(12) United States Patent
Kurn

(10) Patent No.: US 8,512,956 B2
(45) Date of Patent: Aug. 20, 2013

(54) METHOD FOR CLONAL AMPLIFICATION

(75) Inventor: Nurith Kurn, Palo Alto, CA (US)

(73) Assignee: Nugen Technologies, Inc., San Carlos, CA (US)

( * ) Notice: Subject to any disclaimer, the term of this patent is extended or adjusted under 35 U.S.C. 154(b) by 0 days.

(21) Appl. No.: 13/206,309

(22) Filed: Aug. 9, 2011

(65) Prior Publication Data

US 2011/0294132 A1 Dec. 1, 2011

Related U.S. Application Data

(63) Continuation of application No. 12/370,514, filed on Feb. 12, 2009, now abandoned.

(60) Provisional application No. 61/085,811, filed on Aug. 1, 2008, provisional application No. 61/074,991, filed on Jun. 23, 2008, provisional application No. 61/028,146, filed on Feb. 12, 2008.

(51) Int. Cl.
*C12Q 1/68* (2006.01)
*C12P 19/34* (2006.01)

(52) U.S. Cl.
USPC .................. 435/6.12; 435/91.1; 435/91.2

(58) Field of Classification Search
USPC ...................... 435/6.12, 91.1, 91.2
See application file for complete search history.

(56) References Cited

U.S. PATENT DOCUMENTS

| | | | |
|---|---|---|---|
| 5,571,669 A | 11/1996 | Lu et al. | |
| 5,824,517 A * | 10/1998 | Cleuziat et al. | 435/91.2 |
| 6,251,639 B1 * | 6/2001 | Kurn | 435/91.2 |
| 6,376,191 B1 | 4/2002 | Yu et al. | |
| 6,946,251 B2 * | 9/2005 | Kurn | 435/6.1 |
| 2005/0037351 A1 | 2/2005 | Kanno et al. | |
| 2006/0183132 A1 | 8/2006 | Fu et al. | |
| 2006/0257879 A1 | 11/2006 | Wilson et al. | |
| 2009/0203531 A1 | 8/2009 | Kurn et al. | |
| 2011/0105364 A1 | 5/2011 | Kurn | |

OTHER PUBLICATIONS

U.S. Appl. No. 13/349,927, filed Jan. 13, 2012, Kurn et al.
U.S. Appl. No. 12/855,611, filed Aug. 12, 2012, Kurn et al.
U.S. Appl. No. 12/880,032, filed Sep. 10, 2012, Kurn et al.
U.S. Appl. No. 13/103,865, filed May 9, 2011, Kurn et al.
U.S. Appl. No. 13/156,294, filed Jun. 8, 2011, Raymond et al.
European search report and search opinion dated Jul. 1, 2011 for Application No. 9711405.2.
Office action dated Aug. 2, 2011 for U.S. Appl. No. 12/792,702.
Office action dated Jan. 19, 2012 for U.S. Appl. No. 12/792,702.
Office action dated Jan. 19, 2012 for U.S. Appl. No. 13/211,996.

(Continued)

*Primary Examiner* — Kenneth Horlick
(74) *Attorney, Agent, or Firm* — Wilson Sonsini Goodrich & Rosati

(57) ABSTRACT

The present method provides methods, libraries, and kits related to the archiving and clonal amplification of sequences related to target polynucleotide sequences. The method allows for the generation and attachment of polynucleotides with defined 3' and 5' ends to solid surfaces. The polynucleotides attached to the solid substrates can be stored or archived as libraries and can subsequently be retrieved for analysis, for example by clonal amplification using a single composite amplification primer comprising a DNA portion and an RNA portion. In some embodiments, nucleotides attached to solid surfaces can be used for sequencing of nucleotide sequences related to the target DNA. The methods are applicable to total RNA and/or total DNA analysis.

14 Claims, 20 Drawing Sheets

(56) References Cited

OTHER PUBLICATIONS

Notice of allowance dated Sep. 2, 2011 for U.S. Appl. No. 12/615,958.
Office action dated Apr. 2, 2012 for U.S. Appl. No. 13/103,865.
Office action dated Apr. 6, 2012 for U.S. Appl. No. 13/282,732.
Office action dated May 1, 2012 for U.S. Appl. No. 13/349,927.
Office action dated Jul. 23, 2012 for U.S. Appl. No. 13/211,996.
Office action dated Sep. 14, 2012 for U.S. Appl. No. 13/282,732.
Office action dated Oct. 31, 2012 for U.S. Appl. No. 13/103,865.
U.S. Appl. No. 13/282,732, filed Oct. 27, 2011, Kurn.
U.S. Appl. No. 13/918,636, filed Jun. 14, 2013, Kurn et al.
U.S. Appl. No. 13/922,146, filed Jun. 19, 2013, Kurn.

* cited by examiner

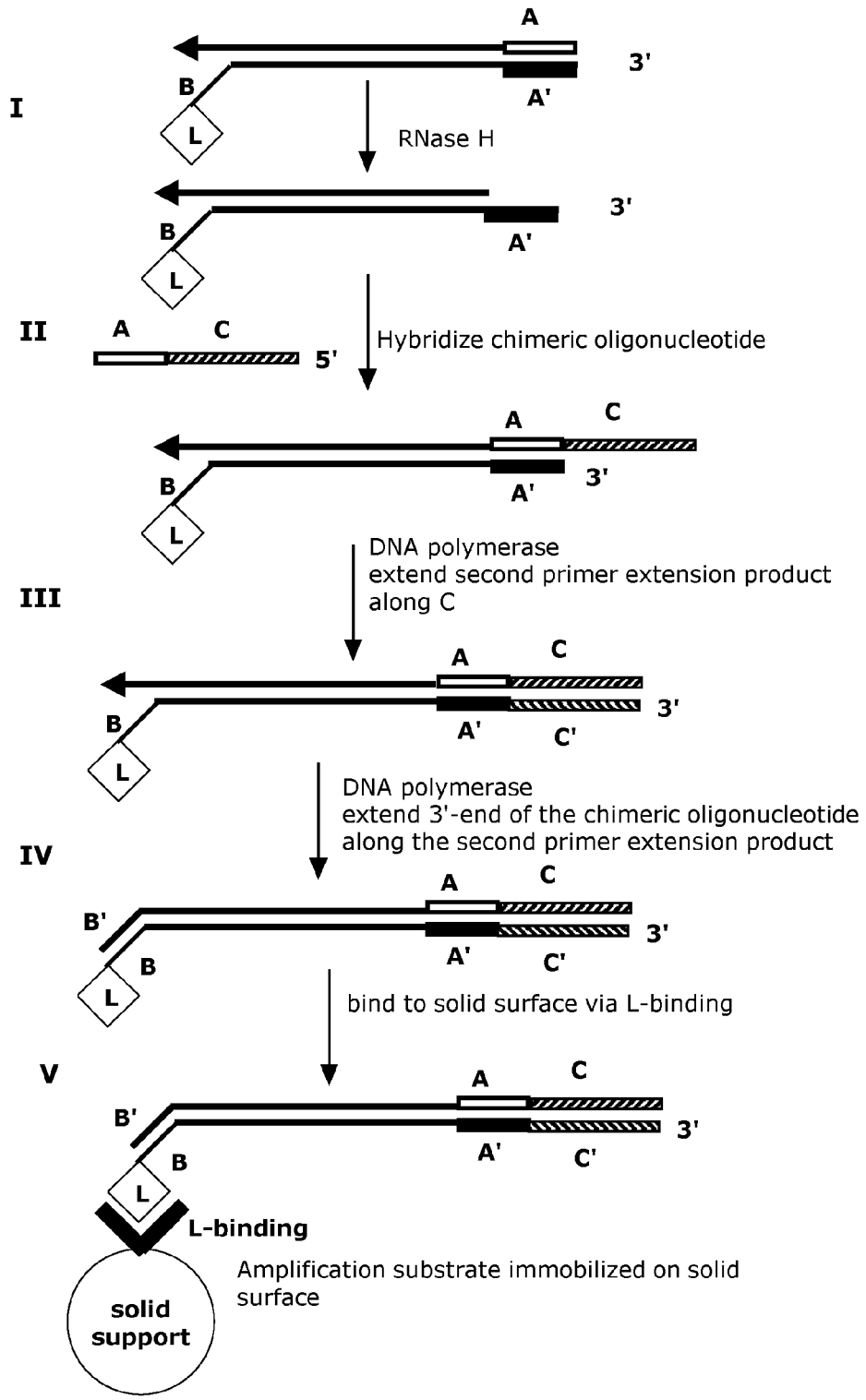

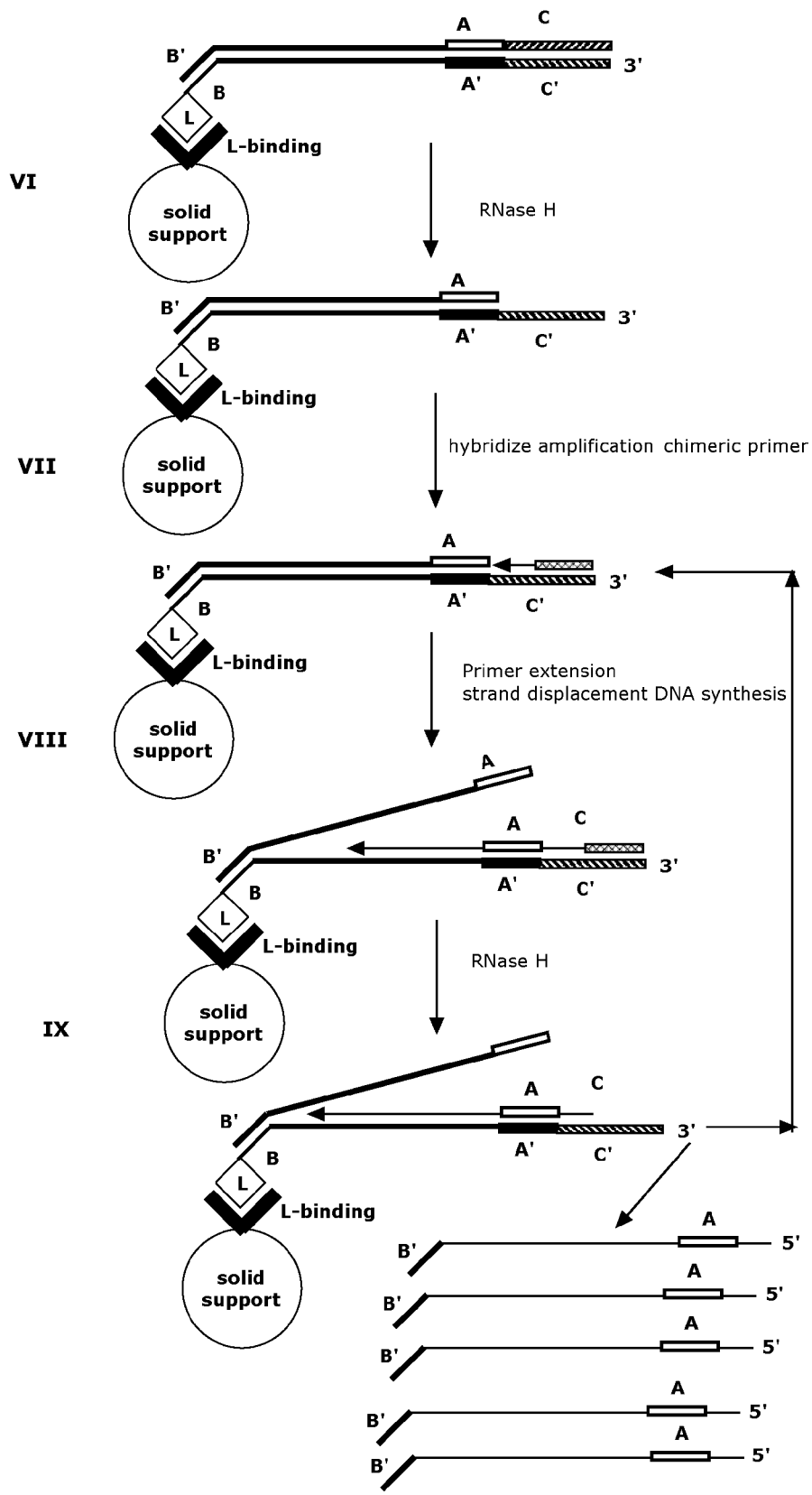

METHOD FOR CLONAL AMPLIFICATION

CROSS-REFERENCE

This application is a continuation of U.S. application Ser. No. 12/370,514 filed on Feb. 12, 2009, now abandoned, which claims the benefit of U.S. Provisional Application Nos. 61/028,146, filed Feb. 12, 2008; 61/074,991, filed Jun. 23, 2008; and 61/085,811, filed Aug. 1, 2008; which applications are incorporated herein by reference in their entirety. This application is also related to the co-pending patent application Ser. No. 12/370,534 filed Feb. 12, 2009, which is incorporated herein by reference in its entirety.

BACKGROUND OF THE INVENTION

The quality and quantity of nucleic acid sample is important for many studies. High-throughput genomic analysis requires large amounts of template for testing, yet typically the yield of nucleic acids from individual patient samples is limited. Forensic and paleoarcheology work also can be severely limited by nucleic acid sample size. The limitation of starting material impacts the ability to carry out large scale analysis of multiple parameters, as is required for, for example, the genotyping of multiple loci in the study of complex diseases. Moreover, it is well accepted that molecular analysis determination of genomic instability in various pathological condition such as cancer, is most precisely carried out in well defined cell populations, such as that obtained by laser capture micro-dissection or cell sorting. Nucleic acid amplification technologies that provide global amplification of very small polynucleotide samples, for example, from one or a very few cells, may provide a solution to the limited starting materials generally available for analysis.

Likewise, the ability to amplify ribonucleic acid (RNA) is an important aspect of efforts to elucidate biological processes. Total cellular mRNA represents gene expression activity at a defined time. Gene expression is affected by cell cycle progression, developmental regulation, response to internal and external stimuli and the like. The profile of expressed genes for any cell type in an organism reflects normal or disease states, response to various stimuli, developmental stages, cell differentiation, and the like. Non-coding RNAs have been shown to be of great importance in regulation of various cellular functions and in certain disease pathologies. Such RNAs are often present in very low levels. Thus, amplification methods capable of amplifying low abundance RNAs, are of great importance.

In addition to the need for amplifying RNA and DNA, there is a need for being able to archive samples, and later retrieve the samples for analysis.

Various methods for global amplification of DNA target molecules (e.g., whole genome amplification) have been described, including methods based on the polymerase chain reaction (PCR). See, e.g., U.S. Pat. Nos. 5,731,171; 6,365,375; Daigo et al., (2001) Am. J. Pathol. 158 (5):1623-1631; Wang et al, (2001); Cancer Res. 61:4169-4174; Zheng et al, (2001) Cancer Epidemiol. 10:697-700; Dietmaier et al (1999) Am. J. Pathol. 154 (1) 83-95; Stoecklein et al (2002) Am. J. Pathol. 161 (1):43-51; U.S. Pat. Nos. 6,124,120; 6,280,949; Dean et al (2002) PNAS 99 (8):5261-5266. However, PCR-based global amplification methods, such as whole genome amplification (WGA), may generate non-specific amplification artifacts, give incomplete coverage of loci, or generate DNA of insufficient length that cannot be used in many applications. PCR-based methods also suffer from the propensity of the PCR reaction to generate products that are preferentially amplified, and thus resulting in biased representation of genomic sequences in the products of the amplification reaction. Methods of global amplification of DNA using composite primers have been described. See e.g. U.S. patent application Ser. No. 10/824,829.

Additionally, a number of methods for the analysis of gene expression have been developed in recent years. See, for example, U.S. Pat. Nos. 6,251,639, 6,692,918, 6,686,156, 5,744,308; 6,143,495; 5,824,517; 5,829,547; 5,888,779; 5,545,522; 5,716,785; 5,409,818; EP 0971039A2; EP0878553A2; and U.S. published patent applications nos. 2002/0115088, 2003/0186234, 2003/0087251, and 2004/0023271. These include quantification of specific mRNAs, and the simultaneous quantification of a large number of mRNAs, as well as the detection and quantification of patterns of expression of known and unknown genes. RNA amplification is most commonly performed using the reverse transcriptase-polymerase chain reaction (RT-PCR) method and variations thereof. These methods are based on replication of RNA by reverse transcriptase to form single stranded DNA complementary to the RNA (cDNA), which is followed by polymerase chain reaction (PCR) amplification to produce multiple copies of double stranded DNA. However, the total amount of sample RNA that is available is frequently limited by the amount of biological sample from which it is derived. Biological samples are often limited in amount and precious. Moreover, the amount of the various RNA species is not equal; some species are more abundant than others are, and these are more likely and easier, to analyze. The ability to amplify RNA sequences enables the analysis of less abundant, rare RNA species. The ability to analyze small samples, by means of nucleic acid amplification, is also advantageous for design parameters of large scale screening of effector molecule libraries, for which reduction in sample volume is a major concern both for the ability to perform very large scale screening or ultra high throughput screening, and in view of the limiting amounts of library components. Methods of amplification from RNA templates have been described, for example in U.S. Pat. No. 6,946,251.

Sequencing of nucleic acids continues to be one of the most important and useful ways to analyze DNA and RNA samples. Recent developments have made possible highly parallel high throughput sequencing. Many of these approaches use an in vitro cloning step to generate many copies of each individual molecule. Emulsion PCR is one method, isolating individual DNA molecules along with primer-coated beads in aqueous bubbles within an oil phase. A polymerase chain reaction (PCR) then coats each bead with clonal copies of the isolated library molecule and these beads are subsequently immobilized for later sequencing. See, e.g. WO04069849A2, WO05010145A2. In other cases, surface methods of clonal amplification have been developed, for example, by the use of polonies (PCR colonies), or by bridge PCR where fragments are amplified upon primers attached to a solid surface. These methods produce many physically isolated locations which each contain many copies of a single fragment. While these methods have provided improvements in sequencing throughput, there is a continuing need to improve the methods of obtaining samples appropriate for sequencing, and of handling, storing, and amplifying such samples.

Therefore, there is a need for improved methods of obtaining, storing, amplifying, and analyzing DNA and RNA samples, including methods which can globally amplify DNA or RNA polynucleotide targets. The invention described herein fulfills this need.

SUMMARY OF THE INVENTION

One aspect of the invention comprises amplifying a target nucleic acid sequence (DNA or RNA) or the complement of a target nucleic acid sequence on a solid support such as a bead, a magnetic bead, a substantially planar array, an isolated surface, or a well in a plate to form a plurality (e.g. 2; 3; 4; 5; 10; 25; 50; 100; 150; 500; 1,000; 5,000; 25,000 or more) of amplified products. In some cases, the plurality of amplified products comprise clonally amplified products such that a given bead, isolated surface, or well contains a plurality of amplified products of substantially identical sequence. The amplification may be performed by linear amplification such as for example single primer isothermal amplification (SPIA), amplification using a single primer such as for example single primer PCR, rolling circle amplification, or SPIA, amplification from a double stranded nucleic acid having a single stranded 3' overhang, amplification using a DNA-RNA chimeric amplification primer, or any combination thereof. In some embodiments of the method, the amplification step results in at least 1,000; 5,000; 10,000; 100,000; 1,000,000; or more copies of the target nucleic acid or a portion thereof. In some embodiments of the method, the amplification step is performed on a linear template. In some embodiments of the method, the target nucleic acid sequence and/or the amplified product is greater than 100; 200; 400; 500; 1,000; 2,000; 5,000 or more base pairs in length.

One aspect of the invention comprises a method for clonally amplifying a target nucleic acid sequence or its complement by delivering a target nucleic acid sequence or a set of target nucleic acid sequences into the aqueous phase of a microdroplet of an emulsion and performing linear amplification of the target nucleic acid or a portion thereof in the aqueous phase of the emulsion such that on average each microdroplet amplifies one or less than one of the target nucleic acid sequence or sequences, or such that on average the step of amplification provides microdroplets that comprise a plurality of amplified products that are substantially identical in sequence. In some cases, the amplification within an emulsion is performed in the presence of a solid substrate such as a bead or isolated surface. In some cases, the solid substrate may comprise capture moieties useful for capturing a target nucleic acid and/or amplified product. In some cases, the amplification is performed such that on average, a given bead or isolated surface captures one or less than one target nucleic acid, or such that a given bead or isolated surface captures a plurality of amplified products that are substantially identical in sequence.

One aspect of the invention comprises a kit for performing the methods of the present invention. The kit may be useful for amplifying DNA or RNA for subsequent analysis such as expression analysis including quantitative PCR or microarray analysis; sequencing including thermocycle sequencing, dye terminator sequencing, sequencing using the methods of Illumina/Solexa, SOLiD (ABI), Roche/454 LifeSciences, Helicos, or Sequenom; alternatively the kit may be useful for archiving DNA or RNA sequencing. In another aspect, the kit may be useful for generating clonally expanded target sequences. In yet another aspect, the kit may be useful for generating one or a plurality of amplified products having a defined 3' and 5' end. The kit comprises an RNA-DNA chimeric first primer for creating a first primer extension product, and an RNA-DNA chimeric oligonucleotide for annealing to an end of a double stranded nucleic acid product having a single stranded 3' overhang at one end. In some embodiments, the kit may further comprise a polymerase having substantial strand-displacement activity. In some embodiments, the kit may further comprise a second primer. In some embodiments, the kit may further comprise RNase H.

One aspect of the invention comprises a method for creating a double stranded nucleic acid comprising an RNA-DNA heteroduplex, wherein the double stranded nucleic acid is suitable for creating amplified products by single primer isothermal linear amplification that have a defined 5' and 3' end. The method comprises (a) annealing to a template nucleic acid and extending a first primer or a set of first primers with a DNA polymerase comprising a DNA segment and a 5' RNA segment, wherein a 3' portion of the primer is complementary to a target nucleic acid sequence of interest, and a portion of the 5' RNA segment, sequence (A), is not complementary to the target nucleic acid. The annealing and the extension produces a first primer extension product or set of products that is hybridized to the target nucleic acid. The extension step may be performed with an RNA-dependant DNA polymerase from an RNA template or a DNA-dependent DNA polymerase from a DNA template. In some cases, step (a) may be performed in the presence of RNA and DNA and an inhibitor such as for example actinomycin to selectively inhibit the formation of an extension product complementary to the DNA.

The method further comprises (b) separating or removing the first primer extension product from the target nucleic acid. The separating step may be performed by heat, enzyme, chemical treatment, or a combination thereof.

The method further comprises step (c) annealing and extending a second primer with a DNA-dependent DNA polymerase. The second primer may comprise a 3' DNA segment and a 5' DNA segment, wherein a portion of the 3' DNA segment is complementary to the first primer extension product or set of first primer extension products and a 5' portion, sequence (B), is not complementary to the first primer extension product or the set of first primer extension products, to produce a double-stranded DNA product or a set of double-stranded DNA products, each product comprising the first primer extension product hybridized to a second primer extension product. The second primer extension product may comprise a DNA sequence (A') that is complementary to and hybridized to the RNA sequence (A) of the first primer extension product at its 3' end, thereby forming a double stranded nucleic acid product or products with an RNA-DNA heteroduplex at one end.

The method further comprises step (d) cleaving the RNA from the RNA-DNA heteroduplex. The cleaving step may be performed using an enzyme that is specific for the RNA portion of an RNA-DNA heteroduplex such as for example RNase H. The cleaving step may provide a double stranded nucleic acid product or products with a single stranded 3' overhang at one end.

The method further comprises step (e) annealing a chimeric oligonucleotide comprising a 5' end, wherein the 5' end comprises sequence (C), and the 5' end further comprises RNA, and a 3' end wherein the 3' end comprises the DNA sequence (A), to the single stranded 3' overhang of the double stranded nucleic acid product or products formed in step (d).

The method further comprises step (f), extending the double stranded nucleic acid product or products with a DNA polymerase to produce a double stranded nucleic acid product with a (C)-(C') RNA-DNA heteroduplex at one end and a (B)-(B') double stranded DNA sequence at the other end.

In some embodiments of the method, the second primer further comprises a ligand at a 5' end of the 5' DNA segment.

In some embodiments of the method, the method further comprises binding the ligand to a solid surface, whereby the first and second primer extension product or products are bound to the solid surface.

In some embodiments of the method, the method further comprises step (g), cleaving the RNA portion of the chimeric oligonucleotide in the DNA-RNA heteroduplex to generate a double stranded nucleic acid or a set of double stranded nucleic acids with a single stranded 3' overhang at one end of sequence (C'). The method may further comprise step (h), annealing a DNA-RNA chimeric amplification primer to the single stranded portion of the second primer extension product. The chimeric amplification primer may comprise a sequence (C) that is complementary to the 3' overhang formed in step (g). The chimeric amplification primer may comprise a DNA portion and a 5' RNA portion. The method may further comprise step (i), extending the amplification primer with a DNA polymerase having strand displacement activity to produce an amplified product hybridized to the second primer extension product. The method may further comprise step (j), cleaving the RNA from the amplified product hybridized to the second primer extension product in the RNA-DNA heteroduplex; and step (k), repeating steps (h) to (j) to produce multiple copies of amplified product comprising a 5' end and a 3' end, wherein the 5' end comprises sequence (A) and the end comprises sequence (B').

In some embodiments of the method, the method comprises use of a first primer that comprises a random annealing sequence such as for example random hexamers or random decamers. Alternatively, the method comprises use of a set of first primers, wherein each member of the set of first primers comprises a distinct 3' DNA annealing sequence, each specific for a target or a region of template nucleic acid. Alternatively, the method comprises use of a first primer that comprises a degenerate annealing sequence for binding to multiple related target sequences. Alternatively, the method comprises use of a first primer that comprises a poly-T sequence, or any sequence that substantially hybridizes to the poly-sequence of messenger RNA. Alternatively, the first primer or set of first primers may comprise a combination thereof.

In some embodiments of the method, the method comprises use of a second primer that comprises a random annealing sequence such as for example random hexamers or random decamers. Alternatively, the method comprises use of a set of second primers, wherein each member of the set of first primers comprises a distinct 3' DNA annealing sequence, each specific for a target or a region of template nucleic acid. Alternatively, the method comprises use of a second primer that comprises a degenerate annealing sequence for binding to multiple related target sequences. Alternatively, the second primer or set of second primers may comprise a combination thereof.

In some embodiments of the method, the amplified products are attached, bound, or covalently linked to a solid surface such as a bead. In some cases, the attached, bound, or covalently linked amplified products comprise a clonally amplified sequence on the surface such as a bead or an isolated area on a surface. In some cases, the bead or isolated area on a surface is the only bead or isolated area on a surface within an isolated liquid volume such as an aqueous droplet in a water/oil emulsion or a liquid volume in the well of a plate, such that the amplified product is contained with such a liquid volume. In some cases, the bead or isolated area comprises covalently attached oligonucleotides comprising sequence (B), at their 3' ends, whereby upon the amplification of step (k) multiple copies of amplified product comprising sequence (B') at their 5' end are hybridized to the bead or isolated area.

In some embodiments of the method, the sequence (B) covalently attached to the bead or isolated area is extended to produce multiple polynucleotides covalently attached to the bead or isolated area that are substantially complementary to the amplified product, wherein the multiple polynucleotides comprise sequence (A') near their 5' ends and sequence (B) near their 3' ends.

In some embodiments of the method, the method further comprises removing the amplified product from the bead or isolated area to render the covalently attached polynucleotides single stranded, and extending a sequencing primer, a portion of which is complementary to a portion of sequence (C') to produce a detectable signal or detectable oligonucleotide fragments characteristic of the sequence of the polynucleotide bound to the bead or isolated area, and thereby perform sequencing. In some cases, the sequencing method comprises the use of cleavable labeled terminators, dye terminators, pyrophosphate detection, an isothermal sequencing method, cycle sequencing, or sequencing by ligation.

One aspect of the invention comprises a method for attaching a target nucleic acid (DNA or RNA) to a solid surface such as a bead or an isolated area. The target nucleic acid attached thereto may be useful for example for clonally amplifying the sequence or a portion thereof. The method comprises step (a), providing a first nucleic acid or a set of first nucleic acids comprising DNA corresponding to a region of a target nucleic acid and further comprising a 5' end and a 3' end, wherein said 5' end of the first nucleic acid or the set of first nucleic acids comprises a sequence (A) and a sequence (C), wherein said sequence (A) is 3' of sequence (C), and wherein sequence (C) comprises RNA, and wherein said 3' end of the first nucleic acid comprises sequence (B'). The first nucleic acid may be from a variety of sources including but not limited to the methods provided herein, single primer polymerase chain reaction products, products, and endonuclease treated rolling circle amplification products. The method further comprises step (b), hybridizing the first nucleic acid or set of first nucleic acids to a solid support comprising an oligonucleotide comprising sequence (B) complementary to sequence (B') of the first nucleic acid. The solid support may be a bead, a substantially planar array, or a magnetic bead. In some cases, the bead or an isolated area of the solid support may comprise only one copy of the first nucleic acid. The method further comprises step (c), extending the oligonucleotide to produce a double stranded product comprising a second nucleic acid hybridized to the first nucleic acid, wherein the second nucleic acid comprises a 3' segment complementary to a portion of the first nucleic acid and a 5' segment complementary to a portion of the first nucleic acid, whereby a portion of the 3' segment comprises a sequence (A') and a portion of the 3' segment comprises a sequence (C'), and wherein the sequence (A') is 5' of the sequence (C'), and whereby a portion of the 5' segment comprises sequence (B). In some cases, the bead or an isolated area of the solid support may thus comprise only one copy of the first and second nucleic acid.

In some embodiments, a plurality of first and second nucleic acids are provided corresponding to different sequences in the target nucleic acid. In some cases, the plurality of first and second nucleic acids are bound to one or a plurality of beads or isolated areas on a surface. In some cases, the plurality of first and second nucleic acids are bound to a plurality of beads or isolated areas on a surface such that generally, or on average, one or fewer than one first and second nucleic acids are bound to one bead or isolated area.

In some embodiments, the method further comprises amplifying the target nucleic acid by treating the first and second nucleic acids bound to the beads or isolated areas with reagents to produce multiple copies of amplification product in an clonal fashion (i.e. multiple copies of substantially one amplification product on each bead or isolated area) that are complementary to all or a portion of the second nucleic acid product. In some cases, the reagents comprise SPIA amplification reagents including but not limited to a DNA-RNA chimeric amplification primer, a DNA-polymerase with substantial strand-displacement activity, and RNase H. In some cases, the bead or isolated area are stored prior to the step of amplification.

One aspect of the invention comprises a method for attaching a polynucleotide sequence that is representative of a sequence within a nucleic acid target molecule to a solid surface comprising: (a) extending a first primer comprising a DNA segment and a 5' RNA segment, wherein a 3' portion of the primer, sequence (P), is complementary to a target nucleic acid and a 5' portion of the of the primer, sequence (A), is not complementary to the target nucleic acid, to form a first primer extension product hybridized to the target nucleic acid; (b) separating or removing the first primer extension product from the target nucleic acid; (c) extending a second primer to produce a double stranded product comprising a second primer extension product hybridized to the first primer extension product, wherein the second primer comprises a 3' segment complementary to a portion of the first primer extension product and a ligand, whereby a portion of the 3' end of the second primer extension product comprises a sequence (A') that is complementary to the sequence (A) of the of the first primer; and (d) binding the ligand to a receptor bound to a solid surface whereby the second primer extension product is attached to the solid surface.

One aspect of the invention comprises a method comprising: (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid; (b) cleaving the target RNA from the RNA/DNA hybrid; and (c) extending a second primer, comprising a ligand and a 3' segment complementary to a portion of the first primer extension product, to produce a double stranded product with a DNA/RNA heteroduplex at one end; wherein the double stranded product comprises a second primer extension product hybridized to the first primer extension product, and whereby a portion of the 3' end of the second primer extension product comprises a sequence (A') that is complementary to the sequence (A) of the of the first primer.

In some embodiments of the method, the 3' portion of the primer that is complementary to the target RNA comprises a random nucleotide sequence. In some embodiments of the method the 3' portion of the primer that is complementary to the target RNA comprises a sequence that is complementary to polyadenosine (poly-A). In some embodiments of the method the 3' portion of the primer that is complementary to the target RNA comprises a specific sequence that is complementary to a multiplicity of targets. In some embodiments of the method, in step (b), the target RNA is cleaved by heat, enzyme treatment, or chemical treatment.

In some embodiments of the method the RNA target is in a sample that also comprises DNA, and wherein actinomycin is added prior to step (a) to selectively inhibit the production of extension product complementary to the DNA during step (a).

In some embodiments of the method the 3' segment of the second primer complementary to a portion of the first primer extension product comprises a random nucleotide sequence, a specific sequence complementary to a specific sequence of the first primer extension product, or a sequence common to multiple first primer extension products. In some embodiments of the method the second primer further comprises a nucleotide sequence (B) that is not complementary to the first primer extension product sequence. In some embodiments of the method the method further comprises step (d) of binding the ligand to a solid surface, whereby the second primer extension product becomes bound to the solid surface. In some embodiments of the method the binding of the ligand results in the double stranded product being bound to the solid surface. In some embodiments of the method the binding of the ligand results in the single stranded second primer extension product being bound to the solid surface.

In some embodiments of the method the method further comprises treating the solid surface with reagents to produce multiple copies of an amplification product that are substantially complementary the second primer extension product. In some embodiments of the method the solid surface comprises a substantially planar array. In some embodiments of the method the solid surface comprises a bead. In some embodiments of the method the bead comprises a magnetic bead. In some embodiments of the method the bead comprises only one copy of second primer extension product. In some embodiments of the method the second primer extension product is single-stranded. In some embodiments of the method the second primer extension product is double-stranded.

In some embodiments of the method a plurality of second primer extension products are produced corresponding to different sequences in the target RNA. In some embodiments of the method the plurality of second primer extension products is bound to one or a plurality of beads or a plurality of isolated areas on a surface. In some embodiments of the method the plurality of second primer extension products is bound to a plurality of beads under conditions such that generally, one or fewer second primer extension products is bound to one bead or one isolated area on a surface.

In some embodiments of the method the method further comprises treating the beads or isolated areas with reagents to produce multiple copies of an amplification product complementary to all or a portion of the second primer extension products. In some embodiments of the method the plurality of beads or isolated areas are contained within a plurality of isolated volumes such that generally one or fewer beads or isolated area is associated with each isolated volume, and whereby the production of multiple copies of amplification product results in multiple copies of substantially one amplification product in each volume. In some embodiments of the method the amplification is carried out with a reaction mixture comprising RNase H, an amplification primer comprising a DNA portion and a 5' RNA portion, and a DNA polymerase with strand displacement activity.

In some embodiments of the method the method further comprises the step of storing the beads or isolated areas comprising generally one or fewer primer extension products per bead or isolated area.

In some embodiments of the method the method further comprises clonally amplifying the primer extension product bound to the beads or isolated areas after storing them.

One aspect of the invention comprises a method for amplifying a nucleic acid representative of a target RNA comprising carrying out steps (a) through (d) above and further comprises the steps of: (e) cleaving the RNA in the heteroduplex from the first primer extension product such that a portion of the second primer extension product that is complementary to sequence (A) is single stranded; (f) annealing an amplification primer to the single stranded portion of the second primer extension product complementary to sequence (A), wherein the amplification primer has a DNA portion and a 5' RNA portion; (g) extending the amplification primer with a DNA polymerase having strand displacement activity to produce an amplified product hybridized to the second primer extension product; (h) cleaving the RNA from the amplified product hybridized to the second primer extension product; and repeating steps (f) to (h) to produce multiple copies of amplified product.

In some embodiments of the method the second primer further comprises a sequence (B that is not complementary to the first primer extension product sequence, whereby the amplification product comprises a sequence at its 3' end which is complementary to (B). In some embodiments of the method the target RNA comprises messenger RNA.

One aspect of the invention comprises a method comprising: (a) denaturing a double-stranded target DNA; (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a plurality of first primer extension products, each with sequence (A) at its 5' end; and (c) extending a second primer comprising a ligand and a 3' DNA region that comprises a random sequence, wherein the primer is optionally a tailed primer comprising a nucleic acid sequence (B) that is 5' of the random sequence, to form a plurality of double-stranded products each comprising a first primer extension product and a second primer extension product whereby the second primer extension product comprises a ligand;

In some embodiments of the method step (b) comprises a first incubation at a temperature below about 30° C., and a second incubation at a temperature above about 40° C. In some embodiments of the method a DNA polymerase which is active at temperatures above about 45° C. is used to extend the first primer.

In some embodiments of the method the method further comprises step (d) of binding the ligand to a solid surface, whereby the plurality of second primer extension products become bound to the solid surface.

In some embodiments of the method the binding of the ligand results in the double stranded product being bound to the solid surface. In some embodiments of the method the binding of the ligand results in the single stranded second primer extension product being bound to the solid surface.

In some embodiments of the method the method further comprises treating the solid surface with reagents to produce multiple copies of amplification products that are substantially complementary to the plurality of second primer extension products. In some embodiments of the method the solid surface comprises a substantially planar array. In some embodiments of the method the solid surface comprises a plurality of beads or a plurality of isolated areas on a surface. In some embodiments of the method the plurality of second primer extension products is bound to a plurality of beads or isolated areas under conditions such that generally, one or fewer copies of a single second primer extension product is bound to one bead or one isolated area.

In some embodiments of the method the method further comprises treating the beads or isolated areas with reagents to produce multiple copies of an amplification product substantially complementary to the second primer extension products. In some embodiments of the method the plurality of beads or isolated areas are contained within a plurality of isolated volumes such that generally one or fewer beads or isolated area is associated with each isolated volume, and whereby the production of multiple copies of amplification product results in multiple copies of substantially one amplification product in each volume. In some embodiments of the method the amplification is carried out with a reaction mixture comprising RNase H, an amplification primer with a DNA portion and a 5' RNA portion, and a DNA polymerase with strand displacement activity.

In some embodiments of the method the method further comprises the step of storing the beads or isolated areas comprising generally one or fewer primer extension products.

In some embodiments of the method the method further comprises clonally amplifying the primer extension product bound to the beads or isolated areas after storing them.

One aspect of the invention comprises a method for amplifying a nucleic acid representative of a target DNA comprising carrying out steps (a) through (d) and further comprising the steps of: (e) cleaving the RNA from the first primer extension products such that a portion of the second primer extension product that is complementary to sequence (A) is single stranded; (f) annealing an amplification primer to the single stranded portion of the second primer extension products complementary to sequence (A), wherein the amplification primer has a DNA portion and a 5' RNA portion; (g) extending the amplification primer with a DNA polymerase having strand displacement activity to produce an amplified product hybridized to the second primer extension product; (h) cleaving the RNA from the amplified product hybridized to the second primer extension product; and repeating steps (f) to (h) to produce multiple copies of amplified product In some embodiments of the method the second primer comprises a tailed primer comprising a nucleic acid sequence (B) that is 5' of the random sequence, whereby the amplified product comprises a portion complementary to sequence (B) at or near its 3' end. In some embodiments of the method the target DNA is genomic DNA. In some embodiments of the method the target DNA comprises multiple genomes.

One aspect of the invention comprises a method for archiving and/or clonal expansion of a nucleotide sequence comprising the steps of: (a) obtaining a plurality of partially double-stranded DNA products comprising a first polynucleotide and a second polynucleotide, wherein the second polynucleotide comprises a sequence (A') at its 3' end and a ligand, wherein the sequence (A') portion of the second polynucleotide is single-stranded, wherein optionally the second polynucleotide comprises a sequence (B) at or near its 5' end; (b) attaching the partially double stranded DNA products to a plurality of beads or a plurality of isolated areas on a surface by binding the ligands to the bead or isolated area; (c) annealing an amplification primer to the single stranded portion of the second polynucleotide complementary to sequence (A'), wherein the amplification primer has a DNA portion and a 5' RNA portion; (d) extending the amplification primer with an enzyme having strand displacement activity to produce a plurality of amplified products hybridized to the second polynucleotide products; (e) cleaving the RNA from the amplified product hybridized to the second polynucleotide products using RNase H; and repeating steps (c) to (e) to produce multiple copies of amplified products.

In some embodiments of the method the ligands of the DNA products are attached to beads or isolated areas, and on average, one DNA product is attached to one or fewer beads or isolated areas.

In some embodiments of the method the method further comprises storing the plurality of beads or isolated areas for later analysis.

In some embodiments of the method the beads or isolated areas are stored after step (b), then later amplified with steps (c) through (f). In some embodiments of the method the amplification is a clonal amplification carried out in multiple isolated volumes wherein on average, one isolated volume has one or fewer beads or isolated areas. In some embodiments of the method the multiple isolated volumes are droplets in a non-aqueous phase.

One aspect of the invention comprises a method comprising: (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid; (b) cleaving the target RNA from the RNA/DNA hybrid; (c) extending a second primer, comprising a ligand and a 3' segment complementary to a portion of the first primer extension product, to produce a double stranded product with a DNA/RNA heteroduplex at one end; wherein the double stranded product comprises a second primer extension product hybridized to the first primer extension product, and wherein a portion of the 3' end of the second primer extension product comprises a sequence (A') that is complementary to the sequence (A) of the of the first primer; (d) cleaving the RNA in the heteroduplex from the first primer extension product such that a portion of the second primer extension product that is complementary to sequence (A) is single stranded; (e) annealing to the second primer extension product an oligonucleotide comprising a 3'-DNA segment that is complementary to sequence (A') and a 5' RNA segment comprising sequence (C); (f) optionally extending the oligonucleotide to form an oligonucleotide extension product hybridized to the second primer extension product; (g) extending the second primer extension product to create a heteroduplex such that the second primer comprises a DNA sequence (C') that is complementary to sequence (C); and (h) cleaving the RNA from the heteroduplex created in step (g) to produce a single-stranded portion of the second primer extension product corresponding to sequence (C').

In some embodiments of the method the 3' portion of the first primer that is complementary to the target RNA comprises a random nucleotide sequence. In some embodiments of the method the 3' portion of the first primer that is complementary to the target RNA comprises a sequence that is complementary to polyadenosine (poly-A). In some embodiments of the method the 3' portion of the primer that is complementary to the target RNA comprises a specific sequence that is complementary to a multiplicity of targets.

In some embodiments of the method the RNA target is contained within a sample that also comprises DNA, and actinomycin is added prior to step (a) to selectively inhibit the production of extension product complementary to the DNA during step (a).

In some embodiments of the method, in step (b), the target RNA is cleaved by chemical heat, or enzyme treatment.

In some embodiments of the method the 3' segment of the second primer complementary to a portion of the first primer extension product comprises a random nucleotide sequence, a specific sequence complementary to a specific sequence of the first primer extension product, or a sequence common to multiple first primer extension products.

In some embodiments of the method the method further comprises: (i) binding the ligand on the second primer extension product to a solid surface. In some embodiments of the method, step (i) of binding the ligand to the solid surface is performed before step (h). In some embodiments of the method, step (i) of binding the ligand to the solid surface is performed after step (h).

One aspect of the invention comprises a method of amplifying a sequence representative of an sequence within an RNA target molecule comprising carrying out steps (a) through (i), and further comprising the steps of: (j) annealing an amplification primer, wherein the amplification primer has a DNA portion and a 5' RNA portion, to the single stranded portion of the second primer extension product complementary to sequence (C'); (k) extending the amplification primer with an enzyme having strand displacement activity to produce an amplified product; (l) cleaving the RNA from the amplified product; and (m) repeating steps (j) to (l) to produce multiple copies of amplified product wherein the 5' portion of the amplified product has a sequence complementary to sequence (A').

In some embodiments of the method, the second primer further comprises a segment (B) that is not complementary to the first primer extension product sequence, whereby the amplified product comprises a sequence (B') at or near its 3' end that is substantially complementary to sequence (B), and a sequence (A) near its 5' end that is complementary to sequence (A'). In some embodiments of the method, the amplification is a clonal amplification. In some embodiments of the method, the solid surface is a bead or an isolated area on a surface. In some embodiments of the method, the bead or isolated area is the only bead or isolated area associated with a isolated liquid volume such that the amplified product is contained within such liquid volume. In some embodiments of the method, the liquid volume is an aqueous droplet within a non-aqueous fluid. In some embodiments of the method, the solid surface is a bead and the droplet is part of a microemulsion. In some embodiments of the method, the liquid volume is a well in a plate. In some embodiments of the method, the solid surface is a substantially planar substrate.

In some embodiments of the method, the bead or isolated area comprises covalently attached thereto multiple oligonucleotides comprising the sequence (B) at their 3' ends, whereby upon the amplification of step (m) multiple copies of amplified product comprising sequence (B') at their 5' end are hybridized to the bead or isolated area.

One aspect of the invention comprises a method of producing a bead or isolated area with multiple copies of a nucleotide sequence covalently attached thereto by attaching the amplified product as described above, and further comprising extending the (B) sequences to produce a multiple polynucleotides covalently attached to the bead or isolated area that are substantially complementary to the amplified product and that comprise sequence (A') near their 5' ends.

One aspect of the invention comprises a sequencing method comprising extending the (B) sequences as described above, further comprising the steps of removing the amplified product to render the covalently attached polynucleotides single-stranded, and extending a primer to sequence (A') to produce detectable oligonucleotide fragments characteristic of the sequence of the polynucleotide bound to the bead or isolated area. In some embodiments of the method, the sequencing method comprises cleavable labeled terminators. In some embodiments of the method, the sequencing method comprises pyrophosphate detection. In some embodiments of the method, the sequencing method is an isothermal sequencing method. In some embodiments of the method the sequencing method comprises cycle sequencing.

One aspect of the invention comprises a method of performing bridge PCR comprising creating amplified product with defined 3' and 5' ends as described herein, and further comprising the steps of exposing the amplified product to a solid substrate comprising oligonucleotide sequences attached thereto complementary to the A and B' sequences on the amplified product in the presence of components necessary for polymerase chain reaction, and thermal cycling the system to perform bridge PCR amplification.

One aspect of the invention comprises a method of performing rolling circle amplification comprising creating amplified product with defined 3' and 5' ends as described herein, and further comprising the steps of: (n) hybridizing the amplified product to a nucleic acid sequence comprising regions complementary to A and B' sequences in close proximity; (o) optionally extending the gap with a DNA polymerase enzyme; (p) ligating to form a circular nucleic acid comprising the amplified product, and performing rolling circle amplification by extending a primer that is complementary to a sequence in the circular nucleic acid. In some embodiments of the method, the primer is complementary to sequence (A), sequence (B'), or a sequence that was between sequences (A) and (B') in the amplified product. In some embodiments of the method, the primer is an oligonucleotide attached to a solid surface.

One aspect of the invention comprises a method of PCR amplification comprising creating amplified product with defined 3' and 5' ends as described herein further comprising the steps of amplifying the amplified product using primers complementary to sequences (A) and (B), or using primers complementary to sequences (A') and (B').

One aspect of the invention comprises a method of strand displacement amplification (SDA) creating amplified product with defined 3' and 5' ends as described herein wherein sequences (A) and (B') in the amplified product are designed to be cleaved by a restriction enzyme, and performing strand displacement amplification on the amplified product.

One aspect of the invention comprises a method comprising: (a) denaturing a double-stranded target DNA; (b) annealing to the target DNA and extending with and enzyme comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a plurality of first primer extension products, each with sequence (A) at its 5' end; (c) extending a second primer comprising a ligand and a 3' DNA region that comprises a random sequence, wherein the primer is optionally a tailed primer comprising a nucleic acid sequence (B) that is 5' of the random sequence, to form a plurality of double-stranded products each comprising a first primer extension product and a second primer extension product whereby the second primer extension product comprises a ligand; (d) cleaving the RNA from the first primer extension products such that a portion of the second primer extension products that are complementary to sequence (A) are single stranded; (e) annealing to the second primer extension product an oligonucleotide comprising a 3'-DNA segment that is complementary to sequence (A') and a 5'-RNA segment comprising sequence (C); (f) optionally extending the oligonucleotide to form a plurality of oligonucleotide extension products hybridized to the second primer extension products; (g) extending the second primer extensions product to create a heteroduplex such that the second primer extension products comprise a DNA sequence (C') that is complementary to sequence (C); and (h) cleaving the RNA from the heteroduplex created in step (g).

In some embodiments of the method the method further comprises: (i) binding the ligand on the second primer extension products to a solid surface. In some embodiments of the method, step (i) of binding the ligand to the solid surface is performed before step (h). In some embodiments of the method, step (i) of binding the ligand to the solid surface is performed after step (h).

One aspect of the invention comprises a method of amplifying a sequence representative of an sequence within n DNA target molecule carrying out steps (a) through (h) above, and further comprising the steps of: (j) annealing an amplification primer, wherein the amplification primer has a DNA portion and a 5' RNA portion, to the single stranded portion of the second primer extension products complementary to sequence (C'); (k) extending the amplification primer with an enzyme having strand displacement activity to produce a amplified products; (l) cleaving the RNA from the amplified products; and (m) repeating steps (j) to (l) to produce multiple copies of amplified products wherein the 5' portion of the amplified product has a sequence complementary to sequence (A').

In some embodiments of the method, the second primer comprises the segment (B) that is not complementary to the first primer extension product sequence, whereby the amplified products comprise a sequence (B') at or near their 3' ends that is substantially complementary to sequence (B), and a sequence (A) near their 5' ends that is complementary to sequence (A'). In some embodiments of the method, the amplification is a clonal amplification. In some embodiments of the method, the solid surface is a bead or isolated area on a surface. In some embodiments of the method, the bead or isolated area is the only bead or isolated area within isolated liquid volume such that the amplified product is contained within such liquid volume. In some embodiments of the method, the liquid volume is an aqueous droplet within a non-aqueous fluid. In some embodiments of the method, the solid surface is a bead and the droplet is part of a microemulsion. In some embodiments of the method, the liquid volume is a well in a plate. In some embodiments of the method, the solid surface is a substantially planar substrate.

In some embodiments of the method, the bead or isolated area comprises covalently attached multiple oligonucleotides comprising the sequence (B) at their 3' ends, whereby upon the amplification of step (m) multiple copies of amplified products comprising sequence (B') at their 5' end are hybridized to the bead or isolated area.

One aspect of the invention comprises a method of producing a bead or isolated area with multiple copies of a nucleotide sequence covalently attached thereto by comprising hybridizing amplified product as described herein further comprising extending the (B) sequences to produce a multiple polynucleotides covalently attached to the bead or isolated area that are substantially complementary to the amplified product and that comprise sequence (A') near their 5' ends.

One aspect of the invention comprises a sequencing method comprising hybridizing amplified product to a solid surface as described herein, further comprising the steps of removing the amplified product to render the covalently attached polynucleotides single-stranded, and extending a primer to sequence (A') to produce detectable oligonucleotide fragments characteristic of the sequence of the polynucleotide bound to the bead or isolated area. In some embodiments of the method, the sequencing method comprises cleavable labeled terminators. In some embodiments of the method the sequencing method comprises pyrophosphate detection. In some embodiments of the method, the sequencing method is an isothermal sequencing method. In some embodiments of the method, the sequencing method comprises cycle sequencing.

One aspect of the invention comprises a method of performing bridge PCR comprising creating amplified product with defined 3' and 5' ends as described herein further comprising the steps of exposing the amplified products to a solid substrate comprising oligonucleotide sequences attached thereto complementary to the A and B' sequences on the amplified products in the presence of components necessary for polymerase chain reaction, and thermal cycling the system to perform bridge PCR amplification.

One aspect of the invention comprises a method of performing rolling circle amplification comprising creating amplified product with defined 3' and 5' ends as described above further comprising the steps of: (n) hybridizing the amplified products to a target nucleic acid comprising regions complementary to A and B' sequences in close proximity; (o) optionally extending the gap with a polymerase enzyme; (p) ligating to form a circular nucleic acid comprising the amplified product, and performing rolling circle amplification by extending a primer that is complementary to a sequence in the circular nucleic acid. In some embodiments of the method, the primer is complementary to sequence (A), sequence (B'), or a sequence that was between sequences (A) and (B') in the amplified product. In some embodiments of the method, the primer is an oligonucleotide attached to a solid surface.

One aspect of the invention comprises a method of PCR amplification comprising creating amplified product with defined 3' and 5' ends as described above further comprising the steps of amplifying the amplified product using primers complementary to sequences (A) and (B), or using primers complementary to sequences (A') and (B').

One aspect of the invention comprises a method of strand displacement amplification (SDA) comprising creating amplified product with defined 3' and 5' ends as described above wherein sequences (A) and (B') in the amplified product are designed to be cleaved by a restriction enzyme, and performing strand displacement amplification on the amplified product.

One aspect of the invention provides an alternative method to produce DNA with defined 3' and 5' sequences from RNA.

One aspect of the invention comprises a method comprising: (a) extending a first primer comprising a 3' portion complementary to a target RNA and a 5' portion, sequence (D), not complementary to the target RNA, to form a first primer extension product hybridized to the target RNA, forming an RNA/DNA hybrid; (b) cleaving the target RNA from the RNA/DNA hybrid; (c) extending a second primer comprising a DNA segment and a 5' RNA segment, wherein a 3' portion of the primer is complementary to the first primer extension product and a 5' portion, sequence (E), of the of the second primer is not complementary to the first primer extension product, to produce a double-stranded DNA product comprising the first primer extension product hybridized to a second primer extension product, whereby the second primer extension product has a sequence (D') that is complementary to sequence (D) at its 3' end; (d) denaturing the double-stranded DNA product; (e) annealing to the second primer extension product and extending a third primer comprising, from its 5' end, a ligand, optionally a sequence (F), and a sequence (D), wherein sequence (D) is complementary to sequence (D') on the second primer extension product to produce a double-stranded DNA product comprising the second primer extension product hybridized to a third primer extension product, whereby the third primer extension product comprises a sequence (E') at its 3' end complementary to sequence (E).

In some embodiments of the method the method further comprises binding the ligand to a solid surface, whereby the third primer extension product is bound to the solid surface.

One aspect of the invention comprises an amplification method comprising carrying out steps (a) through (e) further comprising the steps of: (f) cleaving the RNA portion of the second primer extension product in the DNA-RNA heteroduplex, whereby sequence (E') of the third primer extension product is single stranded. (g) annealing an oligonucleotide comprising a 3' DNA segment (E) that is complementary to sequence (E') and a 5' RNA segment comprising sequence (G); (h) extending the third primer extension product to produce a sequence (G') at its 3' end complementary to sequence (G); cleaving the RNA from the heteroduplex created in step (h) to produce a single-stranded portion of the third primer extension product corresponding to sequence (G'). In some embodiments of the method the method further comprises binding the ligand to a solid surface, whereby the third primer extension product comprising sequence (G') is bound to the solid surface. In some embodiments of the method, the 3' portion of the first primer that is complementary to the target RNA comprises a random nucleotide sequence. In some embodiments of the method, the 3' portion of the first primer that is complementary to the target RNA comprises a sequence that is complementary to polyadenosine (poly-A). In some embodiments of the method, the RNA target is contained within a sample that also comprises DNA, and actinomycin is added prior to step (a) to selectively inhibit the production of extension product complementary to the DNA during step (a).

In some embodiments of the method, in step (b), the target RNA is cleaved by heat, enzyme treatment, or chemical treatment or enzymes.

In some embodiments of the method, the 3' segment of the second primer complementary to a portion of the first primer extension product comprises a random nucleotide sequence, a specific sequence complementary to a specific sequence of the first primer extension product, or a sequence common to multiple first primer extension products.

One aspect of the invention comprises a method of amplifying a sequence representative of an sequence within an RNA target molecule carrying out steps (a) through (i) and further comprising the steps of: (j) annealing an amplification primer, wherein the amplification primer has a DNA portion and a 5' RNA portion, to the single stranded portion of the third primer extension product complementary to sequence (G'); (k) extending the amplification primer with an enzyme having strand displacement activity to produce an amplified product; (l) cleaving the RNA from the amplified product; and (m) repeating steps (j) to (l) to produce multiple copies of amplified product wherein the 5' portion of the amplified product has a sequence (E) complementary to sequence (E') and the 3' end of the amplified product has sequence (D') complementary to sequence (D) and optionally sequence (F') complementary to sequence (F).

In some embodiments of the method, the amplification is a clonal amplification. In some embodiments of the method, the solid surface is a bead or an isolated area on a surface. In some embodiments of the method, the bead or isolated area is the only bead or isolated area within isolated liquid volume such that the amplified product is contained within such liquid volume. In some embodiments of the method, the liquid volume is an aqueous droplet within a non-aqueous fluid. In some embodiments of the method, the droplet is part of a microemulsion. In some embodiments of the method, the liquid volume is a well in a plate. In some embodiments of the method, the solid surface is a substantially planar substrate.

In some embodiments of the method, the bead or isolated area comprises covalently attached thereto multiple oligonucleotides comprising the sequence (D), and/or sequence (F) at their 3' ends, whereby upon the amplification of step (m) multiple copies of amplified product comprising sequence (D') (and/or F') at their 5' end are hybridized to the bead or isolated area.

One aspect of the invention comprises a method of producing a bead or isolated area with multiple copies of a nucleotide sequence covalently attached thereto by hybridizing amplified product as described above, further comprising extending the oligonucleotide at the (D), and/or (F) sequences to produce a multiple polynucleotides covalently attached to the bead or isolated area that are substantially complementary to the amplified product comprising sequence (E') near their 5' ends.

One aspect of the invention comprises a sequencing method comprising producing a bead with multiple copies of a nucleotide sequence covalently attached thereto, further comprising the steps of removing the amplified product to render the covalently attached polynucleotides single-stranded, and extending a primer to sequence (E') to produce detectable oligonucleotide fragments characteristic of the sequence of the polynucleotide bound to the bead or isolated area. In some embodiments of the method, the sequencing method comprises cleavable labeled terminators. In some embodiments of the method, the sequencing method comprises pyrophosphate detection. In some embodiments of the method, the sequencing method is an isothermal sequencing method. In some embodiments of the method, the sequencing method comprises cycle sequencing.

One aspect of the invention comprises alternative methods to produce DNA with defined 3' and 5' sequences from a DNA target One aspect of the invention comprises a method comprising: (a) denaturing a double-stranded target DNA; (b) annealing to the target DNA and extending a first primer comprising a 3' portion comprising a random sequence and a 5' portion, sequence (D), which is not complementary to the target DNA, to form a plurality of first primer extension products, each comprising sequence (D) at its 3' end; (c) extending a second primer comprising a DNA segment and a 5' RNA segment, wherein a 3' portion comprises a random sequence, and a 5' portion, sequence (E), of the of the second primer is not complementary to the first primer extension products, to produce a plurality of double-stranded DNA products comprising a first primer extension product hybridized to a second primer extension product, whereby the second primer extension products have a sequence (D') that is complementary to sequence (D) at their 3' ends; (d) denaturing the double-stranded DNA products; e) annealing to the second primer extension products and extending a third primer comprising, from its 5' end, a ligand, optionally a sequence (F), and a sequence (D), wherein sequence (D) is complementary to sequence (D') on the second primer extension products to produce double-stranded DNA products comprising second primer extension products hybridized to third primer extension products, whereby the third primer extension products comprise a sequence (E') at its 3' end complementary to sequence (E) in a DNA-RNA heteroduplex.

In some embodiments of the method the method further comprises binding the ligand to a solid surface, whereby the third primer extension products are bound to the solid surface.

In some embodiments of the method the method further comprises the steps of: (f) cleaving the RNA portion of the second primer extension products in the DNA-RNA heteroduplex, whereby sequence (E') of the third primer extension products is single stranded. (g) annealing an oligonucleotide comprising a 3' DNA segment (E) that is complementary to sequence (E') and a 5' RNA segment comprising sequence (G); (h) extending the third primer extension products to produce a sequence (G') at their 3' ends complementary to sequence (G); (i) cleaving the RNA from the heteroduplex created in step (h) to produce single-stranded portions of the third primer extension products corresponding to sequence (G').

In some embodiments of the method the method further comprises binding the ligand to a solid surface, whereby the third primer extension products comprising sequence (G') are bound to the solid surface.

One aspect of the invention comprises a method of amplifying a sequence representative of a sequence within a DNA target molecule comprising following the steps (a) through (i), further comprising the steps of: (j) annealing an amplification primer to the single stranded portion of the third primer extension products complementary to sequence (G'); wherein the amplification primer has a DNA portion and a 5' RNA portion, (k) extending the amplification primer with an enzyme having strand displacement activity to produce a amplified products; (l) cleaving the RNA from the amplified products; and (m) repeating steps (j) to (l) to produce multiple copies of amplified products wherein the 5' portion of the amplified products have a sequence (E) complementary to sequence (E') and the 3' end of the amplified products have sequence (D') complementary to sequence (D) and optionally sequence (F') complementary to sequence (F).

In some embodiments of the method, the amplification is a clonal amplification. In some embodiments of the method, the solid surface is a plurality of beads or a plurality of isolated areas on a surface.

In some embodiments of the method, each bead or isolated area in the plurality of beads or isolated areas is the only bead or isolated area within isolated liquid volume such that the amplified product corresponding to the sequence on that bead or isolated area is associated with such liquid volume. In some embodiments of the method, the liquid volume is an aqueous droplet within a non-aqueous fluid. In some embodiments of the method, the droplet is part of a microemulsion. In some embodiments of the method, the liquid volume is a well in a plate. In some embodiments of the method, the solid surface is a substantially planar substrate.

In some embodiments of the method, the bead or isolated area comprises covalently attached thereto multiple oligonucleotides comprising the sequence (D), and/or sequence (F) at their 3' ends, whereby upon the amplification of step (m) multiple copies of amplified product comprising sequence (D') (and/or sequence (F') at their 5' end are hybridized to the bead or isolated area.

One aspect of the invention comprises a method of producing a bead or isolated area with multiple copies of a nucleotide sequence covalently attached thereto further comprising extending the (D), and/or (F) sequences to produce a multiple polynucleotides covalently attached to the bead or isolated area that are substantially complementary to the amplified product comprising sequence (E') near their 5' ends.

One aspect of the invention comprises a sequencing method comprising creating amplified product with defined 3' and 5' ends as described above, further comprising the steps of removing the amplified product to render the covalently attached polynucleotides single-stranded, and extending a primer to sequence (E') to produce detectable oligonucleotide fragments characteristic of the sequence of the polynucleotide bound to the bead or isolated area. In some embodiments of the method, the sequencing method comprises cleavable labeled terminators. In some embodiments of the method, the sequencing method comprises pyrophosphate detection. In some embodiments of the method, the sequencing method is an isothermal sequencing method. In some embodiments of the method, the sequencing method comprises cycle sequencing.

In one aspect the invention comprises a library of nucleic acid sequences.

One aspect of the invention comprises a library comprising a plurality of double-stranded oligonucleotides each of the oligonucleotides comprising: (a) a first strand comprising DNA which has, proceeding from its 5' end (i) a ligand, (ii) a specific sequence (B, D, or DF), (iii) a sequence corresponding to or complementary to a sequence within a nucleic acid target, (iv) a specific sequence (A' or E'); and a specific sequence (C' or G'); and (b) a second strand having from its 5' end, (i) a specific RNA sequence (C or G) complementary to specific sequence C' or G', (ii) a specific sequence (A or E) complementary to sequence (A' or E'), (iii) a sequence complementary to or corresponding to a sequence within a target nucleic acid. In some embodiments, the ligands are bound to a solid surface. In some embodiments, the solid surface comprises a plurality of beads. In some embodiments, each of the plurality of beads comprises a single molecule of double-stranded oligonucleotide. In some embodiments, the solid surface comprises a plurality of isolated areas on a surface.

One aspect of the invention relates to kits comprising reagents that can be used, for example, for carrying out the methods of the invention.

One aspect of the invention comprises kit comprising: (a) a first primer comprising a 3'-DNA portion and a 5'-RNA portion, wherein the 5' RNA portion further comprises sequence (A); (b) a second primer comprising a 5'-ligand; (c) an RNA dependent DNA polymerase; (d) a DNA dependent DNA polymerase with strand displacement activity; (e) RNase H; and (f) an amplification chimeric primer comprising a 3'-DNA portion and a 5'-RNA portion wherein the sequence of the amplification primer is the substantial the same sequence as the (A) sequence. In some embodiments, the 3'-DNA portion of the first primer comprises a random sequence. In some embodiments, the second primer is a DNA primer that comprises a random sequence at its 3' end. In some embodiments, the 3'-DNA portion of the first primer comprises a random sequence, and the second primer is a DNA primer that comprises a random sequence at its 3' end.

One aspect of the invention comprises a kit comprising: (a) a first primer comprising a 3'-DNA portion and a 5'-RNA portion, wherein the 5' RNA portion further comprises sequence (A); (b) a second primer comprising a 5'-ligand; (c) an RNA dependent DNA polymerase; (d) a DNA dependent DNA polymerase with strand displacement activity; (e) RNase H; (f) a chimeric oligonucleotide comprising a 3'-DNA portion substantially comprising sequence (A) and a 5'-RNA sequence (C); and (g) a chimeric amplification primer comprising a 3'-DNA portion and a 5'-RNA portion, wherein the chimeric amplification primer comprises a sequence which is substantially the same as sequence (C). In some embodiments, the 3'-DNA portion of the first primer comprises a random sequence. In some embodiments, the second primer is a DNA primer that comprises a random sequence at its 3' end. In some embodiments, the 3'-DNA portion of the first primer comprises a random sequence, and the second primer is a DNA primer that comprises a random sequence at its 3' end. In some embodiments, the second primer further comprises a sequence (B) at or near the 5'-end. In some embodiments, the kit further comprises solid support with immobilized receptor to the ligand on it surface. In some embodiments, the kit further comprises solid surface with an oligonucleotide attached to the surface by the 5'-end and comprising a sequence substantially the same as sequence (B).

In some embodiments, the kit further comprises solid surface with an oligonucleotide attached to the surface by the 5'-end hybridizable to sequence (A).

In some embodiments, the kit further comprises an inhibitor of the DNA dependent DNA polymerase. In some embodiments, the inhibitor of the DNA dependent DNA polymerase is Actinomycin.

One aspect of the invention comprises a kit comprising: (a) a first primer that is a tailed DNA primer comprising a 5'-tail sequence (D); (b) a second primer that is a chimeric primer comprising a 3'-DNA portion and a 5'-RNA portion wherein the 5'-end comprises a tail sequence (E); (c) a third primer which is a tailed primer comprising a 3'-sequence that comprises a sequence substantially the same as sequence (D), optionally a 5'-tail sequence (F), and 5'-ligand; (d) an RNA dependent DNA polymerase; e) a DNA dependent DNA polymerase with strand displacement activity; (f) RNase H; and (g) a chimeric amplification primer comprising a 3'-DNA portion and a 5'-RNA portion wherein the chimeric amplification primer comprises a sequence which is substantially the same a sequence (E).

In some embodiments, the 3'-DNA portion of the first primer comprises a random sequence. In some embodiments, the second primer is a DNA primer that comprises a random sequence at its 3' end. In some embodiments, the 3'-DNA portion of the first primer comprises a random sequence, and the second primer is a DNA primer that comprises a random sequence at its 3' end.

One aspect of the invention comprises a kit comprising: (a) a first primer that is a tailed DNA primer comprising a 5'-tail sequence (D); (b) a second primer that is a chimeric primer comprising a 3'-DNA portion and a 5'-RNA portion wherein the 5'-end comprises a tail sequence (E); (c) a third primer which is a tailed primer comprising a 3'-sequence that comprises a sequence substantially the same as sequence (D), optionally a 5'-tail sequence (F), and 5'-ligand; (d) an RNA dependent DNA polymerase; e) a DNA dependent DNA polymerase with strand displacement activity; (f) RNase H; (g) a chimeric oligonucleotide comprising a 3'-DNA sequence (E) and a 5'-RNA sequence G; and (h) a chimeric amplification primer comprising a 3'-DNA portion and a 5'-RNA portion wherein the chimeric amplification primer comprises a sequence which is substantially the same as sequence (G). In some embodiments, the 3'-DNA portion of the first primer comprises a random sequence. In some embodiments, the second primer is a DNA primer that comprises a random sequence at its 3' end. In some embodiments, the 3'-DNA portion of the first primer comprises a random sequence, and the second primer is a DNA primer that comprises a random sequence at its 3' end. In some embodiments, the kit further comprises an inhibitor of the DNA dependent DNA polymerase, In some embodiments, the inhibitor of the DNA dependent DNA polymerase is Actinomycin.

One aspect of the invention comprises a method for attaching a polynucleotide sequence that is representative of a sequence within a nucleic acid target molecule to a solid surface comprising: (a) extending a first primer comprising a DNA segment and a 5' RNA segment, wherein a 3' portion of the primer, sequence (P), is complementary to a target nucleic acid and a 5' portion of the of the primer, sequence (A), is not complementary to the target nucleic acid, to form a first primer extension product hybridized to the target nucleic acid; (b) separating or removing the first primer extension product from the target nucleic acid; (c) extending a second primer to produce a double-stranded product comprising a second primer extension product hybridized to the first primer extension product, wherein the second primer comprises a 3' segment complementary to a portion of the first primer extension product and 5' segment non-complementary sequence (B) to the first primer extension product, whereby a portion of the 3' end of the second primer extension product comprises a sequence (A') that is complementary to the sequence (A) of the of the first primer and a portion of the 5' end of the second primer extension product comprises non-complementary sequence (B); (d) adding an exonuclease to the double-stranded DNA/RNA hybrid, whereby single stranded 3' nucleotides are removed from the first primer extension product; (e) extending the first primer extension product to produce a sequence (B'), complementary to sequence (B) on the second primer extension product; (f) denaturing the first and second primer extension products; (g) binding the sequence (B') of the first primer extension product to a third primer comprising sequence (B) bound to a solid surface, whereby the first primer extension product is attached to the solid surface; and (h) extending the sequence (B) of the third primer to produce a double-stranded product comprising a third primer extension product hybridized to the first primer extension product, wherein the 5' end of the third primer comprises a sequence (B) complementary to the sequence (B') of the first primer extension product, whereby a portion of the 3' end of the third primer extension product comprises a sequence (A') that is complementary to the sequence (A) of the of the first primer.

One aspect of the invention comprises a method comprising: (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid; (b) removing the target RNA from the RNA/DNA hybrid; (c) extending a second primer, comprising a 3' segment complementary to a portion of the first primer extension product and a 5' segment non-complementary to the first primer extension product comprising sequence (B), to produce a double-stranded DNA product with a DNA/RNA heteroduplex at one end, wherein the double-stranded product comprises a second primer extension product hybridized to the first primer extension product and wherein a portion of the 3' end of the second primer extension product comprises a sequence (A') that is complementary to the sequence (A) of the of the first primer; (d) adding an exonuclease to the double-stranded DNA product, whereby single stranded 3' nucleotides are removed from the 3' region of the first primer extension product that is not hybridized to the second primer extension product; (e) extending the first primer extension product to produce a sequence (B'), complementary to sequence (B) on the second primer extension product; (f) denaturing the double-stranded DNA product; (g) attaching the single-stranded first primer extension product to a solid support by annealing sequence (B') to the solid support comprising an oligonucleotide attached thereto, comprising a sequence (B); and (h) extending sequence (B) on the solid support to produce a third primer extension product, hybridized to the first extension product, wherein the third primer extension product comprises a 3' sequence (A'), whereby a DNA/RNA heteroduplex at one end is generated.

One aspect of the invention comprises a method for amplifying a nucleic acid representative of a target RNA comprising carrying out steps (a) through (h) above and further comprising the steps of: (i) cleaving the RNA region from the first polynucleotide product hybridized to the third primer extension product using RNase H; (j) annealing an amplification primer to sequence (A') on the single-stranded portion of the third primer extension product, wherein the amplification primer has a DNA portion and a 5' RNA portion; (k) extending the amplification primer with an enzyme having strand displacement activity to produce an amplified product hybridized to the third primer extension product on the solid support; (l) repeating steps (i) to (k) to produce multiple copies of an amplified product wherein the amplified product comprises sequence (B') at its 3' end; and (m) capturing the amplified product on the solid support wherein the solid support comprises sequence (B).

In some embodiments, the 3' portion of the primer that is complementary to the target RNA comprises a random nucleotide sequence. In some embodiments, the 3' portion of the primer that is complementary to the target RNA comprises a sequence that is complementary to polyadenosine (poly-A). In some embodiments, the 3' portion of the primer that is complementary to the target RNA comprises a specific sequence that is complementary to a multiplicity of targets. In some embodiments, the target RNA is cleaved by heat, enzyme treatment, or chemical treatment in step (b).

In some embodiments, the RNA target is in a sample that also comprises DNA, and wherein actinomycin is added prior to step (a) to selectively inhibit the production of extension product complementary to the DNA during step (a). In some embodiments, the 3' portion of the second primer complementary to a portion of the first primer extension product comprises a random nucleotide sequence, a specific sequence complementary to a specific sequence of the first primer extension product, or a sequence common to multiple first primer extension products.

In some embodiments, the solid support comprises a bead. In other embodiments, the solid support comprises an isolated area. In some embodiments, the solid support comprises a plurality of beads or a plurality of isolated areas on a surface. In some embodiments, the solid support comprises a substantially planar array. In some embodiments, the bead comprises a magnetic bead. In some embodiments, the bead comprises only one copy of the first primer extension product.

In some embodiments, the first primer extension product is single-stranded. In some embodiments, a plurality of first primer extension products are produced corresponding to different sequences in the target RNA. In some embodiments, the plurality of first primer extension products is bound to a solid support comprising either one or a plurality of beads or a plurality of isolated areas on a surface. In some embodiments, the plurality of first primer extension products is bound to a plurality of beads under conditions such that generally, one or fewer first primer extension products is bound to one bead or one isolated area on a surface. In some embodiments, the plurality of beads or isolated areas are contained within a plurality of isolated volumes such that generally one or fewer beads or isolated area is associated with each isolated volume, and whereby the production of multiple copies of amplification product results in multiple copies of substantially one amplification product in each volume.

In some embodiments, the method further comprises the step of storing the beads or isolated areas comprising generally one or fewer primer extension products per bead or isolated area. In some embodiments, the method further comprises clonally amplifying the primer extension product bound to the beads or isolated areas after storing them. In other embodiments, the target RNA comprises messenger RNA.

One aspect of the invention comprises a method comprising: (a) denaturing a double-stranded target DNA; (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the primer comprises sequence (A), which is not complementary to the target DNA; to form a plurality of first primer extension product hybridized to the target DNA and comprising sequence (A) at its 5' end; (c) separating the first primer extension product from the target DNA; (d) annealing to the first primer extension product and extending a second primer comprising a 3' complementary DNA region that comprises a random sequence, wherein the second primer is a tailed primer comprising a 5' sequence (B), to form a double-stranded product comprising a first primer extension product and a second primer extension product, whereby a double-stranded product with a DNA/RNA heteroduplex at one end is generated; (e) adding an exonuclease to the double-stranded DNA product, whereby single stranded 3' nucleotides are removed from the 3' region of the first primer extension product that is not hybridized to the second primer extension product; (f) extending the first primer extension product to produce a sequence (B'), complementary to sequence (B) on the second primer extension product; (g) denaturing the double-stranded DNA product; (h) attaching the single-stranded first primer extension product to a solid support by annealing sequence (B') to the solid support comprising an oligonucleotide attached thereto, comprising a sequence (B), whereby a plurality of first primer extension products become bound to the solid surface; and (i) extending sequence (B) on the solid support to produce a third primer extension product, hybridized to the first primer extension product, comprising a 3' sequence (A'), whereby a DNA/RNA heteroduplex at one end is generated.

One aspect of the invention comprises a method for amplifying a nucleic acid representative of a target RNA comprising carrying out steps (a) through (i) above and further comprising the steps of: (j) cleaving the RNA from the first polynucleotide product hybridized to the amplified product using RNase H; (k) annealing an amplification primer to the single-stranded portion of the amplified product complementary to sequence (A'), wherein the amplification primer has a DNA portion and a 5' RNA portion; (l) extending the amplification primer with an enzyme having strand displacement activity to produce an amplified product hybridized to the third primer extension product on the bead or isolated area; (m) repeating steps (j) to (l) to produce multiple copies of an amplified product wherein the amplified product comprises sequence (B') at its 3' end; and (n) capturing the amplified product on the solid support comprising sequence (B).

In some embodiments, step (b) above comprises a first incubation at a temperature below about 30° C., and a second incubation at a temperature above about 40° C. In some embodiments, a DNA polymerase which is active at temperatures above about 45° C. is used to extend the first primer.

In some embodiments, the solid support comprises a bead. In some embodiments, the solid support comprises an isolated area. In some embodiments, the solid support comprises a plurality of beads or a plurality of isolated areas on a surface. In some embodiments, the solid support comprises a substantially planar array. In some embodiments, the bead comprises a magnetic bead.

In some embodiments, the plurality of first primer extension products is bound to a plurality of beads or isolated areas under conditions such that generally, one or fewer copies of a single first primer extension product is bound to one bead or one isolated area. In some embodiments, the plurality of beads or isolated areas are contained within a plurality of isolated volumes such that generally one or fewer beads or isolated area is associated with each isolated volume, and whereby the production of multiple copies of amplification product results in multiple copies of substantially one amplification product in each volume.

In some embodiments, the method further comprises the step of storing the beads or isolated areas comprising generally one or fewer primer extension products. In some embodiments, the method further comprises clonally amplifying the primer extension product bound to the beads or isolated areas after storing them. In some embodiments, the target DNA is genomic DNA. In some embodiments, the target DNA comprises multiple genomes.

One aspect of the invention for preparing DNA with defined 3' and 5' sequences comprises a method comprising: (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid; (b) removing the target RNA from the RNA/DNA hybrid; (c) extending a second primer, comprising a 3' segment complementary to a portion of the first primer extension product and a 5' segment non-complementary to the first primer extension product comprising sequence (B), to produce a double-stranded product with a DNA/RNA heteroduplex at one end; wherein the double-stranded product comprises a second primer extension product hybridized to the first primer extension product, and whereby a portion of the 3' end of the second primer extension product comprises a sequence (A') that is complementary to the sequence (A) of the of the first primer; (d) cleaving the RNA in the heteroduplex from the first primer extension product such that a portion of the second primer extension product that is complementary to sequence (A) is single-stranded; (e) annealing to the second primer extension product an oligonucleotide comprising a 3'-DNA sequence (A) that is complementary to sequence (A') and a 5'-RNA segment comprising sequence (C) that is non-complementary to the second primer extension product; (f) extending the oligonucleotide at the 3' segment to form an oligonucleotide extension product hybridized to the second primer extension product; (g) denaturing the double-stranded DNA product; (h) attaching the single-stranded first primer extension product to a solid support by annealing sequence (B') to the solid support comprising a sequence (B); and (i) extending sequence (B) on the solid support to produce a third primer extension product, comprising a 3' sequence (A') and (C'), whereby a DNA/RNA heteroduplex at one end is generated.

One aspect of the invention comprises a method for amplifying a nucleic acid representative of a target RNA comprising carrying out steps (a) through (i) above and further comprising the steps of: (j) cleaving the RNA from the heteroduplex polynucleotide product hybridized to the amplified product using RNase H to produce a single-stranded portion of the third primer extension product corresponding to sequence (C'); (k) annealing an amplification primer to the single-stranded portion of the third primer extension product complementary to sequence (C'), wherein the amplification primer has a DNA portion and a 5' RNA portion; (l) extending the amplification primer with an enzyme having strand displacement activity to produce an amplified product hybridized to the third primer extension product on the solid support; (m) repeating steps (j) to (l) to produce multiple copies of the amplified product comprising sequences (A) and (B'); and (n) capturing the amplified product on the solid support wherein the solid support comprises sequence (B).

In some embodiments, the method further comprises extending sequence (B), whereby multiple copies are bound to solid support through sequence (B) having sequence (A') at 3' end. In some embodiments, the method further comprises sequencing by synthesis using a sequence (A) complementary to (A') as the priming sequence. In some embodiments, the 3' portion of the first primer that is complementary to the target RNA comprises a random nucleotide sequence. In some embodiments, the 3' portion of the first primer that is complementary to the target RNA comprises a sequence that is complementary to polyadenosine (poly-A). In some embodiments, the 3' portion of the primer that is complementary to the target RNA comprises a specific sequence that is complementary to a multiplicity of targets. In some embodiments, the RNA target is contained within a sample that also comprises DNA, and actinomycin is added prior to step (a) to selectively inhibit the production of extension product complementary to the DNA during step (a). In some embodiments, the target RNA is cleaved by chemical heat, or enzyme treatment in step (b)

In some embodiments, the 3' segment of the second primer complementary to a portion of the first primer extension product comprises a random nucleotide sequence, a specific sequence complementary to a specific sequence of the first primer extension product, or a sequence common to multiple first primer extension products. In some embodiments, the amplification is a clonal amplification.

In some embodiments, the solid support is a bead. In some embodiments, the solid support is an isolated area on a surface. In some embodiments, the bead or isolated area is the only bead or isolated area associated with an isolated liquid volume such that the amplified product is contained within such liquid volume. In some embodiments, the liquid volume is an aqueous droplet within a non-aqueous fluid. In some embodiments, the solid surface is a bead and the droplet is part of a microemulsion. In some embodiments, the liquid volume is a well in a plate. In some embodiments, the solid support is a substantially planar substrate. In some embodiments, a method of producing a solid support with multiple copies of a nucleotide sequence covalently attached thereto by performing the method described above, and further comprising extending the (B) sequences to produce multiple polynucleotides covalently attached to the solid support that are substantially complementary to the amplified product and that comprise sequence (A') near their 3' ends.

In some embodiments, a sequencing method comprises performing the method described above and further comprises the steps of removing the third primer extension product to render the covalently attached polynucleotides single-stranded, and extending a primer to sequence (A) to produce detectable oligonucleotide fragments characteristic of the sequence of the polynucleotide bound to the bead or isolated area. In some embodiments the sequencing method comprises cleavable labeled terminators. In some embodiments the sequencing method comprises pyrophosphate detection. In some embodiments the sequencing method is an isothermal sequencing method. In some embodiments the sequencing method comprises cycle sequencing.

In some embodiments a method of performing bridge PCR comprising performing the method described above and further comprising the steps of exposing the amplified product to a solid substrate comprising oligonucleotide sequences attached thereto complementary to the A and B' sequences on the amplified product in the presence of components necessary for polymerase chain reaction, and thermal cycling the system to perform bridge PCR amplification.

In some embodiments a method of performing rolling circle amplification comprising performing the method described previously and further comprising the steps of: (o) hybridizing the amplified product to a nucleic acid sequence comprising regions complementary to A and B' sequences in close proximity; (p) optionally extending the gap with a DNA polymerase enzyme; (q) ligating to form a circular nucleic acid comprising the amplified product, and performing rolling circle amplification by extending a primer that is complementary to a sequence in the circular nucleic acid.

In some embodiments the primer is complementary to sequence (A), sequence (B'), or a sequence that was between sequences (A) and (B') in the amplified product. In some embodiments the primer is an oligonucleotide attached to a solid surface.

In some embodiments, a method of PCR amplification comprising performing the method previously described and further comprising the steps of amplifying the amplified product using primers complementary to sequences (A) and (B), or using primers complementary to sequences (A') and (B'). In some embodiments, a method of strand displacement amplification (SDA) comprising performing the method previously described wherein sequences (A) and (B') in the amplified product are designed to be cleaved by a restriction enzyme, and performing strand displacement amplification on the amplified product.

One aspect of the invention for preparing DNA with defined 3' and 5' sequences comprises a method comprising: (a) denaturing a double-stranded target DNA; (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a first primer extension product hybridized to the target DNA and comprising sequence (A) at its 5' end; (c) separating the first primer extension product from the target DNA; (d) annealing to the first primer extension product and extending a second primer comprising a 3' complementary DNA region that comprises a random sequence, wherein the second primer is a tailed primer comprising a 5' sequence (B), to form a double-stranded product comprising a first primer extension product and a second primer extension product, whereby a double-stranded product with a DNA/RNA heteroduplex at one end is generated; (e) cleaving the RNA in the heteroduplex from the first primer extension product such that a portion of the second primer extension product that is complementary to sequence (A) is single stranded; (f) annealing to the second primer extension product an oligonucleotide comprising a 3'-DNA segment that is complementary to sequence (A') and a 5' RNA segment comprising sequence (C); (g) extending the oligonucleotide along the second primer extension product to form an oligonucleotide extension product comprising a sequence (B'), complementary to sequence (B) on the second primer extension product; (h) denaturing the double-stranded DNA product; (i) attaching the single-stranded first primer extension product to solid support by annealing sequence (B') to the bead or isolated area comprising a sequence (B); and (j) extending sequence (B) on the solid support to produce a third primer extension product, hybridized to the oligonucleotide extension product, comprising a 3' sequence (A') and (C'), whereby a DNA/RNA heteroduplex at one end is generated.

One aspect of the invention comprises a method for amplifying a nucleic acid representative of a target DNA comprising carrying out steps (a) through (j) above and further comprising the steps of: (k) cleaving the RNA from the heteroduplex polynucleotide product hybridized to the amplified product using RNase H to produce a single-stranded portion of the second primer extension product corresponding to sequence (C'); (l) annealing an amplification primer to the single-stranded portion of the amplified product complementary to sequence (C'), wherein the amplification primer has a DNA portion and a 5' RNA portion; (m) extending the amplification primer with an enzyme having strand displacement activity to produce an amplified product hybridized to the amplified product on the bead or isolated area; and (n) repeating steps (k) to (m) to produce multiple copies of the second polynucleotide product comprising sequences (A) and (B').

In some embodiments, the amplification is a clonal amplification. In some embodiments, the solid support is a bead or isolated area on a surface. In some embodiments, the bead or isolated area is the only bead or isolated area within isolated liquid volume such that the amplified product is contained within such liquid volume. In some embodiments, the liquid volume is an aqueous droplet within a non-aqueous fluid. In some embodiments, the solid surface is a bead and the droplet is part of a microemulsion. In some embodiments, the liquid volume is a well in a plate. In some embodiments, the solid support is a substantially planar substrate. In some embodiments, the bead or isolated area comprises covalently attached multiple oligonucleotides comprising the sequence (B) at their 3' ends, whereby upon the amplification of step (m), multiple copies of amplified products comprising sequence (B') at their 5' end are hybridized to the bead or isolated area.

In some embodiments, a method of producing a bead or isolated area with multiple copies of a nucleotide sequence covalently attached thereto by performing the method previously described and further comprising extending the (B) sequences to produce a multiple polynucleotides covalently attached to the bead or isolated area that are substantially complementary to the amplified product and that comprise sequence (A') near their 5' ends.

In some embodiments, a sequencing method comprising performing the method previously described, further comprising the steps of removing the amplified product to render the covalently attached polynucleotides single-stranded, and extending a primer to sequence (A') to produce detectable oligonucleotide fragments characteristic of the sequence of the polynucleotide bound to the bead or isolated area. In some embodiments, the sequencing method comprises cleavable labeled terminators. In some embodiments, the sequencing method comprises pyrophosphate detection. In some embodiments, the sequencing method is an isothermal sequencing method. In some embodiments, the sequencing method comprises cycle sequencing.

In some embodiments, a method of performing bridge PCR comprising performing the method previously described and further comprising the steps of exposing the amplified products to a solid substrate comprising oligonucleotide sequences attached thereto complementary to the A and B' sequences on the amplified products in the presence of components necessary for polymerase chain reaction, and thermal cycling the system to perform bridge PCR amplification.

In some embodiments, a method of performing rolling circle amplification comprising performing the method previously described and further comprising the steps of: (o) hybridizing the amplified products to a target nucleic acid comprising regions complementary to A and B' sequences in close proximity; (p) optionally extending the gap with a polymerase enzyme; (q) ligating to form a circular nucleic acid comprising the amplified product, and performing rolling circle amplification by extending a primer that is complementary to a sequence in the circular nucleic acid.

In some embodiments, the primer is complementary to sequence (A), sequence (B'), or a sequence that was between sequences (A) and (B') in the amplified product. In some embodiments, the primer is an oligonucleotide attached to a solid surface.

In some embodiments, a method of PCR amplification comprising performing the method previously described and further comprising the steps of amplifying the amplified product using primers complementary to sequences (A) and (B), or using primers complementary to sequences (A') and (B').

In some embodiments, a method of strand displacement amplification (SDA) comprising performing the method previously described wherein sequences (A) and (B') in the amplified product are designed to be cleaved by a restriction enzyme, and performing strand displacement amplification on the amplified product.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A shows a method of producing a second primer extension product comprising, from its 5' end, a ligand, a defined sequence (B), a sequence representative of a target polynucleotide, a sequence (A') and a sequence (C'). The Figure also illustrates binding the second primer extension product to a solid surface.

FIG. 5B illustrates an isothermal amplification using a composite primer utilizing the second primer extension product produced as illustrated in FIG. 5A bound to the bead.

DETAILED DESCRIPTION OF THE INVENTION

Figure 1:
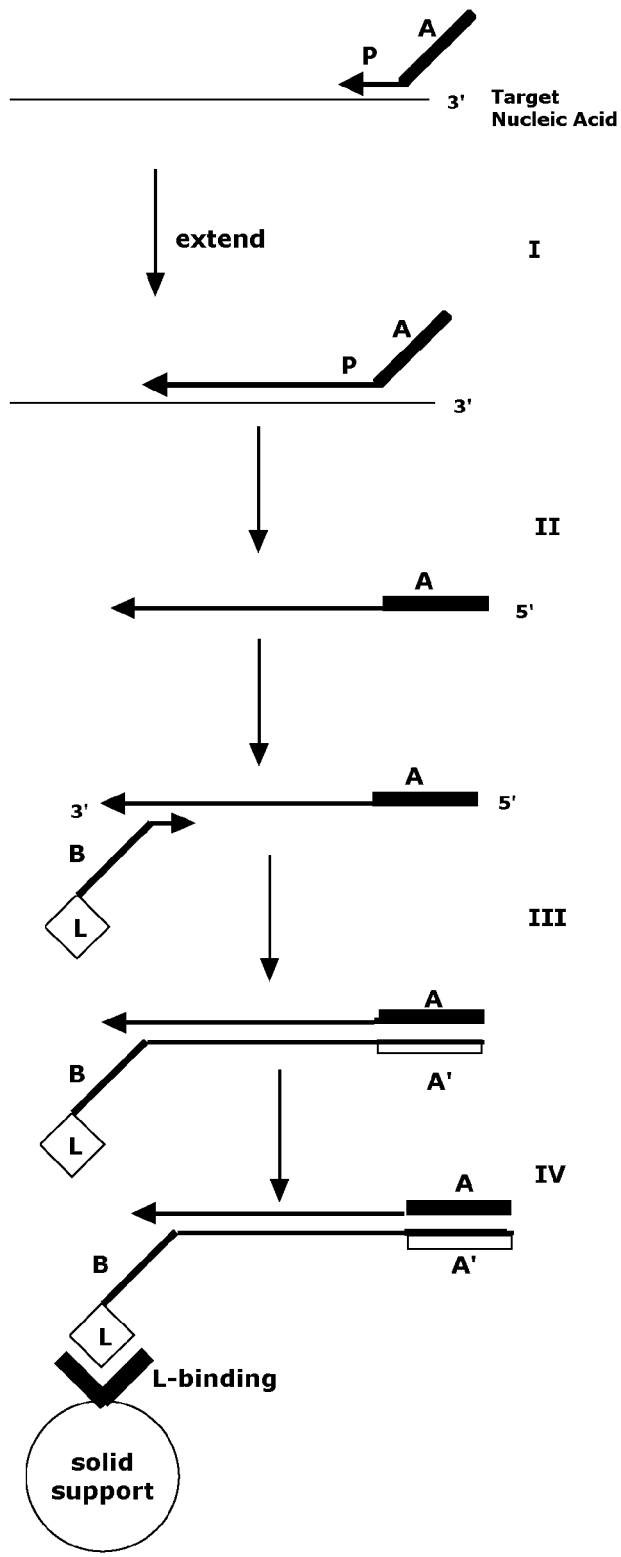
FIG. 1 illustrates a method of producing a polynucleotide bound to a solid support wherein the polynucleotide comprises sequences related to a target nucleic acid and comprises a defined sequence (A') at its 3' end.

The invention provides methods, compositions, and kits useful in the analysis of nucleic acids. Some aspects of the invention relate to the preparation of polynucleotides comprising ligands and binding such ligands to solid surfaces for analysis and for archiving. The polynucleotides bound to the surface are generally produced in a manner that allows for them to be readily manipulated, for example, by incorporating defined 3' and/or 5' regions into the polynucleotides. The bound polynucleotides can then treated by the methods described herein to produce amplified product. The methods of the invention provide for producing amplified product with defined 3' and/or 5' ends. The amplified products having defined 3' and 5' ends can be used for further manipulation and analysis. They can be used, for example in molecular inversion probe (MIP) analysis.

The polynucleotides and amplified product of the present invention generally comprise sequences that are related to (i.e. either equivalent to or complementary to) the target RNA or target DNA from which they are derived. In some embodiments, the methods of the invention can be used for the global isolation and amplification of target RNA or DNA, e.g. messenger RNA (mRNA) or genomic DNA. Thus, the methods can be used to produce a plurality of polynucleotides and/or amplification products having sequence related to the target RNA or DNA, and also having defined, e.g. universal, sequences at their 3' and/or 5' ends. This plurality of polynucleotides and or amplification products can be representative of the target nucleic acid or subset of the target nucleic acid such as to comprise a library of representative sequences.

One aspect of the invention relates to the clonal amplification of nucleic acid sequences of interest. The polynucleotides of the present invention attached to solid substrates can be attached in a manner in which polynucleotides of different specific sequences representative of the target nucleic acid are isolated from one another, for example, each attached to a different bead, or each attached to an isolated area on a surface. In one embodiment, a plurality of polynucleotides, each comprising a specific sequence is bound to a plurality of beads or isolated areas such that only one copy of each polynucleotide is bound to each bead or each isolated surface area. These isolated polynucleotides can then be clonally amplified such that, for example each bead or surface area is retained within an isolated volume. This can be accomplished with beads, for example, by using a microemulsion in which, on average, each droplet comprises one or fewer beads per droplet. The methods of the present invention allow for the archiving of the polynucleotides bound to the beads and the subsequent analysis of the polynucleotides, for example, using clonal amplification.

In one aspect of the invention, the polynucleotide bound to the surface is produced in a manner that is amenable to the sequencing of the polynucleotide, thus revealing information about the target nucleic acid from which it is derived.

Method for Generating Polynucleotide Bound to a Solid Surface

One aspect of the invention is a method for attaching a polynucleotide sequence that is representative of a sequence within a nucleic acid target molecule to a solid surface. The polynucleotide sequence that is produced is representative of the sequence within a nucleic acid target molecule if it is either the same as, or complementary to the sequence within the target nucleic acid. Where the target nucleic acid is double stranded, the method can produce sequences that are representative of both of the strands. The polynucleotide can be, for example either DNA or RNA.

The first step of the method comprises: (a) extending a first primer comprising a DNA segment and a 5' RNA segment, wherein a 3' portion of the primer, sequence (P), is complementary to a target nucleic acid, and a 5' portion of the of the primer, sequence (A), is not complementary to the target nucleic acid, to form a first primer extension product hybridized to the target nucleic acid. The first primer may be extended by a DNA polymerase such as an RNA-dependent DNA polymerase for extending the first primer along an RNA target nucleic acid, or a DNA-dependent DNA polymerase for extending the first primer along a DNA target nucleic acid. In some embodiments, the 3' portion of the primer that is complementary to the target nucleic acid is a specific sequence. For example, where a specific region of interest of a target nucleic acid that is known or suspected to be upstream of a specific sequence on the target nucleic acid, sequence (P) of the composite primer can be designed to hybridize to this specific sequence on the target nucleic acid such that extension of the primer results in producing a first primer extension product that is complementary to such upstream region. The specific sequence may be common to a family of target RNA. A combination of primers with various specific sequences at the 3' end can also be useful. The specific sequence may be common to a family of target RNA. A combination of primers with various specific sequences at the 3' end can also be useful. In some embodiments, such as where the target nucleic acid comprises mRNA, and the mRNA comprises a plurality of sequences, each having a 3' poly-A segment; the specific sequence (P) can comprise a sequence that can hybridize to the poly-A region of the mRNA, thus allowing the extension of the first primer to produce a plurality of first primer extension products, each of which is complementary to the region of an mRNA molecule adjacent to the poly-A region. In some embodiments, the sequence (P) comprises a random sequence, such that the extension of the first primer results in a plurality of first primer extension products complementary to the sequences adjacent to the sequence where each random species hybridizes. The use of a random sequence such as sequence (P) at the 3' end of the primer can be useful for performing a global amplification of a nucleic acid target, generating a plurality of sequences which together can represent, for example substantially the whole sequence of the target nucleic acid. In some embodiments, the relative amounts of the various sequences can be used to quantitate the relative amount of a given sequence in a sample, for example to determine the level of expression in an mRNA sample, or to determine gene copy number in a DNA sample.

The first primer extension product comprises a 5' portion comprising sequence (A). Sequence A comprises RNA. In some embodiments, sequence (A) is RNA, and sequence (P) is DNA. In other embodiments, sequence (A) may comprise some (DNA). In some embodiments, sequence (P) may comprise some RNA. In some embodiments, sequence (A) and sequence (P) are adjacent.

The method further comprises step (b) separating or removing the first primer extension product from the target nucleic acid. The first primer extension product can be separated from the target nucleic acid by a variety of methods. In some cases the separation can be affected by denaturing the complex comprising the first primer extension product and the nucleic acid. Denaturation can be performed, for example by heating the sample, or by adding a denaturing agent, or using a combination of heating the sample and adding denaturing agents. Other methods of separating the first primer extension product from the target nucleic acid involve selectively cleaving or degrading the target nucleic acid. Where the target nucleic acid is RNA, the cleaving or degrading can be accomplished with an enzyme that cleaves RNA from an RNA/DNA hybrid such as RNase H, or chemically, for example with the addition of alkali. In some embodiments, the target nucleic acid is completely cleaved or degraded. In other embodiments, the target nucleic acid is only partly cleaved or degraded. The amount of cleavage or degradation required is that amount which allows the extension of the second primer. In some embodiments, the cleavage or degradation is carried out partially, and the fragments of the target nucleic acid that remain can constitute the second primer for step (c).

The method further comprises step (c) extending a second primer to produce a double stranded product comprising a second primer extension product hybridized to the first primer extension product, wherein the second primer comprises a 3' segment complementary to a portion of the first primer extension product and a ligand, whereby a portion of the 3' end of the second primer extension product comprises a sequence (A') that is complementary to the sequence (A) of the of the first primer. The extension of the second primer is carried out with a DNA polymerase as described herein. The second primer can comprise RNA, DNA, or can be a composite primer comprising both RNA and DNA. The second primer can be a tailed primer having a 3' portion which is complementary to the first primer extension product, and a 5' portion, sequence (B), which is not complementary to the first primer extension product. In some embodiments, the second primer can comprise a specific primer sequence that is designed to hybridize to a specific sequence in the first primer extension product. In some embodiments the second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target RNA or target DNA, whereby a plurality of second primer extension products are produced which is representative of the sequence of the target nucleic acid. In some embodiments, for example where the first primer is designed to hybridize to a specific sequence on a target RNA, or a sequence common to a family of RNA targets, random priming by the second primer may ensure amplification of the entire selected target or family of selected targets. In some cases, random primer by the second primer in combination with extension by a polymerase having substantial strand-displacement activity may ensure amplification of the entire selected target, an entire transcriptome, an entire genome, an entire family of selected targets, or a substantial portion thereof. In this embodiment, the second primer extension products comprise sequences which are the same or substantially the same as the sequences in the target nucleic acid (sense copies), for example, the second primer extension products or the amplicons therefrom may comprise sequences that are 95%, 99%, 99.9%, 99.999%, 99.9999%, 99.999999% or more identical to the sequences in the target nucleic acid or their complement. The second primer comprises a ligand that is a member of a ligand-receptor pair. In some embodiments, the ligand is attached to the primer at the 5' end of the primer. In some embodiments, the ligand is a small molecule, such as biotin or digoxigenin. In some embodiments, the receptor is an antibody, and the ligand is a molecule or portion of a molecule recognized by the antibody.

The second primer extension product is extended such that the 3' portion of the second primer extension product comprises a sequence (A') which is complementary to sequence (A) of the first primer. Since sequence (A) on the first primer extension product comprises RNA, both DNA dependent DNA polymerase activity and RNA dependent DNA polymerase activity are used in step (c). The primer extension results in a product that is at least partially double stranded.

The method further comprises step (d) binding the ligand to a receptor bound to a solid surface whereby the second primer extension product is attached to the solid surface. The solid surface may comprise a bead or a set of beads, a magnetic bead or a set of beads, a substantially planar array, a well in a plate, a series of wells in a plate, an isolated surface, or a set of isolated surfaces. The ligand-receptor pair may comprise any pair of binding agents that are capable of specifically associating. For example, the ligand receptor pair may be avidin and biotin or biotin and avidin respectively. Similarly, the ligand-receptor pair may be any pair of proteins, peptides or small molecules that bind to each other. Additionally, the ligand-receptor pair may comprise nucleic acid sequences such a RNA, DNA, peptide nucleic acids or their analogs that bind or hybridize specifically. Other examples of receptors include aptamers, antibodies, affibodies, enzymes, or any protein, peptide, macromolecule, or small molecule specifically capable of binding to a ligand. Other examples of ligands include any protein, peptide, macromolecule, or small molecule specifically capable of binding to a receptor.

The receptor is a member of the ligand-receptor pair such that binding of the ligand results in attaching the second primer extension product to the solid surface. In some embodiments, the second primer extension product is still hybridized to the first primer extension product when it is attached to the solid surface. In some embodiments, the first primer extension product is removed from the second primer extension product such that a single stranded polynucleotide is attached to the solid surface. The method produces a nucleic acid that is bound to a solid surface that has a specific sequence (A') at its 3' end. The specific, or universal, sequence (A') can be a site for primer hybridization and further analysis or amplification of the nucleic acid bound to the bead. As described above, in some embodiments, the nucleic acid bound to the bead also comprises sequence (B) at or near its 5' end.

One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification. In some embodiments, for example where random sequences at the 3' end of the first and/or second primer are used, a plurality of different nucleic acids bound to a solid surface is created in which each of the nucleic acids has a specific sequence (A') at its 3' end (and in some embodiments also a specific sequence (B) at its 5' end), and where the different nucleic acids have different intervening sequences, wherein the intervening sequences are identical to or substantially identical to the sequences in the target nucleic acid. The set of bound nucleic acids thus generated can be analyzed, for example, by sequencing in order to provide information about the sequence of the target nucleic acid.

Step (d) of binding the polynucleotides to the solid surface through the ligand can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

A schematic exemplary of an embodiment of the invention relating to method for generating polynucleotide bound to a solid surface is shown in FIG. 1. Step I shows the extension of a first primer comprising a DNA segment and a 5' RNA segment, wherein a 3' portion of the primer, sequence (P), is complementary to a target nucleic acid and a 5' portion of the of the primer, sequence (A), is not complementary to the target nucleic acid, to form a first primer extension product hybridized to the target nucleic acid. The target nucleic acid can be, for example, DNA or RNA. The target nucleic acid as shown is single stranded. The target nucleic acid may be single stranded in the sample, or can be double stranded, and rendered single stranded, for example, but denaturation with heat. The sequence (P) can represent a specific sequence, a sequence that will hybridize to Poly-A, a sequence common to a plurality of regions (consensus sequence), or a random sequence. Step II illustrates the separating or removing of the first primer extension product from the target nucleic acid. The separation or removing can be accomplished for instance by denaturation of the complex, or by selective degradation of the target nucleic acid. For example, where the target nucleic acid is RNA, the separation/removing/degradation can be accomplished by alkali, or by enzymatic cleavage, for example by RNase H. Step III illustrates extending a second primer to produce a double stranded product comprising a second primer extension product hybridized to the first primer extension product, wherein the second primer comprises a 3' segment complementary to a portion of the first primer extension product and a ligand, whereby a portion of the 3' end of the second primer extension product comprises a sequence (A') that is complementary to the sequence (A) of the of the first primer. In the embodiment shown the second primer comprises a sequence (B) that is 5' to the segment that is complementary to the first primer extension product, and the ligand is attached 5' to the sequence (B). This step requires both DNA dependent DNA polymerase activity and RNA dependent DNA polymerase activity to product the second primer extension product. Step IV illustrates binding of the ligand to a receptor bound to a solid surface whereby the second primer extension product is attached to the solid surface. In the embodiment shown, the second primer extension product is bound to the solid substrate in double stranded form while still hybridized to the first primer extension product. In some embodiments, the second primer extension product is rendered single stranded before binding of the ligand to the solid surface. The bound second primer extension product comprises defined sequence (B) at its 5' end and defined sequence (A') at its 3' end. The bound second primer extension product can be stored or archived, and later used for analysis and amplification, for example clonal amplification as described herein.

Method for Generating a Polynucleotide Comprising a Ligand for Binding to a Solid Surface from an RNA Target The invention provides methods, compositions and kits for copying, storing, and amplifying polynucleotides having sequences related to target ribonucleic acid (RNA) sequences. The methods provide for amplification of a single RNA species or pool of RNA species. The methods are suitable for, for example, generation of libraries, including cDNA libraries. The methods can generate single stranded RNA or DNA products, which are readily suitable for multiplex analysis by microarray technologies, as well as electrophoresis-based technologies such as differential display, and for sequencing.

The methods of the invention can copy, store, and amplify of one or more species of RNA, such as a pool of RNA sequences, and is most particularly suitable for the amplification of all RNA (such as whole transcriptome or total RNA) sequences in a biological sample. Thus, one of the major advantages of the methods of the invention is the ability to copy, store, and amplify an entire pool of sequences, which is essential for the ability to analyze the gene expression profile in cells, such as the cells in a biological sample of interest. The methods of the invention have the potential of amplifying a multiplicity, a large multiplicity, and in some embodiments all RNA (such as whole transcriptome or total RNA in a sample) sequences in a sample.

Insofar as many mRNAs have a unique polyA 3'-end, the amplification initiated from the 3'-end sequence of mRNAs is most common for preparation of cDNA libraries and subsequent sequence analysis for determination of gene expression profiling or other applications. The methods of the invention are similarly suited for preparation of libraries of amplified 3'-portions of mRNAs. The sequence of the first primer used in the methods of invention can be designed to be complementary to a multiplicity, or all, of the mRNA species in the sample by using random sequences, according to methods known in the art. The methods are also useful for whole transcriptome amplification. The methods of the invention can be used for the total RNA in samples such as viral RNA.

The method for generating a polynucleotide comprising a ligand for binding to a solid surface from an RNA target comprise the step of (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid. In some embodiments, the 3' portion of the primer that is complementary to the target RNA is a specific sequence. For example, where a specific region of interest of a target RNA that is known or suspected to be upstream of a specific sequence on the target RNA, the sequence that is complementary to the target RNA of the first primer can be designed to hybridize to this specific sequence on the target RNA such that extension of the primer results in producing a first primer extension product that is complementary to such upstream region. The specific sequence may be common to a family of target RNA. A combination of primers with various specific sequences at the 3' end can also be useful. The specific sequence may be common to a family of target RNA. A combination of primers with various specific sequences at the 3' end can also be useful. In some embodiments, such as where the target RNA comprises mRNA, and the mRNA comprises a plurality of sequences, each having a 3' poly-A segment; the specific sequence that is complementary to the target RNA can comprise a sequence that will hybridize to the poly-A region of the mRNA, thus allowing the extension of the first primer to produce a plurality of first primer extension products, each of which is complementary to the region of an mRNA molecule adjacent to the poly-A region. In some embodiments, the sequence that is complementary to the target RNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a target RNA, generating a plurality of sequences which together can represent, for example substantially the whole sequence of the target RNA. In some embodiments, the relative amounts of the various sequences can be used to quantitate the relative amount of a given sequence in a sample, for example to determine the level of expression in an mRNA sample. In some embodiments more than one type of sequence that is complementary to the target RNA can be used, for instance both a primer with a random sequence and a primer, or combination of primers with a specific sequence complementary to RNA can be used. In some embodiments, multiple primers comprising different specific sequences can be used.

The method further comprises the step of: (b) cleaving the target RNA from the RNA/DNA hybrid. In some embodiments, the cleaving of the target RNA from the RNA/DNA hybrid involves selectively cleaving or degrading the target RNA. In some cases the cleaving can be affected by denaturing the complex comprising the first primer extension product and the nucleic acid. Denaturation can be performed, for example by heating the sample, or by adding a denaturing agent, or using a combination of heating the sample and adding denaturing agents. The cleaving can be accomplished with an enzyme that cleaves RNA from an RNA/DNA hybrid such as RNase H, or a combination of RNase enzymes, or chemically. In some embodiments, the target RNA is completely cleaved. In other embodiments, the target RNA is only partly cleaved or degraded. The amount of cleaving required is that amount which will allow the extension of the second primer. In some embodiments, the cleaving is carried out partially, and the fragments of the target RNA that remain can constitute the second primer for step (c).

The method further comprises: step (c) extending a second primer, comprising a ligand and a 3' segment complementary to a portion of the first primer extension product, to produce a double stranded product with a DNA/RNA heteroduplex at one end; wherein the double stranded product comprises a second primer extension product hybridized to the first primer extension product, and whereby a portion of the 3' end of the second primer extension product comprises a sequence (A') that is complementary to the sequence (A) of the of the first primer. The extension of the second primer is carried out with a DNA polymerase as described herein. The second primer can comprise RNA, DNA, or can be a composite primer comprising both RNA and DNA. The second primer can be a tailed primer having a 3' portion which is complementary to the first primer extension product, and a 5' portion, sequence (B), which is not complementary to the first primer extension product. In some embodiments, the second primer can comprise a specific primer sequence that is designed to hybridize to a specific sequence in the first primer extension product. In some embodiments the second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target RNA, whereby a plurality of second primer extension products are produced which is representative of the sequence of the target RNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target RNA (sense copies). The second primer comprises a ligand that is a member of a ligand-receptor pair. In some embodiments, the ligand is attached to the primer at the 5' end of the primer. In some embodiments, the ligand is a small molecule, such as biotin or digoxigenin. In some embodiments, the receptor is an antibody, and the ligand is a molecule or portion of a molecule recognized by the antibody.

The second primer extension product is extended such that the 3' portion of the second primer extension product comprises a sequence (A') which is complementary to sequence (A) of the first primer. Since sequence (A) on the first primer extension product comprises RNA, both DNA dependent DNA polymerase activity and RNA dependent DNA polymerase activity are used in step (c). The primer extension results in a product that is at least partially double stranded. The method produces a nucleic acid that comprises a ligand allowing it to be bound to a solid surface and that has a specific sequence (A') at its 3' end. The specific, or universal, sequence (A') can be a site for primer hybridization and further analysis or amplification of the nucleic acid bound to the bead. As described above, in some embodiments, the nucleic acid attached to the ligand also comprises sequence (B) at or near its 5' end.

In some embodiments, the sample comprising the target RNA is in a sample that also comprises DNA. In such cases, it can be advantageous to add a selective DNA dependent DNA polymerase inhibitor such as actinomycin such that it is present during step (a) to selectively inhibit the production of extension product complementary to the DNA during step (a). The presence of a DNA dependent DNA polymerase inhibitor such as actinomycin is particularly advantageous when a first primer comprising a random sequence is used, as the inhibitor allows for the selective creation of first primer extension products to RNA without the need of separating the RNA from the DNA. This is also advantageous when the priming is carried out at specific target sequences since the sequence may be the same on the DNA when the DNA and RNA in the sample represent total nucleic acid from the same biological entity, for example, human tissue, animal tissue, and the like. The use of DNA dependent DNA polymerase inhibitors such as actinomycin is described in copending applications.

In some embodiments, the method further comprises step (d) binding the ligand to a receptor bound to a solid surface whereby the second primer extension product is attached to the solid surface. The receptor bound to the solid surface is a member of the ligand-receptor pair such that binding of the ligand results in attaching the second primer extension product to the solid surface. In some embodiments, the second primer extension product is still hybridized to the first primer extension product when it is attached to the solid surface. In some embodiments, the first primer extension product is removed from the second primer extension product such that a single stranded polynucleotide is attached to the solid surface. The method produces a nucleic acid that is bound to a solid surface that has a specific sequence (A') at its 3' end. The specific, or universal, sequence (A') can be a site for primer hybridization and further analysis or amplification of the nucleic acid bound to the bead. As described above, in some embodiments, the nucleic acid bound to the bead also comprises sequence (B) at or near its 5' end. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification.

In some embodiments, the amplification of the second primer extension product comprises the steps of: (e) cleaving the RNA in the heteroduplex from the first primer extension product such that a portion of the second primer extension product that is complementary to sequence (A) is single stranded; (f) annealing an amplification primer to the single stranded portion of the second primer extension product complementary to sequence (A), wherein the amplification primer has a DNA portion and a 5' RNA portion; (g) extending the amplification primer with a DNA polymerase having strand displacement activity to produce an amplified product hybridized to the second primer extension product; (h) cleaving the RNA from the amplified product hybridized to the second primer extension product; and (i) repeating steps (f) to (h) to produce multiple copies of amplified product. Where this method of amplification is used, and a sequence (B) is incorporated into the second primer extension product as described above, amplification product is generated which comprises sequence (B') complementary to sequence B at or near its 3' end.

In some embodiments, for example where random sequences at the 3' end of the first and/or second primer are used, a plurality of different nucleic acids bound to a solid surface is created in which each of the nucleic acids has a specific sequence (A') at its 3' end (and in some embodiments also a specific sequence (B) at its 5' end), and where the different nucleic acids have different intervening sequences, wherein the intervening sequences are identical to or substantially identical to the sequences in the target RNA. The set of bound nucleic acids thus generated can be analyzed, for example, by sequencing in order to provide information about the sequence of the target RNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through the ligand, step (d), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments, the method further comprises treating the solid surface with reagents to produce multiple copies of an amplification product that are substantially complementary the second primer extension product. This step comprises carrying out an amplification reaction wherein the bound nucleic acid acts as a template for the amplification. Generally, the amplification is carried out using the sequence (A') on the second primer extension product for the hybridization of primer. In some embodiments, the amplification produces single stranded amplified product, In some embodiments, the amplification provides double stranded product. In some embodiments, the second primer comprises a specific sequence (B), which becomes incorporated into the second primer extension product. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the second primer extension product comprises both as sequence (B) at or near its 5' end and a sequence (A') at or near its 3' end, a set of primers, one designed to hybridize to all or a portion of the sequence (A') and the other designed to hybridize to sequence (B'), the complement of sequence (B), can be used to carry out a PCR reaction to exponentially produce double stranded amplified product.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (A) or sequence (B'), that allows it to be captured to another solid surface or other portion of the solid surface by hybridization to a complementary sequence bound to such surface (e.g. sequence (A') or sequence (B)). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer second primer extension product molecules are bound per bead. The beads are dispersed into an aqueous solution, and a plurality of microreactors, e.g. droplets, are produced such that on average one or fewer beads is contained within each of the plurality of microreactors. The amplification of the second primer extension products bound to the beads is then carried out such that the clonal amplification of each of the plurality of second primer extension products in the separate microreactors is achieved. This clonal amplification in microreactors can be performed on a sample of target RNA, such as whole transcriptome or total RNA, wherein the plurality of second primer extension products comprise sequences that correspond to most, to substantially all, or to all of the sequences in the target RNA. In some embodiments, the amplified products are captured by bead having attached thereto a plurality of oligonucleotides comprising complementary sequences bound to such surface (e.g. sequence (A') or sequence (B)), which are complementary to sequence (A) or sequence (B') on the amplified product.

In some embodiments, the plurality of beads, produced as described above, with each bead comprising a single second primer extension product can comprise a library. These libraries can be stored, then later clonally amplified. In some embodiments, a library of beads can comprise a plurality of beads wherein each bead had multiple copies of a single amplification product generated from a second primer extension product. These libraries can be analyzed, for example by sequencing. The libraries can be stored, and later analyzed. In some embodiments the libraries can be stored, then analyzed multiple times.

Figure 2:
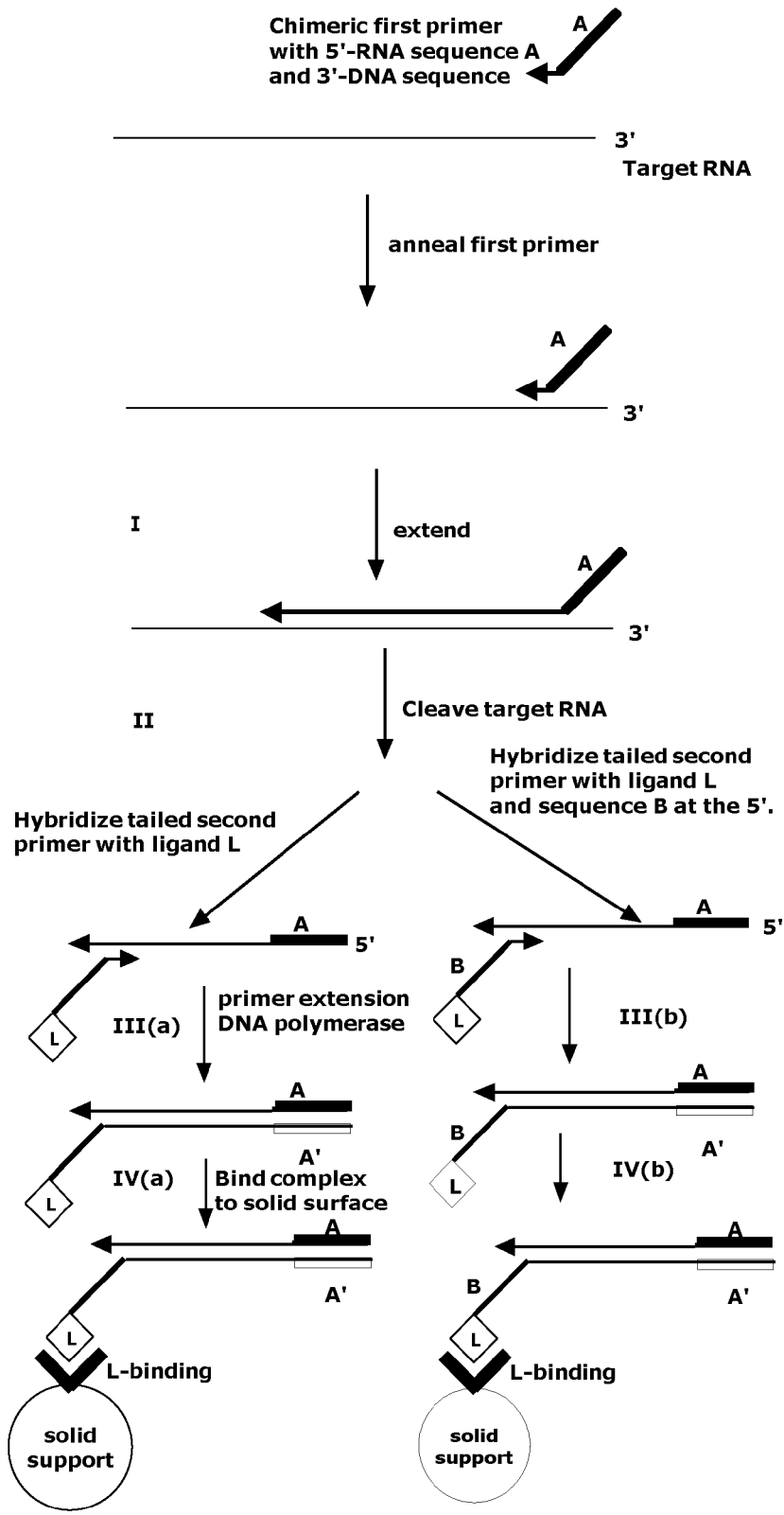
FIG. 2 illustrates a method of producing a polynucleotide comprising a ligand, sequences related to a target RNA, and a defined sequence (A') at its 3' end. The Figure also illustrates binding such polynucleotide to a solid surface.

A schematic exemplary of an embodiment of the invention relating to method for generating a polynucleotide comprising a ligand for binding to a solid surface from an RNA target is shown in FIG. 2. FIG. 2 shows a target RNA and a chimeric RNA/DNA first primer. The primer is first annealed to the target RNA. Step I illustrates extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid. The sequence complementary to a target RNA can be a specific sequence, a sequence that will hybridize to Poly-A, a sequence common to a plurality of regions (consensus sequence), or a random sequence. Step II represents cleaving the target RNA from the RNA/DNA hybrid. Cleaving can be accomplished thermally, chemically, or enzymatically, e.g. with RNase H. The second primer comprising a ligand is then annealed to the first primer extension product. Step III(a) and step III(b) illustrate extending a second primer, comprising a ligand and a 3' segment complementary to a portion of the first primer extension product, to produce a double stranded product with a DNA/RNA heteroduplex at one end; wherein the double stranded product comprises a second primer extension product hybridized to the first primer extension product, and whereby a portion of the 3' end of the second primer extension product comprises a sequence (A') that is complementary to the sequence (A) of the of the first primer. Step III(a) shows step III for a second primer that does not comprise sequence (B). Step III(b) shows step III for a second primer that comprises a sequence (B) that is 5' of the segment complementary to a portion of the first primer extension product. In each case the second primer is shown with a ligand attached to the 5' end. The second primer extension product comprising a ligand and a defined sequence (A) at its 3' end is useful for storage, archiving and analysis as it has a ligand capable of binding to a solid surface. Such second primer extension product also comprises a sequence that is representative of (identical to or substantially identical to) a sequence in the target RNA, so analysis of this product provides information about the target RNA. Step IV shows the binding the ligand to a solid surface, whereby the second primer extension product becomes bound to the solid surface.

Method for Generating a Polynucleotide Comprising a Ligand for Binding to a Solid Surface from a DNA Target The methods of the present invention can be used to analyze the DNA (e.g. genomic DNA) samples that are important for many studies. The methods can be used for high-throughput genomic analysis, and can be used for forensic and paleoarcheology work which can be severely limited by nucleic acid sample size. The methods can be used, for example, for the genotyping of multiple loci in the study of complex diseases. The methods can also be used for the determination of genomic instability in various pathological conditions such as cancer, which is most precisely carried out in well defined cell populations, such as that obtained by laser capture microdissection or cell sorting. The DNA amplification technologies described herein provide global amplification of very small polynucleotide samples, for example, from one or a very few cells.

One aspect of the invention is a method for generating from a DNA target a polynucleotide comprising a ligand for binding to a solid surface.

The method comprises the steps of: (a) denaturing a double-stranded target DNA. Double stranded DNA can be denatured, for example by heating, or by the addition of denaturing agents.

The method further comprises step (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a plurality of first primer extension products, each with sequence (A) at its 5' end. The enzyme that carries out step (b) is generally a DNA polymerase. In some cases a mixture of DNA polymerases can be used. The sequence that is complementary to the target DNA comprises a random sequence, such that the extension of the first primer results in a plurality of first primer extension products complementary to the sequences adjacent to the sequence where each random species hybridizes. The use of a random sequence at the 3' end of the primer as sequence can be useful for performing a global amplification of a DNA target, generating a plurality of sequences which together can represent, for example substantially the whole sequence of the target DNA. In some embodiments, the relative amounts of the various sequences can be used to quantitate the relative amount of a given sequence in a sample, for example to determine the number of gene copies in a DNA sample, or obtaining sequence information. In some embodiments, the extension of one first primer, will result in the release of a downstream first primer extension product. This can occur throughout the target DNA resulting in the release of multiple first primer extension products from the target DNA. This process can occur simultaneously on both of the strands of the double-stranded DNA target, thus creating first primer extension products complementary to sequences in both strands.

In some embodiments, the first primer extension step is carried out with a DNA polymerase capable of extension at elevated temperature that is not compatible with subsequent hybridization of the random sequence to the displaced primer-extension product. For example, Bst DNA polymerase can be used which is active at elevated temperature. The reaction can be carried out stepwise, first with an incubation at a lower temperature such as about 25° C., followed by an incubation at higher temperature such as about 50° C. In some embodiments, the first incubation is carried out below about 30° C., and the second incubation is carried out above about 40° C. In some embodiments, a DNA polymerase which is active at temperatures above about 45° C. is used to extend the first primer. Mixtures of DNA polymerases can also be useful.

The method further comprises step (c) extending a second primer comprising a ligand and a 3' DNA region that comprises a random sequence, wherein the primer is optionally a tailed primer comprising a nucleic acid sequence (B) that is 5' of the random sequence, to form a plurality of double-stranded products each comprising a first primer extension product and a second primer extension product whereby the second primer extension product comprises a ligand. This step may be carried out with or without prior denaturation. If carried out without denaturation, generally, only the single stranded displaced first primer extension product will hybridize to the second primer. Generally the second primer does not comprise RNA. The extension of the second primer is carried out with a DNA polymerase as described herein. The second primer can be a tailed primer having a 3' portion which is complementary to the first primer extension product, and a 5' portion, sequence (B), which is not complementary to the first primer extension product. The second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target DNA, whereby a plurality of second primer extension products are produced which is representative of the sequence of the target DNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target DNA. The second primer comprises a ligand that is a member of a ligand-receptor pair. In some embodiments, the ligand is attached to the primer at the 5' end of the primer. In some embodiments, the ligand is a small molecule, such as biotin or digoxigenin. In some embodiments, the receptor is an antibody, and the ligand is a molecule or portion of a molecule recognized by the antibody.

The second primer extension product is extended such that the 3' portion of the second primer extension product comprises a sequence (A') which is complementary to sequence (A) of the first composite primer. Since sequence (A) on the first primer extension product comprises RNA, both DNA dependent DNA polymerase activity and RNA dependent DNA polymerase activity are used in step (c). The primer extension results in a product that is at least partially double stranded. The method produces a nucleic acid that comprises a ligand allowing it to be bound to a solid surface and that has a specific sequence (A') at its 3' end. The specific, or universal, sequence (A') can be a site for primer hybridization and further analysis or amplification of the nucleic acid bound to the bead. As described above, in some embodiments, the nucleic acid attached to the ligand also comprises sequence (B) at or near its 5' end.

In some embodiments, The method further comprises step (d) binding the ligand to a receptor bound to a solid surface whereby the second primer extension product is attached to the solid surface. The receptor bound to the solid surface is a member of the ligand-receptor pair such that binding of the ligand results in attaching the second primer extension product to the solid surface. In some embodiments, the second primer extension product is still hybridized to the first primer extension product when it is attached to the solid surface. In some embodiments, the first primer extension product is removed from the second primer extension product such that a single stranded polynucleotide is attached to the solid surface. The method produces a nucleic acid that is bound to a solid surface that has a specific sequence (A') at its 3' end. The specific, or universal, sequence (A') can be a site for primer hybridization and further analysis or amplification of the nucleic acid bound to the bead. As described above, in some embodiments, the nucleic acid bound to the bead also comprises sequence (B) at or near its 5' end. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification.

In some embodiments, the amplification of the second primer extension product comprises the steps of: (e) cleaving the RNA in the heteroduplex from the first primer extension product such that a portion of the second primer extension product that is complementary to sequence (A) is single stranded; (f) annealing an amplification primer to the single stranded portion of the second primer extension product complementary to sequence (A), wherein the amplification primer has a DNA portion and a 5' RNA portion; (g) extending the amplification primer with a DNA polymerase having strand displacement activity to produce an amplified product hybridized to the second primer extension product; (h) cleaving the RNA from the amplified product hybridized to the second primer extension product; and (i) repeating steps (f) to (h) to produce multiple copies of amplified product. Where this method of amplification is used, and a sequence (B) is incorporated into the second primer extension product as described above, amplification product is generated which comprises sequence (B') complementary to sequence B at or near its 3' end.

In some embodiments, a plurality of different nucleic acids bound to a solid surface is created in which each of the nucleic acids has a specific sequence (A') at its 3' end (and in some embodiments also a specific sequence (B) at its 5' end), and where the different nucleic acids have different intervening sequences, wherein the intervening sequences are identical to or substantially identical to the sequences in the target DNA. The set of bound nucleic acids thus generated can be analyzed, for example, by sequencing in order to provide information about the sequence of the target DNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through the ligand, step (d), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments, the method further comprises treating the solid surface with reagents to produce multiple copies of an amplification product that are substantially complementary the second primer extension product. This step comprises carrying out an amplification reaction wherein the bound nucleic acid acts as a template for the amplification. Generally, the amplification is carried out using the sequence (A') on the second primer extension product for the hybridization of primer. In some embodiments, the amplification produces single stranded amplified product, In some embodiments, the amplification provides double stranded product. In some embodiments, the second primer comprises a specific sequence (B), which becomes incorporated into the second primer extension product. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the second primer extension product comprises both as sequence (B) at or near its 5' end and a sequence (A') at or near its 3' end, a set of primers, one designed to hybridize to all or a portion of the sequence (A') and the other designed to hybridize to sequence (B'), the complement of sequence (B), can be used to carry out a PCR reaction to exponentially produce double stranded amplified product.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (A) or sequence (B'), that allows it to be captured to another solid surface or other portion of the solid surface by hybridization to a complementary sequence bound to such surface (e.g. sequence (A') or sequence (B)). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer second primer extension product molecules are bound per bead. The beads are dispersed into an aqueous solution, and a plurality of microreactors, e.g. droplets, are produced such that on average one or fewer beads is contained within each of the plurality of microreactors. The amplification of the second primer extension products bound to the beads is then carried out such that the clonal amplification of each of the plurality of second primer extension products in the separate microreactors is achieved. This clonal amplification in microreactors can be performed on a sample of target DNA, such as genomic DNA, wherein the plurality of second primer extension products comprise sequences that correspond to most, to substantially all, or to all of the sequences in the target DNA. In some embodiments, the amplified products are captured by bead having attached thereto a plurality of oligonucleotides comprising complementary sequences bound to such surface (e.g. sequence (A') or sequence (B)), which are complementary to sequence (A) or sequence (B') on the amplified product.

In some embodiments, the plurality of beads, produced as described above, with each bead comprising a single second primer extension product can comprise a library. These libraries can be stored, then later clonally amplified. In some embodiments, a library of beads can comprise a plurality of beads wherein each bead had multiple copies of a single amplification product generated from a second primer extension product. These libraries can be analyzed, for example by sequencing. The libraries can be stored, and later analyzed. In some embodiments the libraries can be stored, then analyzed multiple times.

Figure 3:
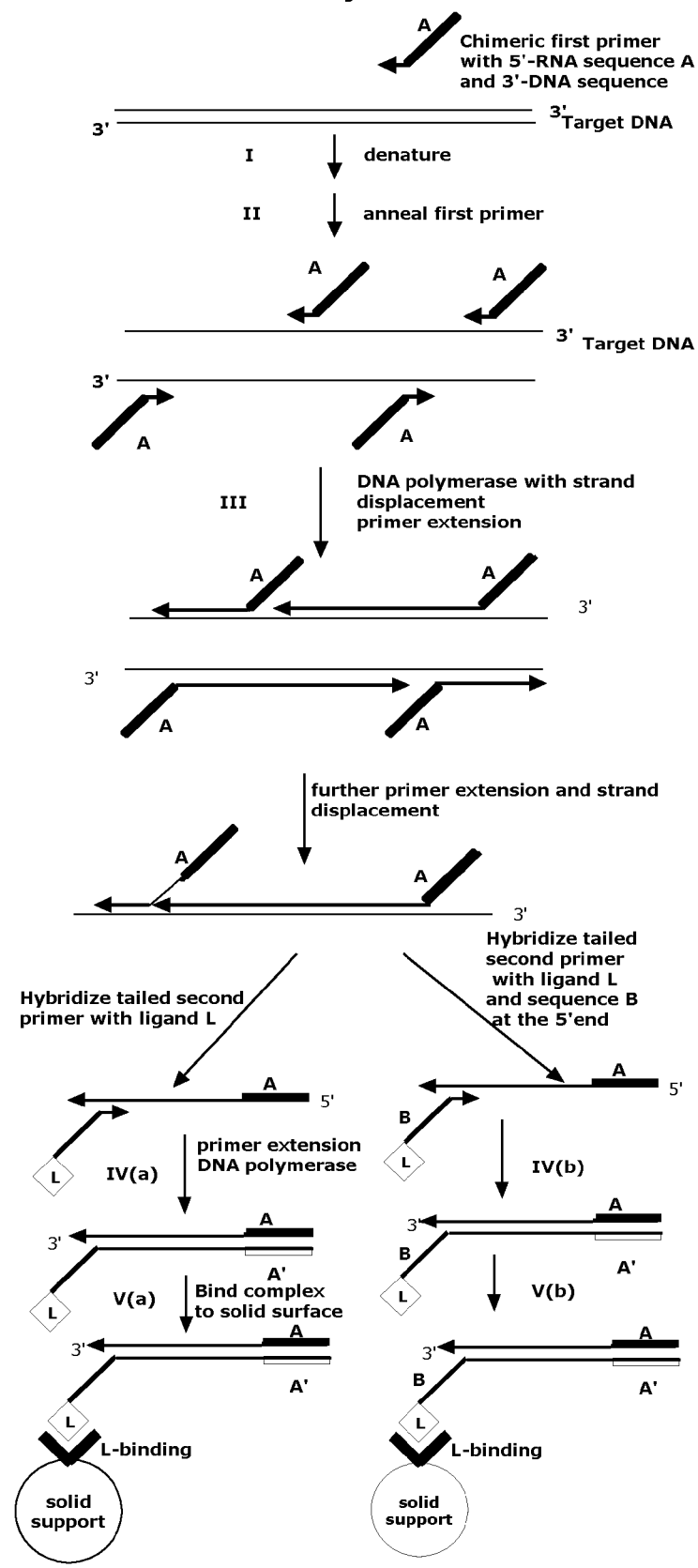
FIG. 3 illustrates a method of producing a polynucleotide comprising a ligand, sequences related to a target DNA and a defined sequence (A') at its 3' end. The Figure also illustrates binding such polynucleotide to a solid surface.

A schematic exemplary of an embodiment of the invention relating to method for generating a polynucleotide comprising a ligand for binding to a solid surface from a DNA target is shown in FIG. 3. Step I represents denaturing a double-stranded target DNA, for example by raising the temperature. Steps II and III illustrate annealing to the target DNA and extending with a DNA polymerase comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a plurality of first primer extension products, each with sequence (A) at its 5' end. The enzyme that carries out step (b) is generally a DNA polymerase. In some cases a mixture of DNA polymerases can be used. In some embodiments, a DNA polymerase with strand displacement activity is used such that a growing first primer extension product can displace a downstream first primer extension product, producing a plurality of first primer extension products, representing different regions of the sequence of the target DNA are produced. Step IV illustrates extending a second primer comprising a ligand and a 3' DNA region that comprises a random sequence, wherein the primer is optionally a tailed primer comprising a nucleic acid sequence (B) that is 5' of the random sequence, to form a plurality of double-stranded products each comprising a first primer extension product and a second primer extension product whereby the second primer extension product comprises a ligand. Step IV(b) shows step IV in which the second primer comprises a segment (B) that is 5' of the 3' DNA region that comprises a random sequence. Step IV(a) shows step IV where the second primer does not comprise a (B) sequence. The second primer extension products comprising a ligand and a defined sequence (A) at its 3' end are useful for storage, archiving and analysis as they have a ligand capable of binding to a solid surface. Such second primer extension products also comprises sequences that are representative of (identical to or substantially identical to) a sequence in the target DNA, so analysis of these products provides information about the target DNA. Step V shows the binding the ligand to a solid surface, whereby the plurality of second primer extension products become bound to the solid surface.

Method for Archiving and Clonal Expansion

An aspect of the invention is a method for archiving and clonal expansion of a nucleotide sequence.

The method comprises the steps of: (a) obtaining a plurality of partially double-stranded DNA products comprising a first polynucleotide and a second polynucleotide, wherein the second polynucleotide comprises a sequence (A') at its 3' end and a ligand, and the sequence (A') portion of the second polynucleotide is single-stranded, wherein optionally the second polynucleotide comprises a sequence (B) at or near its 5' end. The plurality of partially double-stranded DNA products comprising a first polynucleotide and a second polynucleotide, wherein the second polynucleotide comprises a sequence (A') at its 3' end and a ligand, and the sequence (A') portion of the second polynucleotide is single-stranded, wherein optionally the second polynucleotide comprises a sequence (B) at or near its 5' end may be obtained, for example, by the methods described above.

The method further comprises step (b) attaching the partially double stranded DNA products to a plurality of beads or a plurality of isolated areas on a surface by binding the ligands to the bead or isolated area. The receptor bound to the solid surface is a member of the ligand-receptor pair such that binding of the ligand results in attaching the second polynucleotide to the solid surface. In some embodiments, the second polynucleotide is still hybridized to the first polynucleotide when it is attached to the solid surface. In some embodiments, the first polynucleotide is removed from the second polynucleotide such that a single stranded polynucleotide is attached to the solid surface. The method produces a polynucleotide that is bound to a solid surface that has a specific sequence (A') at its 3' end. The specific, or universal, sequence (A') can be a site for primer hybridization and further analysis or amplification of the polynucleotide bound to the bead. As described above, in some embodiments, the polynucleotide bound to the bead also comprises sequence (B) at or near its 5' end. One aspect of the invention comprises amplification of the polynucleotide bound to the bead. In some embodiments, a plurality of different polynucleotides bound to a solid surface is created in which each of the polynucleotides has a specific sequence (A') at its 3' end (and in some embodiments also a specific sequence (B) at its 5' end), and where the different polynucleotides have different intervening sequences, wherein the intervening sequences are identical to or substantially identical to the sequences in the target nucleic acid. The set of bound polynucleotides thus generated can be analyzed, for example, by sequencing in order to provide information about the sequence of the target nucleic acid.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through the ligand, step (b), can be carried out such that only one polynucleotide is bound to an isolated area of a surface or only one polynucleotide is bound to a single bead. This isolated binding of polynucleotides can be used for clonal amplification of the specific bound polynucleotide in that area or on that bead. Such bound, isolated polynucleotides can also be stored and archived for later analysis, for example by sequencing. The bound, isolated polynucleotides can be amplified, stored, and analyzed multiple times.

The method further comprises the steps of: (c) annealing an amplification primer to the single stranded portion of the second polynucleotide complementary to sequence (A'), wherein the amplification primer has a DNA portion and a 5' RNA portion; (d) extending the amplification primer with an enzyme having strand displacement activity to produce a plurality of amplified products hybridized to the second polynucleotide products; (e) cleaving the RNA from the amplified product hybridized to the second polynucleotides using RNase H; and (f) repeating steps (c) to (e) to produce multiple copies of amplified products.

In some embodiments, the DNA products are attached to beads or isolated areas of the solid surface, and on average, one DNA product is attached to one or fewer beads or isolated areas. The plurality of beads or isolated areas can be stored for later analysis, and in some cases can later be amplified with steps (c) through (f). In some embodiments, the amplification is a clonal amplification carried out in multiple isolated volumes wherein, on average, one isolated volume has one or fewer beads or isolated areas.

Figure 4:
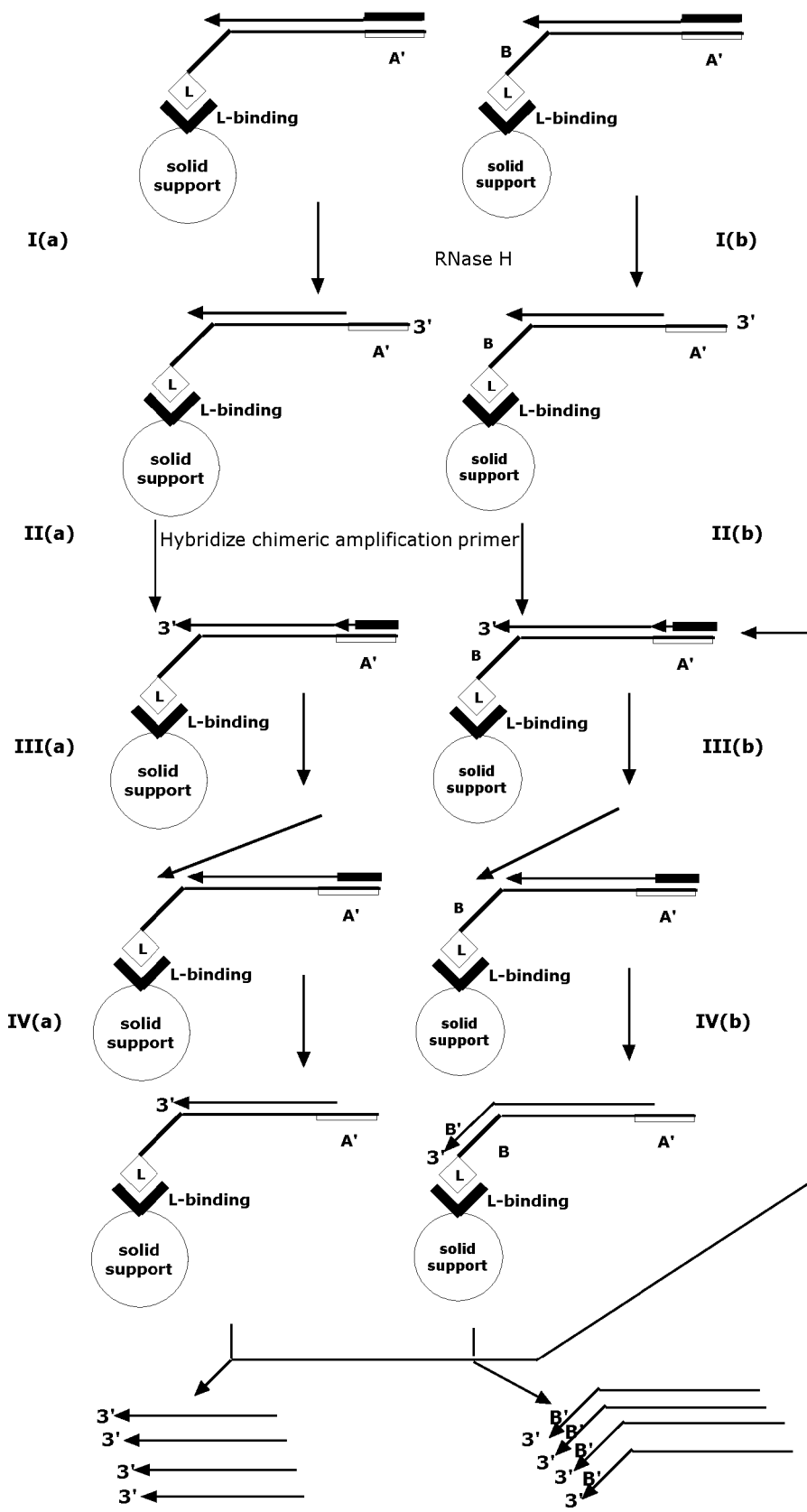
FIG. 4 shows a method of producing amplified product from a nucleotide, bound to the bead through a ligand, wherein the amplified product comprises sequences related to the target nucleic acid and a defined sequence (B') at its 3' end.

A schematic exemplary of an embodiment of the invention relating to amplification of polynucleotides bound to a solid surface is shown in FIG. 4. The polynucleotides bound to the solid surface can be generated, for example from RNA or from DNA by the methods described above. A polynucleotides bound to the solid surface can be a second primer extension product comprising a sequence (A') at its 3' end. In some embodiments, as in those shown in FIG. 4, the polynucleotides bound to the surface are hybridized to a first primer extension product comprising and RNA sequence (A). For clarity, the polynucleotides are referred to as second primer extension products. It will be understood, however, by those of ordinary skill in the art that polynucleotides of the same structure as shown here can be used in the present amplification methods. Where the polynucleotides are single stranded, it would be understood by those skilled in the art that the amplification can be carried out without the first RNase H step (Step I). In FIG. 4, the steps labeled (b), e.g. Step I(b), represents the method for the case in which the second primer comprises a sequence (B) 5' to the 3' sequence that is complementary to the first primer extension product, while steps labeled (a), e.g. Step I(a) represent the method in which the second primer, and therefore the second primer extension product, does not include sequence (B).

In FIG. 4, Step I illustrates cleaving the RNA from the first primer extension products such that a portion of the second primer extension product that is complementary to sequence (A) is single stranded. As shown, the cleavage is performed using RNase H. Chemical and thermal means can alternatively be employed. Step II shows annealing an amplification primer to the single stranded portion of the second primer extension products complementary to sequence (A), wherein the amplification primer has a DNA portion and a 5' RNA portion. Step III illustrates extending the amplification primer with an enzyme having strand displacement activity to produce an amplified product hybridized to the second primer extension product. Step IV illustrates the step of cleaving the RNA from the amplified product hybridized to the second primer extension product. The product of step IV can be the starting point for another round of amplification in that Step II, the hybridization of and amplification primer, can occur, followed by the subsequent steps. Thus, steps II-IV can be repeated to produce multiple copies of amplified product. Note that for case (b) the amplified product that is produced comprises the sequence (B'), complementary to sequence (B) at its 3' end.

In some embodiments, the amplification illustrated in FIG. 4 can be carried out on beads. In some embodiments, the beads have only one bound second primer extension product. In some embodiments such beads are individually in isolated volumes or microreactors allowing for clonal amplification.

Method for Generating a Polynucleotide Having a Defined 3' and 5' Sequences from an RNA Target One aspect of the invention is a method for generating a polynucleotide having a defined 3' and 5' sequences from an RNA target. The method utilizes a composite RNA/DNA oligonucleotide in order to extend the second primer extension product such that the second primer extension product comprises a sequence (C') at its 3' end than can be used as a site for isothermal amplification in a manner such that the sequence (A) is present at or near the 5' end of the amplified product produced in this amplification.

The method comprises the steps: (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid. In some embodiments, the 3' portion of the primer that is complementary to the target RNA is a specific sequence. For example, where a specific region of interest of a target RNA that is known or suspected to be upstream of a specific sequence on the target RNA, the sequence that is complementary to the target RNA of the first primer can be designed to hybridize to this specific sequence on the target RNA such that extension of the primer results in producing a first primer extension product that is complementary to such upstream region. The specific sequence may be common to a family of target RNA. A combination of primers with various specific sequences at the 3' end can also be useful. In some embodiments, such as where the target RNA comprises mRNA, and the mRNA comprises a plurality of sequences, each having a 3' poly-A segment; the specific sequence that is complementary to the target RNA can comprise a sequence that will hybridize to the poly-A region of the mRNA, thus allowing the extension of the first primer to produce a plurality of first primer extension products, each of which is complementary to the region of an mRNA molecule adjacent to the poly-A region. In some embodiments, the sequence that is complementary to the target RNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a RNA target, generating a plurality of sequences which together can represent, for example substantially the whole sequence of the target RNA. In some embodiments, the relative amounts of the various sequences can be used to quantitate the relative amount of a given sequence in a sample, for example to determine the level of expression in an mRNA sample. In some embodiments more than one type of sequence that is complementary to the target RNA can be used, for instance both a primer with a random sequence and a primer, or combination of primers with a specific sequence complementary to RNA can be used. In some embodiments, multiple primers comprising different specific sequences can be used.

The method further comprises step (b) cleaving the target RNA from the RNA/DNA hybrid. In some embodiments, the cleaving of the target RNA from the RNA/DNA hybrid involves selectively cleaving or degrading the target RNA. In some cases the cleaving can be affected by denaturing the complex comprising the first primer extension product and the nucleic acid. Denaturation can be performed, for example by heating the sample, or by adding a denaturing agent, or using a combination of heating the sample and adding denaturing agents. The cleaving can be accomplished with an enzyme that cleaves RNA from an RNA/DNA hybrid such as RNase H, or a combination of RNase enzymes, or chemically. In some embodiments, the target RNA is completely cleaved. In other embodiments, the target RNA is only partly cleaved or degraded. The amount of cleaving required is that amount which will allow the extension of the second primer. In some embodiments, the cleaving is carried out partially, and the fragments of the target RNA that remain can constitute the second primer for step (c).

The method further comprises step (c) extending a second primer, comprising a ligand and a 3' segment complementary to a portion of the first primer extension product, to produce a double stranded product with a DNA/RNA heteroduplex at one end; wherein the double stranded product comprises a second primer extension product hybridized to the first primer extension product, and wherein a portion of the 3' end of the second primer extension product comprises a sequence (A') that is complementary to the sequence (A) of the of the first primer. The extension of the second primer is carried out with a DNA polymerase as described herein. The second primer can comprise RNA, DNA, or can be a composite primer comprising both RNA and DNA. The second primer can be a tailed primer having a 3' portion which is complementary to the first primer extension product, and a 5' portion, sequence (B), which is not complementary to the first primer extension product. In some embodiments, the second primer can comprise a specific primer sequence that is designed to hybridize to a specific sequence in the first primer extension product. In some embodiments the second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target RNA, whereby a plurality of second primer extension products are produced which is representative of the sequence of the target RNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target RNA (sense copies). The second primer comprises a ligand that is a member of a ligand-receptor pair. In some embodiments, the ligand is attached to the primer at the 5' end of the primer. In some embodiments, the ligand is a small molecule, such as biotin or digoxigenin.

In some embodiments, the receptor is an antibody, and the ligand is a molecule or portion of a molecule recognized by the antibody.

The second primer extension product is extended such that the 3' portion of the second primer extension product comprises a sequence (A') which is complementary to sequence (A) of the first primer. Since sequence (A) on the first primer extension product comprises RNA, both DNA dependent DNA polymerase activity and RNA dependent DNA polymerase activity are used in step (c). The primer extension results in a product that is at least partially double stranded. The product further comprises a DNA-RNA heteroduplex region. The method produces a nucleic acid that comprises a ligand allowing it to be bound to a solid surface and that has a specific sequence (A') at its 3' end. The specific, or universal, sequence (A') can be a site for primer hybridization and further analysis or amplification of the nucleic acid bound to the bead. As described above, in some embodiments, the nucleic acid attached to the ligand also comprises sequence (B) at or near its 5' end.

In some embodiments, the sample comprising the target RNA is in a sample that also comprises DNA. In such cases, it can be advantageous to add a selective DNA dependent DNA polymerase inhibitor such as actinomycin such that it is present during step (a) to selectively inhibit the production of extension product complementary to the DNA during step (a). The presence of a DNA dependent DNA polymerase inhibitor such as actinomycin is particularly advantageous when a first primer comprising a random sequence is used, as the inhibitor allows for the selective creation of first primer extension products to RNA without the need of separating the RNA from the DNA. This is also advantageous when the priming is carried out at specific target sequences since the sequence may be the same on the DNA when the DNA and RNA in the sample represent total nucleic acid from the same biological entity, for example, human tissue, animal tissue, and the like. The use of DNA dependent DNA polymerase inhibitors such as actinomycin is described in copending application.

The method further comprises step (d) cleaving the RNA in the heteroduplex from the first primer extension product such that a portion of the second primer extension product that is complementary to sequence (A) is single stranded. The cleaving of RNA can be performed, for example by treatment with RNase H, which will selectively cleave the RNA portion of the DNA/RNA partial heteroduplex formed in step (c).

The method further comprises step (e) annealing to the second primer extension product an oligonucleotide comprising a 3'-DNA segment that is complementary to sequence (A') and a 5' RNA segment comprising sequence (C). The oligonucleotide comprises at least one DNA and at least one RNA portion. In some embodiments the 5' DNA segment is complementary to all of sequence (A'), in other embodiments, the 5' DNA segment is complementary to portion of sequence (A'). In some embodiments, 5' RNA segment comprising sequence (C) is partly complementary to sequence (A').

The method optionally comprises step: (f) extending the oligonucleotide to form an oligonucleotide extension product hybridized to the second primer extension product. In some embodiments, the oligonucleotide is optionally extended from its 3' end to produce an oligonucleotide extension product hybridized to the second primer extension product and displacing the DNA portion of the first primer extension product. In some embodiments, the second primer comprises a sequence (B), such that the oligonucleotide extension product will comprise a sequence (B') at or near its 3' end that is complementary to sequence (B).

The method further comprises step (g) extending the second primer extension product to create a heteroduplex such that the second primer comprises a DNA sequence (C') that is complementary to sequence (C). The DNA sequence (C') is created by a DNA polymerase that has RNA dependent DNA polymerase activity. This step creates an RNA/DNA heteroduplex region that can be used for further manipulation of the second primer extension product.

The method further comprises step (h) cleaving the RNA from the heteroduplex created in step (g) to produce a single-stranded portion of the second primer extension product corresponding to sequence (C'). The RNA can be cleaved from the heteroduplex, for example, by RNase H.

In some embodiments, The method further comprises step (i) binding the ligand on the second primer extension product to a solid surface. The binding can be performed at various stages or steps during the procedure depending, for example, on whether it is advantageous to carry out the subsequent steps on a solid surface. The binding step is generally performed after step (c). In some embodiments, the binding the ligand to the solid surface is performed before step (h). In some embodiments, the binding the ligand to the solid surface is performed after step (h). The receptor bound to the solid surface is a member of the ligand-receptor pair such that binding of the ligand results in attaching the second primer extension product to the solid surface. In some embodiments, the second primer extension product is still hybridized to the first primer extension product when it is attached to the solid surface. In some embodiments, the first primer extension product is removed from the second primer extension product such that a single stranded polynucleotide is attached to the solid surface. The method produces a nucleic acid that is bound to a solid surface that has a specific sequence (A') and (C') at its 3' end. The specific sequence (C') can be a site for primer hybridization and further analysis or amplification of the nucleic acid bound to the bead. As described above, in some embodiments, the nucleic acid bound to the bead also comprises sequence (B) at or near its 5' end. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (C') acts as the site to which the composite RNA/DNA amplification primer hybridizes, allowing for amplification. When the sequence (C') acts as a site to which a composite amplification primer binds, the amplified product that is produced has the sequence (A) (and a portion of sequence (C) at its 5' end. Where the second primer comprises the sequence (B), the amplified product also has the sequence (B'), complementary to (B) at or near its 3' end. Thus the method produced amplified product with defined sequences at or near both its 3' and 5' ends.

In some embodiments, for example where random sequences at the 3' end of the first and/or second primer are used, a plurality of different nucleic acids bound to a solid surface is created in which each of the nucleic acids has a specific sequence (A') and (C') at its 3' end (and in some embodiments also a specific sequence (B) at its 5' end), and where the different nucleic acids have different intervening sequences, wherein the intervening sequences are identical to or substantially identical to the sequences in the target RNA. The set of bound nucleic acids thus generated can be analyzed, for example, by sequencing in order to provide information about the sequence of the target RNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through the ligand, step (i), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments, the method further comprises treating the solid surface with reagents to produce multiple copies of an amplification product that are substantially complementary the second primer extension product. This step comprises carrying out an amplification reaction wherein the bound nucleic acid acts as a template for the amplification. Generally, the amplification is carried out using the sequence (C') on the second primer extension product for the hybridization of primer. In some embodiments, the amplification produces single stranded amplified product, In some embodiments, the amplification provides double stranded product. In some embodiments, the second primer comprises a specific sequence (B), which becomes incorporated into the second primer extension product. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the second primer extension product comprises both as sequence (B) at or near its 5' end and a sequence (C') at or near its 3' end, a set of primers, one designed to hybridize to all or a portion of the sequence (C') and the other designed to hybridize to sequence (B'), the complement of sequence (B), can be used to carry out a PCR reaction to exponentially produce double stranded amplified product.

In some embodiments, the amplification is performed by a method comprising the following steps: (j) annealing an amplification primer, wherein the amplification primer has a DNA portion and a 5' RNA portion, to the single stranded portion of the second primer extension product complementary to sequence (C'); (k) extending the amplification primer with an enzyme having strand displacement activity to produce an amplified product; (l) cleaving the RNA from the amplified product; and (m) repeating steps (j) to (l) to produce multiple copies of amplified product wherein the 5' portion of the amplified product has a sequence complementary to sequence (A'). Where the second primer further comprises a segment (B) that is not complementary to the first primer extension product sequence, this amplification method, utilizing sequence (C'), allows for the production of an amplified product comprises a sequence (B') at or near its 3' end that is substantially complementary to sequence (B), and a sequence (A) near its 5' end that is complementary to sequence (A'), thus producing an amplified polynucleotide product with defined 3' and 5' ends.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (A) or sequence (B'), that allows it to be captured to another solid surface or other portion of the solid surface by hybridization to a complementary sequence bound to such surface (e.g. sequence (A') or sequence (B). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer second primer extension product molecules are bound per bead. The beads are dispersed into an aqueous solution, and a plurality of microreactors, e.g. droplets, are produced such that on average one or fewer beads is contained within each of the plurality of microreactors. The amplification of the second primer extension products bound to the beads is then carried out such that the clonal amplification of each of the plurality of second primer extension products in the separate microreactors is achieved. This clonal amplification in microreactors can be performed on a sample of target RNA, such as whole transcriptome or total RNA, wherein the plurality of second primer extension products comprise sequences that correspond to most, to substantially all, or to all of the sequences in the target RNA. In some embodiments, the amplified products are captured by bead having attached thereto a plurality of oligonucleotides comprising complementary sequences bound to such surface (e.g. sequence (A') or sequence (B)), which are complementary to sequence (A) or sequence (B') on the amplified product.

In some embodiments, the plurality of beads, produced as described above, with each bead comprising a single second primer extension product can comprise a library. These libraries can be stored, then later clonally amplified. In some embodiments, a library of beads can comprise a plurality of beads wherein each bead had multiple copies of a single amplification product generated from a second primer extension product. These libraries can be analyzed, for example by sequencing. The libraries can be stored, and later analyzed. In some embodiments the libraries can be stored, then analyzed multiple times.

In some embodiments, a bead or isolated area of the solid surface comprises covalently attached thereto multiple oligonucleotides comprising the sequence (B) at their 3' ends, whereby upon the amplification of step (m) multiple copies of amplified product comprising sequence (B') at their 5' end are hybridized to the bead or isolated area. For example, where beads are used, a plurality of beads in a plurality of microreactors wherein, the plurality of beads has, on average one or fewer second primer extension products bound to it and there are, on average, one or fewer beads in each microreactor, a clonal amplification of the plurality of second primer extension products can be carried out, and the amplified products in each of the microreactors will bind to the bead through the sequence (B') on the amplified product to the sequence (B) on the beads. This approach produces a plurality of beads, each with multiple copies of a different sequence bound to it. Where these sequences are representative of the target RNA, the plurality of beads can constitute a library representative of such RNA.

After the amplified products are bound to the beads by hybridization, the (B) sequences on the beads can be extended along the amplified product by a DNA polymerase or mixture of polymerases to produce a multiple polynucleotides covalently attached to the bead or isolated area that are substantially complementary to the amplified product and also comprise sequence (A') near their 5' ends. Where the (B) sequences are covalently attached to the beads, this method provides for the production of beads with polynucleotides complementary to amplified product covalently attached to the beads. Covalently attached polynucleotides such as those produce here are more robust than nucleotides that are attached only by hybridization to the beads. Thus, the covalently attached polynucleotides can be more stable and can be used with analysis methods and sequencing methods that have harsher conditions which would result in the displacement of polynucleotides bound only by hybridization.

In some embodiments, the amplified product is removed from the covalently bound polynucleotide to render the polynucleotide single stranded. Such single stranded covalently bound polynucleotides comprise a specific sequence at their 3' ends comprising sequence (A') and a portion of sequence (C'). This specific sequence at the 3' end of the covalently bound polynucleotide can act as a hybridization site for a primer complementary to sequence (A') that can act as a primer to carry out sequencing by any of a variety of sequencing methods, for example, those described herein.

The sequencing methods can comprise the use of cleavable labeled terminators. The sequencing method can comprise pyrophosphate detection. The sequencing method can comprise an isothermal sequencing method, for example using chimeric primers, RNase H, and a polymerase with strand displacement activity. The sequencing method can also comprise cycle sequencing.

In some embodiments, the sequencing methods comprise sequencing by ligation. Sequencing by ligation involves using a DNA ligase. Although commonly represented as joining two pairs of ends at once, as in the ligation of restriction enzyme fragments, ligase can also join the ends on only one of the two strands (for example, when the other strand either already continuous or lacks a terminal phosphate necessary for ligation). DNA ligase is sensitive to the structure of DNA and has very low efficiency when there are mismatches between the bases of the two strands. Sequencing by ligation relies upon the sensitivity of DNA ligase for base-pairing mismatches.

The target molecule to be sequenced is a single strand of unknown DNA sequence, flanked on at least one end by a known sequence. A short "anchor" strand is brought in to bind the known sequence. A mixed pool of probe oligonucleotides is then brought in (eight or nine bases long), labeled (typically with fluorescent dyes or other detection means) according to the position that will be sequenced. These molecules hybridize to the target DNA sequence, next to the anchor sequence, and DNA ligase preferentially joins the molecule to the anchor when its bases match the unknown DNA sequence. Based on the fluorescence or other signal produced by the molecule, one can infer the identity of the nucleotide at this position in the unknown sequence. The oligonucleotide probes may also be constructed with cleavable linkages which can be cleaved after identifying the label. This will both remove the label and regenerate a 5' phosphate on the end of the ligated probe, preparing the system for another round of ligation.

This cycle can be repeated several times to read longer sequences. This sequences every Nth base, where N is the length of the probe left behind after cleavage. To sequence the skipped positions, the anchor and ligated oligonucleotides may be stripped off the target DNA sequence, and another round of sequencing by ligation started with an anchor one or more bases shorter. A simpler, albeit more limited, technique is to do repeated rounds of a single ligation where the label corresponds to different position in the probe, followed by stripping the anchor and ligated probe. Sequencing by ligation can proceed in either direction (either 5'-3' or 3'-5') depending on which end of the probe oligonucleotides are blocked by the label. The 3'-5' direction is more efficient for doing multiple cycles of ligation. Note that this is the opposite direction to polymerase based sequencing methods.

One feature unique to sequencing by ligation is the possibility of labeling the probe oligonucleotides according to various combinations of bases at more than one position. This has error detection capabilities not available to polymerase-based sequencing methods. The Applied Biosystems SOLiD sequencing system uses 2-base encoding to improve its error rates.

In some embodiments the methods of the invention provide for performing bridge PCR comprising making amplified product as described above with defined 3' and 5' ends, and further comprising the steps of exposing the amplified product to a solid substrate comprising oligonucleotide sequences attached thereto complementary to the defined 3' and 5' sequences, for example, A and B' sequences, on the amplified product in the presence of components necessary for polymerase chain reaction, and thermal cycling the system to perform bridge PCR amplification.

In some embodiments the methods of the invention provide for making amplified product as described above with defined 3' and 5' ends and further performing rolling circle amplification comprising performing the steps of: (n) hybridizing the amplified product to an oligonucleotide comprising regions complementary to A and B' sequences in close proximity; (o) optionally extending the gap with a polymerase enzyme; (p) ligating to form a circular nucleic acid comprising the amplified product, and performing rolling circle amplification by extending a primer that is complementary to a sequence in the circular nucleic acid. In some embodiments, the rolling circle amplification uses primers complementary to sequence (A), sequence (B'), or a sequence that was between sequences (A) and (B') in the amplified product. In some cases, such a primer can be an oligonucleotide attached to a solid surface, thus resulting in amplified product bound to the surface In some embodiments the methods of the invention provide for performing PCR comprising making amplified product as described above with defined 3' and 5' ends, further comprising the steps of amplifying the amplified product using primers complementary to sequences (A) and (B), or using primers complementary to sequences (A') and (B').

In some embodiments the methods of the invention provide for performing strand displacement amplification (SDA) comprising making amplified product as described above with defined 3' and 5' ends, wherein the defined 3' and 5' ends, for example, sequences (A) and (B'), in the amplified product are designed to be cleaved by a restriction enzyme, and performing strand displacement amplification on the amplified product.

Method for Generating a Polynucleotide Having a Defined 3' and 5' Sequences from a DNA Target One aspect of the invention is a method for generating a polynucleotide having a defined 3' and 5' sequences from a DNA target. The method utilizes a composite RNA/DNA oligonucleotide in order to extend the second primer such that the second primer extension products comprise a sequence (C') at its 3' end than can be used as a site for isothermal amplification in a manner such that the sequence (A) is present at or near the 5' end of the amplified product produced in this amplification, and where a second primer comprising sequence (B) is used, amplified products with defined sequences at both the 3' and 5' ends can be produced.

The method comprises the step: (a) denaturing a double-stranded target DNA. Double stranded DNA can be denatured, for example by heating, or by the addition of denaturing agents.

The method further comprises step (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a plurality of first primer extension products, each with sequence (A) at its 5' end. The sequence that is complementary to the target DNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a target DNA, generating a plurality of sequences which together can represent, for example substantially the whole sequence of the target DNA. In some embodiments, the relative amounts of the various sequences can be used to quantitate the relative amount of a given sequence in a sample, for example to determine the number of gene copies in a DNA sample, or obtaining sequence information. In some embodiments, the extension of one first primer, will result in the release of a downstream first primer extension product. This can occur throughout the target DNA resulting in the release of multiple first primer extension products from the target DNA. This process can occur simultaneously on both of the strands of the double-stranded DNA target, thus creating first primer extension products complementary to sequences in both strands.

In some embodiments, the first primer extension step is carried out with a DNA polymerase capable of extension at elevated temperature that is not compatible with subsequent hybridization of the random sequence to the displaced primer-extension product. For example, Bst DNA polymerase can be used which is active at elevated temperature. The reaction can be carried out stepwise, first with an incubation at a lower temperature such as about 25° C., followed by an incubation at higher temperature such as about 50° C. In some embodiments, the first incubation is carried out below about 30° C., and the second incubation is carried out above about 40° C. In some embodiments, a DNA polymerase which is active at temperatures above about 45° C. is used to extend the first primer. Mixtures of DNA polymerases can also be useful.

The method further comprises step (c), extending a second primer, comprising a ligand and a 3' segment complementary to a portion of the first primer extension product, to produce a double stranded product with a DNA/RNA heteroduplex at one end; wherein the double stranded product comprises a second primer extension product hybridized to the first primer extension product, and wherein a portion of the 3' end of the second primer extension product comprises a sequence (A') that is complementary to the sequence (A) of the of the first primer. In this step, a second primer comprising a ligand and a 3' DNA region that comprises a random sequence is used. The primer is optionally a tailed primer comprising a nucleic acid sequence (B) that is 5' of the random sequence, to form a plurality of double-stranded products each comprising a first primer extension product and a second primer extension product whereby the second primer extension products comprise a ligand. This step may be carried out with or without prior denaturation. If carried out without denaturation, generally, only the single stranded displaced first primer extension products will hybridize to the second primer. Generally the second primer does not comprise RNA. The extension of the second primer is carried out with a DNA polymerase as described herein. The second primer can be a tailed primer having a 3' portion which is complementary to the first primer extension products, and a 5' portion, sequence (B), which is not complementary to the first primer extension products. The second primer comprises a random primer sequence that randomly binds to the first primer extension products. Extension of the second primer comprising a random sequence produces a plurality of second primer extension products. The use of a random sequence at the 3' end of the primer is useful, for example, in performing global amplification of a target DNA, whereby a plurality of second primer extension products are produced which is representative of the sequence of the target DNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target DNA. The second primer comprises a ligand that is a member of a ligand-receptor pair. In some embodiments, the ligand is attached to the primer at the 5' end of the primer. In some embodiments, the ligand is a small molecule, such as biotin or digoxigenin. In some embodiments, the receptor is an antibody, and the ligand is a molecule or portion of a molecule recognized by the antibody.

The second primer extension products are extended such that the 3' portion of the second primer extension product comprises a sequence (A') which is complementary to sequence (A) of the first composite primer. Since sequence (A) on the first primer extension products comprise RNA, both DNA dependent DNA polymerase activity and RNA dependent DNA polymerase activity are used in step (c). The primer extension results in a products that are at least partially double stranded. The method produces a nucleic acid that comprises a ligand allowing it to be bound to a solid surface and that has a specific sequence (A') at its 3' end. The specific, or universal, sequence (A') can be a site for primer hybridization and further analysis or amplification of the nucleic acid bound to the bead. As described above, in some embodiments, the nucleic acid attached to the ligand also comprises sequence (B) at or near its 5' end.

The method further comprises step (d) cleaving the RNA from the first primer extension products such that a portion of the second primer extension products that are complementary to sequence (A) is single stranded. The cleaving of RNA can be performed, for example by treatment with RNase H, which will selectively cleave the RNA portion of the DNA/RNA partial heteroduplex formed in step (c).

The method further comprises step (e) annealing to the second primer extension products an oligonucleotide comprising a 3'-DNA segment that is complementary to sequence (A') and a 5' RNA segment comprising sequence (C). The oligonucleotide comprises at least one DNA and at least one RNA portion. In some embodiments the 5' DNA segment is complementary to all of sequence (A'), in other embodiments, the 5' DNA segment is complementary to portion of sequence (A'). In some embodiments, 5' RNA segment comprising sequence (C) is partly complementary to sequence (A').

The method optionally comprises step: (f) extending the oligonucleotide to form a plurality of oligonucleotide extension products hybridized to the second primer extension products. In some embodiments, the oligonucleotide is optionally extended from its 3' end to produce a plurality of oligonucleotide extension products hybridized to the second primer extension product and displacing the DNA portion of the first primer extension product. In some embodiments, the second primer comprises a sequence (B), such that the oligonucleotide extension products will comprise a sequence (B') at or near their 3' ends that are complementary to sequence (B).

The method further comprises step (g) extending the second primer extension products to create a heteroduplex such that the second primer comprises a DNA sequence (C') that is complementary to sequence (C). The DNA sequence (C') is created by a DNA polymerase that has RNA dependent DNA polymerase activity. This step creates an RNA/DNA heteroduplex region that can be used for further manipulation of the second primer extension products.

The method further comprises step (h) cleaving the RNA from the heteroduplex created in step (g) to produce a single-stranded portion of the second primer extension products corresponding to sequence (C'). The RNA can be cleaved from the heteroduplex, for example, by RNase H.

In some embodiments, The method further comprises step (i) binding the ligand on the second primer extension products to a solid surface. The binding step can be performed at various stages or steps during the procedure depending, for example, on whether it is advantageous to carry out the subsequent steps on a solid surface. The binding step is generally performed after step (c). In some embodiments, the binding the ligand to the solid surface is performed before step (h). In some embodiments, the binding the ligand to the solid surface is performed after step (h). The receptor bound to the solid surface is a member of the ligand-receptor pair such that binding of the ligand results in attaching the second primer extension products to the solid surface. In some embodiments, the second primer extension products are still hybridized to the first primer extension products when they are attached to the solid surface. In some embodiments, the first primer extension products are removed from the second primer extension products such that a single stranded polynucleotide is attached to the solid surface. The method produces polynucleotides that are bound to a solid surface that have a specific sequence (A') and (C') at their 3' ends. The specific sequence (C') can be a site for primer hybridization and further analysis or amplification of the nucleic acid bound to the bead. As described above, in some embodiments, the nucleic acid bound to the bead also comprises sequence (B) at or near its 5' end. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (C') acts as the site to which the composite RNA/DNA amplification primer hybridizes, allowing for amplification. When the sequence (C') acts as a site to which a composite amplification primer binds, the amplified products that are produced have the sequence (A) (and a portion of sequence (C) at their 5' ends)). Where the second primer comprises the sequence (B), the amplified products also have the sequence (B'), complementary to (B) at or near their 3' ends. Thus the method produced amplified products with defined sequences at or near both its 3' and 5' ends.

Due to the use of random priming, a plurality of different nucleic acids bound to a solid surface is created in which each of the nucleic acids has a specific sequence (A') and (C') at its 3' end (and in some embodiments also a specific sequence (B) at its 5' end), and where the different nucleic acids have different intervening sequences, wherein the intervening sequences are identical to or substantially identical to the sequences in the target DNA. The set of bound nucleic acids thus generated can be analyzed, for example, by sequencing in order to provide information about the sequence of the target DNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through the ligand, step (i), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times. This allows, for example, for the analysis of an individuals genes, or a portion of the individual genes at one time, then allows for archiving the genetic material at a later date by the same or by different tests.

In some embodiments, the method further comprises treating the solid surface with reagents to produce multiple copies of amplification products that are substantially complementary to the second primer extension products. This step comprises carrying out an amplification reaction wherein the bound nucleic acid acts as a template for the amplification. Generally, the amplification is carried out using the sequence (C') on the second primer extension products as for primer hybridization. In some embodiments, the amplification produces single stranded amplified products. In some embodiments, the amplification provides double stranded products. In some embodiments, the second primer comprises a specific sequence (B), which becomes incorporated into the second primer extension products. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the second primer extension products comprises both as sequence (B) at or near its 5' end and a sequence (C') at or near its 3' end, a set of primers, one designed to hybridize to all or a portion of the sequence (C') and the other designed to hybridize to sequence (B'), the complement of sequence (B), can be used to carry out a PCR reaction to exponentially produce double stranded amplified products.

In some embodiments, the amplification is performed by a method comprising the following steps: (j) annealing an amplification primer, wherein the amplification primer has a DNA portion and a 5' RNA portion, to the single stranded portion of the second primer extension products complementary to sequence (C'); (k) extending the amplification primer with an enzyme having strand displacement activity to produce an amplified products; (l) cleaving the RNA from the amplified products; and (m) repeating steps (j) to (l) to produce multiple copies of amplified products wherein the 5' portion of the amplified products have a sequence complementary to sequence (A'). Where the second primer further comprises a segment (B) that is not complementary to the first primer extension products sequence, this amplification method, utilizing sequence (C'), allows for the production of amplified products comprises a sequence (B') at or near their 3' ends that is substantially complementary to sequence (B), and a sequence (A) near their 5' end that are complementary to sequence (A'), thus producing an amplified polynucleotide products with defined 3' and 5' ends.

In some embodiments the amplification is carried out such that the amplified products are not attached to the substrate, but is freely dissolved in the solution. In other embodiments, the amplification is carried out such that the amplified products remains bound to the substrate, for example by performing solid phase PCR such as bridge PCR. In yet other embodiments, amplified products are generated that may float freely in solution, but which comprise a sequence, for example sequence (A) or sequence (B'), that allows them to be captured to another solid surface or other portion of the solid surface by hybridization to a complementary sequence bound to such surface (e.g. sequence (A') or sequence (B). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer second primer extension product molecules are bound per bead. The beads are dispersed into an aqueous solution, and a plurality of microreactors, e.g. droplets, are produced such that on average one or fewer beads is contained within each of the plurality of microreactors. The amplification of the second primer extension products bound to the beads is then carried out such that the clonal amplification of each of the plurality of second primer extension products in the separate microreactors is achieved. This clonal amplification in microreactors can be performed on a sample of target DNA, such as genomic DNA, wherein the plurality of second primer extension products comprise sequences that correspond to most, to substantially all, or to all of the sequences in the target DNA. In some embodiments, the amplified products are captured by bead having attached thereto a plurality of oligonucleotides comprising complementary sequences bound to such surface (e.g. sequence (A') or sequence (B)), which are complementary to sequence (A) or sequence (B') on the amplified products.

In some embodiments, the plurality of beads, produced as described above, with each bead comprising a single second primer extension product can comprise a library. The library can represent, for example, the genomic DNA of an individual, or the genomic DNA from a group of cells or from a single cell. These libraries can be stored, then later clonally amplified. In some embodiments, a library of beads can comprise a plurality of beads wherein each bead had multiple copies of a single amplification product generated from a second primer extension product. These libraries can be analyzed, for example by sequencing. The libraries can be stored, and later analyzed. In some embodiments the libraries can be stored, then analyzed multiple times.

In some embodiments, a bead or isolated area of the solid surface comprises covalently attached thereto multiple oligonucleotides comprising the sequence (B) at their 3' ends, whereby upon the amplification of step (m) multiple copies of amplified product comprising sequence (B') at their 5' end are hybridized to the bead or isolated area. For example, where beads are used, a plurality of beads in a plurality of microreactors wherein, the plurality of beads has, on average one or fewer second primer extension products bound to it and there are, on average, one or fewer beads in each microreactor, a clonal amplification of the plurality of second primer extension products can be carried out, and the amplified products in each of the microreactors will bind to the bead through the sequence (B') on the amplified product to the sequence (B) on the beads. This approach produces a plurality of beads, each with multiple copies of a different sequence bound to it. Where these sequences are representative of the target DNA, the plurality of beads can constitute a library representative of such DNA.

After the amplified products are bound to the beads by hybridization, the (B) sequences on the beads can be extended to produce a multiple polynucleotides covalently attached to the bead or isolated area that are substantially complementary to the amplified product and also comprise sequence (A') near their 5' ends. Where the (B) sequences are covalently attached to the beads, this method provides for the production of beads with polynucleotides complementary to amplified product covalently attached to the beads. Covalently attached polynucleotides such as those produce here are more robust than nucleotides that are attached only by hybridization to the beads. Thus, the covalently attached polynucleotides can be more stable and can be used with analysis methods and sequencing methods that have harsher conditions which would result in the displacement of polynucleotides bound only by hybridization.

In some embodiments, the amplified product is removed from the covalently bound polynucleotide to render the polynucleotide single stranded. Such single stranded covalently bound polynucleotides comprise a specific sequence at their 3' ends comprising sequence (A') and a portion of sequence (C'). This specific sequence at the 3' end of the covalently bound polynucleotide can act as a hybridization site for a primer complementary to sequence (A) that can act as a primer to carry out sequencing by any of a variety of sequencing methods, for example, those described herein. The single stranded covalently bound polynucleotides derived from DNA can be sequenced as described above for the single stranded covalently bound polynucleotides derived from DNA, such as pyrosequencing, cycle sequencing, isothermal sequencing and other methods such as those described below.

The sequencing methods can comprise the use of cleavable labeled terminators. The sequencing method can comprise pyrophosphate detection. The sequencing method can comprise an isothermal sequencing method, for example using chimeric primers, RNase H, and a polymerase with strand displacement activity. The sequencing method can also comprise cycle sequencing.

In some embodiments the methods of the invention provide for performing bridge PCR comprising making amplified product as described above with defined 3' and 5' ends, and further comprising the steps of exposing the amplified product to a solid substrate comprising oligonucleotide sequences attached thereto complementary to the defined 3' and 5' sequences, for example, A and B' sequences, on the amplified product in the presence of components necessary for polymerase chain reaction, and thermal cycling the system to perform bridge PCR amplification. The bridge PCR can be carried out such that isolated lawns of amplified product are obtained wherein each lawn comprises polynucleotides having sequences representative of a portion of the sequence of the target DNA.

In some embodiments the methods of the invention provide for making amplified product as described above with defined 3' and 5' ends and further performing rolling circle amplification comprising performing the steps of: (n) hybridizing the amplified product to a target DNA comprising regions complementary to A and B' sequences in close proximity; (o) optionally extending the gap with a polymerase enzyme; (p) ligating to form a circular nucleic acid comprising the amplified product, and performing rolling circle amplification by extending a primer that is complementary to a sequence in the circular nucleic acid. In some embodiments, the rolling circle amplification uses primers complementary to sequence (A), sequence (B'), or a sequence that was between sequences (A) and (B') in the amplified product. In some cases, such a primer can be an oligonucleotide attached to a solid surface, thus resulting in amplified product bound to the surface In some embodiments the methods of the invention provide for performing PCR comprising making amplified product as described above with defined 3' and 5' ends, further comprising the steps of amplifying the amplified product using primers complementary to sequences (A) and (B), or using primers complementary to sequences (A') and (B').

In some embodiments the methods of the invention provide for performing strand displacement amplification (SDA) comprising making amplified product as described above with defined 3' and 5' ends, wherein the defined 3' and 5' ends, for example, sequences (A) and (B'), in the amplified product are designed to be cleaved by a restriction enzyme, and performing strand displacement amplification on the amplified product.

A schematic exemplary of an embodiment of the invention relating to generating a polynucleotide having a defined 3' and 5' sequences is shown in FIGS. 5A and 5B. The starting material in 5A can be generated as described in the methods herein. The starting material can be generated, for example, from the methods above from a target RNA or a target DNA. While the starting material is described as, for example first primer extension product, it will be understood that a complex of the same structure as shown and described can be used in the method described here.

In FIG. 5A, step I shows the step of: cleaving the RNA from the first primer extension product in the DNA-RNA heteroduplex such that a portion of the second primer extension product that is complementary to sequence (A) is single stranded. As shown, the cleavage is performed using RNase H. Chemical and thermal means can alternatively be employed. Step II illustrates annealing to the second primer extension product an oligonucleotide comprising a 3'-DNA segment that is complementary to sequence (A') and a 5' RNA segment comprising sequence (C). Step III illustrates extending the second primer extension product to create a DNA-RNA heteroduplex such that the second primer comprises a DNA sequence (C') that is complementary to sequence (C). Step IV illustrates the optional step of extending the oligonucleotide to form an oligonucleotide extension product hybridized to the second primer extension product. Step V illustrates binding the ligand to a solid surface resulting in binding of the second primer extension product to the solid surface. While the step of binding the ligand to the solid surface is shown at step V is to be understood that the binding step can be performed at many steps in the process. For example, in this case, the binding step could alternately have been carried out before step I, or could be carried out after amplification.

In FIG. 5B, step VI illustrates cleaving the RNA from the DNA-RNA heteroduplex created in step III to produce a single-stranded portion of the second primer extension product corresponding to sequence (C'). Step VII illustrates annealing an amplification primer, wherein the amplification primer has a DNA portion and a 5' RNA portion, to the single stranded portion of the second primer extension product complementary to sequence (C'). Step VIII illustrates extending the amplification primer with a DNA polymerase having strand displacement activity to produce an amplified product. Step IX illustrates the step of cleaving the RNA from the extended hybridized amplification primer in the DNA-RNA heteroduplex. The product of step IX is now capable of hybridizing another amplification primer, allowing for steps VII to IX to occur again, resulting in the generation of another amplified product. These steps can thus be repeated to produce multiple copies of amplified product wherein the 5' portion of the amplified product has a sequence complementary to sequence (A'). In the embodiment illustrated in FIGS. 5A and 5B the second primer comprised a sequence (B), and as such, the amplified product shown in FIG. 5B comprises a defined sequences on both the 5' and 3' ends.

Figure 6:
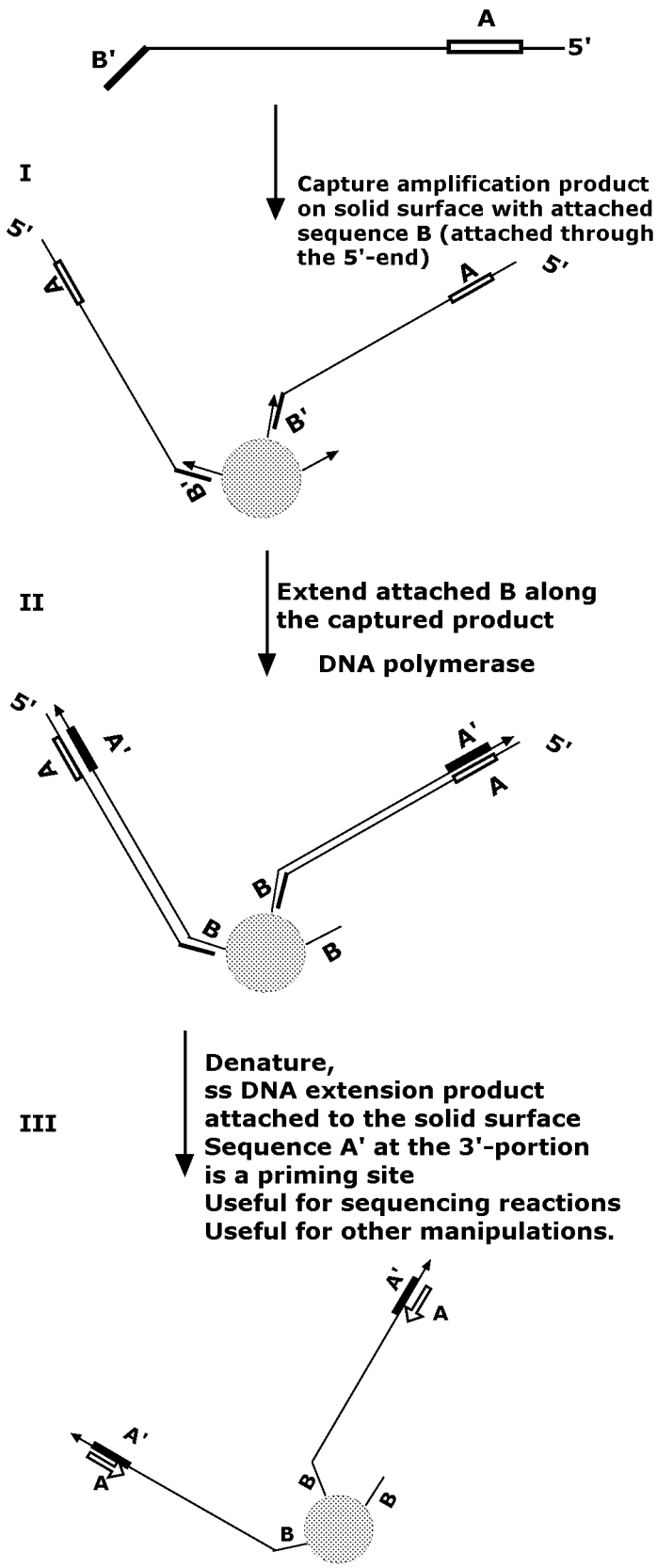
FIG. 6 illustrates the capture by the solid surface comprising oligonucleotides of sequence (B) of amplification product having defined 3' and 5' sequences by hybridization to (B'), the 3' defined sequence of the amplified product. The Figure also shows the extension of the sequence (B) bound to the solid surface to produce a polynucleotide bound to the solid surface. The Figure also illustrates the use of sequencing primers (A) to sequence the bound polynucleotide.

A schematic exemplary of an embodiment of the invention relating to the capture of amplification product on a solid surface is shown in FIG. 6. In some embodiments, the amplified product can be captured onto a surface by hybridization to the defined sequences on the 5' and/or 3' ends of the amplified product. This approach can be useful for example, where a clonal amplification of a given sequence or plurality of sequences that are representative of a target RNA or target DNA produces multiple copies of a specific sequence having defined 5' and 3' ends. The clonal amplification can be carried out in an isolated volume, or on in an isolated area on a surface. In some embodiments, the clonal amplification is carried out with beads in droplets of an inverse emulsion, wherein each droplet has on average one or fewer beads. In some embodiments, it is useful to capture the amplified product on a solid surface, for example a bead. FIG. 6 illustrates how a solid surface, for example the surface of a bead can have multiple oligonucleotides attached thereto. In the embodiment illustrated, the amplified product has a defined sequence (B') at its 3' end and a defined sequence (A) near its 5' end. The bead has multiple oligonucleotides attached to its surface comprising the sequence (B), which is complementary to the sequence (B') at the 3' end of an amplified product. The bead can capture the amplified product as shown by hybridization under the right conditions. The capture of amplified product is illustrated in step I. This type of bead can be used as a library, and can be used for sequencing, for example, by extending from sequence (B). FIG. 6 also illustrates in step II that the (B) sequences on the bead can be extended along the amplified product to produce a polynucleotide attached to the bead which has sequence (A') at or near its 3' end and sequence (B) at its 5' end. Such a polynucleotide can be made single stranded, for example by heat or chemical denaturation, and washing as illustrated in step III. The bead with single stranded polynucleotide which has sequence (A') at or near its 3' end and sequence (B) at its 5' end can be more stable than a bead to which a polynucleotide is held by hybridization alone. The polynucleotide attached to the bead can be covalently bound. The beads made in this fashion can be used to create libraries with long storage life. The single stranded product of step III can be used for archiving, storage, and a variety of manipulations made possible by the defined sequences at the 5' and 3' ends. For example, as shown in FIG. 6, a sequencing primer (A) can be hybridized to sequence (A') to allow the sequencing of the polynucleotide attached to the bead by methods such as those described herein.

Figure 7:
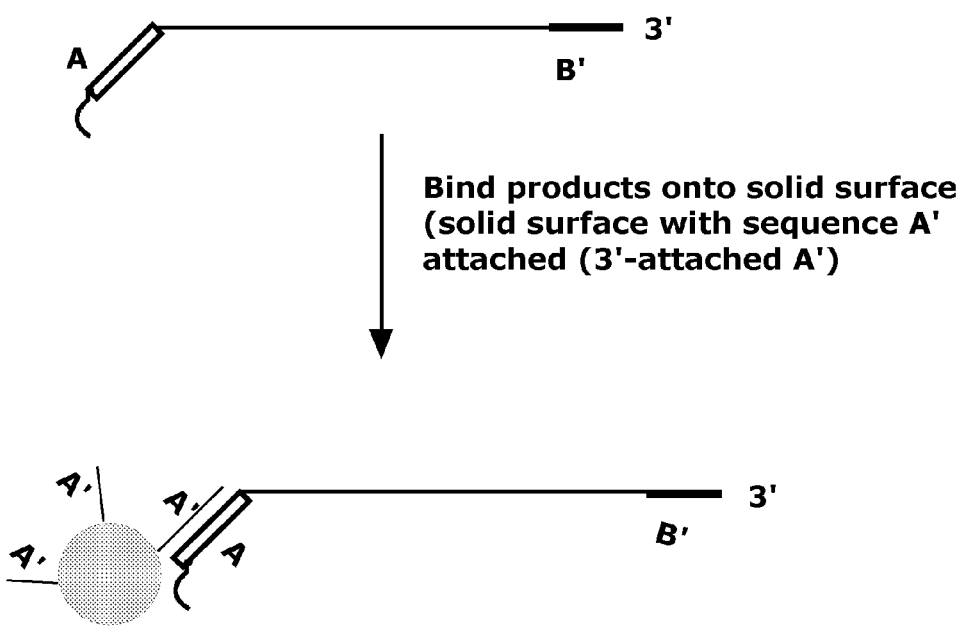
FIG. 7 shows the capture by the solid surface comprising oligonucleotides of sequence (A') of amplification product having defined 3' and 5' sequences by hybridization to (A), the 5' defined sequence of the amplified product.

FIG. 7 illustrates that the amplified product with a defined sequence (B') at its 3' end and a defined sequence (A) near its 5' end can also be captured onto surfaces such as beads by hybridization to an oligonucleotide attached to the solid surface that comprises the sequence (A'). In some cases, the capture is by specific nucleic acid hybridization of sequence (A) of the amplified product to the complementary sequence (A'). In other cases, the oligonucleotide attached to the surface of the solid surface may not be a perfect complement of at least a portion of the 5' end of the amplified product. For example, the oligonucleotide may differ by about 1, 2, 3, 4, 5, 6, 7, 8, 9, 10, 12, 15, 20, or more nucleotides from the perfect complement of sequence (A). The oligonucleotide may be attached to the solid surface by any method known in the art. For example, the oligonucleotide may be attached via non-covalent interaction such as by ionic, hydrogen, or hydrophobic interaction or a combination thereof. In some cases, the oligonucleotide may be attached by one or more covalent bonds between the oligonucleotide and the solid surface. In some cases, the oligonucleotide may be attached by interaction between a receptor ligand pair such as for example an avidin molecule on the surface and a biotin molecule on the oligonucleotide, or any receptor ligand pair known in the art.

Figure 8:
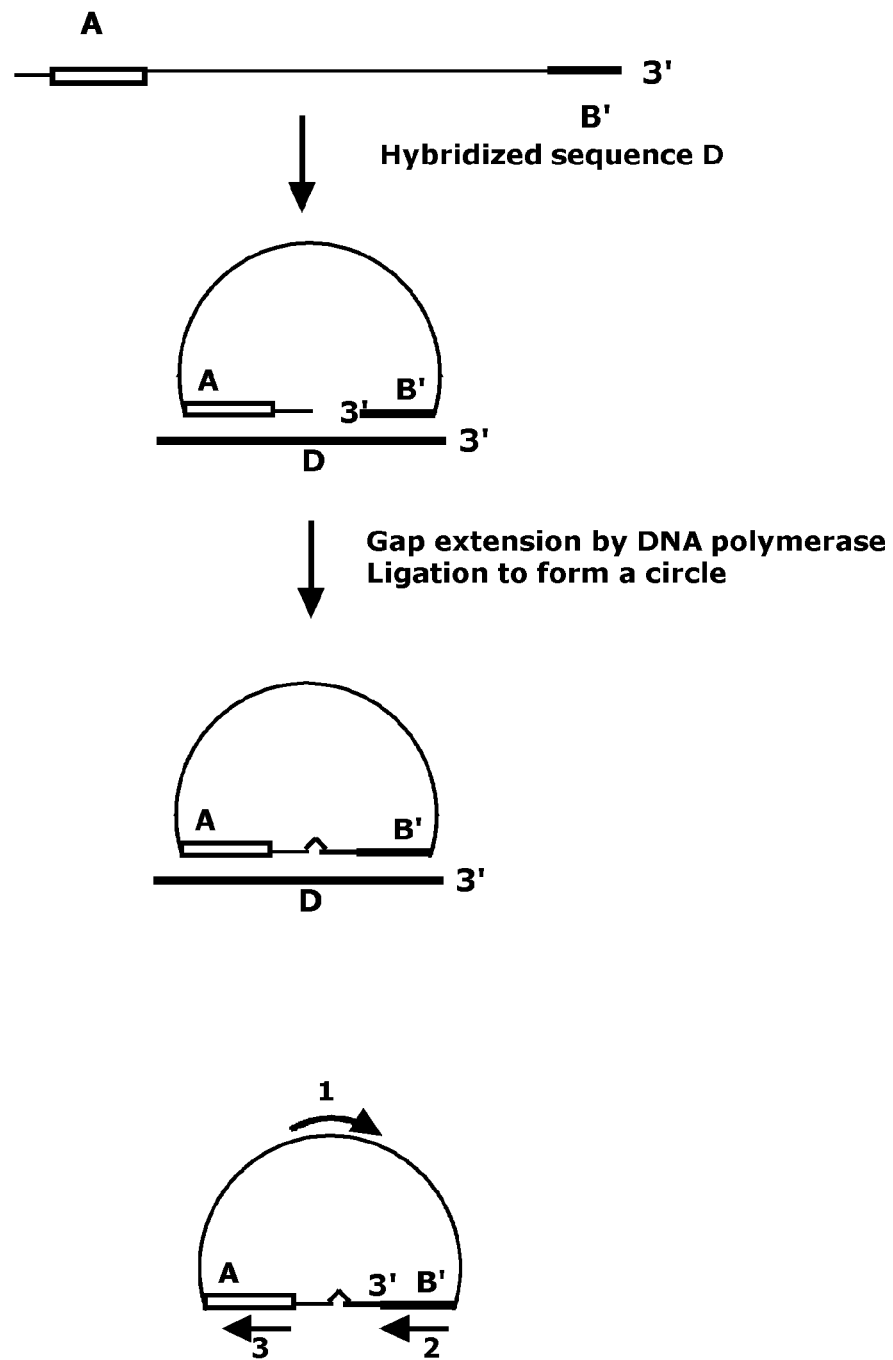
FIG. 8 shows how the of amplification product having defined 3' and 5' sequences can be used for analysis of sequence D by hybridization, gap ligation, and rolling circle amplification.

FIG. 8 illustrates that the amplified products with defined 3' and 5' sequences can be used for gap ligation to create a circular polynucleotide which can then be amplified and characterized using rolling circle amplification. In FIG. 8, the amplified product with a defined sequence (B') at its 3' end and a defined sequence (A) near its 5' end is hybridized to a sequence D with sequences complementary to sequence (A) and sequence (B') (with B' hybridizes upstream from (A), wherein the hybridization of sequences (A) and (B') leave a gap. The gap is closed with a ligase and alternatively with a polymerase for larger gaps. The circular polynucleotide, e.g. DNA, can then be amplified and characterized using rolling circle amplification. Primers for rolling circle amplification can hybridize (3) to sequence (A), (2) to sequence (B'), or (1) to the sequence between (A) and (B') on the amplified product. These methods can be used for the accurate determination of mutations such as single nucleotide polymorphisms (SNPs).

Alternative Method for Generating a Polynucleotide Having a Defined 3' and 5' Sequences from an RNA Target One aspect of the present invention is an alternative method for generating a polynucleotide having a defined 3' and 5' sequences from an RNA target. Unlike the methods described in detail above, this method generally does not use a composite RNA/DNA primer as the first primer. Here, a tailed primer, usually not comprising RNA, composed, for example, of DNA is used to create the first primer extension product. In this method, the second primer comprises a composite RNA/DNA primer, and the third primer comprises a ligand for binding the third primer extension product to a solid surface.

The method comprises step: (a) extending a first primer comprising a 3' portion complementary to a target RNA and a 5' portion, sequence (D), not complementary to the target RNA, to form a first primer extension product hybridized to the target RNA, forming an RNA/DNA hybrid. The first primer generally does not comprise RNA, and may be all DNA. The first primer is a tailed primer comprising a 5' portion, sequence (D) which is generally not complementary to the target RNA, and does not hybridize to the target RNA. In some embodiments, the 3' portion of the primer that is complementary to the target RNA is a specific sequence. For example, where a specific region of interest of a target RNA that is known or suspected to be upstream of a specific sequence on the target RNA, the sequence that is complementary to the target RNA of the first primer can be designed to hybridize to this specific sequence on the target RNA such that extension of the primer results in producing a first primer extension product that is complementary to such upstream region. The specific sequence may be common to a family of target RNA. A combination of primers with various specific sequences at the 3' end can also be useful. In some embodiments, such as where the target RNA comprises mRNA, and the mRNA comprises a plurality of sequences, each having a 3' poly-A segment; the specific sequence that is complementary to the target RNA can comprise a sequence that will hybridize to the poly-A region of the mRNA, thus allowing the extension of the first primer to produce a plurality of first primer extension products, each of which is complementary to the region of an mRNA molecule adjacent to the poly-A region. In some embodiments, the sequence that is complementary to the target RNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a RNA target, generating a plurality of sequences which together can represent, for example substantially the whole sequence of the target RNA. In some embodiments, the relative amounts of the various sequences can be used to quantitate the relative amount of a given sequence in a sample, for example to determine the level of expression in an mRNA sample. In some embodiments more than one type of sequence that is complementary to the target RNA can be used, for instance both a primer with a random sequence and a primer, or combination of primers with a specific sequence complementary to RNA can be used. In some embodiments, multiple primers comprising different specific sequences can be used.

The method further comprises step (b) cleaving the target RNA from the RNA/DNA hybrid. In some cases the cleaving can be accomplished by denaturing the complex comprising the first primer extension product and the nucleic acid. Denaturation can be performed, for example by heating the sample, or by adding a denaturing agent, or using a combination of heating the sample and adding denaturing agents. The cleaving can be accomplished with an enzyme that cleaves RNA from an RNA/DNA hybrid such as RNase H, or a combination of RNase enzymes, or chemically. In some embodiments, the target RNA is completely cleaved. In other embodiments, the target RNA is only partly cleaved or degraded. The amount of cleaving required is that amount which will allow the extension of the second primer.

The method further comprises step (c) extending a second primer comprising a DNA segment and a 5' RNA segment, wherein a 3' portion of the primer is complementary to the first primer extension product and a 5' portion, sequence (E), of the of the second primer is not complementary to the first primer extension product, to produce a double-stranded DNA product comprising the first primer extension product hybridized to a second primer extension product, whereby the second primer extension product has a sequence (D') that is complementary to sequence (D) at its 3' end. The extension of the second primer is carried out with a DNA polymerase as described herein. The second primer is a composite RNA/DNA primer having a 3' portion which is complementary to the first primer extension product, and a 5' portion, sequence (E), which is not complementary to the first primer extension product. In some embodiments, the second primer can comprise a specific primer sequence that is designed to hybridize to a specific sequence in the first primer extension product. In some embodiments the second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target RNA, whereby a plurality of second primer extension products are produced which is representative of the sequence of the target RNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target RNA (sense copies).

The second primer extension product is extended such that the 3' portion of the second primer extension product comprises a sequence (D') which is complementary to sequence (D) of the first primer. The primer extension results in a product that is at least partially double stranded.

In some embodiments, the sample comprising the target RNA is in a sample that also comprises DNA. In such cases, it can be advantageous to add a selective DNA dependent DNA polymerase inhibitor such as actinomycin such that it is present during step (a) to selectively inhibit the production of extension product complementary to the DNA during step (a). The presence of a DNA dependent DNA polymerase inhibitor such as actinomycin is particularly advantageous when a first primer comprising a random sequence is used, as the inhibitor allows for the selective creation of first primer extension products to RNA without the need of separating the RNA from the DNA. This is also advantageous when the priming is carried out at specific target sequences since the sequence may be the same on the DNA when the DNA and RNA in the sample represent total nucleic acid from the same biological entity, for example, human tissue, animal tissue, and the like. The use of DNA dependent DNA polymerase inhibitors such as actinomycin is described in copending application.

The method further comprises step (d) denaturing the double-stranded DNA product. Double stranded DNA can be denatured, for example by heating, or by the addition of denaturing agents.

The method further comprises step (e) annealing to the second primer extension product and extending a third primer comprising, from its 5' end, a ligand, optionally a sequence (F), and a sequence (D), wherein sequence (D) is complementary to sequence (D') on the second primer extension product to produce a double-stranded DNA product comprising the second primer extension product hybridized to a third primer extension product, whereby the third primer extension product comprises a sequence (E') at its 3' end complementary to sequence (E) in a DNA-RNA heteroduplex. The third primer comprises a ligand that is a member of a ligand-receptor pair. In some embodiments, the ligand is attached to the primer at the 5' end of the primer. In some embodiments, the ligand is a small molecule, such as biotin or digoxigenin. In some embodiments, the receptor is an antibody, and the ligand is a molecule or portion of a molecule recognized by the antibody. The method produces a nucleic acid that comprises a ligand allowing it to be bound to a solid surface and that has a specific sequence (E') at its 3' end. The specific sequence (E') can be a site for primer hybridization and further analysis or amplification of the nucleic acid bound to the bead. As described above, the nucleic acid attached to the ligand also comprises sequence (D') at or near its 5' end, and in some embodiments comprises the sequence (F').

In some embodiments, the method further comprises the step of binding the ligand to a solid surface, whereby the third primer extension product is bound to the solid surface.

In some embodiments, the method further comprises the steps of: (f) cleaving the RNA portion of the second primer extension product in the DNA-RNA heteroduplex, whereby sequence (E') of the third primer extension product is single stranded, (g) annealing an oligonucleotide comprising a 3' DNA segment (E) that is complementary to sequence (E') and a 5' RNA segment comprising sequence (G), (h) extending the third primer extension product to produce a sequence (G') at its 3' end complementary to sequence (G), and (i) cleaving the RNA from the heteroduplex created in step (h) to produce a single-stranded portion of the third primer extension product corresponding to sequence (G'). The cleaving of RNA in steps (f) and (i) can be performed, for example by treatment with RNase H, which will selectively cleave the RNA portion of the DNA/RNA partial heteroduplex formed in step (e). The oligonucleotide comprises at least one DNA and at least one RNA portion. In some embodiments the 3' DNA segment is complementary to all of sequence (E'), in other embodiments, the 3' DNA segment is complementary to portion of sequence (E'). In some embodiments, 5' RNA segment comprising sequence (G) is partly complementary to sequence (E'). In some embodiments, the oligonucleotide is optionally extended from its 3' end to produce an oligonucleotide extension product hybridized to the third primer extension product and displacing the DNA portion of the second primer extension product. In some embodiments, the third primer comprises a sequence (F), such that the oligonucleotide extension product will comprise a sequence (F') at or near its 3' end that is complementary to sequence (F). The DNA sequence (G') is created by a DNA polymerase that has RNA dependent DNA polymerase activity. This step creates an RNA/DNA heteroduplex region that can be used for further manipulation of the second primer extension product.

In some embodiments the method further comprises binding the ligand to a solid surface, whereby the third primer extension product comprising sequence (G') is bound to the solid surface. The solid surface can be any of a variety of surfaces, some described in more detail below. The solid surface can be, for example a planar surface, for example, a planar array. In some embodiments the solid surface comprises a plurality of beads. In some embodiments the beads are magnetic. The receptor bound to the solid surface is a member of the ligand-receptor pair such that binding of the ligand results in attaching the second primer extension product to the solid surface. In some embodiments, the second primer extension product is still hybridized to the first primer extension product when it is attached to the solid surface. In some embodiments, the second primer extension product is removed from the third primer extension product such that a single stranded polynucleotide is attached to the solid surface. The method produces a nucleic acid that is bound to a solid surface that has a specific sequence (E') and (G') at its 3' end. The specific sequence (G') can be a site for primer hybridization and further analysis or amplification of the nucleic acid bound to the bead. As described above, in some embodiments, the nucleic acid bound to the bead also comprises sequence (F) at or near its 5' end. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (G') acts as the site to which the composite RNA/DNA amplification primer hybridizes, allowing for amplification. When the sequence (G') acts as a site to which a composite amplification primer binds, the amplified product that is produced has the sequence (E) (and a portion of sequence (G) at its 5' end. The amplified product has a sequence (D') at or near its 3' end. Where the third primer comprises the sequence (F), the amplified product also has the sequence (F'), complementary to (F) at or near its 3' end. Thus the method produced amplified product with defined sequences at or near both its 3' and 5' ends.

In some embodiments, for example where random sequences at the 3' end of the first and/or second primer are used, a plurality of different nucleic acids bound to a solid surface is created in which each of the nucleic acids has a specific sequence (E') and (G') at its 3' end, the sequence (D) at or near its 5' end (and in some embodiments also a specific sequence (F) at its 5' end), and where the different nucleic acids have different intervening sequences, wherein the intervening sequences are identical to or substantially identical to the sequences in the target RNA. The set of bound nucleic acids thus generated can be analyzed, for example, by sequencing in order to provide information about the sequence of the target RNA.

In some embodiments, the method further comprises treating the solid surface with reagents to produce multiple copies of an amplification product that are substantially complementary the second primer extension product. This step comprises carrying out an amplification reaction wherein the bound nucleic acid acts as a template for the amplification. Generally, the amplification is carried out using the sequence (G') on the third primer extension product for the hybridization of primer. In some embodiments, the amplification produces single stranded amplified product, In some embodiments, the amplification provides double stranded product. The third primer extension product comprises the specific sequence (D). In some embodiments, the third primer comprises a specific sequence (F), which thus becomes incorporated into the third primer extension product. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the third primer extension product comprises both as sequence (F) at or near its 5' end and a sequence (G') at or near its 3' end, a set of primers, one designed to hybridize to all or a portion of the sequence (G') and the other designed to hybridize to sequence (F'), complementary to sequence (F), and/or to sequence (D') to exponentially produce double stranded amplified product.

One aspect of the invention is a method of amplifying a sequence representative of a sequence within a target RNA comprising the above steps and further comprising: (j) annealing an amplification primer, wherein the amplification primer has a DNA portion and a 5' RNA portion, to the single stranded portion of the third primer extension product complementary to sequence (G'); (k) extending the amplification primer with an enzyme having strand displacement activity to produce an amplified product; (l) cleaving the RNA from the amplified product; and (m) repeating steps (j) to (l) to produce multiple copies of amplified product wherein the 5' portion of the amplified product has a sequence (E) complementary to sequence (E') and the 3' end of the amplified product has sequence (D') complementary to sequence (D) and optionally sequence (F') complementary to sequence (F).

The step of binding the polynucleotides to the solid surface through the ligand can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (E) or sequence (D'), that allows it to be captured by another solid surface or other portion of the solid surface by hybridization to a complementary sequence bound to such surface (e.g. sequence (E') or sequence (D). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer third primer extension product molecules are bound per bead. The beads are dispersed into an aqueous solution, and a plurality of microreactors, e.g. droplets, are produced such that on average one or fewer beads is contained within each of the plurality of microreactors. The amplification of the third primer extension products bound to the beads is then carried out such that the clonal amplification of a plurality of third primer extension products is achieved. This clonal amplification in microreactors can be performed on a sample of target RNA, such as whole transcriptome or total RNA, wherein the plurality of third primer extension products comprise sequences that correspond to most, to substantially all, or to all of the sequences in the target RNA. In some embodiments, the amplified products are captured by bead having attached thereto a plurality of oligonucleotides comprising complementary sequences bound to such surface (e.g. sequence (E') or sequence (D)), which are complementary to sequence (E) or sequence (D') on the amplified product.

In some embodiments, the plurality of beads, produced as described above, with each bead comprising a single third primer extension product can comprise a library. These libraries can be stored, then later clonally amplified. In some embodiments, a library of beads can comprise a plurality of beads wherein each bead had multiple copies of a single amplification product generated from a third primer extension product. These libraries can be analyzed, for example by sequencing. The libraries can be stored, and later analyzed. In some embodiments the libraries can be stored, then analyzed multiple times.

In some embodiments, a bead or isolated area of the solid surface comprises covalently attached thereto multiple oligonucleotides comprising the sequence (D) (or F) at their 3' ends, whereby upon the amplification of step (m) multiple copies of amplified product comprising sequence (D') (or F') at their 5' end are hybridized to the bead or isolated area. For example, where beads are used, a plurality of beads in a plurality of microreactors wherein, the plurality of beads has, on average one or fewer third primer extension products bound to it and there are, on average, one or fewer beads in each microreactor, a clonal amplification of the plurality of third primer extension products can be carried out, and the amplified products in each of the microreactors will bind to the bead through the sequence (D') (and/or F') on the amplified product to the sequence (D) (and/or F) on the beads. This approach produces a plurality of beads, each with multiple copies of a different sequence bound to it. Where these sequences are representative of the target RNA, the plurality of beads can constitute a library representative of such RNA.

After the amplified products are bound to the beads by hybridization, the (D) sequences on the beads can be extended to produce a multiple polynucleotides covalently attached to the bead or isolated area that are substantially complementary to the amplified product and also comprise sequence (E') near their 5' ends. Where the (D) (and or F) sequences are covalently attached to the beads, this method provides for the production of beads with polynucleotides complementary to amplified product covalently attached to the beads. Covalently attached polynucleotides such as those produce here are more robust than nucleotides that are attached only by hybridization to the beads. Thus, the covalently attached polynucleotides can be more stable and can be used with analysis methods and sequencing methods that have harsher conditions which would result in the displacement of polynucleotides bound only by hybridization.

In some embodiments, the amplified product is removed from the covalently bound polynucleotide to render the polynucleotide single stranded. Such single stranded covalently bound polynucleotides comprise a specific sequence at their 3' ends comprising sequence (E') and a portion of sequence (G'). This specific sequence at the 3' end of the covalently bound polynucleotide can act as a hybridization site for a primer complementary to sequence (E) that can act as a primer to carry out sequencing by any of a variety of sequencing methods, for example, those described herein.

The sequencing methods can comprise the use of cleavable labeled terminators. The sequencing method can comprise pyrophosphate detection. The sequencing method can comprise an isothermal sequencing method, for example using chimeric primers, RNase H, and a polymerase with strand displacement activity. The sequencing method can also comprise cycle sequencing.

The amplified products with defined 3' and 5' ends can be used in the methods described herein for the amplified products produced by the other methods. They can be used, for example, for bridge PCR, rolling circle amplification, and strand displacement amplification.

Figure 9:
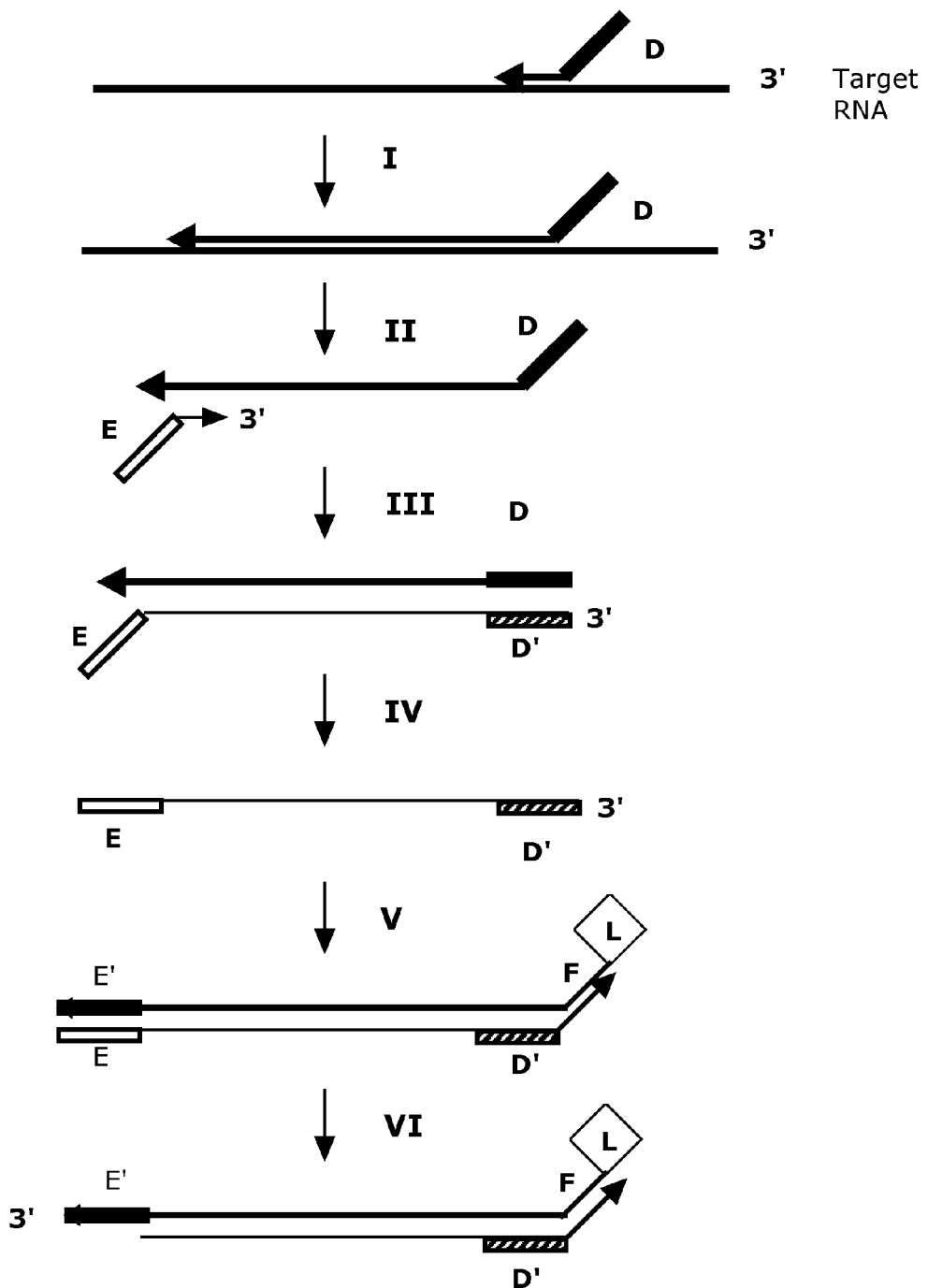
FIG. 9 illustrates an alternative method of producing a polynucleotide comprising a ligand that can be bound to a solid support that comprises sequences related to a target nucleic acid and comprises a defined sequence (E') at its 3' end.

A schematic exemplary of an embodiment of the invention relating to an alternative method for generating a polynucleotide having a defined 3' and 5' sequences from an RNA target is shown in FIG. 9. Step I illustrates the step of extending a DNA first primer comprising a 3' portion complementary to a target RNA and a 5' portion, sequence (D), not complementary to the target RNA, to form a first primer extension product hybridized to the target RNA, forming an RNA/DNA hybrid. Step II illustrates cleaving the target RNA from the RNA/DNA hybrid, and hybridizing the second primer. Step III illustrates extending a second primer comprising a DNA segment and a 5' RNA segment, wherein a 3' portion of the primer is complementary to the first primer extension product and a 5' portion, sequence (E), of the of the second primer is not complementary to the first primer extension product, to produce a double-stranded DNA product comprising the first primer extension product hybridized to a second primer extension product, whereby the second primer extension product has a sequence (D') that is complementary to sequence (D) at its 3' end. Step IV illustrates denaturing the double-stranded DNA product. Step V illustrates annealing to the second primer extension product and extending a third primer comprising, from its 5' end, a ligand, optionally a sequence (F), and a sequence (D), wherein sequence (D) is complementary to sequence (D') on the second primer extension product to produce a double-stranded DNA product comprising the second primer extension product hybridized to a third primer extension product, whereby the third primer extension product comprises a sequence (E') at its 3' end complementary to sequence (E). The products of steps V and VI may be useful for SPIA amplification of a target RNA sequence or its complement.

Step VI illustrates the step of cleaving the RNA portion of the second primer extension product in the DNA-RNA heteroduplex, whereby sequence (E') of the third primer extension product is single stranded.

Figure 10:
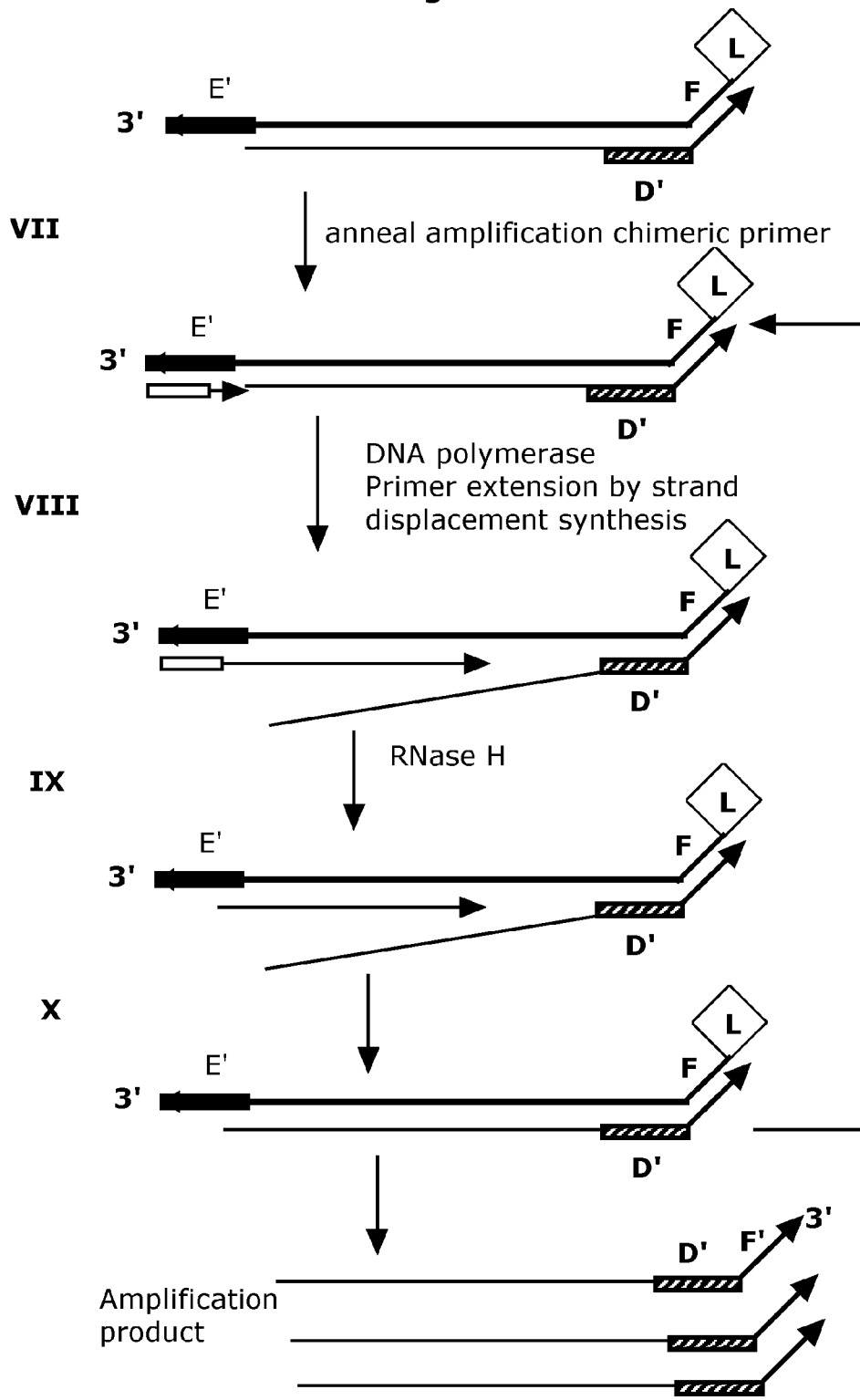
FIG. 10 shows how the polynucleotide produced as shown in FIG. 9 can be used to produce amplified product.
Figure 11:
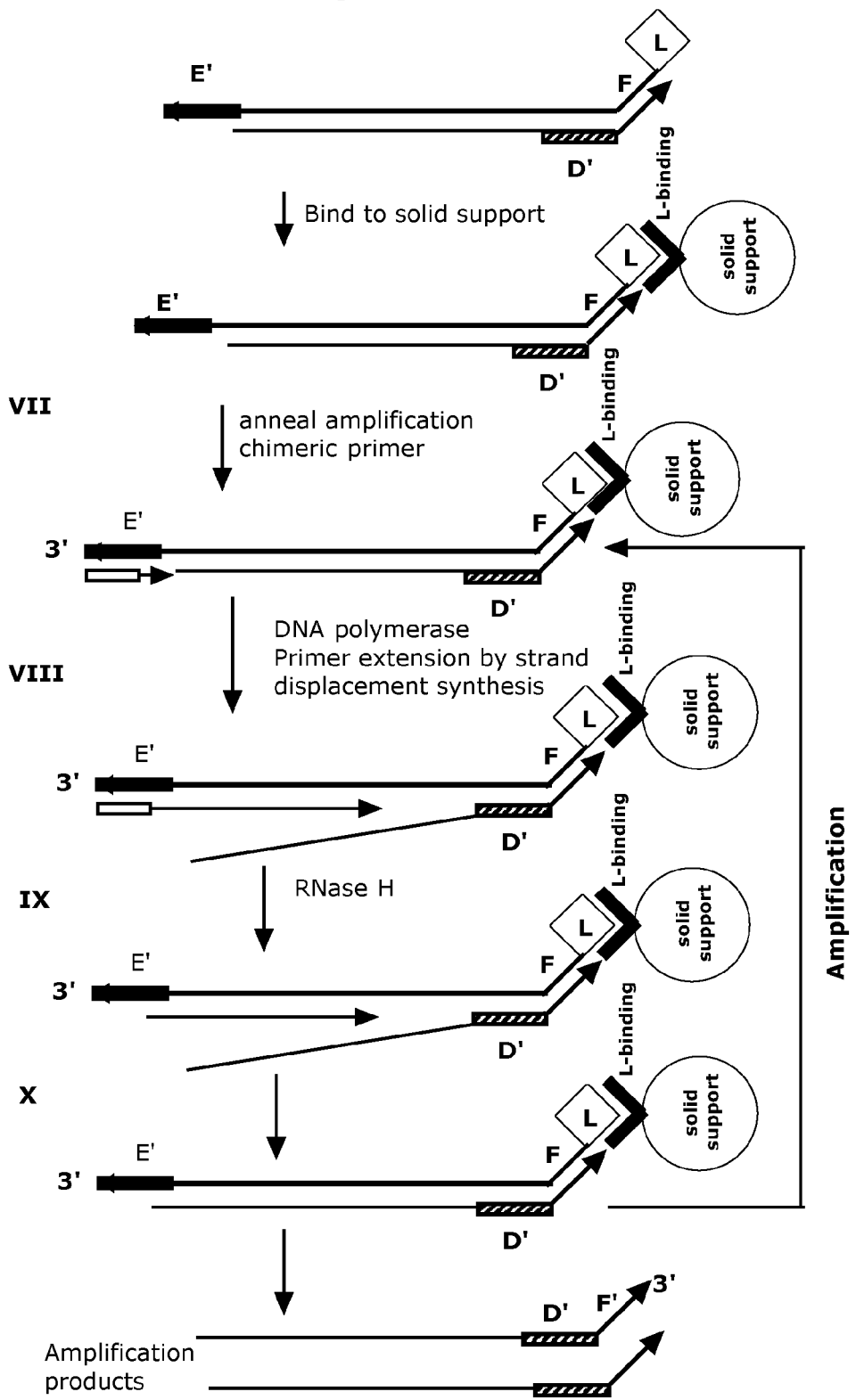
FIG. 11 shows how the amplification illustrated in FIG. 10 can be carried out while the polynucleotide is bound to a solid surface.

FIG. 10 illustrates the isothermal amplification starting from the partially double-stranded polynucleotide produced either from RNA described above, or from DNA as described below. Step VII comprises annealing an amplification primer comprising 5' RNA and 3' DNA segments. Step VIII shows the extension of the amplification primer by a DNA polymerase with strand displacement activity. Step IX shows the cleavage of the RNA portion of the amplification primer. Step X illustrates the continued extension of the amplification primer by a DNA polymerase with strand displacement activity to produce an amplified product comprising sequence (D') and sequence (F') at its 3' end. The product of step X can hybridize to another amplification primer, and steps VII through X can be repeated to produce multiple copies of amplified product. While the ligand is unbound in this embodiment, it is to be understood that the ligand can be bound to the surface at various steps in the process. For example, it can be advantageous to have the species bound during the amplification step. FIG. 11 illustrates the process shown in FIG. 10 where the ligand and third primer extension product are bound to the support during amplification.

Alternative Method for Generating a Polynucleotide Having a Defined 3' and 5' Sequences from a DNA Target One aspect of the invention is an alternative method for generating a polynucleotide having a defined 3' and 5' sequences from a DNA target. This method generally does not use a composite RNA/DNA primer as the first primer. Here, a tailed primer, usually not comprising RNA, composed, for example, of DNA is used to create a plurality of first primer extension products. In this method, the second primer comprises a composite RNA/DNA primer, and the third primer comprises a ligand for binding the third primer extension products to a solid surface.

The method comprises step: (a) denaturing a double-stranded target DNA. Double stranded DNA can be denatured, for example by heating, or by the addition of denaturing agents.

The method further comprise step: (b) annealing to the target DNA and extending a first primer comprising a 3' portion comprising a random sequence and a 5' portion, sequence (D), which is not complementary to the target DNA, to form a plurality of first primer extension products, each comprising sequence (D) at its 3' end. The first primer generally does not comprise RNA, and may be all DNA. The first primer is a tailed primer comprising a 5' portion, sequence (D) which is generally not complementary to the target DNA, and does not hybridize to the target DNA. The sequence that is complementary to the target DNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a DNA target, generating a plurality of sequences which together can represent, for example substantially the whole sequence of the target DNA. In some embodiments, the relative amounts of the various sequences can be used to quantitate the relative amount of a given sequence in a sample, for example to determine the number of gene copies in a target DNA sample. In some embodiments more than one type of sequence that is complementary to the target DNA can be used, for instance both a primer with a random sequence and a primer with a sequence complementary to DNA can be used. In some embodiments, multiple primers comprising different specific sequences can be used.

The method further comprises step (c): extending a second primer comprising a DNA segment and a 5' RNA segment, wherein a 3' portion comprises a random sequence, and a 5' portion, sequence (E), of the of the second primer is not complementary to the first primer extension products, to produce a plurality of double-stranded DNA products comprising a first primer extension product hybridized to a second primer extension product, whereby the second primer extension products have a sequence (D') that is complementary to sequence (D) at their 3' ends. The extension of the second primer is carried out with a DNA polymerase as described herein. The second primer is a composite RNA/DNA primer having a 3' portion which is complementary to the first primer extension product, and a 5' portion, sequence (E), which is not complementary to the first primer extension product. The second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target DNA, whereby a plurality of second primer extension products are produced which is representative of the sequence of the target DNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target DNA (sense copies).

The second primer extension products are extended such that the 3' portion of the second primer extension products comprises a sequence (D') which is complementary to sequence (D) of the first primer. The primer extension results in products that are at least partially double stranded.

The method further comprises step (d) denaturing the double-stranded DNA product. Double stranded DNA can be denatured, for example by heating, or by the addition of denaturing agents.

The method further comprises step (e) annealing to the second primer extension product and extending a third primer comprising, from its 5' end, a ligand, optionally a sequence (F), and a sequence (D), wherein sequence (D) is complementary to sequence (D') on the second primer extension products to produce double-stranded DNA products comprising second primer extension products hybridized to a third primer extension products, whereby the third primer extension products comprise a sequence (E') at its 3' end complementary to sequence (E). The third primer comprises a ligand that is a member of a ligand-receptor pair. In some embodiments, the ligand is attached to the primer at the 5' end of the primer. In some embodiments, the ligand is a small molecule, such as biotin or digoxigenin. In some embodiments, the receptor is an antibody, and the ligand is a molecule or portion of a molecule recognized by the antibody. The method produces nucleic acids that comprise a ligand allowing them to be bound to a solid surface and that has a specific sequence (E') at its 3' end. The specific sequence (E') can be a site for primer hybridization and further analysis or amplification of the nucleic acid bound to the bead. As described above, the nucleic acid attached to the ligand also comprises sequence (D') at or near its 5' end, and in some embodiments comprises the sequence (F').

In some embodiments, the method further comprises the step of binding the ligand to a solid surface, whereby the third primer extension product is bound to the solid surface.

In some embodiments, the method further comprises the steps of: (f) cleaving the RNA portion of the second primer extension products in the DNA-RNA heteroduplex, whereby sequence (E') of the third primer extension products is single stranded, (g) annealing an oligonucleotide comprising a 3' DNA segment (E) that is complementary to sequence (E') and a 5' RNA segment comprising sequence (G), (h) extending the third primer extension products to produce a sequence (G') at their 3' end complementary to sequence (G), and (i) cleaving the RNA from the heteroduplex created in step (h) to produce a single-stranded portion of the third primer extension products corresponding to sequence (G'). The cleaving of RNA in steps (f) and (i) can be performed, for example by treatment with RNase H, which will selectively cleave the RNA portion of the DNA/RNA partial heteroduplex formed in step (e). The oligonucleotide comprises at least one DNA and at least one RNA portion. In some embodiments the 3' DNA segment is complementary to all of sequence (E'), in other embodiments, the 3' DNA segment is complementary to portion of sequence (E'). In some embodiments, 5' RNA segment comprising sequence (G) is partly complementary to sequence (E'). In some embodiments, the oligonucleotide is optionally extended from its 3' end to produce a plurality of oligonucleotide extension products hybridized to the third primer extension products and displacing the DNA portion of the second primer extension products. In some embodiments, the third primer comprises a sequence (F), such that the oligonucleotide extension products will comprise a sequence (F') at or near their 3' end that is complementary to sequence (F). The DNA sequence (G') is created by a DNA polymerase that has RNA dependent DNA polymerase activity. This step creates an RNA/DNA heteroduplex region that can be used for further manipulation of the second primer extension products.

In some embodiments the method further comprises binding the ligand to a solid surface, whereby the third primer extension products comprising sequence (G') are bound to the solid surface. The solid surface can be any of a variety of surfaces, some described in more detail below. The solid surface can be, for example a planar surface, for example, a planar array. In some embodiments the solid surface comprises a plurality of beads. In some embodiments the beads are magnetic. The receptor bound to the solid surface is a member of the ligand-receptor pair such that binding of the ligand results in attaching the second primer extension products to the solid surface. In some embodiments, the second primer extension products are still hybridized to the first primer extension product when they are attached to the solid surface. In some embodiments, the second primer extension products are removed from the third primer extension products such that single stranded polynucleotides are attached to the solid surface. The method produces nucleic acids that are bound to a solid surface having a defined sequence (E') and (G') at their 3' ends. The specific sequence (G') can be a site for primer hybridization and further analysis or amplification of the nucleic acids bound to the beads. As described above, in some embodiments, the nucleic acid bound to the bead also comprises sequence (F) at or near its 5' end. One aspect of the invention comprises amplification of the nucleic acids bound to the bead. In some embodiments, the amplification is carried out using isothermal amplification using a composite RNA/DNA primer, RNase H, and a polymerase with strand displacement activity. For this embodiment, the sequence (G') acts as the site to which the composite RNA/DNA amplification primer hybridizes, allowing for amplification. When the sequence (G') acts as a site to which a composite amplification primer binds, the amplified products that are produced have the sequence (E) (and a portion of sequence (G) at their 5' ends. The amplified products have a sequence (D') at or near their 3' ends. Where the third primer comprises the sequence (F), the amplified products also have the sequence (F'), complementary to (F) at or near their 3' ends. Thus the method produces amplified product with defined sequences at or near both its 3' and 5' ends.

In some embodiments, for example where random sequences at the 3' end of the first and/or second primer are used, a plurality of different nucleic acids bound to a solid surface is created in which each of the nucleic acids has a specific sequence (E') and (G') at its 3' end, the sequence (D) at or near its 5' end (and in some embodiments also a specific sequence (F) at its 5' end), and where the different nucleic acids have different intervening sequences, wherein the intervening sequences are identical to or substantially identical to the sequences in the target DNA. The set of bound nucleic acids thus generated can be analyzed, for example, by sequencing in order to provide information about the sequence of the target DNA.

In some embodiments, the method further comprises treating the solid surface with reagents to produce multiple copies of amplification products that are substantially complementary the second primer extension products. This step comprises carrying out an amplification reaction wherein the bound nucleic acid acts as a template for the amplification. Generally, the amplification is carried out using the sequence (G') on the third primer extension product for the hybridization of primer. In some embodiments, the amplification produces single stranded amplified products, In some embodiments, the amplification provides double stranded products. The third primer extension products comprise the specific sequence (D'). In some embodiments, the third primer comprises a specific sequence (F), which thus becomes incorporated into the third primer extension products. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the third primer extension products comprise both as sequence (F) at or near its 5' end and a sequence (G') at or near its 3' end, a set of primers, one designed to hybridize to all or a portion of the sequence (G') and the other designed to hybridize to sequence (F'), the complement of sequence (B), or sequence (D), can be used to carry out a PCR reaction to exponentially produce double stranded amplified products.

One aspect of the invention is a method of amplifying a sequence representative of a sequence within a target DNA comprising the above steps and further comprising: (j) annealing an amplification primer, wherein the amplification primer has a DNA portion and a 5' RNA portion, to the single stranded portion of the third primer extension products complementary to sequence (G'); (k) extending the amplification primer with an enzyme having strand displacement activity to produce an amplified products; (l) cleaving the RNA from the amplified products; and (m) repeating steps (j) to (l) to produce multiple copies of amplified products wherein the 5' portion of the amplified products have a sequence (E) complementary to sequence (E') and the 3' end of the amplified products have sequence (D') complementary to sequence (D) and optionally sequence (F') complementary to sequence (F).

The step of binding the polynucleotides to the solid surface through the ligand can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments the amplification is carried out such that the amplified products are not attached to the substrate, but is freely dissolved in the solution. In other embodiments, the amplification is carried out such that the amplified products remains bound to the substrate, for example by performing solid phase PCR such as bridge PCR. In yet other embodiments, amplified products are generated that may float freely in solution, but which comprise a sequence, for example sequence (E) or sequence (D'), that allows them to be captured to another solid surface or other portion of the solid surface by hybridization to a complementary sequence bound to such surface (e.g. sequence (E') or sequence (D). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer third primer extension product molecules are bound per bead. The beads are dispersed into an aqueous solution, and a plurality of microreactors, e.g. droplets, are produced such that on average one or fewer beads is contained within each of the plurality of microreactors. The amplification of the third primer extension products bound to the beads is then carried out such that the clonal amplification of a plurality of third primer extension products is achieved. This clonal amplification in microreactors can be performed on a sample of target DNA such as genomic, wherein the plurality of third primer extension products comprise sequences that correspond to most, to substantially all, or to all of the sequences in the target DNA. In some embodiments, the amplified products are captured by bead having attached thereto a plurality of oligonucleotides comprising complementary sequences bound to such surface (e.g. sequence (E') or sequence (D)), which are complementary to sequence (E) or sequence (D') on the amplified product.

In some embodiments, the plurality of beads, produced as described above, with each bead comprising a single third primer extension product can comprise a library. These libraries can be stored, then later clonally amplified. In some embodiments, a library of beads can comprise a plurality of beads wherein each bead had multiple copies of a single amplification product generated from a third primer extension product. These libraries can be analyzed, for example by sequencing. The libraries can be stored, and later analyzed. In some embodiments the libraries can be stored, then analyzed multiple times.

In some embodiments, a bead or isolated area of the solid surface comprises covalently attached thereto multiple oligonucleotides comprising the sequence (D) (or F) at their 3' ends, whereby upon the amplification of step (m) multiple copies of amplified product comprising sequence (D') (or F') at their 5' end are hybridized to the bead or isolated area. For example, where beads are used, a plurality of beads in a plurality of microreactors wherein, the plurality of beads has, on average one or fewer third primer extension products bound to it and there are, on average, one or fewer beads in each microreactor, a clonal amplification of the plurality of third primer extension products can be carried out, and the amplified products in each of the microreactors will bind to the bead through the sequence (D') (and/or F') on the amplified product to the sequence (D) (and/or F) on the beads. This approach produces a plurality of beads, each with multiple copies of a different sequence bound to it. Where these sequences are representative of the target DNA, the plurality of beads can constitute a library representative of such DNA.

After the amplified products are bound to the beads by hybridization, the (D) sequences on the beads can be extended to produce a multiple polynucleotides covalently attached to the bead or isolated area that are substantially complementary to the amplified product and also comprise sequence (E') near their 5' ends. Where the (D) (and or F) sequences are covalently attached to the beads, this method provides for the production of beads with polynucleotides complementary to amplified product covalently attached to the beads. Covalently attached polynucleotides such as those produce here are more robust than nucleotides that are attached only by hybridization to the beads. Thus, the covalently attached polynucleotides can be more stable and can be used with analysis methods and sequencing methods that have harsher conditions which would result in the displacement of polynucleotides bound only by hybridization.

In some embodiments, the amplified product is removed from the covalently bound polynucleotide to render the polynucleotide single stranded. Such single stranded covalently bound polynucleotides comprise a specific sequence at their 3' ends comprising sequence (E') and a portion of sequence (G'). This specific sequence at the 3' end of the covalently bound polynucleotide can act as a hybridization site for a primer complementary to sequence (E) that can act as a primer to carry out sequencing by any of a variety of sequencing methods, for example, those described herein.

The sequencing can be used to reveal information about the target DNA, for example the genomic DNA. The sequencing methods can comprise the use of cleavable labeled terminators. The sequencing method can comprise pyrophosphate detection. The sequencing method can comprise an isothermal sequencing method, for example using chimeric primers, RNase H, and a polymerase with strand displacement activity. The sequencing method can also comprise cycle sequencing.

The amplified products with defined 3' and 5' ends can be used in the methods described herein for the amplified products produced by the other methods. They can be used, for example, for bridge PCR, rolling circle amplification, and strand displacement amplification.

Figure 12:
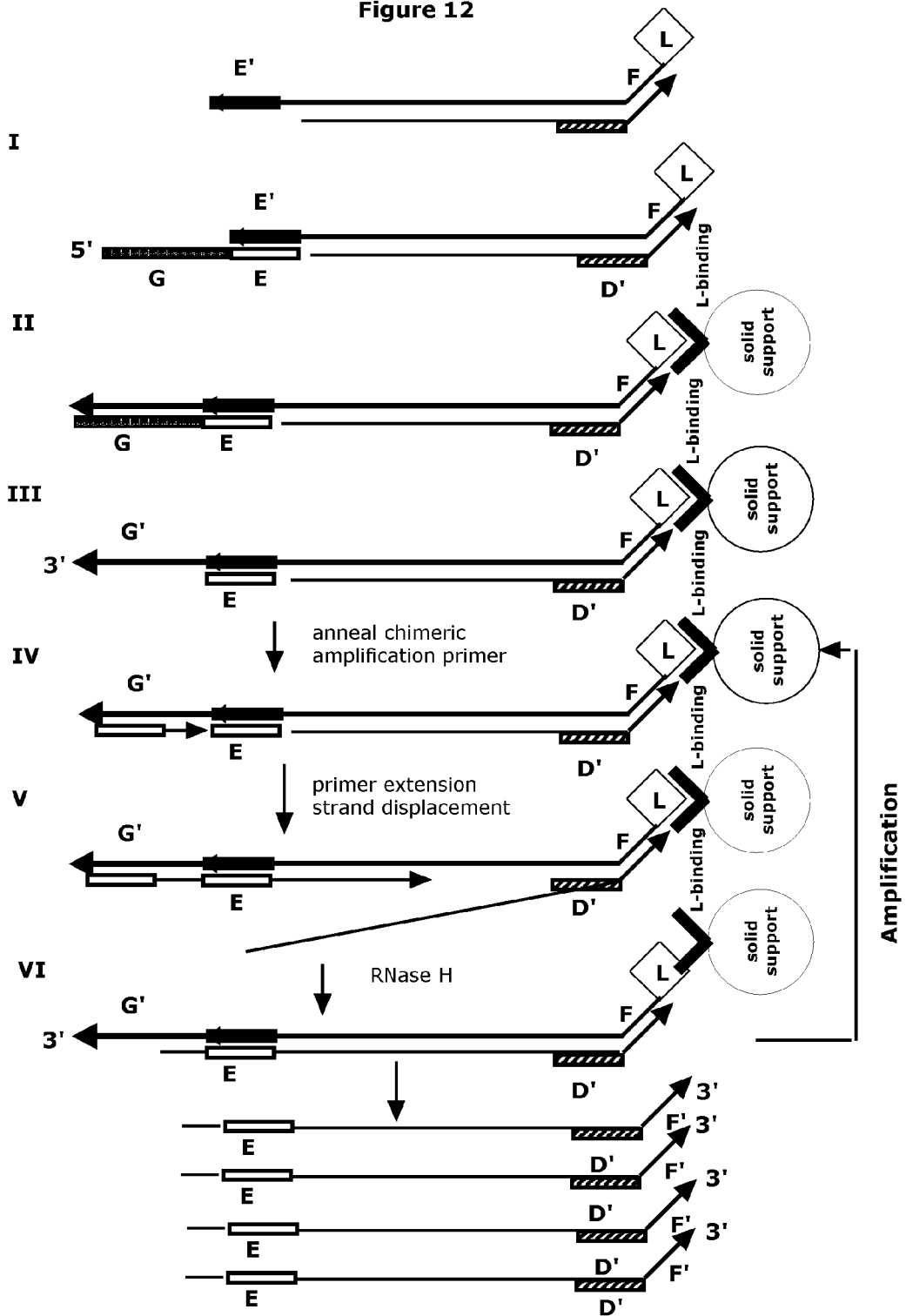
FIG. 12 shows how a chimeric RNA/DNA oligonucleotide (G/E) can be used with the product of the method illustrated in FIG. 9 to produce amplified product with defined sequences at its 3' and 5' ends.

A schematic exemplary of an embodiment of the invention relating to an alternative method for generating a polynucleotide having a defined 3' and 5' sequences from an RNA target is shown in FIG. 12. The steps shown in FIG. 12 are applicable to product that is generated from the alternative method for either RNA or from DNA as described above. Step I comprises the steps of annealing an oligonucleotide comprising a 3' DNA segment (E) that is complementary to sequence (E') and a 5' RNA segment comprising sequence (G). Step II comprises extending the third primer extension product to produce a sequence (G') at its 3' end complementary to sequence (G). Step III comprises cleaving the RNA from the heteroduplex created in step II to produce a single-stranded portion of the third primer extension product corresponding to sequence (G').

Step IV comprises annealing an amplification primer, wherein the amplification primer has a DNA portion and a 5' RNA portion, to the single stranded portion of the third primer extension product complementary to sequence (G'). Step V comprises extending the amplification primer with an enzyme having strand displacement activity to produce an amplified product. Step VI comprises cleaving the RNA from the amplified product. The product of step VI can hybridize to another amplification primer, thus allowing steps IV to VI to be repeated to produce multiple copies of amplified product wherein the 5' portion of the amplified product has a sequence (E) complementary to sequence (E') and the 3' end of the amplified product has sequence (D') complementary to sequence (D) and optionally sequence (F') complementary to sequence (F).

Alternative Method for Generating a Polynucleotide Bound to a Solid Surface

One aspect of the invention is a method for attaching a polynucleotide sequence that is representative of a sequence within a nucleic acid target molecule to a solid surface. The terms solid surface and solid support are used interchangeably herein. The polynucleotide sequence that is produced is representative of the sequence within a nucleic acid target molecule if it is either the same as, or complementary to the sequence within the target nucleic acid. Where the target nucleic acid is double stranded, the method can produce sequences that are representative of both of the strands. The polynucleotide can be, for example either DNA or RNA.

The first step of the method comprises step: (a) extending a first primer comprising a DNA segment and a 5' RNA segment, wherein a 3' portion of the primer, sequence (P), is complementary to a target nucleic acid and a 5' portion of the of the primer, sequence (A), is not complementary to the target nucleic acid, to form a first primer extension product hybridized to the target nucleic acid. In some embodiments, the 3' portion of the primer that is complementary to the target nucleic acid is a specific sequence. For example, where a specific region of interest of a target nucleic acid that is known or suspected to be upstream of a specific sequence on the target nucleic acid, sequence (P) of the composite primer can be designed to hybridize to this specific sequence on the target nucleic acid such that extension of the primer results in producing a first primer extension product that is complementary to such upstream region. The specific sequence may be common to a family of target RNA. A combination of primers with various specific sequences at the 3' end can also be useful. In some embodiments, such as where the target nucleic acid comprises mRNA, and the mRNA comprises a plurality of sequences, each having a 3' poly-A segment; the specific sequence (P) can comprise a sequence that will hybridize to the poly-A region of the mRNA, thus allowing the extension of the first primer to produce a plurality of first primer extension products, each of which is complementary to the region of an mRNA molecule adjacent to the poly-A region. In some embodiments, the sequence (P) comprises a random sequence, such that the extension of the first primer results in a plurality of first primer extension products complementary to the sequences adjacent to the sequence where each random species hybridizes. The use of a random sequence such as sequence (P) at the 3' end of the primer can be useful for performing a global amplification of a nucleic acid target, generating a plurality of sequences which together can represent, for example substantially the whole sequence of the target nucleic acid. In some embodiments, the relative amounts of the various sequences can be used to quantitate the relative amount of a given sequence in a sample, for example to determine the level of expression in an mRNA sample, or to determine gene copy number in a DNA sample.

The first primer extension product comprises a 5' portion comprising sequence (A). Sequence A comprises RNA. In some embodiments, sequence (A) is RNA, and sequence (P) is DNA. In other embodiments, sequence (A) will comprise some DNA. In some embodiments, sequence (P) will comprise some RNA. In some embodiments, sequence (A) and sequence (P) are adjacent.

The method further comprises step: (b) separating or removing the first primer extension product from the target nucleic acid. The first primer extension product can be separated from the target nucleic acid by a variety of methods. In some cases the separation can be affected by denaturing the complex comprising the first primer extension product and the nucleic acid. Denaturation can be performed, for example by heating the sample, or by adding a denaturing agent, or using a combination of heating the sample and adding denaturing agents. Other methods of separating the first primer extension product from the target nucleic acid involve selectively cleaving or degrading the target nucleic acid. Where the target nucleic acid is RNA, the cleaving or degrading can be accomplished by denaturing or heating the sample to degrade RNA or with an enzyme that cleaves RNA from an RNA/DNA hybrid such as RNase H, or chemically. In some embodiments, the target nucleic acid is completely cleaved or degraded. In other embodiments, the target nucleic acid is only partly cleaved or degraded. The amount of cleavage or degradation required is that amount which will allow the extension of the second primer. In some embodiments, the cleavage or degradation is carried out partially, and the fragments of the target nucleic acid that remain can constitute the second primer for step (c).

The method further comprises step: (c) extending a second primer to produce a double-stranded product comprising a second primer extension product hybridized to the first primer extension product, wherein the second primer comprises a 3' segment complementary to a portion of the first primer extension product and 5' segment non-complementary sequence (B) to the first primer extension product, whereby a portion of the 3' end of the second primer extension product comprises a sequence (A') that is complementary to the sequence (A) of the of the first primer and a portion of the 5' end of the second primer extension product comprises non-complementary sequence (B).

The extension of the second primer is carried out with a DNA polymerase as described herein. The second primer can comprise RNA, DNA, or can be a composite primer comprising both RNA and DNA. The second primer is generally a tailed primer having a 3' portion which is complementary to the first primer extension product, and a 5' portion, sequence (B), which is not complementary to the first primer extension product. In some embodiments, the second primer can comprise a specific primer sequence that is designed to hybridize to a specific sequence in the first primer extension product. In some embodiments the second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target RNA or target DNA, whereby a plurality of second primer extension products are produced which is representative of the sequence of the target nucleic acid. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target nucleic acid (sense copies). The second primer comprises a sequence (B) that is homologous to a sequence (B) on a solid support.

The second primer extension product is extended such that the 3' portion of the second primer extension product comprises a sequence (A') which is complementary to sequence (A) of the first primer. Since sequence (A) on the first primer extension product comprises RNA, both DNA dependent DNA polymerase activity and RNA dependent DNA polymerase activity are used in step (c). The primer extension results in a product that is at least partially double stranded since sequence (B) is not hybridized to the first primer extension product.

The method further comprises step: (d) adding an exonuclease to the double-stranded DNA/RNA hybrid, whereby single stranded 3' nucleotides are removed from the first primer extension product. Non-limiting examples of an exonuclease include single-strand specific 3'-exonucleases such as exonuclease 1. The exonuclease should remove all of the single-stranded 3' nucleotides which are not hybridized to sequence (B). In some embodiments, the exonuclease may remove additional 3' nucleotides which are hybridized to the second primer extension product. In other embodiments, a polymerase comprising exonuclease activity may be used. Non-limiting examples include a T4 polymerase comprising 3' exonuclease activity.

The method further comprises step: (e) extending the first primer extension product to produce a sequence (B'), complementary to sequence (B) on the second primer extension product. The extension of the first primer extension product is carried out with a DNA polymerase as described herein and is generally carried out with a DNA-dependent DNA polymerase if the second primer extension product contains only DNA or with RNA-dependent DNA polymerase if the second primer extension product contains a RNA sequence. The primer extension results in a product that is double stranded and comprises sequences (A) and (B') on the first primer extension product and sequences (B) and (A') on the second primer extension product.

The method further comprises step: (f) denaturing the first and second primer extension products. The first primer extension product can be separated from the second primer extension product by denaturation. Denaturation can be performed, for example by heating the sample, or by adding a denaturing agent, or using a combination of heating the sample and adding denaturing agents.

The method further comprises step: (g) binding the sequence (B') of the first primer extension product to a third primer comprising sequence (B) bound to a solid surface, whereby the first primer extension product is attached to the solid surface. The third primer comprises an oligonucleotide with sequence (B) that is complementary to the sequence (B') of the first primer extension product and results in attaching the single stranded first primer extension product to the solid surface. The method produces a nucleic acid that is bound to a solid surface that has a specific sequence (A) at its 5' end. As described above, in some embodiments, the nucleic acid bound to the bead also comprises sequence (B') at or near its 3' end.

Step (g) of binding the polynucleotides to the solid surface sequence (B) can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

The method further comprises step: (h) extending the sequence (B) of the third primer to produce a double-stranded product comprising a third primer extension product hybridized to the first primer extension product, wherein the 5' end of the third primer comprises a sequence (B) complementary to the sequence (B') of the first primer extension product, whereby a portion of the 3' end of the third primer extension product comprises a sequence (A') that is complementary to the sequence (A) of the of the first primer.

The extension of the third primer is carried out with a DNA polymerase as described herein. The primer extension results in a product that is double stranded and comprises sequences (A) and (B') on the first primer extension product and sequences (B) and (A') on the third primer extension product.

The specific, or universal, sequence (A') can be a site for primer hybridization and further analysis or amplification of the nucleic acid bound to the bead. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification. In some embodiments, for example where random sequences at the 3' end of the first and/or second primer are used, a plurality of different nucleic acids bound to a solid surface is created in which each of the nucleic acids has a specific sequence (A') at its 3' end (and in some embodiments also a specific sequence (B) at its 5' end), and where the different nucleic acids have different intervening sequences, wherein the intervening sequences are identical to or substantially identical to the sequences in the target nucleic acid. The set of bound nucleic acids thus generated can be analyzed, for example, by sequencing in order to provide information about the sequence of the target nucleic acid.

Figure 13:
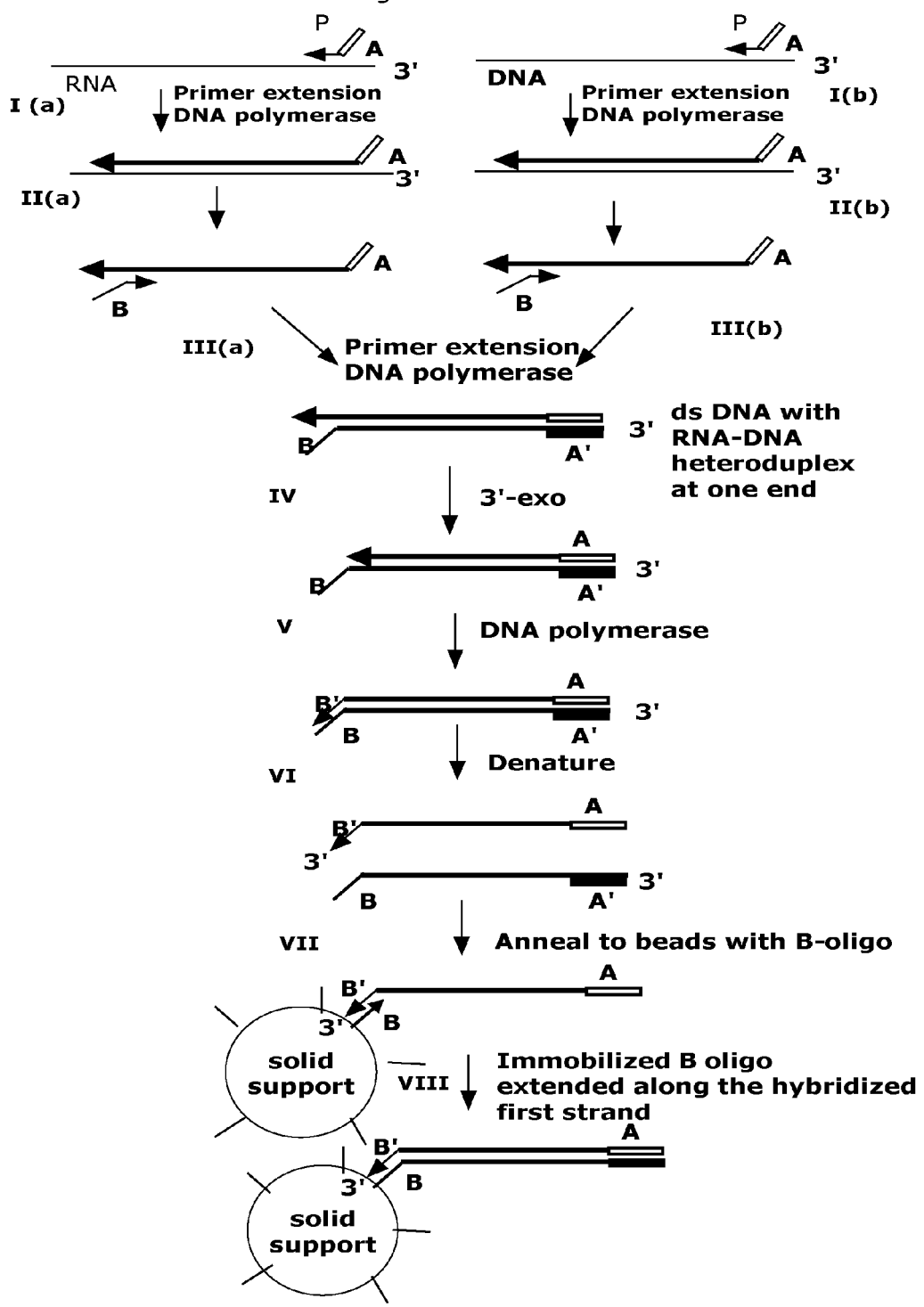
FIG. 13 illustrates an alternative method of producing a polynucleotide bound to a solid support wherein the polynucleotide comprises sequences related to a target nucleic acid and comprises a defined sequence (A') at its 3' end.

A schematic exemplary of an embodiment of the invention relating to an alternative method for generating polynucleotide bound to a solid surface is shown in FIG. 13. The figure shows a target nucleic acid (RNA or DNA) and a chimeric RNA/DNA first primer. The primer is first annealed to the target nucleic. Step Ia (RNA target) and Ib (DNA target) illustrates extending a first primer comprising a DNA segment and a 5' RNA segment, wherein a 3' portion of the primer is complementary to a target nucleic acid and a 5' portion, sequence (A), of the of the primer is not complementary to the target nucleic acid, to form a first primer extension product hybridized to the target nucleic acid, forming an RNA/DNA hybrid. The sequence complementary to a target nucleic acid can be a specific sequence, a sequence that will hybridize to Poly-A, a sequence common to a plurality of regions (consensus sequence), or a random sequence. Step IIa (RNA target) and IIb (DNA target) represent separating the target nucleic acid from the RNA/DNA hybrid. Separation of the target nucleic acid can be accomplished thermally, chemically, or enzymatically, e.g. with RNase H. The second primer comprising a 5' sequence (B) is then annealed to the first primer extension product. Step IIIa and IIIb illustrate extending a second primer, comprising a 5' sequence (B) and a 3' segment complementary to a portion of the first primer extension product, to produce a double stranded product with a DNA/RNA heteroduplex at one end; wherein the double stranded product comprises a second primer extension product hybridized to the first primer extension product, and whereby a portion of the 3' end of the second primer extension product comprises a sequence (A') that is complementary to the sequence (A) of the of the first primer. This embodiment provides for attachment of the first primer extension product to the solid surface by creating a sequence (B'), allowing attachment to a solid surface comprising sequences (B) attached thereto. Step IV shows the removal of 3' nucleotides from the 3' region of the first primer extension product that is not hybridized to the second primer extension product. This step may be done using exonucleases or using DNA polymerase comprising exonuclease activity. Step V shows extension of the first primer extension product by DNA polymerase to generate a sequence (B'), complementary to the sequence (B) of the second primer extension product. Step VI shows the denaturation of the first and second primer extension product by methods described previously. The first primer extension product comprising a sequence (B') and a defined sequence (A) at its 3' end is useful for storage, archiving and analysis as it has a sequence (B') capable of binding to a solid surface. Such first primer extension product also comprises a sequence that is representative of (identical to or substantially identical to) a sequence in the target RNA, so analysis of this product provides information about the target RNA. Step VII shows the binding of sequence (B') of the first primer extension product to a sequence (B) on a solid surface, whereby the first primer extension product becomes bound to the solid surface. Step VIII shows extension of the immobilized sequence (B) oligonucleotide on the solid support using DNA and RNA-dependent DNA polymerase, resulting in another DNA/RNA heteroduplex.

Alternative Method for Generating a Polynucleotide for Binding to a Solid Surface from an RNA Target The invention provides methods, compositions and kits for copying, storing, and amplifying polynucleotides having sequences related to target ribonucleic acid (RNA) sequences. The methods provide for amplification of a single RNA species or pool of RNA species. The methods are suitable for, for example, generation of libraries, including cDNA libraries. The methods can generate single stranded RNA or DNA products, which are readily suitable for multiplex analysis by microarray technologies, as well as electrophoresis-based technologies such as differential display, and for sequencing.

The methods of the invention can copy, store, and amplify one or more species of RNA, such as a pool of RNA sequences, and is most particularly suitable for the amplification of all RNA (such as whole transcriptome or total RNA) sequences in a biological sample. Thus, one of the major advantages of the methods of the invention is the ability to copy, store, and amplify an entire pool of sequences, which is essential for the ability to analyze the gene expression profile in cells, such as the cells in a biological sample of interest. The methods of the invention have the potential of amplifying a multiplicity, a large multiplicity, and in some embodiments all RNA (such as whole transcriptome or total RNA in a sample) sequences in a sample.

Insofar as many mRNAs have a unique polyA 3'-end, the amplification initiated from the 3'-end sequence of mRNAs is most common for preparation of cDNA libraries and subsequent sequence analysis for determination of gene expression profiling or other applications. The methods of the invention are similarly suited for preparation of libraries of amplified 3'-portions of mRNAs. The sequence of the first primer used in the methods of invention can be designed to be complementary to a multiplicity, or all, of the mRNA species in the sample by using random sequences, according to methods known in the art. The methods are also useful for whole transcriptome amplification. The methods of the invention can be used for the total RNA in samples such as viral RNA.

An aspect of the invention is a method for generating a polynucleotide comprising a sequence (B') for binding to a solid surface from a RNA target comprising the step of: (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid. This extension is generally performed with an enzyme comprising RNA-dependent DNA polymerase activity.

In some embodiments, the 3' portion of the primer that is complementary to the target RNA is a specific sequence. For example, where a specific region of interest of a target RNA that is known or suspected to be upstream of a specific sequence on the target RNA, the sequence that is complementary to the target RNA of the first primer can be designed to hybridize to this specific sequence on the target RNA such that extension of the primer results in producing a first primer extension product that is complementary to such upstream region. The specific sequence may be common to a family of target RNA. A combination of primers with various specific sequences at the 3' end can also be useful. In some embodiments, such as where the target RNA comprises mRNA, and the mRNA comprises a plurality of sequences, each having a 3' poly-A segment; the specific sequence that is complementary to the target RNA can comprise a sequence that will hybridize to the poly-A region of the mRNA, thus allowing the extension of the first primer to produce a plurality of first primer extension products, each of which is complementary to the region of an mRNA molecule adjacent to the poly-A region. In some embodiments, the sequence that is complementary to the target RNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a target RNA, generating a plurality of sequences which together can represent, for example substantially the whole sequence of the target RNA. In some embodiments, the relative amounts of the various sequences can be used to quantitate the relative amount of a given sequence in a sample, for example to determine the level of expression in an mRNA sample. In some embodiments more than one type of sequence that is complementary to the target RNA can be used, for instance both a primer with a random sequence and a primer, or combination of primers with a specific sequence complementary to RNA can be used. In some embodiments, multiple primers comprising different specific sequences can be used.

The method further comprises the step of: (b) removing the target RNA from the RNA/DNA hybrid. In some embodiments, the removal of the target RNA from the RNA/DNA hybrid involves selectively cleaving or degrading the target RNA. In some cases, the complex comprising the first primer extension product and the nucleic acid can be heated in reaction conditions comprising Mg, which leads to cleaving the RNA including the RNA in the RNA/DNA hybrid. The RNA can also be removed from the RNA/DNA hybrid by denaturation, performed, for example by heating the sample (thermal methods), or by adding denaturing agents or using a combination of heating the sample and adding denaturing agents. The cleaving can be accomplished with an enzyme that cleaves RNA from an RNA/DNA hybrid such as RNase H, or a combination of RNase enzymes, or chemically. In some embodiments, the target RNA is completely cleaved. In other embodiments, the target RNA is only partly cleaved or degraded. The amount of cleaving required is that amount which will allow the extension of the second primer.

The method further comprises the step of: (c) extending a second primer, comprising a 3' segment complementary to a portion of the first primer extension product and a 5' segment non-complementary to the first primer extension product comprising sequence (B), to produce a double-stranded DNA product with a DNA/RNA heteroduplex at one end, wherein the double-stranded product comprises a second primer extension product hybridized to the first primer extension product and wherein a portion of the 3' end of the second primer extension product comprises a sequence (A') that is complementary to the sequence (A) of the of the first primer.

The extension of the second primer is carried out with a DNA polymerase as described herein. In some embodiments, a DNA polymerase comprising both DNA and RNA dependent DNA polymerase activities is used here. In other embodiments, both a RNA dependent DNA polymerase and a DNA dependent DNA polymerase are used. The second primer can comprise RNA, DNA, or can be a composite primer comprising both RNA and DNA. In some embodiments, the second primer can comprise a specific primer sequence that is designed to hybridize to a specific sequence in the first primer extension product. In some embodiments the second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target RNA, whereby a plurality of second primer extension products are produced which is representative of the sequence of the target RNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target RNA (sense copies). The second primer comprises a sequence (B) that is homologous to a sequence (B) on a solid support.

The second primer extension product is extended such that the 3' portion of the second primer extension product comprises a sequence (A') which is complementary to sequence (A) of the first primer. Since sequence (A) on the first primer extension product comprises RNA, both DNA dependent DNA polymerase activity and RNA dependent DNA polymerase activity are used in step (c). The primer extension results in a product that is at least partially double stranded since sequence (B) on the second primer does not hybridize to the first primer extension product.

The method further comprises the step of: (d) adding an exonuclease to the double-stranded DNA product, whereby single stranded 3' nucleotides are removed from the 3' region of the first primer extension product that is not hybridized to the second primer extension product. Non-limiting examples of an exonuclease include single-strand specific 3'-exonucleases such as exonuclease 1. The exonuclease should remove all of the single-stranded 3' nucleotides which are not hybridized to sequence (B). In some embodiments, the exonuclease may remove additional 3' nucleotides which are hybridized to the second primer extension product. In other embodiments, a polymerase comprising exonuclease activity may be used. Non-limiting examples include a T4 polymerase comprising 3' exonuclease activity.

The method further comprises the step of: (e) extending the first primer extension product to produce a sequence (B'), complementary to sequence (B) on the second primer extension product. The extension of the first primer extension product is carried out with a DNA polymerase as described herein and is generally carried out with a DNA-dependent DNA polymerase if the second primer extension product contains only DNA or with RNA-dependent DNA polymerase if the second primer extension product contains a RNA sequence. The primer extension results in a product that is double stranded and comprises sequences (A) and (B') on the first primer extension product and sequences (B) and (A') on the second primer extension product.

The method further comprises the step of: (f) denaturing the double-stranded DNA product. The first primer extension product can be separated from the second primer extension product by denaturation. Denaturation can be performed, for example by heating the sample, or by adding a denaturing agent, or using a combination of heating the sample and adding denaturing agents.

The method further comprises the step of: (g) attaching the single-stranded first primer extension product to a solid support by annealing sequence (B') to the solid support comprising an oligonucleotide attached thereto, comprising a sequence (B). The oligonucleotide or third primer comprises an oligonucleotide sequence (B) that is complementary to the sequence (B') of the first primer extension product and results in attaching the single stranded first primer extension product to the solid surface. The method produces a nucleic acid that is bound to a solid surface that has a specific sequence (A) at its 5' end. As described above, in some embodiments, the nucleic acid bound to the bead also comprises sequence (B') at or near its 3' end.

Step (g) of binding the polynucleotides to the solid surface sequence (B) can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

The method further comprises the step of: (h) extending sequence (B) on the solid support to produce a third primer extension product, hybridized to the second extension product, wherein the third primer extension product comprises a 3' sequence (A'), whereby a DNA/RNA heteroduplex at one end is generated. The extension of the third primer is carried out with a DNA polymerase as described herein. In some embodiments, a DNA polymerase comprising both DNA and RNA dependent DNA polymerase activities is used here. In other embodiments, both a RNA dependent DNA polymerase and a DNA dependent DNA polymerase are used. The primer extension results in a product that is double stranded and comprises sequences (A) and (B') on the first primer extension product and sequences (B) and (A') on the third primer extension product.

The method produces a nucleic acid that is bound to a solid surface that has a specific sequence (A') at its 3' end. The specific, or universal, sequence (A') can be a site for primer hybridization and further analysis or amplification of the nucleic acid bound to the bead. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification. In some embodiments, for example where random sequences at the 3' end of the first and/or second primer are used, a plurality of different nucleic acids bound to a solid surface is created in which each of the nucleic acids has a specific sequence (A') at its 3' end (and in some embodiments also a specific sequence (B) at its 5' end), and where the different nucleic acids have different intervening sequences, wherein the intervening sequences are identical to or substantially identical to the sequences in the target nucleic acid. The set of bound nucleic acids thus generated can be analyzed, for example, by sequencing in order to provide information about the sequence of the target nucleic acid.

In some embodiments, the sample comprising the target RNA is in a sample that also comprises DNA. In such cases, it can be advantageous to add a selective DNA dependent DNA polymerase inhibitor such as actinomycin such that it is present during step (a) to selectively inhibit the production of extension product complementary to the DNA during step (a). The presence of a DNA dependent DNA polymerase inhibitor such as actinomycin is particularly advantageous when a first primer comprising a random sequence is used, as the inhibitor allows for the selective creation of first primer extension products to RNA without the need of separating the RNA from the DNA. This is also advantageous when the priming is carried out at specific target sequences since the sequence may be the same on the DNA when the DNA and RNA in the sample represent total nucleic acid from the same biological entity, for example, human tissue, animal tissue, and the like. The use of DNA dependent DNA polymerase inhibitors such as actinomycin is described in co-pending application.

One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification.

In some embodiments, the amplification comprises the steps of: (i) cleaving the RNA region from the first polynucleotide product hybridized to the third primer extension product using RNase H; (j) annealing an amplification primer to sequence (A') on the single-stranded portion of the third primer extension product, wherein the amplification primer has a DNA portion and a 5' RNA portion; (k) extending the amplification primer with an enzyme having strand displacement activity to produce an amplified product hybridized to the third primer extension product on the solid support; (l) repeating steps (i) to (k) to produce multiple copies of an amplified product wherein the amplified product comprises sequence (B') at its 3' end; and (m) capturing the amplified product on the solid support wherein the solid support comprises sequence (B).

In some embodiments, for example where random sequences at the 3' end of the first and/or second primer are used, a plurality of different nucleic acids bound to a solid surface is created in which each of the bound nucleic acids has a specific sequence (A') at its 3' end and also a specific sequence (B) at its 5' end, and where the different nucleic acids have different intervening sequences, wherein the intervening sequences are identical to or substantially identical to the sequences in the target RNA. The set of bound nucleic acids thus generated can be analyzed, for example, by sequencing in order to provide information about the sequence of the target RNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of attaching or binding the polynucleotides to the solid surface through the sequence (B), step (g), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments, the method further comprises treating the solid surface with reagents to produce multiple copies of an amplification product that are substantially complementary to the third primer extension product. This step comprises carrying out an amplification reaction wherein the bound nucleic acid acts as a template for the amplification. Generally, the amplification is carried out using the sequence (A') on the third primer extension product for the hybridization of primer. In some embodiments the amplification is an isothermal amplification reaction comprising a composite RNA/DNA primer, RNase H, and a DNA polymerase with strand displacement activity. In some embodiments, the amplification is carried out using polymerase chain reaction (PCR). For example where the third primer extension product comprises both as sequence (B) at or near its 5' end and a sequence (A') at or near its 3' end, a set of primers, one designed to hybridize to all or a portion of the sequence (A') and the other designed to hybridize to sequence (B'), the complement of sequence (B), can be used to carry out a PCR reaction to exponentially produce double stranded amplified product.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (A) or sequence (B'), that allows it to be captured to another solid surface or other portion of the solid surface by hybridization to a complementary sequence bound to such surface, e.g. sequence (A') or sequence (B). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer first primer extension product molecules are bound per bead. The beads are dispersed into an aqueous solution, and a plurality of microreactors, e.g. droplets, are produced such that on average one or fewer beads is contained within each of the plurality of microreactors. The amplification of the first primer extension products bound to the beads is then carried out such that the clonal amplification of each of the plurality of second primer extension products in the separate microreactors is achieved. This clonal amplification in microreactors can be performed on a sample of target RNA, such as whole transcriptome or total RNA, wherein the plurality of first primer extension products comprise sequences that correspond to most, to substantially all, or to all of the sequences in the target RNA. In some embodiments, the amplified products are captured by bead having attached thereto a plurality of oligonucleotides comprising complementary sequences bound to such surface, e.g. sequence (A') or sequence (B), which are complementary to sequence (A) or sequence (B') on the amplified product.

In some embodiments, the plurality of beads, produced as described above, with each bead comprising a single first primer extension product can comprise a library. These libraries can be stored, then later clonally amplified. In some embodiments, a library of beads can comprise a plurality of beads wherein each bead had multiple copies of a single amplification product generated from a second primer extension product. These libraries can be analyzed, for example by sequencing. The libraries can be stored, and later analyzed. In some embodiments the libraries can be stored, then analyzed multiple times.

Figure 14:
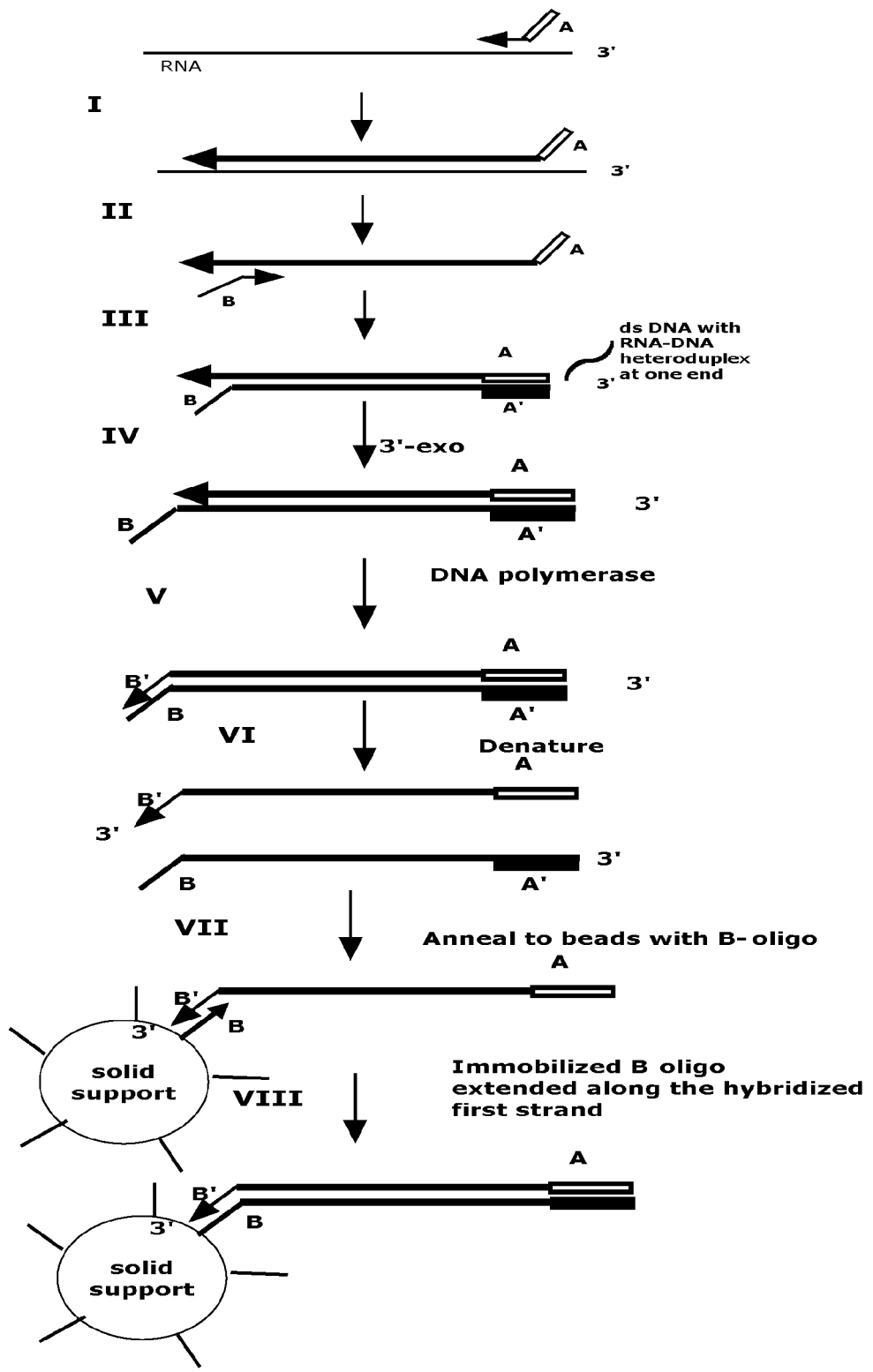
FIG. 14 illustrates an alternative method of producing a polynucleotide bound to a solid support wherein the polynucleotide comprises sequence B, sequences related to a target RNA, and a defined sequence (A') at its 3' end.

A schematic exemplary of an embodiment of the invention relating to this method for generating a polynucleotide for binding to a solid surface from an RNA target is shown in FIG. 14. The figure shows a target RNA and a chimeric RNA/DNA first primer. The primer is first annealed to the target RNA. Step I illustrates extension of the first primer comprising a DNA segment and a 5' RNA segment, wherein a 3' portion of the primer is complementary to a target RNA and a 5' portion, sequence (A), of the of the primer is not complementary to the target RNA, to form a first primer extension product hybridized to the target RNA, forming an RNA/DNA hybrid. The sequence complementary to a target RNA can be a specific sequence, a sequence that will hybridize to Poly-A, a sequence common to a plurality of regions (consensus sequence), or a random sequence. Step II represents separation of the target RNA from the RNA/DNA hybrid. The separation can be accomplished thermally, chemically, or enzymatically, e.g. with RNase H. The second primer comprising a 5' sequence (B) is then annealed to the first primer extension product. Step III illustrate extending a second primer, comprising a 5' sequence (B) and a 3' segment complementary to a portion of the first primer extension product, to produce a double stranded product with a DNA/RNA heteroduplex at one end; wherein the double stranded product comprises a second primer extension product hybridized to the first primer extension product, and whereby a portion of the 3' end of the second primer extension product comprises a sequence (A') that is complementary to the sequence (A) of the of the first primer. This embodiment provides for attachment of the first primer extension product to the solid surface by creating a sequence (B'), allowing attachment to a solid surface comprising sequences (B) attached thereto. Step IV shows the removal of 3' nucleotides from the 3' region of the first primer extension product that is not hybridized to the second primer extension product. This step may be done using exonucleases or using DNA polymerase comprising exonuclease activity. Step V shows extension of the first primer extension product by DNA polymerase to generate a sequence (B'), complementary to the sequence (B) of the second primer extension product. Step VI shows the denaturation of the first and second primer extension product by methods described previously. The first primer extension product comprising a sequence (B') and a defined sequence (A) at its 3' end is useful for storage, archiving and analysis as it has a sequence (B') capable of binding to a solid surface. Such first primer extension product also comprises a sequence that is representative of (identical to or substantially identical to) a sequence in the target RNA, so analysis of this product provides information about the target RNA. Step VII shows the binding of sequence (B') of the first primer extension product to a sequence (B) on a solid surface, whereby the first primer extension product becomes bound to the solid surface. Step VIII shows extension of the immobilized sequence (B) oligonucleotide on the solid support using DNA and RNA-dependent DNA polymerase, resulting in another DNA/RNA heteroduplex.

Figure 15:
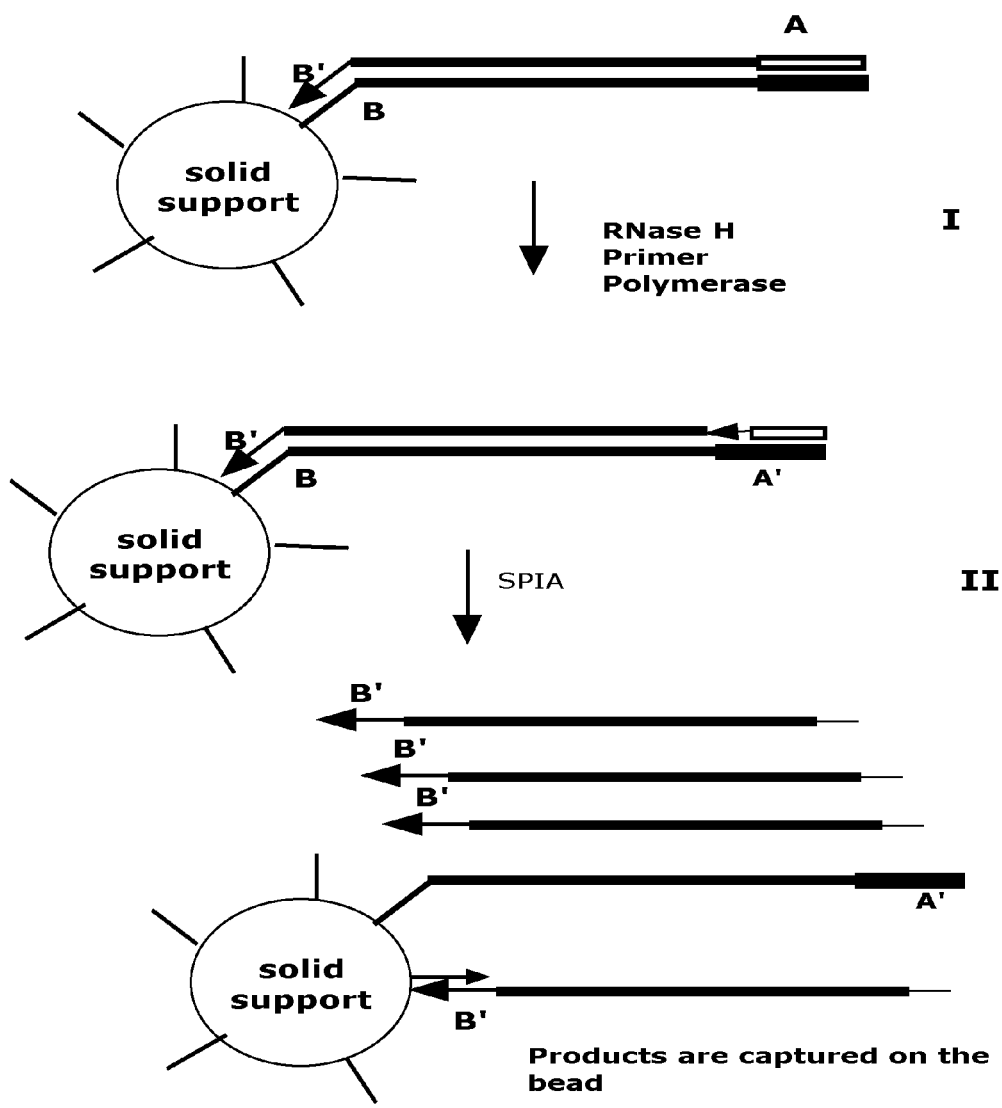
FIG. 15 shows a method of producing amplified product from a polynucleotide, bound to the bead through sequence B, wherein the amplified product comprises sequences complementary to the target nucleic acid and a defined sequence (B') at its 3' end.

In FIG. 15, Step I illustrates amplification using single primer isothermal linear amplification (SPIA) wherein RNaseH cleaves the RNA from the DNA/RNA heteroduplex, a chimeric RNA/DNA primer binds to sequence (A'), and DNA polymerase with strand displacement activity is used to extend the chimeric primer to produce amplified product of the first primer extension product. Step II illustrates amplified products that are produced from repeated rounds of SPIA from Step I of the figure. Since the amplification products are generated in close proximity to access sequence (B) on the solid support, the amplified products are captured on the solid support through hybridization of the 3' sequence (B') to sequence (B) for further manipulations as described herein such as clonal amplification.

Alternative Method for Generating a Polynucleotide for Binding to a Solid Surface from a DNA Target The methods of the present invention can be used to analyze the DNA (e.g. genomic DNA) samples that are important for many studies. The methods can be used for high-throughput genomic analysis, and can be used for forensic and paleoarcheology work which can be severely limited by nucleic acid sample size. The methods can be used, for example, for the genotyping of multiple loci in the study of complex diseases. The methods can also be used for the determination of genomic instability in various pathological conditions such as cancer, which is most precisely carried out in well defined cell populations, such as that obtained by laser capture microdissection or cell sorting. The DNA amplification technologies described herein provide global amplification of very small polynucleotide samples, for example, from one or a very few cells.

One aspect of the invention is a method for generating from a DNA target a polynucleotide comprising a sequence for binding to a solid surface comprising the steps of: (a) denaturing a double-stranded target DNA. Double stranded DNA can be denatured, for example by heating, or by the addition of denaturing agents, or using a combination of heating the sample and adding denaturing agents.

The method further comprises step: (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the primer comprises sequence (A), which is not complementary to the target DNA; to form a plurality of first primer extension product hybridized to the target DNA and comprising sequence (A) at its 5' end. The enzyme that carries out step (b) is generally a DNA polymerase. In some cases a mixture of DNA polymerases can be used. This extension is generally performed with an enzyme comprising DNA-dependent DNA polymerase activity. The sequence that is complementary to the target DNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a DNA target, generating a plurality of sequences which together can represent, for example substantially the whole sequence of the target DNA. In some embodiments, the relative amounts of the various sequences can be used to quantitate the relative amount of a given sequence in a sample, for example to determine the number of gene copies in a DNA sample, or obtaining sequence information. In some embodiments, the extension of one first primer, will result in the release of a downstream first primer extension product. This can occur throughout the target DNA resulting in the release of multiple first primer extension products from the target DNA. This process can occur simultaneously on both of the strands of the double-stranded DNA target, thus creating first primer extension products complementary to sequences in both strands.

In some embodiments, the first primer extension step is carried out with a DNA polymerase capable of extension at elevated temperature that is not compatible with subsequent hybridization of the random sequence to the displaced primer-extension product. For example, Bst DNA polymerase can be used which is active at elevated temperature. The reaction can be carried out stepwise, first with incubation at a lower temperature such as about 25° C., followed by incubation at higher temperature such as about 50° C. In some embodiments, the first incubation is carried out below about 30° C., and the second incubation is carried out above about 40° C. In some embodiments, a DNA polymerase which is active at temperatures above about 45° C. is used to extend the first primer. Mixtures of DNA polymerases can also be useful.

The method further comprises step: (c) separating the first primer extension product from the target DNA. In some embodiments, the separation can be affected by denaturing the complex comprising the first primer extension product and the nucleic acid. Denaturation can be performed, for example by heating the sample, or by adding a denaturing agent, or using a combination of heating the sample and adding denaturing agents. The amount of cleaving required is that amount which will allow the extension of the second primer.

The method further comprises step: (d) annealing to the first primer extension product and extending a second primer comprising a 3' complementary DNA region that comprises a random sequence, wherein the second primer is a tailed primer comprising a 5' sequence (B), to form a double stranded product comprising a first primer extension product and a second primer extension product, whereby a double-stranded product with a DNA/RNA heteroduplex at one end is generated. In some embodiments, a DNA polymerase comprising both DNA and RNA dependent DNA polymerase activities is used here. In other embodiments, both a RNA dependent DNA polymerase and a DNA dependent DNA polymerase are used. This step may be carried out with or without prior denaturation. If carried out without denaturation, generally, only the single stranded displaced first primer extension product will hybridize to the second primer. Generally the second primer does not comprise RNA. The extension of the second primer is carried out with a DNA polymerase as described herein. The second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target DNA, whereby a plurality of second primer extension products are produced which is representative of the sequence of the target DNA. In some embodiments, for example where the first primer is designed to hybridize to a specific sequence on a target DNA, or a sequence common to a family of DNA targets, random priming by the second primer ensures amplification of the entire selected target or family of selected targets. In this embodiment, the second primer extension products comprise sequences which are the same or substantially the same as the sequences in the target DNA.

The second primer extension product is extended such that the 3' portion of the second primer extension product comprises a sequence (A') which is complementary to sequence (A) of the first composite primer. Since sequence (A) on the first primer extension product comprises RNA, both DNA dependent DNA polymerase activity and RNA dependent DNA polymerase activity are used in step (d). The primer extension results in a product that is at least partially double stranded since sequence (B) not does hybridize to the first primer extension product. The method produces a nucleic acid that comprises a sequence (B), allowing it to be bound to a solid surface by hybridization to its complement, which is immobilized on the solid surface and that has a specific sequence (A') at its 3' end. The specific, or universal, sequence (A') can be a site for primer hybridization and further analysis or amplification of the nucleic acid bound to the bead.

The method further comprises step: (e) adding an exonuclease to the double-stranded DNA product, whereby single stranded 3' nucleotides are removed from the 3' region of the first primer extension product that is not hybridized to the second primer extension product. Non-limiting examples of an exonuclease include single-strand specific 3'-exonucleases such as exonuclease 1. The exonuclease should remove all of the single-stranded 3' nucleotides which are not hybridized to sequence (B). In some embodiments, the exonuclease may remove additional 3' nucleotides which are hybridized to the second primer extension product. In other embodiments, a polymerase comprising exonuclease activity may be used. Non-limiting examples include a T4 polymerase comprising 3' exonuclease activity.

The method further comprises step: (f) extending the first primer extension product to produce a sequence (B'), complementary to sequence (B) on the second primer extension product. The extension of the first primer extension product is carried out with a DNA polymerase as described herein and is generally carried out with a DNA-dependent DNA polymerase if the second primer extension product contains only DNA or with RNA-dependent DNA polymerase if the second primer extension product contains a RNA sequence. The primer extension results in a product that is double stranded and comprises sequences (A) and (B') on the first primer extension product and sequences (B) and (A') on the second primer extension product.

The method further comprises step: (g) denaturing the double-stranded DNA product. The first primer extension product can be separated from the second primer extension product by denaturation. Denaturation can be performed, for example by heating the sample, or by adding a denaturing agent, or using a combination of heating the sample and adding denaturing agents.

The method further comprises step: (h) attaching the single-stranded first primer extension product to a solid support by annealing sequence (B') to the solid support comprising an oligonucleotide attached thereto, comprising a sequence (B), whereby a plurality of first primer extension products become bound to the solid surface. The oligonucleotide or third primer comprises a sequence or oligo (B) that is complementary to the sequence (B') of the first primer extension product and results in attaching the single stranded first primer extension product to the solid surface. The method produces a nucleic acid that is hybridize to a sequence on the solid surface and has a specific sequence (A) at its 5' end.

Step (h) of binding the polynucleotides to the solid surface sequence (B) can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

The method further comprises step: (i) extending sequence (B) on the solid support to produce a third primer extension product, hybridized to the first primer extension product, wherein the third primer extension product comprises a 3' sequence (A'), whereby a DNA/RNA heteroduplex at one end is generated.

The extension of the third primer is carried out with a DNA polymerase as described herein. In some embodiments, a DNA polymerase comprising both DNA and RNA dependent DNA polymerase activities is used here. In other embodiments, both a RNA dependent DNA polymerase and a DNA dependent DNA polymerase are used. The primer extension results in a product that is double stranded and comprises sequences (A) and (B') on the first primer extension product and sequences (B) and (A') on the third primer extension product.

The method produces a nucleic acid that is bound to a solid surface that has a specific sequence (A') at its 3' end. The specific, or universal, sequence (A') can be a site for primer hybridization and further analysis or amplification of the nucleic acid bound to the bead. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification. In some embodiments, for example where random sequences at the 3' end of the first and/or second primer are used, a plurality of different nucleic acids bound to a solid surface is created in which each of the nucleic acids has a specific sequence (A') at its 3' end (and in some embodiments also a specific sequence (B) at its 5' end), and where the different nucleic acids have different intervening sequences, wherein the intervening sequences are identical to or substantially identical to the sequences in the target nucleic acid. The set of bound nucleic acids thus generated can be analyzed, for example, by sequencing in order to provide information about the sequence of the target nucleic acid.

One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (A') acts as the site to which the composite RNA/DNA amplification primer hybridizes, allowing for amplification.

In some embodiments, the amplification comprises the steps of: (j) cleaving the RNA from the first polynucleotide product hybridized to the amplified product using RNase H; (k) annealing an amplification primer to the single-stranded portion of the amplified product complementary to sequence (A'), wherein the amplification primer has a DNA portion and a 5' RNA portion; (l) extending the amplification primer with an enzyme having strand displacement activity to produce an amplified product hybridized to the third primer extension product on the bead or isolated area; (m) repeating steps (j) to (l) to produce multiple copies of an amplified product wherein the amplified product comprises sequence (B') at its 3' end; and (n) capturing the amplified product on the solid support comprising sequence (B).

In some embodiments, a plurality of different nucleic acids bound to a solid surface is created in which each of the nucleic acids has a specific sequence (A') at its 3' end and also a specific sequence (B) at its 5' end, and where the different nucleic acids have different intervening sequences, wherein the intervening sequences are identical to or substantially identical to the sequences in the target DNA. The set of bound nucleic acids thus generated can be analyzed, for example, by sequencing in order to provide information about the sequence of the target DNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through the sequence (B), step (h), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments, the method further comprises treating the solid surface with reagents to produce multiple copies of an amplification product that are substantially complementary to the third primer extension product. This step comprises carrying out an amplification reaction wherein the bound nucleic acid acts as a template for the amplification. Generally, the amplification is carried out using the sequence (A') on the third primer extension product for the hybridization of primer. In some embodiments the amplification is an isothermal amplification reaction comprising a composite RNA/DNA primer, RNase H, and a DNA polymerase with strand displacement activity. In some embodiments, the amplification is carried out using polymerase chain reaction (PCR). For example where the third primer extension product comprises both as sequence (B) at or near its 5' end and a sequence (A') at or near its 3' end, a set of primers, one designed to hybridize to all or a portion of the sequence (A') and the other designed to hybridize to sequence (B'), the complement of sequence (B), can be used to carry out a PCR reaction to exponentially produce double stranded amplified product.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (A) or sequence (B'), that allows it to be captured to another solid surface or other portion of the solid surface by hybridization to a complementary sequence bound to such surface, e.g. sequence (A') or sequence (B). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer first primer extension product molecules are bound per bead. The beads are dispersed into an aqueous solution, and a plurality of microreactors, e.g. droplets, are produced such that on average one or fewer beads is contained within each of the plurality of microreactors. The amplification of the second primer extension products bound to the beads is then carried out such that the clonal amplification of each of the plurality of second primer extension products in the separate microreactors is achieved. This clonal amplification in microreactors can be performed on a sample of target DNA, such as genomic DNA, wherein the plurality of second primer extension products comprise sequences that correspond to most, to substantially all, or to all of the sequences in the target DNA. In some embodiments, the amplified products are captured by bead having attached thereto a plurality of oligonucleotides comprising complementary sequences bound to such surface (e.g. sequence (A') or sequence (B)), which are complementary to sequence (A) or sequence (B') on the amplified product.

In some embodiments, the plurality of beads, produced as described above, with each bead comprising a single first primer extension product can comprise a library. These libraries can be stored, then later clonally amplified. In some embodiments, a library of beads can comprise a plurality of beads wherein each bead had multiple copies of a single amplification product generated from a second primer extension product. These libraries can be analyzed, for example by sequencing. The libraries can be stored, and later analyzed. In some embodiments the libraries can be stored, then analyzed multiple times.

Figure 16:
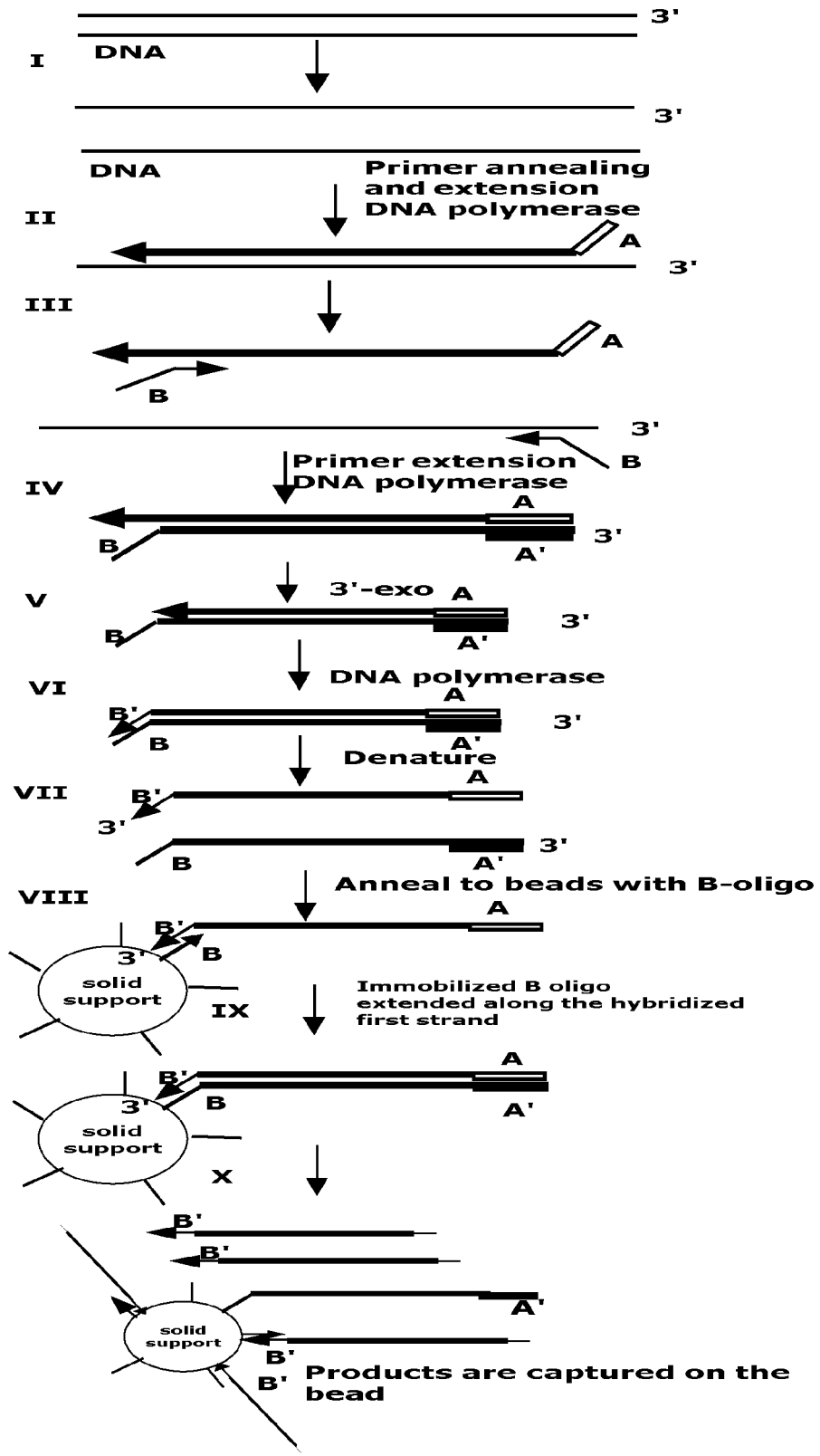
FIG. 16 shows an alternative method of producing a polynucleotide bound to a solid support wherein the polynucleotide comprises sequence B, sequences related to a target DNA and a defined sequence (A') at its 3' end. The figure also illustrates production of amplified product from the bound polynucleotide, wherein the amplified product comprises defined sequence B' at its 3' end.

A schematic exemplary of an embodiment of the invention relating to method for generating a polynucleotide comprising a sequence (B) for binding to a solid surface from a DNA target is shown in FIG. 16. Step I represents denaturing a double-stranded target DNA, for example by raising the temperature. Steps II illustrate annealing to the target DNA and extending with a DNA polymerase comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a plurality of first primer extension products, each with sequence (A) at its 5' end. The enzyme that carries out Step II is generally a DNA polymerase. In some cases a mixture of DNA polymerases can be used. In some embodiments, a DNA polymerase with strand displacement activity is used such that a growing first primer extension product can displace a downstream first primer extension product, producing a plurality of first primer extension products, representing different regions of the sequence of the target DNA are produced. Step III illustrates annealing a second primer to the first primer extension product that has been denatured from the target DNA. Step IV illustrates extending a second primer comprising a 3' DNA region that comprises a random sequence, wherein the primer is a tailed primer comprising a nucleic acid sequence (B) that is 5' of the random sequence, to form a plurality of double-stranded products each comprising a first primer extension product and a second primer extension product. Step V shows the removal of single stranded 3' nucleotides from the 3' region of the first primer extension product that is not hybridized to the second primer extension product. This step may be done using exonucleases. Step VI shows extension of the first primer extension product by DNA polymerase to generate a sequence (B'), complementary to sequence (B) of the second primer extension product. Step VII shows the denaturation of the first and second primer extension product by methods described previously. Step VIII shows the binding of sequence (B') of the first primer extension product to a sequence (B) on a solid surface, whereby the first primer extension product becomes hybridized to the solid surface. The immobilized sequence (B) oligonucleotide on the solid support is extended using DNA and RNA-dependent DNA polymerase, resulting in another DNA/RNA heteroduplex, as illustrated in step IX. Amplification of the first primer extension product takes place using repeated cycles of single primer isothermal linear amplification (SPIA), which comprises the following steps not shown in the figure: RNaseH cleaves the RNA from the DNA/RNA heteroduplex, a chimeric RNA/DNA primer binds to sequence (A'), and DNA polymerase with strand displacement activity is used to extend the chimeric primer to produce amplified product of the first primer extension product. As shown in step X, since the amplification products are generated in close proximity to access sequence (B) on the solid support, the amplified products are captured on the solid support through hybridization of the 3' sequence (B') to sequence (B) for further manipulations as described herein such as clonal amplification.

Alternative Method for Generating a Polynucleotide Having a Defined 3' and 5' Sequences from an RNA Target One aspect of the invention is a method for generating a polynucleotide having defined 3' and 5' sequences from a RNA target. The method utilizes a composite RNA/DNA oligonucleotide to generate an oligonucleotide extension product comprising sequences (A) and (C), which will allow extension of the third primer on the solid surface such that the third primer extension product comprises a sequence (C') at its 3' end than can be used as a site for isothermal amplification in a manner such that the sequence (A) is present at or near the 5' end of the amplified product produced in this amplification.

The method comprises the steps: (a) extending a first primer comprising a DNA segment and a 5' RNA segment, wherein a 3' portion of the primer is complementary to a target RNA and a 5' portion, sequence (A), of the of the primer is not complementary to the target RNA; to form a first primer extension product hybridized to the target RNA, forming an RNA/DNA hybrid. This extension is generally performed with an enzyme comprising RNA-dependent DNA polymerase activity. In some embodiments, the 3' portion of the primer that is complementary to the target RNA is a specific sequence. For example, where a specific region of interest of a target RNA that is known or suspected to be upstream of a specific sequence on the target RNA, the sequence that is complementary to the target RNA of the first primer can be designed to hybridize to this specific sequence on the target RNA such that extension of the primer results in producing a first primer extension product that is complementary to such upstream region. The specific sequence may be common to a family of target RNA. A combination of primers with various specific sequences at the 3' end can also be useful. In some embodiments, such as where the target RNA comprises mRNA, and the mRNA comprises a plurality of sequences, each having a 3' poly-A segment; the specific sequence that is complementary to the target RNA can comprise a sequence that will hybridize to the poly-A region of the mRNA, thus allowing the extension of the first primer to produce a plurality of first primer extension products, each of which is complementary to the region of an mRNA molecule adjacent to the poly-A region. In some embodiments, the sequence that is complementary to the target RNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a RNA target, generating a plurality of sequences which together can represent, for example substantially the whole sequence of the target RNA. In some embodiments, the relative amounts of the various sequences can be used to quantitate the relative amount of a given sequence in a sample, for example to determine the level of expression in an mRNA sample. In some embodiments more than one type of sequence that is complementary to the target RNA can be used, for instance both a primer with a random sequence and a primer, or combination of primers with a specific sequence complementary to RNA can be used. In some embodiments, multiple primers comprising different specific sequences can be used.

The method further comprises step: (b) removing the target RNA from the RNA/DNA hybrid. In some embodiments, the cleaving of the target RNA from the RNA/DNA hybrid involves selectively cleaving or degrading the target RNA. In some cases the complex comprising the first primer extension product and the nucleic acid can be heated in reaction conditions comprising Mg, which leads to cleaving the RNA including the RNA in the RNA/DNA hybrid. The RNA can also be removed from the RNA/DNA hybrid by denaturation, performed, for example by heating the sample (thermal methods), or by adding a denaturing agent, or using a combination of heating the sample and adding denaturing agents. The cleaving can be accomplished with an enzyme that cleaves RNA from an RNA/DNA hybrid such as RNase H, or a combination of RNase enzymes, or cleaving can be accomplished chemically or by heating. In some embodiments, the target RNA is completely cleaved. In other embodiments, the target RNA is only partly cleaved or degraded. The amount of cleaving required is that amount which will allow the extension of the second primer.

The method further comprises step: (c) extending a second primer, comprising a 3' segment complementary to a portion of the first primer extension product and a 5' segment non-complementary to the first primer extension product comprising sequence (B), to produce a double-stranded product with a DNA/RNA heteroduplex at one end; wherein the double-stranded product comprises a second primer extension product hybridized to the first primer extension product, and whereby a portion of the 3' end of the second primer extension product comprises a sequence (A') that is complementary to the sequence (A) of the of the first primer.

The extension of the second primer is carried out with a DNA polymerase as described herein. In some embodiments, a DNA polymerase comprising both DNA and RNA dependent DNA polymerase activities is used here. In other embodiments, both a RNA dependent DNA polymerase and a DNA dependent DNA polymerase are used.

The second primer can comprise RNA, DNA, or can be a composite primer comprising both RNA and DNA. In some embodiments, the second primer can comprise a specific primer sequence that is designed to hybridize to a specific sequence in the first primer extension product. In some embodiments the second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target RNA, whereby a plurality of second primer extension products are produced which is representative of the sequence of the target RNA. In some embodiments, for example where the first primer is designed to hybridize to a specific sequence on a target RNA, or a sequence common to a family of RNA targets, random priming by the second primer ensures amplification of the entire selected target or family of selected targets. In this embodiment, the second primer extension products comprise sequences which are the same or substantially the same as the sequences in the target RNA (sense copies).

The second primer extension product is extended such that the 3' portion of the second primer extension product comprises a sequence (A') which is complementary to sequence (A) of the first primer. Since sequence (A) on the first primer extension product comprises RNA, both DNA dependent DNA polymerase activity and RNA dependent DNA polymerase activity are used in step (c). The primer extension results in a product that is at least partially double stranded since sequence (B) does not hybridize to the first primer extension product. The product further comprises a DNA-RNA heteroduplex region. The specific, or universal, sequence (A') can be a site for primer hybridization and further analysis or amplification of the nucleic acid bound to the bead.

In some embodiments, the sample comprising the target RNA is in a sample that also comprises DNA. In such cases, it can be advantageous to add a selective DNA dependent DNA polymerase inhibitor such as actinomycin such that it is present during step (a) to selectively inhibit the production of extension product complementary to the DNA during step (a). The presence of a DNA dependent DNA polymerase inhibitor such as actinomycin is particularly advantageous when a first primer comprising a random sequence is used, as the inhibitor allows for the selective creation of first primer extension products to RNA without the need of separating the RNA from the DNA. This is also advantageous when the priming is carried out at specific target sequences since the sequence may be the same on the DNA when the DNA and RNA in the sample represent total nucleic acid from the same biological entity, for example, human tissue, animal tissue, and the like. The use of DNA dependent DNA polymerase inhibitors such as actinomycin is described in copending application.

The method further comprises step: (d) cleaving the RNA in the heteroduplex from the first primer extension product such that a portion of the second primer extension product that is complementary to sequence (A) is single-stranded. The cleaving of RNA can be performed, for example by treatment with RNase H, which will selectively cleave the RNA portion of the DNA/RNA partial heteroduplex formed in step (c).

The method further comprises step: (e) annealing to the second primer extension product an oligonucleotide comprising a 3'-DNA sequence (A) that is complementary to sequence (A') and a 5'-RNA segment comprising sequence (C) that is non-complementary to the second primer extension product. The oligonucleotide comprises at least one DNA and at least one RNA portion. In some embodiments the 5' DNA segment is complementary to all of sequence (A'), in other embodiments, the 5' DNA segment is complementary to portion of sequence (A'). In some embodiments, 5' RNA segment comprising sequence (C) is partly complementary to sequence (A').

The method further comprises step: (f) extending the oligonucleotide at the 3' segment to form an oligonucleotide extension product hybridized to the second primer extension product. In some embodiments, the oligonucleotide is extended from its 3' end to produce an oligonucleotide extension product hybridized to the second primer extension product and displaces the first primer extension product. The second primer comprises a sequence (B), such that the oligonucleotide extension product will comprise a sequence (B') at or near its 3' end that is complementary to sequence (B). An optional step that may be added using a DNA polymerase that has RNA dependent DNA polymerase activity is extension of the second primer extension product to create a heteroduplex such that the second primer comprises a DNA sequence (C') that is complementary to sequence (C). This step creates an RNA/DNA heteroduplex region.

The method further comprises step: (g) denaturing the double-stranded DNA product. The first primer extension product can be separated from the second primer extension product by denaturation. Denaturation can be performed, for example by heating the sample, or by adding a denaturing agent, or using a combination of heating the sample and adding denaturing agents.

The method further comprises step: (h) attaching the single-stranded first primer extension product to a solid support by annealing sequence (B') to the solid support comprising a sequence (B). The oligonucleotide bound to the solid surface comprises sequence (B) such that binding of sequence (B') of the oligonucleotide primer extension product results in attaching the oligonucleotide primer extension product to the solid surface. The method produces a nucleic acid that is hybridized to sequence (B) on a solid surface that has a specific sequence (A) and (C) at its 5' end.

The method further comprises step: (i) extending sequence (B) on the solid support to produce a third primer extension product, comprising a 3' sequence (A') and (C'), whereby a DNA/RNA heteroduplex at one end is generated.

The extension of the third primer is carried out with a DNA polymerase as described herein. In some embodiments, a DNA polymerase comprising both DNA and RNA dependent DNA polymerase activities is used here. In other embodiments, both a RNA dependent DNA polymerase and a DNA dependent DNA polymerase are used.

The primer extension results in a product that is double stranded and comprises sequences (B'), (A), (C) on the oligonucleotide primer extension product and sequences (B), (A') and (C') on the third primer extension product.

In some embodiments, the sample comprising the target RNA is in a sample that also comprises DNA. In such cases, it can be advantageous to add a selective DNA dependent DNA polymerase inhibitor such as actinomycin such that it is present during step (a) to selectively inhibit the production of extension product complementary to the DNA during step (a). The presence of a DNA dependent DNA polymerase inhibitor such as actinomycin is particularly advantageous when a first primer comprising a random sequence is used, as the inhibitor allows for the selective creation of first primer extension products to RNA without the need of separating the RNA from the DNA. This is also advantageous when the priming is carried out at specific target sequences since the sequence may be the same on the DNA when the DNA and RNA in the sample represent total nucleic acid from the same biological entity, for example, human tissue, animal tissue, and the like. The use of DNA dependent DNA polymerase inhibitors such as actinomycin is described in co-pending application.

The method produces a nucleic acid that is bound to a solid surface that has a specific sequence (A') and (C') at its 3' end and a sequence (B) at or near its 5' end. The specific, or universal, sequence (A') or (C') can be a site for primer hybridization and further analysis or amplification of the nucleic acid bound to the bead. The specific sequence (C') can be a site for primer hybridization and further analysis or amplification of the nucleic acid bound to the bead. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (C') acts as the site to which the composite RNA/DNA amplification primer hybridizes, allowing for amplification. When the sequence (C') acts as a site to which a composite amplification primer binds, the amplified product that is produced has the sequence (A) and a portion of sequence (C) at its 5' end. The third primer comprises the sequence (B) and the amplified product also has the sequence (B'), complementary to (B) at or near its 3' end. Thus the method produced amplified product with defined sequences at or near both its 3' and 5' ends.

In some embodiments, for example where random sequences at the 3' end of the first and/or second primer are used, a plurality of different nucleic acids hybridized to a solid surface is created in which each of the nucleic acids has a specific sequence (A) and (C) at its 5' end and also a specific sequence (B') at its 3' end, and where the different nucleic acids have different intervening sequences, wherein the intervening sequences are identical to or substantially identical to the sequences in the target RNA. The set of bound nucleic acids thus generated can be analyzed, for example, by sequencing in order to provide information about the sequence of the target RNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through sequence (B'), step (i), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments, the method further comprises treating the solid surface with reagents to produce multiple copies of an amplification product that are substantially complementary to the third primer extension product. This step comprises carrying out an amplification reaction wherein the bound nucleic acid acts as a template for the amplification.

Generally, the amplification is carried out using the sequence (C') on the third primer extension product for the hybridization of a primer such as a composite RNA/DNA amplification primer hybridizes, allowing for amplification. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the third primer extension product comprises both a sequence (B) at or near its 5' end and a sequence (C') at or near its 3' end, a set of primers, one designed to hybridize to all or a portion of the sequence (C') and the other designed to hybridize to sequence (B), can be used to carry out a PCR reaction to exponentially produce double stranded amplified product.

In some embodiments, the amplification is performed by a method comprising the following steps: (j) cleaving the RNA from the heteroduplex polynucleotide product hybridized to the amplified product using RNase H to produce a single-stranded portion of the third primer extension product corresponding to sequence (C'); (k) annealing an amplification primer to the single-stranded portion of the third primer extension product complementary to sequence (C'), wherein the amplification primer has a DNA portion and a 5' RNA portion; (l) extending the amplification primer with an enzyme having strand displacement activity to produce an amplified product hybridized to the third primer extension product on the solid support; (m) repeating steps (j) to (l) to produce multiple copies of the amplified product comprising sequences (A) and (B'); and (n) capturing the amplified product on the solid support wherein the solid support comprises sequence (B).

This amplification method, utilizing a sequence (B) and (C'), allows for the production of an amplified product comprising a sequence (B') at or near its 3' end that is substantially complementary to sequence (B), and a sequence (A) near its 5' end that is complementary to sequence (A'), thus producing an amplified polynucleotide product with defined 3' and 5' ends.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (A) or sequence (B'), that allows it to be captured to another solid surface or other portion of the solid surface by hybridization to a complementary sequence bound to such surface, e.g. sequence (A') or sequence (B). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer oligonucleotide primer extension product molecules are bound per bead. The beads are dispersed into an aqueous solution, and a plurality of microreactors, e.g. droplets, are produced such that on average one or fewer beads is contained within each of the plurality of microreactors. The amplification of the third primer extension products bound to the beads is then carried out such that the clonal amplification of each of the plurality of second primer extension products in the separate microreactors is achieved. This clonal amplification in microreactors can be performed on a sample of target RNA, such as whole transcriptome or total RNA, wherein the plurality of third primer extension products comprise sequences that correspond to most, to substantially all, or to all of the sequences in the target RNA. In some embodiments, the amplified products are captured by bead having attached thereto a plurality of oligonucleotides comprising complementary sequences bound to such surface (e.g. sequence (A') or sequence (B)), which are complementary to sequence (A) or sequence (B') on the amplified product.

In some embodiments, the plurality of beads, produced as described above, with each bead comprising a single third primer extension product can comprise a library. These libraries can be stored, then later clonally amplified. In some embodiments, a library of beads can comprise a plurality of beads wherein each bead had multiple copies of a single amplification product generated from a second primer extension product. These libraries can be analyzed, for example by sequencing. The libraries can be stored, and later analyzed. In some embodiments the libraries can be stored, then analyzed multiple times.

In some embodiments, a bead or isolated area of the solid surface comprises covalently attached thereto multiple oligonucleotides comprising the sequence (B) at their 5' ends, whereby upon the amplification of step (n) multiple copies of amplified product comprising sequence (B') at their 3' end are hybridized to the bead or isolated area. For example, where beads are used, a plurality of beads in a plurality of microreactors wherein, the plurality of beads has, on average one or fewer third primer extension products bound to it and there are, on average, one or fewer beads in each microreactor, a clonal amplification of the plurality of third primer extension products can be carried out, and the amplified products in each of the microreactors will bind to the bead through the sequence (B') on the amplified product to the sequence (B) on the beads. This approach produces a plurality of beads, each with multiple copies of a different sequence bound to it. Where these sequences are representative of the target RNA, the plurality of beads can constitute a library representative of such RNA.

Since the amplification products are generated in close proximity to access sequence (B) on the solid support, the amplified products are captured on the solid support through hybridization of the 3' sequence (B') to sequence (B) for further manipulations as described herein. The (B) sequences on the beads can be extended along the amplified product by a DNA polymerase or mixture of polymerases to produce a multiple polynucleotides covalently attached to the bead or isolated area that are substantially complementary to the amplified product and also comprise sequence (A') near their 3' ends. This method provides for the production of beads with polynucleotides complementary to amplified product covalently attached to the beads. Covalently attached polynucleotides such as those produce here are more robust than nucleotides that are attached only by hybridization to the beads. Thus, the covalently attached polynucleotides can be more stable and can be used with analysis methods and sequencing methods that have harsher conditions which would result in the displacement of polynucleotides bound only by hybridization.

In some embodiments, the amplified product is removed from the covalently bound polynucleotide to render the polynucleotide single stranded. Such single stranded covalently bound polynucleotides comprise a specific sequence at their 3' ends comprising sequence (A') and a portion of sequence (C'). Here, the portion of sequence (C') is the DNA portion of the chimeric amplification primer (C) that does is generally not cleaved by RNase H and therefore becomes incorporated into the amplified product. This specific sequence at the 3' end of the covalently bound polynucleotide can act as a hybridization site for a primer complementary to sequence (A') that can act as a primer to carry out sequencing by any of a variety of sequencing methods, for example, those described herein.

The sequencing methods can comprise the use of cleavable labeled terminators. The sequencing method can comprise pyrophosphate detection. The sequencing method can comprise an isothermal sequencing method, for example using chimeric primers, RNase H, and a polymerase with strand displacement activity. The sequencing method can also comprise cycle sequencing.

In some embodiments the methods of the invention provide for performing bridge PCR comprising making amplified product as described above with defined 3' and 5' ends, and further comprising the steps of exposing the amplified product to a solid substrate comprising oligonucleotide sequences attached thereto complementary to the defined 3' and 5' sequences, for example, A and B' sequences, on the amplified product in the presence of components necessary for polymerase chain reaction, and thermal cycling the system to perform bridge PCR amplification.

In some embodiments the methods of the invention provide for making amplified product as described above with defined 3' and 5' ends and further performing rolling circle amplification comprising performing the steps of: (o) hybridizing the amplified product to a nucleic acid sequence comprising regions complementary to A and B' sequences in close proximity; (p) optionally extending the gap with a DNA polymerase enzyme; (q) ligating to form a circular nucleic acid comprising the amplified product, and performing rolling circle amplification by extending a primer that is complementary to a sequence in the circular nucleic acid.

In some embodiments, the rolling circle amplification uses primers complementary to sequence (A), sequence (B'), or a sequence that was between sequences (A) and (B') in the amplified product. In some cases, such a primer can be an oligonucleotide attached to a solid surface, thus resulting in amplified product bound to the surface In some embodiments the methods of the invention provide for performing PCR comprising making amplified product as described above with defined 3' and 5' ends, further comprising the steps of amplifying the amplified product using primers complementary to sequences (A) and (B), or using primers complementary to sequences (A') and (B').

In some embodiments the methods of the invention provide for performing strand displacement amplification (SDA) comprising making amplified product as described above with defined 3' and 5' ends, wherein the defined 3' and 5' ends, for example, sequences (A) and (B'), in the amplified product are designed to be cleaved by a restriction enzyme, and performing strand displacement amplification on the amplified product.

Figure 17:
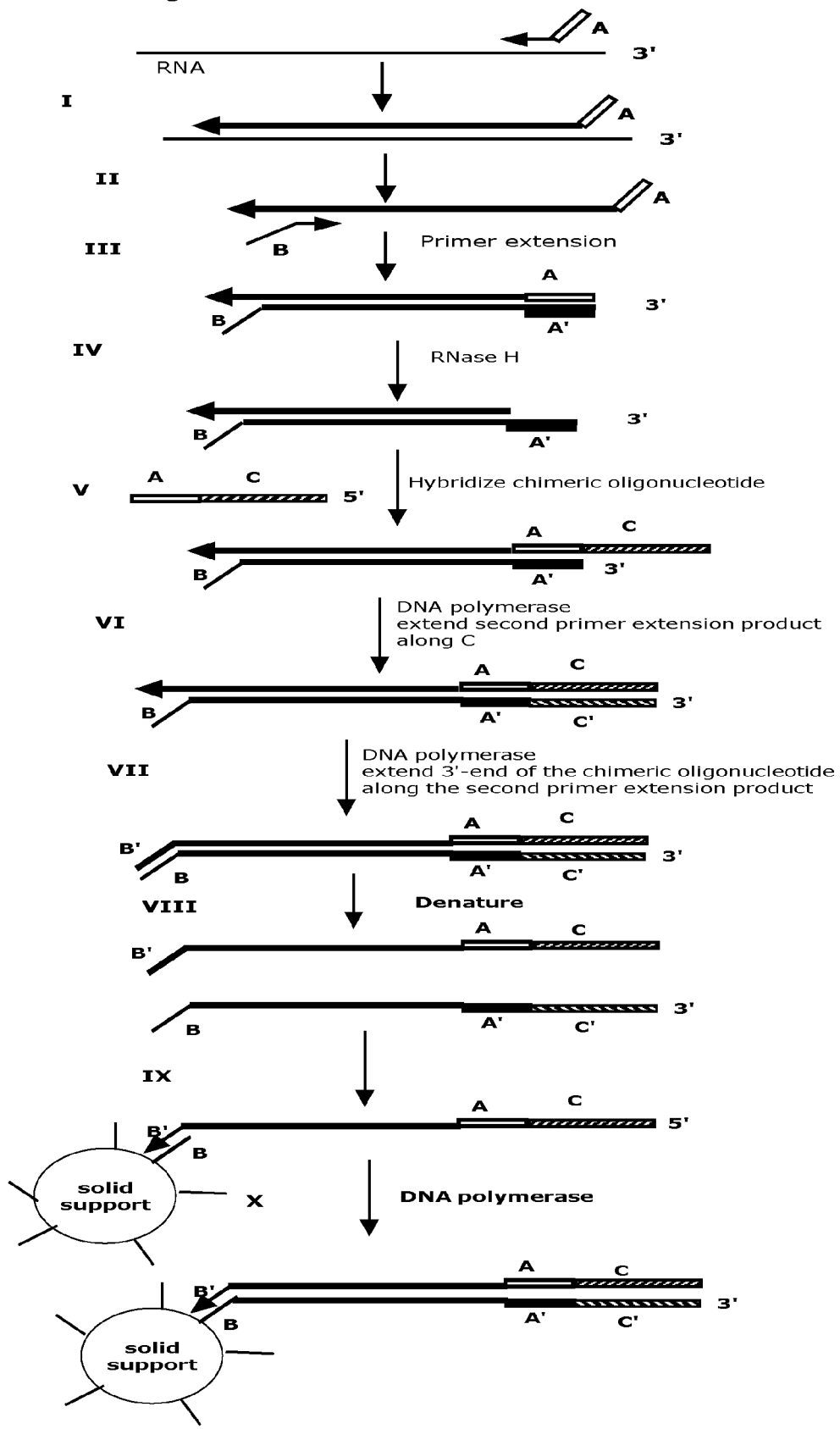
FIG. 17 shows an alternative method of producing a polynucleotide having defined 3' and 5' sequences from a RNA target and a chimeric oligonucleotide primer. A chimeric oligonucleotide extension product is bound to a solid support through sequence B' and is used to generate a bound polynucleotide which comprises from its 5' end, a defined sequence (B), a sequence representative of a target polynucleotide, a sequence (A') and a sequence (C').

A schematic exemplary of an embodiment of the invention relating to generating a polynucleotide having a defined 3' and 5' sequences is shown in FIG. 17. The figure shows a target RNA and a chimeric RNA/DNA first primer. The primer is first annealed to the target RNA. Step I illustrates extension of the first primer comprising a DNA segment and a 5' RNA segment, wherein a 3' portion of the primer is complementary to a target RNA and a 5' portion, sequence (A), of the of the primer is not complementary to the target RNA, to form a first primer extension product hybridized to the target RNA, forming an RNA/DNA hybrid. The sequence complementary to a target RNA can be a specific sequence, a sequence that will hybridize to Poly-A, a sequence common to a plurality of regions (consensus sequence), or a random sequence. Step II represents separation of the target RNA from the RNA/DNA hybrid. The separation can be accomplished thermally, chemically, or enzymatically, e.g. with RNase H. The second primer comprising a 5' sequence (B) is then annealed to the first primer extension product. Step III illustrate extending a second primer, comprising a 5' sequence (B) and a 3' segment complementary to a portion of the first primer extension product, to produce a double stranded product with a DNA/RNA heteroduplex at one end; wherein the double stranded product comprises a second primer extension product hybridized to the first primer extension product, and whereby a portion of the 3' end of the second primer extension product comprises a sequence (A') that is complementary to the sequence (A) of the of the first primer. In step IV, cleavage of the RNA from the first primer extension product in the DNA- RNA heteroduplex occurs such that a portion of the second primer extension product that is complementary to sequence (A) is single stranded. As shown, the cleavage is performed using RNase H. Chemical and thermal means can alternatively be employed. Step V illustrates annealing to the second primer extension product a chimeric oligonucleotide comprising a 3'-DNA segment that is complementary to sequence (A') and a 5' RNA segment comprising sequence (C). Step VI is an optional step and may occur when there is DNA polymerase comprising RNA-dependent DNA polymerase activity. In this step the second primer extension product is extended along sequence C. Step VII illustrates extension of the oligonucleotide at the 3' end, generating an oligonucleotide extension product which is hybridized to the second primer extension product and comprises a sequence (B'), complementary to sequence (B) on the second primer extension product. The first primer extension product is displaced during 3'-extension of the oligonucleotide. Step VIII illustrates the denaturation of the chimeric oligonucleotide extension product from the second primer extension product. Step IX illustrates binding of the chimeric oligonucleotide extension product to a third primer comprising sequence (B) on the solid surface. Step X illustrates extension of the third primer to create a strand complementary to the chimeric oligonucleotide extension product comprising sequence (C') and (A').

Figure 18:
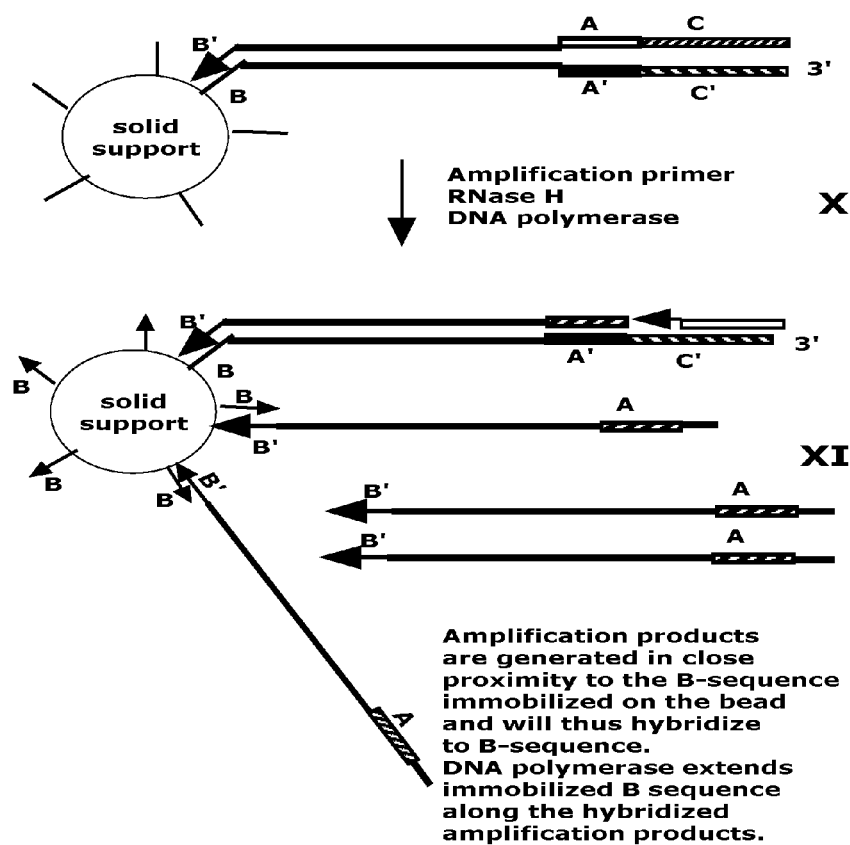
FIG. 18 illustrates an isothermal amplification using a composite primer and the bound polynucleotide product produced in FIG. 17.

In FIG. 18, Step I illustrates the steps of: cleaving the RNA from the DNA-RNA heteroduplex created in step X above to produce a single-stranded portion of the third primer extension product corresponding to sequence (C'); annealing an amplification primer to sequence (C'), wherein the amplification primer has a DNA portion and a 5' RNA portion, to the single stranded portion of the second primer extension product complementary to sequence (C'); extending the amplification primer with a DNA polymerase having strand displacement activity to produce an amplified product. These steps can be repeated to produce multiple copies of amplified product wherein the 5' portion of the amplified product has a sequence complementary to sequence (A'). In the embodiment illustrated, the amplified product shown comprises a defined sequences on both the 5' and 3' ends. Step II illustrates that the amplification products are generated in close proximity to the sequence (B) immobilized on the bead and will thus allow the amplification product to be captured on the bead via hybridization of its sequence (B'). DNA polymerase extends immobilized sequence (B) along the hybridized amplification product to generate bound nucleic acid comprising specific sequences (B) and (A'). Also shown on the amplified product is a portion of sequence (C') that is the DNA portion of the chimeric amplification primer (C). This portion does not generally become cleaved by RNase H and therefore becomes incorporated into the amplified product.

Alternative Method for Generating a Polynucleotide Having a Defined 3' and 5' Sequences from a DNA Target The method utilizes a composite RNA/DNA oligonucleotide to generate an oligonucleotide extension product comprising sequences (A) and (C), which will allow extension of the third primer on the solid surface such that the third primer extension product comprises a sequence (C') at its 3' end than can be used as a site for isothermal amplification in a manner such that the sequence (A) is present at or near the 5' end of the amplified product produced in this amplification, and where a second primer comprising sequence (B) is used, amplified products with defined sequences at both the 3' and 5' ends can be produced.

The method comprises the step: (a) denaturing a double-stranded target DNA. Double stranded DNA can be denatured, for example by heating, or by the addition of denaturing agents.

The method further comprises step: (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the of the primer comprises sequence (A), which is not complementary to the target DNA; to form a first primer extension product hybridized to the target DNA and comprising sequence (A) at its 5' end. This extension is generally performed with an enzyme comprising DNA-dependent DNA polymerase activity. The sequence that is complementary to the target DNA comprises a random sequence, such that the extension of the first primer results in a plurality of first primer extension products complementary to the sequences adjacent to the sequence where each random species hybridizes. The use of a random sequence at the 3' end of the primer can be useful for performing a global amplification of a target DNA, generating a plurality of sequences which together can represent, for example substantially the whole sequence of the target DNA. In some embodiments, the relative amounts of the various sequences can be used to quantitate the relative amount of a given sequence in a sample, for example to determine the number of gene copies in a DNA sample, or obtaining sequence information. In some embodiments, the extension of one first primer, will result in the release of a downstream first primer extension product. This can occur throughout the target DNA resulting in the release of multiple first primer extension products from the target DNA. This process can occur simultaneously on both of the strands of the double-stranded DNA target, thus creating first primer extension products complementary to sequences in both strands.

In some embodiments, the first primer extension step is carried out with a DNA polymerase capable of extension at elevated temperature that is not compatible with subsequent hybridization of the random sequence to the displaced primer-extension product. For example, Bst DNA polymerase can be used which is active at elevated temperature. The reaction can be carried out stepwise, first with an incubation at a lower temperature such as about 25° C., followed by an incubation at higher temperature such as about 50° C. In some embodiments, the first incubation is carried out below about 30° C., and the second incubation is carried out above about 40° C. In some embodiments, a DNA polymerase which is active at temperatures above about 45° C. is used to extend the first primer. Mixtures of DNA polymerases can also be useful.

The method further comprises step: (c) separating the first primer extension product from the target DNA. In some embodiments, the separation can be affected by denaturing the complex comprising the first primer extension product and the nucleic acid. Denaturation can be performed, for example by heating the sample, or by adding a denaturing agent, or using a combination of heating the sample and adding denaturing agents. The amount of cleaving required is that amount which will allow the extension of the second primer.

The method further comprises step: (d) annealing to the first primer extension product and extending a second primer comprising a 3' complementary DNA region that comprises a random sequence, wherein the second primer is a tailed primer comprising a 5' sequence (B), to form a double-stranded product comprising a first primer extension product and a second primer extension product, whereby a double-stranded product with a DNA/RNA heteroduplex at one end is generated. In some embodiments, a DNA polymerase comprising both DNA and RNA dependent DNA polymerase activities is used here. In other embodiments, both a RNA dependent DNA polymerase and a DNA dependent DNA polymerase are used.

This step may be carried out with or without prior denaturation. If carried out without denaturation, generally, only the single stranded displaced first primer extension product will hybridize to the second primer. Generally the second primer does not comprise RNA. The extension of the second primer is carried out with a DNA polymerase as described herein. The second primer comprises a random primer sequence that randomly binds to the first primer extension product. Extension of the second primer comprising a random sequence produces a plurality of second primer extension products. The use of a random sequence at the 3' end of the primer is useful, for example, in performing global amplification of a target DNA, whereby a plurality of second primer extension products are produced which is representative of the sequence of the target DNA. In some embodiments, for example where the first primer is designed to hybridize to a specific sequence on a target DNA, or a sequence common to a family of DNA targets, random priming by the second primer ensures amplification of the entire selected target or family of selected targets. In this embodiment, the second primer extension products comprise sequences which are the same or substantially the same as the sequences in the target DNA.

The second primer extension product is extended such that the 3' portion of the second primer extension product comprises a sequence (A') which is complementary to sequence (A) of the first composite primer. Since sequence (A) on the first primer extension product comprises RNA, both DNA dependent DNA polymerase activity and RNA dependent DNA polymerase activity are used in step (d). The primer extension results in a product that is at least partially double stranded since sequence (B) does not hybridize to the first primer extension product. The method produces a nucleic acid that comprises a sequence (B), allowing it to be bound to a solid surface by hybridization to its complement, which is immobilized on the solid surface and that has a specific sequence (A') at its 3' end. The specific, or universal, sequence (A') can be a site for primer hybridization and further analysis or amplification of the nucleic acid bound to the bead.

The method further comprises step: (e) cleaving the RNA in the heteroduplex from the first primer extension product such that a portion of the second primer extension product that is complementary to sequence (A) is single stranded. The cleaving of RNA can be performed, for example by treatment with RNase H, which will selectively cleave the RNA portion of the DNA/RNA partial heteroduplex formed in step (d).

The method further comprises step: (f) annealing to the second primer extension product an oligonucleotide comprising a 3'-DNA segment that is complementary to sequence (A') and a 5' RNA segment comprising sequence (C).

The oligonucleotide comprises at least one DNA and at least one RNA portion. In some embodiments the 5' DNA segment is complementary to all of sequence (A'), in other embodiments, the 5' DNA segment is complementary to portion of sequence (A'). In some embodiments, 5' RNA segment comprising sequence (C) is partly complementary to sequence (A').

The method further comprises step: (g) extending the oligonucleotide along the second primer extension product to form an oligonucleotide extension product comprising a sequence (B'), complementary to sequence (B) on the second primer extension product. In some embodiments, the oligonucleotide is extended from its 3' end to produce an oligonucleotide extension product hybridized to the second primer extension product and displaces the first primer extension product. The second primer comprises a sequence (B), such that the oligonucleotide extension product will comprise a sequence (B') at or near its 3' end that is complementary to sequence (B). An optional step that may be added using a DNA polymerase that has RNA dependent DNA polymerase activity is extension of the second primer extension product to create a heteroduplex such that the second primer comprises a DNA sequence (C') that is complementary to sequence (C). This step creates an RNA/DNA heteroduplex region.

The method further comprises step: (h) denaturing the double-stranded DNA product. The oligonucleotide primer extension product can be separated from the second primer extension product by denaturation. Denaturation can be performed, for example by heating the sample, or by adding a denaturing agent, or using a combination of heating the sample and adding denaturing agents.

The method further comprises step: (i) attaching the single-stranded oligonucleotide extension product to solid support by annealing sequence (B') to the bead or isolated area comprising a sequence (B). The third primer comprises an oligonucleotide sequence (B) that is complementary to the sequence (B') of the oligonucleotide primer extension product and results in attaching the single stranded oligonucleotide primer extension product to the solid surface. The method produces a nucleic acid that is hybridized to a solid surface that has a specific sequence (A) at its 5' end.

Step (i) of binding the polynucleotides to the solid surface sequence (B) can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

The method further comprises the step of: (j) extending sequence (B) on the solid support to produce a third primer extension product, hybridized to the oligonucleotide extension product, comprising a 3' sequence (A') and (C'), whereby a DNA/RNA heteroduplex at one end is generated. The extension of the third primer is carried out with a DNA polymerase as described herein. In some embodiments, a DNA polymerase comprising both DNA and RNA dependent DNA polymerase activities is used here. In other embodiments, both a RNA dependent DNA polymerase and a DNA dependent DNA polymerase are used. The primer extension results in a product that is double stranded and comprises sequences (B'), (A), (C) on the first primer extension product and sequences (B), (A') and (C') on the third primer extension product.

The method produces a nucleic acid that is bound to a solid surface that has a specific sequence (A') and (C') at its 3' end and a sequence (B) at or near its 5' end. The specific, or universal, sequence (A') or (C') can be a site for primer hybridization and further analysis or amplification of the nucleic acid bound to the bead. The specific, or universal, sequence (C') can be a site for primer hybridization and further analysis or amplification of the nucleic acid bound to the bead. One aspect of the invention comprises amplification of the nucleic acid bound to the bead. In some embodiments, the amplification is carried out using isothermal amplification using a composite RNA/DNA primer, RNase H, and a polymerase with strand displacement activity. For this embodiment, the sequence (C') acts as the site to which the composite RNA/DNA amplification primer hybridizes, allowing for amplification. In some embodiments, for example where random sequences at the 3' end of the first and/or second primer are used, a plurality of different nucleic acids bound to a solid surface is created in which each of the nucleic acids has a specific sequence (C') at its 3' end and also a specific sequence (B) at its 5' end, and where the different nucleic acids have different intervening sequences, wherein the intervening sequences are identical to or substantially identical to the sequences in the target nucleic acid. The set of bound nucleic acids thus generated can be analyzed, for example, by sequencing in order to provide information about the sequence of the target nucleic acid.

In some embodiments, for example where random sequences at the 3' end of the first and/or second primer are used, a plurality of different nucleic acids hybridized to a solid surface is created in which each of the nucleic acids has a specific sequence (A) and (C) at its 5' end and also a specific sequence (B') at its 3' end, and where the different nucleic acids have different intervening sequences, wherein the intervening sequences are identical to or substantially identical to the sequences in the target DNA. The set of bound nucleic acids thus generated can be analyzed, for example, by sequencing in order to provide information about the sequence of the target DNA.

The solid surface can be any of a variety of surfaces, some described in more detail below. The solid surface can be, for example a planar surface, for example, a planar array. In some embodiments the solid surface comprises a plurality of beads. In some embodiments the beads are magnetic.

The step of binding the polynucleotides to the solid surface through sequence (B'), step (i), can be carried out such that only one nucleic acid is bound to an isolated area of a surface or only one nucleic acid is bound to a single bead. This isolated binding of nucleic acids can be used for clonal amplification of the specific bound nucleic acid in that area or on that bead. Such bound, isolated nucleic acids can also be stored and archived for later analysis, for example by sequencing. The bound, isolated nucleic acids can be amplified, stored, and analyzed multiple times.

In some embodiments, the method further comprises treating the solid surface with reagents to produce multiple copies of an amplification product that are substantially complementary to the third primer extension product. This step comprises carrying out an amplification reaction wherein the bound nucleic acid acts as a template for the amplification.

Generally, the amplification is carried out using the sequence (C') on the third primer extension product for the hybridization of a primer such as a composite RNA/DNA amplification primer hybridizes, allowing for amplification. In some embodiments the amplification is an isothermal amplification reaction comprising a composite RNA/DNA primer, RNase H, and a DNA polymerase with strand displacement activity. In some embodiments, the amplification is carried out using polymerase chain reaction, (PCR). For example where the second primer extension product comprises both as sequence (B) at or near its 5' end and a sequence (C') at or near its 3' end, a set of primers, one designed to hybridize to all or a portion of the sequence (C') and the other designed to hybridize to sequence (B), can be used to carry out a PCR reaction to exponentially produce double stranded amplified product.

In some embodiments, the amplification is performed by a method comprising the following steps: (k) cleaving the RNA from the heteroduplex polynucleotide product hybridized to the amplified product using RNase H to produce a single-stranded portion of the second primer extension product corresponding to sequence (C'); (l) annealing an amplification primer to the single-stranded portion of the amplified product complementary to sequence (C'), wherein the amplification primer has a DNA portion and a 5' RNA portion; (m) extending the amplification primer with an enzyme having strand displacement activity to produce an amplified product hybridized to the amplified product on the bead or isolated area; and (n) repeating steps (k) to (m) to produce multiple copies of the second polynucleotide product comprising sequences (A) and (B'). This amplification method, utilizing a sequence (B) and (C'), allows for the production of an amplified product comprises a sequence (B') at or near its 3' end that is substantially complementary to sequence (B), and a sequence (A) near its 5' end that is complementary to sequence (A'), thus producing an amplified polynucleotide product with defined 3' and 5' ends.

In some embodiments the amplification is carried out such that the amplified product is not attached to the substrate, but is freely dissolved in the solution. In other embodiments, the amplification is carried out such that the amplified product remains bound to the substrate, for example by performing solid phase PCR such as bridge PCR. In yet other embodiments, an amplified product is generated that may float freely in solution, but which comprises a sequence, for example sequence (A) or sequence (B'), that allows it to be captured to another solid surface or other portion of the solid surface by hybridization to a complementary sequence bound to such surface, e.g. sequence (A') or sequence (B). In some embodiments, the amplified product is a single-stranded product and, because it is generated at the solid surface, the amplified product readily captured by complementary sequences, e.g. sequence (B), bound to the surface.

In one aspect of the invention, a plurality of beads is used, and the methods described above are carried out such that on average, one or fewer oligonucleotide primer extension product molecules are bound per bead. The beads are dispersed into an aqueous solution, and a plurality of microreactors, e.g. droplets, are produced such that on average one or fewer beads is contained within each of the plurality of microreactors. The amplification of the third primer extension products bound to the beads is then carried out such that the clonal amplification of each of the plurality of second primer extension products in the separate microreactors is achieved. This clonal amplification in microreactors can be performed on a sample of target DNA, such as whole transcriptome or total DNA, wherein the plurality of third primer extension products comprise sequences that correspond to most, to substantially all, or to all of the sequences in the target RNA. In some embodiments, the amplified products are captured by bead having attached thereto a plurality of oligonucleotides comprising complementary sequences bound to such surface (e.g. sequence (A') or sequence (B)), which are complementary to sequence (A) or sequence (B') on the amplified product.

In some embodiments, the plurality of beads, produced as described above, with each bead comprising a single oligonucleotide primer extension product can comprise a library. These libraries can be stored, then later clonally amplified. In some embodiments, a library of beads can comprise a plurality of beads wherein each bead had multiple copies of a single amplification product generated from a third primer extension product. These libraries can be analyzed, for example by sequencing. The libraries can be stored, and later analyzed. In some embodiments the libraries can be stored, then analyzed multiple times.

In some embodiments, a bead or isolated area of the solid surface comprises covalently attached thereto multiple oligonucleotides comprising the sequence (B) at their 5' ends, whereby upon the amplification of step (m) multiple copies of amplified product comprising sequence (B') at their 3' end are hybridized to the bead or isolated area. For example, where beads are used, a plurality of beads in a plurality of microreactors wherein, the plurality of beads has, on average one or fewer oligonucleotide primer extension products bound to it and there are, on average, one or fewer beads in each microreactor, a clonal amplification of the plurality of third primer extension products can be carried out, and the amplified products in each of the microreactors will bind to the bead through the sequence (B') on the amplified product to the sequence (B) on the beads. This approach produces a plurality of beads, each with multiple copies of a different sequence bound to it. Where these sequences are representative of the target DNA, the plurality of beads can constitute a library representative of such DNA.

After the amplified products are bound to the beads by hybridization, the (B) sequences on the beads can be extended along the amplified product by a DNA polymerase or mixture of polymerases to produce a multiple polynucleotides covalently attached to the bead or isolated area that are substantially complementary to the amplified product and also comprise sequence (A') near their 3' ends. This method provides for the production of beads with polynucleotides complementary to amplified product covalently attached to the beads. Covalently attached polynucleotides such as those produce here are more robust than nucleotides that are attached only by hybridization to the beads. Thus, the covalently attached polynucleotides can be more stable and can be used with analysis methods and sequencing methods that have harsher conditions which would result in the displacement of polynucleotides bound only by hybridization.

In some embodiments, the amplified product is removed from the covalently bound polynucleotide to render the polynucleotide single stranded. Such single stranded covalently bound polynucleotides comprise a specific sequence at their 3' ends comprising sequence (A') and a portion of sequence (C'). Here, the portion of sequence (C') is the DNA portion of the chimeric amplification primer (C) that does is generally not cleaved by RNase H and therefore becomes incorporated into the amplified product. This specific sequence at the 3' end of the covalently bound polynucleotide can act as a hybridization site for a primer complementary to sequence (A') that can act as a primer to carry out sequencing by any of a variety of sequencing methods, for example, those described herein.

The sequencing methods can comprise the use of cleavable labeled terminators. The sequencing method can comprise pyrophosphate detection. The sequencing method can comprise an isothermal sequencing method, for example using chimeric primers, RNase H, and a polymerase with strand displacement activity. The sequencing method can also comprise cycle sequencing.

In some embodiments the methods of the invention provide for performing bridge PCR comprising making amplified product as described above with defined 3' and 5' ends, and further comprising the steps of exposing the amplified product to a solid substrate comprising oligonucleotide sequences attached thereto complementary to the defined 3' and 5' sequences, for example, A and B' sequences, on the amplified product in the presence of components necessary for polymerase chain reaction, and thermal cycling the system to perform bridge PCR amplification.

In some embodiments the methods of the invention provide for making amplified product as described above with defined 3' and 5' ends and further performing rolling circle amplification comprising performing the steps of: (o) hybridizing the amplified products to a target nucleic acid comprising regions complementary to A and B' sequences in close proximity; (p) optionally extending the gap with a polymerase enzyme; and (q) ligating to form a circular nucleic acid comprising the amplified product, and performing rolling circle amplification by extending a primer that is complementary to a sequence in the circular nucleic acid.

In some embodiments, the rolling circle amplification uses primers complementary to sequence (A), sequence (B'), or a sequence that was between sequences (A) and (B') in the amplified product. In some cases, such a primer can be an oligonucleotide attached to a solid surface, thus resulting in amplified product bound to the surface In some embodiments the methods of the invention provide for performing PCR comprising making amplified product as described above with defined 3' and 5' ends, further comprising the steps of amplifying the amplified product using primers complementary to sequences (A) and (B), or using primers complementary to sequences (A') and (B').

In some embodiments the methods of the invention provide for performing strand displacement amplification (SDA) comprising making amplified product as described above with defined 3' and 5' ends, wherein the defined 3' and 5' ends, for example, sequences (A) and (B'), in the amplified product are designed to be cleaved by a restriction enzyme, and performing strand displacement amplification on the amplified product.

Figure 19:
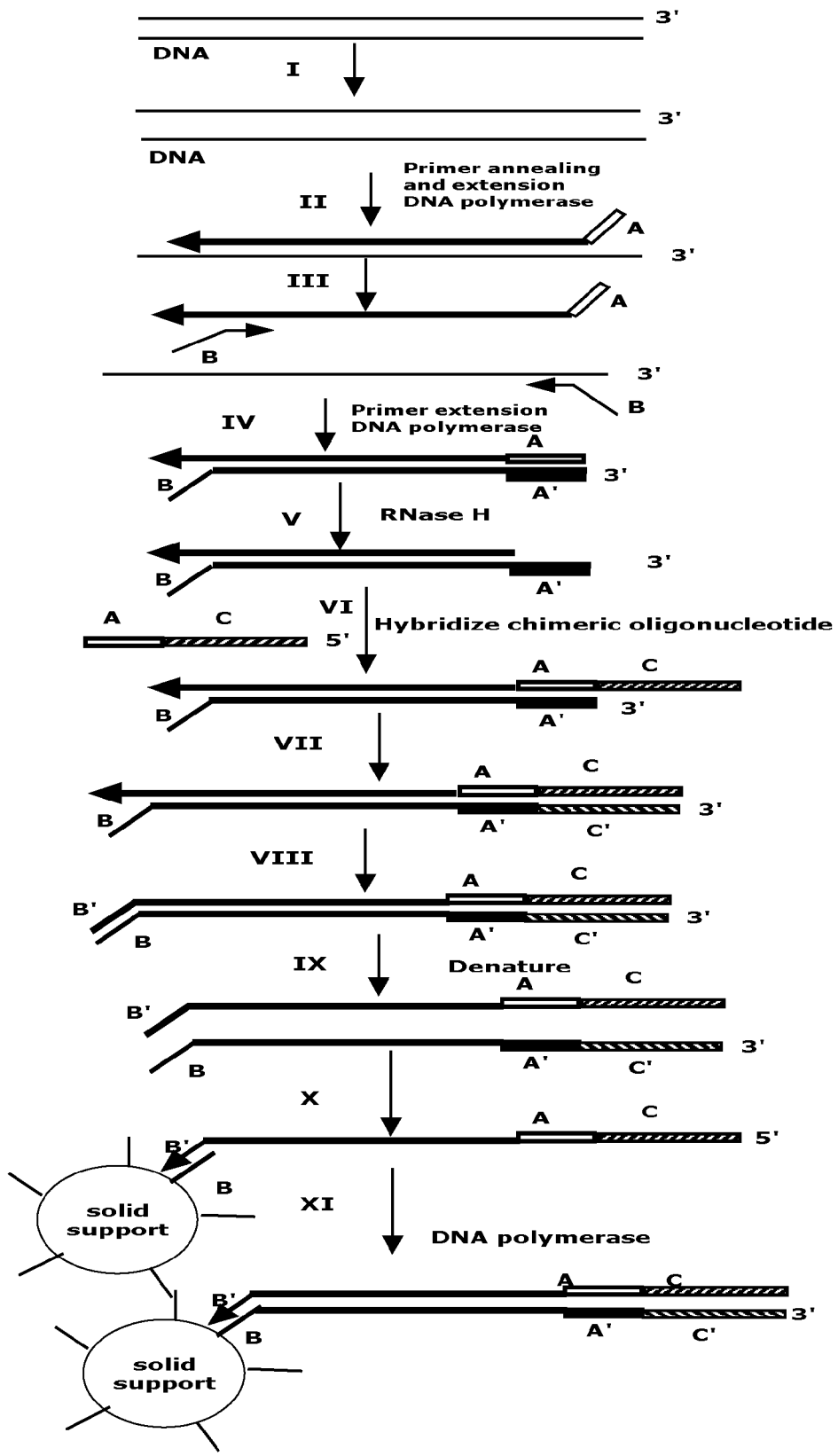
FIG. 19 shows an alternative method of producing a polynucleotide having defined 3' and 5' sequences from a DNA target and a chimeric oligonucleotide primer. A chimeric oligonucleotide extension product is bound to a solid support through sequence B' and is used to generate a bound polynucleotide which comprises from its 5' end, a defined sequence (B), a sequence representative of a target polynucleotide, a sequence (A') and a sequence (C').

A schematic exemplary of an embodiment of the invention relating to generating a polynucleotide having a defined 3' and 5' sequences is shown in FIG. 19. The figure shows a double stranded target DNA that is denatured in step I. In step II, a chimeric RNA/DNA first primer is first annealed to the target DNA and is extended to form a first primer extension product hybridized to the target DNA, forming a RNA/DNA hybrid. The first primer comprises a DNA segment and a 5' RNA segment, wherein a 3' portion of the primer is complementary to a target RNA and a 5' portion, sequence (A), of the of the primer is not complementary to the target DNA. The sequence complementary to a target DNA can be a specific sequence, a sequence that will hybridize to Poly-A, a sequence common to a plurality of regions (consensus sequence), or a random sequence. Step III represents separation of the target DNA from the RNA/DNA hybrid. The separation can be accomplished thermally, chemically, or enzymatically, e.g. with RNase H. A second primer comprising a 5' sequence (B) is then annealed to the first primer extension product. Step IV illustrate extension of the second primer, comprising a 5' sequence (B) and a 3' segment complementary to a portion of the first primer extension product, to produce a double stranded product with a DNA/RNA heteroduplex at one end; wherein the double stranded product comprises a second primer extension product hybridized to the first primer extension product, and whereby a portion of the 3' end of the second primer extension product comprises a sequence (A') that is complementary to the sequence (A) of the of the first primer. In step V, cleavage of the RNA from the first primer extension product in the DNA-RNA heteroduplex occurs such that a portion of the second primer extension product that is complementary to sequence (A) is single stranded. As shown, the cleavage is performed using RNase H. Chemical and thermal means can alternatively be employed. Step VI illustrates annealing to the second primer extension product a chimeric oligonucleotide comprising a 3'-DNA segment that is complementary to sequence (A') and a 5' RNA segment comprising sequence (C). Step VII is an optional step and may occur when there is DNA polymerase comprising RNA-dependent DNA polymerase activity. In this step the second primer extension product is extended along sequence C. Step VIII illustrates extension of the oligonucleotide at the 3' end, generating an oligonucleotide extension product which is hybridized to the second primer extension product and comprises a sequence (B'), complementary to sequence (B) on the second primer extension product. The first primer extension product is displaced during 3'-extension of the oligonucleotide. Step IX illustrates the denaturation of the chimeric oligonucleotide extension product from the second primer extension product. Step X illustrates binding of the chimeric oligonucleotide extension product to a third primer comprising sequence (B) on the solid surface. Step XI illustrates extension of the third primer to create a strand complementary to the chimeric oligonucleotide extension product comprising sequence (C') and (A'). Amplification of the oligonucleotide extension product comprising specific sequences (B) and (A') at the 3' and 5' ends, respectively, take place by carrying out the steps illustrated in FIG. 18.

In one aspect of the present invention, methods are provided for amplifying a target nucleic acid or its complement on a solid support to form a plurality of amplified products comprising clonally amplifying said target sequence or its complement by linear amplification. In some embodiments, the method comprises amplification using a single primer. In some embodiments, the method comprises amplification from a double-stranded nucleic acid having a single-stranded 3' overhang at one end. In some embodiments, the method comprises amplification using a DNA-RNA chimeric primer. In some embodiments, the method comprises a combination of linear amplification using a single primer from a double-stranded nucleic acid having a single-stranded 3' overhang at one end using a DNA-RNA chimeric primer. In some embodiments, the target nucleic acid sequence is coupled to a solid support. In some cases, the amplification is isothermal. In some cases, the solid support is a bead. In some cases, the amplification results in at least 10,000; 100,000; one million or more copies of the target sequence, its complement, or a portion thereof. In some cases, the solid surface comprises a plurality of primers of substantially identical sequence. In some cases, the solid surface consists of a plurality of primers of substantially identical sequence. In some cases, the target nucleic acid sequence is a linear template. In some cases, the target nucleic acid sequence is greater than about 150, 200, 250, 300, 400, 500, 1 kb, 2 kb, 5 kb, 10 kb or more in length. In some cases, the target nucleic acid is less than about 1 megabase, 100 kb, 50 kb, 10 kb, 5 kb, or less in length.

In one aspect of the present invention, methods are provided for clonally amplifying a target nucleic acid sequence or its complement by delivering the target nucleic acid sequence into an emulsion and performing linear amplification of the target nucleic acid sequence inside the emulsion. In some cases, the method further comprises the step of forming the emulsion first. In some cases, the emulsion is formed around the target nucleic acid and/or the target nucleic acid in a reaction mixture comprising amplification reagents including but not limited to buffers; one or more enzymes such as a DNA polymerase with substantial strand displacement activity, exonuclease, and RNase H; salts; primers including chimeric primers, amplification primers, and all-DNA primers, oligonucleotides including chimeric oligonucleotides; and dNTPs. In some cases, the method may further comprise amplifying the target nucleic acid in the presence of a solid surface such as a bead, a substantially planar array, an isolated surface, or a well in a plate. In some cases the amplification results in a plurality of non-multimerized individual amplification products. These are physically separated or chemically separated amplified products. In some cases, the amplification results in a lower error rate than PCR such as for example fewer errors than 2 in every 100,000 nucleotides incorporated into amplified product.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

The terms "Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The oligonucleotide(s) are generally comprised of a sequence of at least 5 nucleotides, generally from about 10 to about 100 nucleotides, about 20 to about 50 nucleotides, and often about 10 to about 30 nucleotides in length. The oligonucleotides of the invention can be DNA, RNA, DNA-RNA, or other polynucleotide. The terms oligo or sequence may be used interchangeable herein.

Various techniques can be employed for preparing an oligonucleotide utilized in the present invention. Such oligonucleotide can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) Methods Enzymol, 101, 20-78.

In the present invention, nucleoside triphosphates are incorporated by a polymerase enzyme in the extension of the primer to produce an extension product. Nucleoside triphosphates are generally nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common triphosphates dATP, dCTP, dGTP and dTTP and ribonucleoside triphosphates such as the four common triphosphates rATP, rCTP, rGTP and rUTP. The term "nucleoside triphosphates" also includes derivatives and analogs thereof, which are exemplified by those derivatives that are recognized in a similar manner to the underivatized nucleoside triphosphates. Examples of such derivatives or analogs, by way of illustration and not limitation, are those which are biotinylated, amine modified, alkylated, and the like and also include phosphorothioate, phosphite, ring atom modified derivatives, and the like.

As used herein, the term "nucleotide" generally refers to a base-sugar-phosphate combination that is the monomeric unit of nucleic acid polymers, i.e., DNA and RNA. In some aspects of the invention modified nucleotides are used, for example, where a nucleotide is connected to a ligand. A modified nucleotide is generally the unit in a nucleic acid polymer that results from the incorporation of a modified nucleoside triphosphate during an amplification reaction and therefore becomes part of the nucleic acid polymer.

As used herein, a nucleoside is generally a base-sugar combination or a nucleotide lacking a phosphate moiety.

A "primer" is generally a nucleotide sequence (i.e. a polynucleotide), generally with a free 3'-OH group, that hybridizes with a template sequence (such as a target RNA, or a primer extension product) and is capable of promoting polymerization of a polynucleotide complementary to the template. A "primer" can be, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer.

The primers of the invention are usually oligonucleotide primers. A primer is generally an oligonucleotide that is employed in an extension on a polynucleotide template. The oligonucleotide primer is usually a synthetic nucleotide that is single stranded, containing a sequence at its 3'-end that is capable of hybridizing with a sequence of the target polynucleotide. Normally, the 3' region of the primer that hybridizes with the target nucleic acid has at least 80%, preferably 90%, more preferably 95%, most preferably 100%, complementarity to a sequence or primer binding site. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence of the target polynucleotide, namely, at least ten nucleotides, at least about 15 nucleotides and generally from about 10 to about 200, usually about 20 to about 50 nucleotides.

A "random primer," as used herein, is a primer that comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. The random primers used herein are generally tailed random primers comprising a 3' segment that acts as a random primer to the target polynucleotide, and a 5' sequence that generally does not hybridize to the target polynucleotide. The sequence of a random primer (or its complement) may or may not be naturally-occurring, or may or may not be present in a pool of sequences in a sample of interest. The amplification of a plurality of polynucleotides, e.g. DNA or RNA species in a single reaction mixture would generally, but not necessarily, employ a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target. In some embodiments one portion of a primer is random, and another portion of the primer comprises a defined sequence. For example, in some embodiments, a 3' portion of the primer will comprise a random sequence, while the 5' portion of the primer comprises a defined sequence. In some embodiments a 3' random portion of the primer will comprise DNA, and a 5' portion defined portion of the primer will comprise RNA, in other embodiments, both the 3' and 5' portions will comprise DNA.

Composite primers are employed in certain embodiments of the invention. Composite primers are primers that are composed of RNA and DNA portions. In some aspects, the composite primer is a tailed composite primer comprising, for example, a 3' DNA portion and a 5' RNA portion. In the tailed composite primer, a 3' portion, all or a portion of which comprises DNA is complementary to a polynucleotide; and a 5' portion, all or a portion of which comprises RNA, is not complementary to the polynucleotide and does not hybridize to the polynucleotide under conditions in which the 3' portion of the tailed composite primer hybridizes to the polynucleotide target. When the tailed composite primer is extended with a DNA polymerase, a primer extension product with a 5' RNA portion comprising a defined sequence can be created. This primer extension product can then have a second primer anneal to it, which can be extended with a DNA polymerase to create a double stranded product with an RNA/DNA heteroduplex comprising a defined sequence at one end. The RNA portion can be selectively cleaved from the partial heteroduplex to create a double stranded DNA with a 3' single stranded overhang which can be useful for a various aspects of the present invention including allowing for isothermal amplification using a composite amplification primer.

In other aspects, the composite primer is an amplification composite primer. In the amplification composite primer, both the RNA and the DNA portions are generally complementary and hybridize to a sequence in the polynucleotide to be copied or amplified. In some embodiments, a 3' portion of the amplification composite primer is DNA and a 5' portion of the composite amplification primer is RNA. The composite amplification primer is designed such that the primer is extended from the 3' DNA portion to create a primer extension product. The 5' RNA portion of this primer extension product, in a DNA-RNA heteroduplex is susceptible to cleavage by RNase H, thus freeing a portion of the polynucleotide to the hybridization of an additional composite amplification primer. The extension of the additional composite primer by a DNA polymerase with strand displacement activity releases the primer extension product from the original primer and creates another copy of the sequence of the polynucleotide. Repeated rounds of primer hybridization, primer extension with strand displacement DNA synthesis, and RNA cleavage create multiple copies of the sequence of the polynucleotide. Composite primers are described in more detail below.

Polymerases are used in the methods of the invention, for example to extend primers to produce extension products. A polymerase, or nucleotide polymerase, is a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, Bst DNA polymerase, reverse transcriptase, Bca polymerase, Vent DNA polymerase, Pfu DNA polymerase, Taq DNA polymerase, and the like, derived from any source such as cells, bacteria, such as E. coli, plants, animals, virus, thermophilic bacteria, and so forth. RNA polymerases include T7 RNA polymerase, AMV polymerase, Q-beta-replicase, and so forth. In some cases, Bst DNA Polymerase Large Fragment can be used. Bst DNA polymerase Large Fragment is the portion of the *Bacillus stearothermophilus* DNA Polymerase protein that contains the 5'→3' polymerase activity, but lacks the 5'→3' exonuclease domain. Where the polymerase forms an extension product on a DNA template, it is referred to herein as a DNA dependent polymerase. Where the polymerase forms an extension product on a RNA template, it is referred to herein as a RNA dependent polymerase.

A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotin-avidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include fluorescent dyes (e.g., fluorescein isothiocyanate, Texas red, rhodamine, green fluorescent protein and the like), radioisotopes (e.g., $^3$H, $^{35}$S, $^{32}$P, $^{33}$P, $^{125}$I, or $^{14}$C), enzymes (e.g., LacZ, horseradish peroxidase, alkaline phosphatase,), digoxigenin, and colorimetric labels such as colloidal gold or colored glass or plastic (e.g., polystyrene, polypropylene, latex, etc.) beads.

The term "double stranded product" is used herein to refer to products that are produced by the extension of a primer. It is understood that the products are at least partially double stranded, for example, in the region comprising the primer extension product and its complement. The double stranded product need not be completely double-stranded, and may have single stranded regions. It is also understood that the double stranded product can have heteroduplex regions in which one strand comprises RNA and the complementary strand comprised DNA in that region.

Amplification

Some aspects of the invention comprise the amplification of polynucleotide molecules or sequences within the polynucleotide molecules. Amplification generally refers to a method that results in the formation of one or more copies of a nucleic acid or polynucleotide molecule or in the formation of one or more copies of the complement of a nucleic acid or polynucleotide molecule. Amplifications can be used in the invention, for example, to amplify or analyze a polynucleotide bound to a solid surface. The amplifications can be performed, for example, after archiving the samples in order to analyze the archived polynucleotide.

In some aspects of the invention, exponential amplification of nucleic acids or polynucleotides is used. These methods often depend on the product catalyzed formation of multiple copies of a nucleic acid or polynucleotide molecule or its complement. The amplification products are sometimes referred to as "amplicons." One such method for the enzymatic amplification of specific double stranded sequences of DNA is known as the polymerase chain reaction (PCR). This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification involves amplification of a single stranded polynucleotide using a single oligonucleotide primer. The single stranded polynucleotide that is to be amplified contains two non-contiguous sequences that are complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving a nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTPs and dNTPs.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTPs, and Q-beta-replicase.

Another method for amplifying nucleic acids is known as 3SR and is similar to NASBA except that the RNAse-H activity is present in the reverse transcriptase. Amplification by 3SR is an RNA specific target method whereby RNA is amplified in an isothermal process combining promoter directed RNA polymerase, reverse transcriptase and RNase H with target RNA.

Another method for amplifying nucleic acids is the Transcription Mediated Amplification (TMA) used by Gen-Probe. The method is similar to NASBA in utilizing two enzymes in a self-sustained sequence replication. See U.S. Pat. No. 6,946,254.

Another method for amplification of nucleic acids is Strand Displacement Amplification (SDA) (Westin et al 2000, Nature Biotechnology, 18, 199-202; Walker et al 1992, Nucleic Acids Research, 20, 7, 1691-1696), which is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Another method for amplification of nucleic acids is Rolling Circle Amplification (RCA) (Lizardi et al. 1998, Nature Genetics, 19:225-232). RCA can be used to amplify single stranded molecules in the form of circles of nucleic acids. In its simplest form, RCA involves the hybridization of a single primer to a circular nucleic acid. Extension of the primer by a DNA polymerase with strand displacement activity results in the production of multiple copies of the circular nucleic acid concatenated into a single DNA strand.

In some embodiments of the invention, RCA is coupled with ligation. For example, a single oligonucleotide can be used both for ligation and as the circular template for RCA. This type of polynucleotide can be referred to as a "padlock probe" or a "RCA probe". For a padlock probe, both termini of the oligonucleotide contains sequences complementary to a domain within a nucleic acid sequence of interest. The first end of the padlock probe is substantially complementary to a first domain on the nucleic acid sequence of interest, and the second end of the padlock probe is substantially complementary to a second domain, adjacent to the first domain near the first domain. Hybridization of the oligonucleotide to the target nucleic acid results in the formation of a hybridization complex. Ligation of the ends of the padlock probe results in the formation of a modified hybridization complex containing a circular polynucleotide. In some cases, prior to ligation, a polymerase can fill in the gap by extending one end of the padlock probe. The circular polynucleotide thus formed can serve as a template for RCA that with the addition of a polymerase results in the formation of an amplified product nucleic acid. The methods of the invention described herein, can produce amplified products with defined sequences on both the 5' and 3' ends. Such amplified products can be used as padlock probes.

Some aspects of the invention utilize the linear amplification of nucleic acids or polynucleotides. Linear amplification generally refers to a method that involve the formation of one or more copies of the complement of only one strand of a nucleic acid or polynucleotide molecule, usually a nucleic acid or polynucleotide analyte. Thus, the primary difference between linear amplification and exponential amplification is that the latter is auto catalyzed, that is, the product serves to catalyze the formation of more product, whereas in the former process the starting sequence catalyzes the formation of product but is not itself replicated. In linear amplification the amount of product formed increases as a linear function of time as opposed to exponential amplification where the amount of product formed is an exponential function of time.

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., Adessi et al., Nucleic Acids Research (2000): 28(20): E87) can be used. In some cases the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). The methods of the invention provide new methods for generating and using polonies.

In some embodiments, amplification methods such as amplification that maintains spatial clustering of identical amplicons, amplification that produces in situ polonies, picotiter amplification, amplification inside microdroplets, amplification inside the aqueous phase of microdroplets of an oil and water emulsion or the like, may provide clonal amplification. "Clonal amplification" as used herein is the amplification of a target sequence or a set of target sequences in a spatially or physically separated manner such that the amplified products are spatially or physically separated from the amplified products of other target sequences. For example, some of the methods of the present invention provide for amplification of a set of target sequences attached to, bound to, or hybridized to a solid surface such as a set of beads, isolated surfaces, or wells in a plate such that each surface on average contains one or fewer target sequences. In some cases, the amplification is carried out under conditions that the amplified products of the target sequence of a given surface are attached to, bound to, or hybridized to that surface. Further, in some cases, the given surface comprises few, substantially no, or no other amplified products from other target sequences. Similarly, clonal amplification may be carried out by separating the target sequences and their products from other target sequences and their products in other ways such as in a set of microreactors such as microdroplets such as in an emulsion, in a set of wells, or by dilution. Additionally clonal amplification may be performed using a combination of compositions and techniques such as by amplifying a set of target sequences on a solid surface or set of solid surfaces such as a bead or set of beads in a set of microdroplets in an emulsion.

Single Primer Isothermal Amplification Using a Complex Comprising an RNA/DNA Partial Heteroduplex as a Template In some aspects of the invention, the amplification method that is used is a single primer isothermal amplification using a complex comprising an RNA/DNA partial heteroduplex as a template. In this method, termed single primer isothermal amplification, a complex comprising an RNA/DNA partial heteroduplex is a substrate for further amplification as follows: an enzyme which cleaves RNA sequence from an RNA/DNA hybrid (such as RNase H) cleaves RNA from the partial heteroduplex, leaving a partially double stranded polynucleotide complex comprising a 3' single stranded DNA sequence. The 3' single stranded sequence (formed by cleavage of RNA in the complex comprising an RNA/DNA partial heteroduplex) is generally the complement of the amplification composite primer, and thus forms a specific binding site for a composite primer. Extension of a bound composite primer by a DNA-dependent DNA polymerase with strand displacement activity produces a primer extension product, which displaces the previously bound cleaved primer extension product, whereby polynucleotide (generally, DNA) product accumulates. See, for example, U.S. Pat. Nos. 6,251,639 and 6,692,918.

Amplification using a complex comprising an RNA/DNA partial heteroduplex as a template for further amplification (also termed single primer isothermal amplification) generally occurs under conditions permitting composite primer hybridization, primer extension by a DNA polymerase with strand displacement activity, cleavage of RNA from an RNA/DNA hybrid and strand displacement. In so far as the composite primer hybridizes to the 3' single stranded portion (of the partially double stranded polynucleotide which is formed by cleaving RNA in the complex comprising an RNA/DNA partial heteroduplex) comprising, generally, the complement of at least a portion of the composite primer sequence, composite primer hybridization may be under conditions permitting specific hybridization.

In some embodiments, the methods of the invention result in amplification of a multiplicity, a large multiplicity, or a very large multiplicity of template polynucleotide sequences. In some embodiments, essentially all of the template polynucleotide present in the initial sample (e.g., all of the mRNA or all of the genomic DNA) is amplified. In other embodiments, at least 1, at least 5, at least 10, at least 20. at least 50, at least 100, at least 200, at least 300, or more distinct sequences (such as a gene or other subsegment of a polynucleotide, transcripts of a nucleic acid target, a marker (such as a SNP or other polymorphism) are amplified, as assessed, e.g., by analysis of marker sequences known to be present in the template sample under analysis, using methods known in the art. Template polynucleotide sequences that are amplified may be present on the same polynucleotide (e.g., a chromosome or portion of a chromosome for genomic DNA template or on the same RNA for RNA template) or on different template polynucleotides (e.g., different chromosome or portions of chromosomes for DNA template, or different RNAs for RNA template). In some case, amplification of genomic DNA is exemplified herein, it will be understood by those of skill in the art, however, that the global amplification methods of the invention are suitable for amplification of any pool or subset of polynucleotides.

In some embodiments, the methods of the invention are used to globally amplify double stranded DNA target. It is understood that in these cases, the amplified product generally is a mixture of sense and antisense copies of the template DNA. In some embodiments, the methods of the invention are used to globally amplify a single stranded DNA or RNA target. In these cases, the amplification product will generally be a copy of either the target polynucleotide (sense copy) or of the complement to the target nucleotide (antisense copy). Whether the sense or antisense copy is produced will depend on the method, as will be understood by one of ordinary skill in the art. In some embodiments, the amplification product of different senses can be annealed to form a double stranded (or partially double stranded) complex. In other embodiments, they can be prevented from annealing (or subsequently denatured) to produce a mixture of single stranded amplification products. The amplified products may be of differing lengths.

As illustrated in these embodiments, all steps are isothermal (in the sense that thermal cycling is not required), although the temperatures for each of the steps may or may not be the same. It is understood that various other embodiments may be practiced, given the general description provided above. For example, as described and exemplified herein, certain steps may be performed as temperature is changed (e.g., raised, or lowered).

For simplicity, the isothermal amplification methods of the invention are described as two distinct steps or phases, above. It is understood that the two phases may occur simultaneously in some embodiments (for example, if the enzyme that cleaves RNA from RNA/DNA hybrid is included in the first reaction mixture).

Although generally only one composite primer is described above, it is further understood that the amplification methods may be performed in the presence of two or more different composite primers that randomly prime template polynucleotide. In addition, the amplification polynucleotide products of two or more separate amplification reactions conducted using two or more different composite primers that randomly prime template polynucleotide can be combined.

Extension of Primers

The methods of the present invention involve the extension of primers. In general, primers hybridize to, and are extended along (chain extended), a sequence within the target polynucleotide and, thus, the target polynucleotide acts as a template. The extended primers are chain "extension products." The sequence over which the primer is extended may lie between two defined sequences but need not be. In general, the primers hybridize with a sequence within the target polynucleotide. The target sequence usually contains from about 30 to 5,000 or more nucleotides, often 50 to 1,000 nucleotides. The target polynucleotide may be a fraction of a larger molecule or it may be substantially the entire molecule (polynucleotide analyte).

Composite Primers

Generation of primers suitable for extension by polymerization is well known in the art, such as described in PCT Pub. No. WO99/42618 (and references cited therein). The composite primer comprises a combination of RNA and DNA, with the 3'-end nucleotide being a nucleotide suitable for nucleic acid extension. The 3'-end nucleotide can be any nucleotide or analog that when present in a primer, is extendable by a DNA polymerase when hybridized to a polynucleotide template. Generally, the 3'-end nucleotide has a 3'-OH. Suitable primers include those that comprise at least one portion of RNA and at least one portion of DNA. For example, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the invention comprises a 3'-DNA portion and at least one intervening RNA portion (i.e., an RNA portion between DNA portions).

Composite Amplification Primers

Composite amplification primers are RNA/DNA composite primers that can be used to create multiple copies of (amplify) a polynucleotide sequence isothermally using RNA cleavage, and DNA polymerase activity with strand displacement. Amplification with such primers is described, for example in U.S. Pat. Nos. 6,251,639, 6,692,918, and 6,946,251. The composite amplification primer comprises sequences capable of hybridizing to a portion of a DNA template, and most often comprises sequences hybridizable to a defined 3'-portion of the DNA.

A composite amplification primer comprises at least one RNA portion that is capable of (a) binding (hybridizing) to a sequence on a DNA template independent of hybridization of the DNA portion(s) to a sequence on the same extension product; and being cleaved with a ribonuclease when hybridized to the DNA template. The composite amplification primers bind to the DNA template to form a partial heteroduplex in which only the RNA portion of the primer is cleaved upon contact with a ribonuclease such as RNase H, while the DNA template remains intact, thus enabling annealing of another composite primer.

The composite amplification primers also comprise a 3' DNA portion that is capable of hybridization to a sequence on the DNA template such that its hybridization to the DNA is favored over that of the nucleic acid strand that is displaced from the DNA template by the DNA polymerase. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the second strand cDNA is favored over the hybridization of the homologous sequence in the 5' end of the displaced strand to the second strand cDNA.

Ligands and Receptors

The present invention utilizes ligands to bind polynucleotides to a solid surface. A ligand is a compound which can bind to a receptor. The ligand and receptor (antiligand) can be members of a specific binding pair of two different molecules. In some cases, the receptor and or ligand have one or more areas on the surface or in a cavity which gives rise to specific binding. The ligand can be complementary with a particular spatial and polar organization of the receptor. The specific binding pair may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like. Examples of ligands and/or receptors include, but are not limited to, agonists and antagonists for cell membrane receptors, toxins and venoms, viral epitopes, hormones such as steroids, hormone receptors, peptides, enzymes and other catalytic polypeptides, enzyme substrates, cofactors, drugs including small organic molecule drugs, opiates, opiate receptors, lectins, sugars, saccharides including polysaccharides, proteins, and antibodies including monoclonal antibodies and synthetic antibody fragments, cells, cell membranes and moieties therein including cell membrane receptors, and organelles. Examples of ligand-receptor pairs include antibody-antigen; lectin-carbohydrate; peptide-cell membrane receptor; protein A-antibody; hapten-antihapten; digoxigenin-anti-digoxigenin; avidin and biotin, enzyme-cofactor and enzyme-substrate.

In one embodiment, the receptor may comprise an antibody. As used herein, the term "antibody" refers to an immunoglobulin molecule or a fragment of an immunoglobulin molecule having the ability to specifically bind to a particular antigen. The antibody may be an anti-receptor antibody specific for the receptor used in the assay. Thus, the antibody may be capable of specifically binding the receptor as the antigen. Antibodies and methods for their manufacture are well known in the art of immunology. The antibody may be produced, for example, by hybridoma cell lines, by immunization to elicit a polyclonal antibody response, or by recombinant host cells that have been transformed with a recombinant DNA expression vector that encodes the antibody. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like. In some embodiments, the receptor is an antibody, and the ligand is a molecule or portion of a molecule that is recognized by the antibody such as an epitope, or a hapten.

In some embodiments it is desirable that the ligand be a small organic molecule, for example, a compound of molecular weight less than about 1500 g/mol, generally between about 100 to about 1000 g/mol, often between about 300 to about 600 g/mol such as biotin or other haptens. The small organic molecule can provide a means for attachment of a nucleotide sequence to a label or to a support.

Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

Attaching the receptors that are specific binders to the ligands to a support or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970).

The ligand and receptor can be members of capture pairs. For example, capture pairs can employ reversible (e.g., cleavable) or irreversible linkages. Non-limiting examples of reversible linkages include thiol-thiol, digoxigenin/antidigoxigenin, and linkages using VECTREX (E Avidin DLA (Vector Laboratories, Burlingame, Calif.), CaptAvidin™, NeutrAvidinN, and D-desthiobiotin (Molecular Probes, Inc., Eugene, Oreg.).

In some embodiments, the ligand-receptor pair can be pairs of reactive molecules that can react to form a covalent bond, thus binding the polynucleotide to the surface. For example, the ligand can comprise an amine group bound to the polynucleotide that can be reacted with a functional group attached to the solid surface to form a covalent bond. The amine on the polynucleotide can react, for example with an activated carbonyl group attached to the surface, e.g. an N-hydroxy succinimide (NHS) ester. Functional groups such as N-acylimidazole, 2- or 3-bromoacrylate, cyanuric chloride, disulfide, N-hydroxysuccinimide ester, hydrazide, iodoacetyl, imidoester, isocyanate, isothiocyanate, maleimide, succinimidyl carbonate, acyl chloride, and sulfonyl chloride can be used in order to form a covalent linkage to the solid surface.

DNA Polymerase, and an Agent Capable of Cleaving an RNA-DNA Hybrid

The isothermal amplification methods of the invention employ the following enzymes: an RNA-dependent DNA polymerase, a DNA-dependent DNA polymerase, and an agent capable of cleaving an RNA strand of an RNA-DNA hybrid (for example, a ribonuclease such as RNase H). One or more of these activities may be found and used in a single enzyme. For example, RNase H activity may be supplied by an RNA-dependent DNA polymerase (such as reverse transcriptase) or may be provided in a separate enzyme. Reverse transcriptases useful for this method may or may not have RNase H activity. Many reverse transcriptases, such as those from avian myeloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a reverse transcriptase which lacks or has reduced levels RNase H activity. Reverse transcriptase devoid of RNase H or with reduced levels of RNase H activity are known in the art, including those comprising a mutation of the wild type reverse transcriptase where the mutation eliminates the RNase H activity. In these cases, the addition of an RNase H from other sources, such as that isolated from *E. coli*, can be employed for the formation of the double stranded cDNA. The RNA-dependent DNA polymerase activity and DNA-dependent DNA polymerase activity may be provided by the same enzyme (for example, Bst polymerase), or these activities may be provided in separate enzymes. DNA polymerases with strand displacement activity are also useful.

One aspect of the invention is the formation of a complex comprising an RNA/DNA partial heteroduplex. This process generally utilizes the enzymatic activities of an RNA-dependent DNA polymerase, a DNA-dependent DNA polymerase. Generally, RNA in the RNA/DNA partial heteroduplex is cleaved by an agent (such as an enzyme, such as a ribonuclease) capable of cleaving RNA from an RNA/DNA hybrid, generating a 3' single stranded portion with sequences that are complementary to RNA in a composite primer (and thus forming a binding site for a composite primer).

RNA-dependent DNA polymerases for use in the methods and compositions of the invention are capable of effecting extension of a primer according to the methods of the invention. Accordingly, a preferred RNA-dependent DNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase and, for example, a DNA polymerase that possesses both DNA-dependent and RNA-dependent DNA polymerase activity, such as Bst DNA polymerase.

DNA-dependent DNA polymerases for use in the methods and compositions of the invention are capable of effecting extension of the composite primer according to the methods of the invention. Accordingly, a preferred polymerase is one that is capable of extending a nucleic acid primer along a nucleic acid template that is comprised at least predominantly of deoxynucleotides. The formation of the complex comprising the RNA/DNA partial heteroduplex can be carried out by a DNA polymerase which comprises both RNA-dependent DNA polymerase and DNA-dependent DNA polymerase activities (such as Bst DNA polymerase, or a reverse transcriptase). Amplification of an RNA sequence according to methods of the invention involves the use of a DNA polymerase that is able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Generally, the DNA polymerase preferably has little or no 5' to 3' exonuclease activity so as to minimize degradation of primer, or primer extension products. Generally, this exonuclease activity is dependent on factors such as pH, salt concentration, whether the template is double stranded or single stranded, and so forth, all of which are familiar to one skilled in the art. Mutant DNA polymerases in which the 5' to 3' exonuclease activity has been deleted, are known in the art and are suitable for the amplification methods described herein. Mutant DNA polymerases which lack both 5' to 3' nuclease and 3' to 5' nuclease activities have also been described, for example, exo$^{-/-}$-Klenow DNA polymerase. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as described in U.S. Pat. No. 5,744,312 (and references cited therein). Generally, the DNA polymerase has little to no proofreading activity Suitable DNA polymerases for use in the methods and compositions of the invention include those disclosed in U.S. Pat. Nos. 5,648,211 and 5,744,312, which include exo$^-$ Vent (New England Biolabs), exo$^-$ Deep Vent (New England Biolabs), Bst (BioRad), exo$^-$ Pfu (Stratagene), Bca (Panvera), sequencing grade Taq (Promega), exo$^{-/-}$ Klenow DNA polymerase, and thermostable DNA polymerases from *Thermoanaerobacter thermohydrosulfuricus*.

One of the ribonuclease for use in the methods and compositions of the invention is capable of cleaving ribonucleotides in an RNA/DNA hybrid or heteroduplex. Preferably, the ribonuclease cleaves ribonucleotides in an RNA/DNA hybrid regardless of the identity and type of nucleotides adjacent to the ribonucleotide to be cleaved. It is preferred that the ribonuclease cleaves independent of sequence identity. Examples of suitable ribonucleases for the methods and compositions of the invention are well known in the art, including ribonuclease H(RNase H), e.g., Hybridase.

As is well known in the art, DNA-dependent DNA polymerase activity, RNA-dependent DNA polymerase activity, and the ability to cleave RNA from a RNA/DNA hybrid may be present in different enzymes, or two or more activities may be present in the same enzyme. Accordingly, in some embodiments, the same enzyme comprises RNA-dependent DNA polymerase activity and cleaves RNA from an RNA/DNA hybrid. In some embodiments, the same enzyme comprises DNA-dependent DNA polymerase activity and cleaves RNA from an RNA/DNA hybrid. In some embodiments, the same enzyme comprises DNA-dependent DNA polymerase activity, RNA-dependent DNA polymerase activity and cleaves RNA from an RNA/DNA hybrid. In some embodiments, different enzymes comprise RNA-dependent DNA polymerase activity and DNA-dependent DNA polymerase activity. In some embodiments, different enzymes comprise RNA-dependent DNA polymerase activity and cleave RNA from an RNA/DNA hybrid. In some embodiments, different enzymes comprise DNA-dependent DNA polymerase activity and cleave RNA from an RNA/DNA hybrid. In other embodiments the RNA targets are degraded by the use of other RNases such as RNase 1, for example, for removing the target RNA following extension of all DNA first primer along the RNA targets by transcription, or a combination of RNase H and other RNases.

Nucleic Acid Target

The DNA, RNA, or polynucleotide target is generally a polymeric nucleotide, which in the intact natural state can have about 30 to 5,000,000 or more nucleotides and in an isolated state can have about 20 to 50,000 or more nucleotides, usually about 100 to 20,000 nucleotides, more frequently 500 to 10,000 nucleotides. The polynucleotide target to be amplified includes nucleic acids from any source in purified or unpurified form, which can be DNA (dsDNA and ssDNA) or RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof. Exemplary RNAs include, but are not limited to, mRNAs, tRNAs, snRNAs, rRNAs, retroviruses, small non-coding RNAs, microRNAs, polysomal RNAs, pre-mRNAs, intronic RNA, viral RNA and fragments thereof. Exemplary DNAs include, but are not limited to, genomic DNA, plasmid DNA, phage DNA, nucleolar DNA, mitochondrial DNA, chloroplast DNA, cDNA, synthetic DNA, yeast artificial chromosomal DNA ("YAC"), bacterial artificial chromosome DNA ("BAC"), other extrachromosomal DNA, primer extension products and fragments thereof. Target polynucleotide includes DNA (e.g., genomic DNA, including human genomic DNA, and mammalian genomic DNA (such as mouse, rat,)) and RNA (e.g., mRNA, ribosomal RNA, and total RNA). It should be understood that template RNA includes coding and non-coding RNA. The sequences can be naturally occurring or recombinant nucleic acid targets, including cloned nucleic fragments of interest. The terms "polynucleotide target", "nucleic acid target", "target polynucleotide" and "polynucleotide target" are used interchangeably. The term "DNA target" is interchangeable with the term "target DNA", and the term "RNA target" is interchangeable with the term "target RNA". The target nucleic acid may be a mixture of DNA and RNA targets.

The target polynucleotide can be only a minor fraction of a complex mixture such as a biological sample and can be obtained from various biological material by procedures well known in the art. Polynucleotides can be obtained from sources containing very small quantities of nucleic acid, such a single cells, small numbers of cells, patient samples, forensic samples, and archeological samples. Obtaining and purifying nucleic acids use standard techniques in the art, including methods designed to isolate one or a very small number of cells, such a cell sorting or laser capture micro-dissection. The methods of the invention are particularly suited for use with genomic DNA (e.g., human and other mammalian genomic DNA), as well as RNA (e.g., total RNA or mRNA samples) or fragments thereof.

The target polynucleotide(s) can be known or unknown and may contain more than one desired specific nucleic acid sequence of interest, each of which may be the same or different from each other. If the target polynucleotide is double stranded (e.g., double stranded DNA or a double stranded DNA/RNA hybrid, such as is produced by first strand cDNA synthesis), the target may first be treated to render it single stranded (e.g., by denaturation or by cleavage of the RNA portion of a DNA/RNA hybrid). Denaturation may also be carried out to remove secondary structure present in a single stranded target molecule (e.g., RNA). In some cases, double stranded DNA target polynucleotide may be first cleaved by one or more restriction endonuclease enzymes.

When the target polynucleotide is DNA, the initial step of the amplification of a target nucleic acid sequence can be rendering the target single stranded. If the target nucleic acid is a double stranded (ds) DNA, the initial step can be target denaturation. The denaturation step may be thermal denaturation or any other method known in the art, such as alkali treatment. If the target nucleic acid is present in a DNA-RNA hybrid, the initial step can be denaturation of the hybrid to obtain a DNA, or removal of the RNA strand using other means known in the art, such as thermal treatment, digestion with an enzyme that cleaves RNA from an RNA/DNA hybrid (such as RNase H) or alkali treatment, to generate single stranded DNA. When the target is RNA, the initial step may be the synthesis of a single stranded cDNA. Techniques for the synthesis of cDNA from RNA are known in the art, and include reverse transcription of RNA strand using a primer that binds to a specific target, such as the poly-A tail of eukaryotic mRNAs or other specific or consensus sequences. In addition, reverse transcription can be primed by a population of degenerate or partially degenerate primers. First strand cDNA can be separated from the complex of RNA and first strand cDNA as described herein.

RNAs can be from any source in purified or unpurified form, which can be RNA such as total RNA, tRNA, mRNA, rRNA, mitochondrial RNA, chloroplast RNA, DNA-RNA hybrids, or mixtures thereof, from any source and/or species, including human, animals, plants, and microorganisms such as bacteria, yeasts, viruses, viroids, molds, fungi, plants, and fragments thereof. It is understood that the RNA can be coding or noncoding RNA (such as untranslated small RNAs). RNAs can be obtained and purified using standard techniques in the art. Use of a DNA target (including genomic DNA target) can involve initial transcription of the DNA target into RNA form, which can be achieved using methods disclosed in Kurn, U.S. Pat. No. 6,251,639 B1, and by other techniques (such as expression systems) known in the art. Thus, RNA template can be itself generated from a DNA source (such as genomic DNA), using methods known in the art, including Kurn, U.S. Pat. No. 6,251,639. RNA copies of genomic DNA would generally include untranscribed sequences generally not found in mRNA, such as introns, regulatory and control elements, etc. RNA targets may also be generated from cloned genomic DNA sequences that can be subjected to in vitro transcription. Use of a DNA-RNA hybrid can involve denaturation of the hybrid to obtain a single stranded RNA, denaturation followed by transcription of the DNA strand to obtain an RNA, or other methods known in the art such as digestion with an RNase H to generate single stranded DNA.

Reaction Conditions and Detection

Appropriate reaction media and conditions for carrying out the methods of the invention include those that permit nucleic acid extension, copying, and amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as Mg.sup.2+, or Mn.sup.2+, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single stranded binding protein (for example, T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as RNasin) that does not inhibit the activity of the RNase employed in the method can also be included. Any aspect of the methods of the invention can occur at the same or varying temperatures. In some embodiments, the amplification reactions (particularly, primer extension and transcription; and generally not the step of denaturing) are performed isothermally, which substantially avoids the thermocycling process. The isothermal amplification reaction is carried out at a temperature that permits hybridization of the oligonucleotides (primer) of the invention to the template polynucleotide and that does not substantially inhibit the activity of the enzymes employed. The temperature can be in the range of preferably about 25° C. to about 85° C., more preferably about 30° C. to about 80° C., and most preferably about 37° C. to about 75° C. The temperature for the transcription steps can be lower than the temperature(s) for the preceding steps. The temperature of the transcription steps can be in the range of preferably about 25° C. to about 85° C., more preferably about 30° C. to about 75° C., and most preferably about 37° C. to about 70° C.

Nucleotide and/or nucleotide analogs, such as deoxyribonucleoside triphosphates, that can be employed for synthesis of the primer extension products in the methods of the invention are provided in the amount of from preferably about 50 to about 2500 µM, more preferably about 100 to about 2000 µM, even more preferably about 200 to about 1700 µM, and most preferably about 250 to about 1500 µm. Nucleotides and/or analogs, such as ribonucleoside triphosphates, that can be employed for synthesis of the RNA transcripts in the methods of the invention are provided in the amount of from preferably about 0.25 to about 6 mM, more preferably about 0.5 to about 5 mM, even more preferably about 0.75 to about 4 mM, and most preferably about 1 to about 3 mM.

The oligonucleotide components of the reactions of the invention are generally in excess of the number of target nucleic acid sequence to be amplified. They can be provided at about or at least about any of the following: 10, $10^2$, $10^4$, $10^6$, $10^8$, $10^{10}$ times the amount of target nucleic acid. Primers can be provided at about or at least about any of the following concentrations: 50 nM, 100 nM, 500 nM, 1000 nM, 2500 nM, 5000 nM.

In the methods of the invention, the steps may be carried out in the order listed or, in some cases, may be carried out in a different order. In some methods a later step depends on the formation of a product from an earlier step, in which case such steps must be carried out in the order listed. One of ordinary skill in the art will understand which steps should be carried out in the order listed, and which steps can be carried out in a different order.

In some embodiments, the foregoing components are added simultaneously at the initiation of the isothermal amplification process. In another embodiment, components are added in any order prior to or after appropriate timepoints during the amplification process, as required and/or permitted by the amplification reaction. Such timepoints, some of which are noted below, can be readily identified by a person of skill in the art. The enzymes used for nucleic acid amplification according to the methods of the invention can be added to the reaction mixture either prior to a denaturation step, following the denaturation step, or following hybridization of a primer to a polynucleotide template, as determined by their thermal stability and/or other considerations known to the person of skill in the art. The first primer extension product and the second primer extension product synthesis reactions can be performed consecutively, followed by an amplification steps. In these embodiments, the reaction conditions and components may be varied between the different reactions.

In some embodiments, the amplification reactions can be stopped at various timepoints, and resumed at a later time. Said timepoints can be readily identified by a person of skill in the art. One timepoint is at the end of a first primer extension product synthesis. Another timepoint is at the end of a second primer extension product synthesis. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (or depleted) enzyme. In some embodiments, one or more of the components of the reactions is replenished prior to, at, or following the resumption of the reactions. Alternatively, the reaction can be allowed to proceed (i.e., from start to finish) without interruption.

In some embodiments the reaction can be allowed to proceed without purification of intermediate complexes, for example, to remove primer. Products can be purified at various timepoints, which can be readily identified by a person of skill in the art. One timepoint is at the end of first primer extension product synthesis. Another timepoint is at the end of second primer extension synthesis. In some embodiments, the removal of primers and/or target at the end of a defined step by enzymes with appropriate nuclease activities are also useful, for example, cleavage of the RNA portion of free composite tailed primer prior to the isothermal amplification step by treatment with RNase 1.

The detection of the amplification product can be indicative of the presence of a target sequence. Quantitative analysis is also an aspect of the instant invention. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the invention can also be extended to analysis of sequence alterations and sequencing of the target nucleic acid. Further, detection could be effected by, for example, examination of translation products from RNA amplification products. The global amplification by the methods of the invention and/or the amplification of selected targets, when present in the sample, are useful for various methods which enable highly parallel nucleic acid interrogations.

Characterization of Nucleic Acids

The methods of the invention are amenable to quantitative analysis, as in some embodiments, amplification can yield sufficient single stranded polynucleotide (generally, DNA and RNA) products which accurately reflect the representation of the various DNA or RNA sequences (e.g. genomic DNA or mRNA) in the starting material. The amplified products can be analyzed using, for example, probe hybridization techniques known in the art, such as Northern blotting, and hybridizing to probe arrays. In addition, the single stranded polynucleotide products may serve as starting material for other starting material for other analytical and/or quantification methods known in the art, such as real time PCR, quantitative TaqMan, quantitative PCR using molecular beacons, methods described in Kurn, U.S. Pat. No. 6,251,639, etc. Thus, the invention includes those further analytical and/or quantification methods as applied to any of the products of the methods herein.

In another embodiment, the amplification methods of the invention are utilized to generate multiple copies of single stranded polynucleotide products from RNA or DNA targets that are labeled by the incorporation of labeled nucleotides during DNA polymerization. For example, amplification according to the methods of the invention can be carried out with suitable labeled dNTPs or rNTPs. These labeled nucleotides can be directly attached to a label, or can comprise a moiety which could be attached to a label. The label may be attached covalently or non-covalently to the amplification products. Suitable labels are known in the art, and include, for example, a ligand which is a member of a specific binding pair which can be detected/quantified using a detectable second member of the binding pair. Thus, amplification of total RNA or mRNA according to the methods of the invention in the presence of, for example, Cy3-dUTP or Cy5-dUTP results in the incorporation of these nucleotides into the amplification products.

The labeled amplified products are suitable for analysis (for example, detection and/or quantification) by contacting them with, for example, microarrays (of any suitable surface, which includes glass, chips, plastic), beads, or particles, that comprise suitable probes such as cDNA and/or oligonucleotide probes. Thus, the invention provides methods to characterize (for example, detect and/or quantify) a DNA or RNA sequence of interest by generating labeled polynucleotide (generally, DNA) products using amplification methods of the invention, and analyzing the labeled products. Analysis of labeled products can be performed by, for example, hybridization of the labeled amplification products to, for example, probes immobilized at, for example, specific locations on a solid or semi-solid substrate, probes immobilized on defined particles, or probes immobilized on blots (such as a membrane), for example arrays. Other methods of analyzing labeled products are known in the art, such as, for example, by contacting them with a solution comprising probes, followed by extraction of complexes comprising the labeled amplification products and probes from solution. The identity of the probes provides characterization of the sequence identity of the amplified products, and thus by extrapolation the identity of the target DNA or target RNA present in a sample. Hybridization of the labeled products is detectable, and the amount of specific labels that are detected is proportional to the amount of the labeled amplification products of a specific DNA or RNA sequence of interest. This measurement is useful for, for example, measuring the relative amounts of the various RNA species in a sample, which are related to the relative levels of gene expression, as described herein or to detect the presence or absence of defined target DNA or RNA in a sample. The measurement is also useful for measuring the relative amounts of various DNA sequences corresponding, for example, to genetic regions in the sample. The amount of labeled products (as indicated by, for example, detectable signal associated with the label) hybridized at defined locations on an array can be indicative of the detection and/or quantification of the corresponding target DNA or target RNA species in the sample.

Sequencing of the Polynucleotide Products of the Invention

As described above, the methods can be used to obtain sequence information about a target RNA or target DNA of interest. The sequencing can be carried out on the primer extension products or amplification products produced by the methods herein. In some embodiments the sequencing is performed on the polynucleotides attached to solid surfaces as described herein. In one embodiment sequencing is performed on polynucleotides that are attached to the beads through oligonucleotides attached to the beads which capture amplified product, and are extended to produce a polynucleotide attached to the surface comprising a defined sequence at its 3' end.

The methods of the invention are useful, for example, for sequencing of a polynucleotide sequence of interest. The sequencing process is carried out as described for the methods described herein.

Known methods for sequencing include, for example, those described in: Sanger, F. et al., Proc. Natl. Acad. Sci. U.S.A. 75, 5463-5467 (1977); Maxam, A. M. & Gilbert, W. Proc Natl Acad Sci USA 74, 560-564 (1977); Ronaghi, M. et al., Science 281, 363, 365 (1998); Lysov, 1. et al., Dokl Akad Nauk SSSR 303, 1508-1511 (1988); Bains W. & Smith G. C. J. Theor Biol 135, 303-307 (1988); Drnanac, R. et al., Genomics 4, 114-128 (1989); Khrapko, K. R. et al., FEBS Lett 256.118-122 (1989); Pevzner P. A. J Biomol Struct Dyn 7, 63-73 (1989); and Southern, E. M. et al., Genomics 13, 1008-1017 (1992). Pyrophosphate-based sequencing reaction as described, e.g., in U.S. Pat. Nos. 6,274,320, 6,258,568 and 6,210,891), may also be used. In some cases, the methods above require that the nucleic acid attached to the solid surface be single stranded. In such cases, the unbound strand may be melted away using any number of commonly known methods such as addition of NaOH, application of low ionic (e.g., salt) strength, enzymatic degradation or displacement of the second strand, or heat processing. Where the solid surface comprises a plurality of beads, following this strand removal step, the beads can be pelleted and the supernatant discarded. The beads can then be resuspended in a buffer, and a sequencing primer or other non-amplification primer can be added. The primer is annealed to the single stranded amplification product. This can be accomplished by using an appropriate annealing buffer and temperature conditions, e.g., as according to standard procedures in the art.

The methods of the invention are useful, for example, for sequencing of an RNA sequence of interest. The sequencing process can be carried out by processing and amplifying a target RNA containing the sequence of interest by any of the methods described herein. Addition of nucleotides during primer extension can be analyzed using methods known in the art, for example, incorporation of a terminator nucleotide or sequencing by synthesis (e.g. pyrosequencing).

In embodiments wherein the end product is in the form of DNA primer extension products, in addition to the nucleotides, such as natural deoxyribonucleotide triphosphates (dNTPs), that are used in the amplification methods, appropriate nucleotide triphosphate analogs, which may be labeled or unlabeled, that upon incorporation into a primer extension product effect termination of primer extension, may be added to the reaction mixture. Preferably, the dNTP analogs are added after a sufficient amount of reaction time has elapsed since the initiation of the amplification reaction such that a desired amount of second primer extension product or fragment extension product has been generated. Said amount of the time can be determined empirically by one skilled in the art.

Suitable dNTP analogs include those commonly used in other sequencing methods and are well known in the art. Examples of dNTP analogs include dideoxyribonucleotides. Examples of rNTP analogs (such as RNA polymerase terminators) include 3'-dNTP. Sasaki et al., Biochemistry (1998) 95:3455-3460. These analogs may be labeled, for example, with fluorochromes or radioisotopes. The labels may also be labels which are suitable for mass spectroscopy. The label may also be a small molecule which is a member of a specific binding pair, and can be detected following binding of the other member of the specific binding pair, such as biotin and streptavidin, respectively, with the last member of the binding pair conjugated to an enzyme that catalyzes the generation of a detectable signal that could be detected by methods such as colorimetry, fluorometry or chemiluminescence. All of the above examples are well known in the art. These are incorporated into the primer extension product or RNA transcripts by the polymerase and serve to stop further extension along a template sequence. The resulting truncated polymerization products are labeled. The accumulated truncated products vary in length, according to the site of incorporation of each of the analogs, which represent the various sequence locations of a complementary nucleotide on the template sequence.

Analysis of the reaction products for elucidation of sequence information can be carried out using any of various methods known in the art. Such methods include gel electrophoresis and detection of the labeled bands using appropriate scanner, sequencing gel electrophoresis and detection of the radiolabeled band directly by phosphorescence, capillary electrophoresis adapted with a detector specific for the labels used in the reaction, and the like. The label can also be a ligand for a binding protein which is used for detection of the label in combination with an enzyme conjugated to the binding protein, such as biotin-labeled chain terminator and streptavidin conjugated to an enzyme. The label is detected by the enzymatic activity of the enzyme, which generates a detectable signal. As with other sequencing methods known in the art, the sequencing reactions for the various nucleotide types (A, C, G, T or U) are carried out either in a single reaction vessel, or in separate reaction vessels (each representing one of the various nucleotide types). The choice of method to be used is dependent on practical considerations readily apparent to one skilled in the art, such as the nucleotide tri phosphate analogs and/or label used. Thus, for example, when each of the analogs is differentially labeled, the sequencing reaction can be carried out in a single vessel. The considerations for choice of reagent and reaction conditions for optimal performance of sequencing analysis according to the methods of the invention are similar to those for other previously described sequencing methods. The reagent and reaction conditions should be as described above for the nucleic acid amplification methods of the invention.

The Solid Surface

In various exemplary embodiments, a solid surface may have a wide variety of forms, including membranes, slides, plates, micromachined chips, microparticles, beads and the like. Solid surfaces may comprise a wide variety of compositions including, but not limited to, glass, plastic, silicon, alkanethiolate derivatized gold, cellulose, low cross linked and high cross linked polystyrene, silica gel, polyamide, and the like, and can have various shapes and features (e.g., wells, indentations, channels, etc.). As used herein, the terms "solid surface" and "solid substrate" are used interchangeably. In some cases these will be referred to as the surface or the support. The surface can be hydrophilic or capable of being rendered hydrophilic and may comprise inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. The surface can have any one of a number of shapes, such as strip, rod, particle, including bead, and the like.

In some embodiments, the solid surface comprises a bead or plurality of beads. The beads may be of any convenient size and fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g, in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex) agarose gel (Sepharose™), and other solid phase supports known to those of skill in the art. The beads are generally about 2 to about 100 um in diameter, or about 5 to about 80 pm in diameter, in some cases, about 10 to about 40, um in diameter. In some embodiments the beads can be magnetic. Having magnetic beads can be useful for isolation and purification of the beads comprising nucleic acids described herein. Other methods to separate beads can also be used. For example, the capture beads may be labeled with a fluorescent moiety which would make the nucleic acid-bead complex fluorescent. The target capture bead complex may be separated, for example, by flow cytometry or fluorescence cell sorter.

Attachment of Oligonucleotides to the Solid Surfaces

One aspect of the invention involves attaching oligonucleotides to solid surfaces such that the oligonucleotides can hybridize with polynucleotides produced by the methods of the invention. Many methods of attaching oligonucleotides to surfaces are known. In some embodiments, the oligonucleotide is attached covalently to the solid surface. In some embodiments such attached oligonucleotides act to capture nucleic acids such as amplification products, and in some cases such attached oligonucleotides also act as primers. Methods of attaching oligonucleotides and primers to a surface are known in the art (see, e.g., Beier et al., 1999, Nucleic Acids Res. 27(9):1970-1977; Brison et al., 1982, Molecular and Cellular Biology 2:578 587; Cheung et al., 1999, Nat. Genet. 21(1 Suppl):15-19; Chrisey et al., 1996, Nucleic Acids Res. 24(15):3031-3039; Cohen et. al., 1997, Nucleic Acids Res. 1997 Feb. 15; 25(4):911-912; Devivar et al., 1999, Bioorg. Med. Chem. Lett. 9(9):1239-1242; Heme et al., 1997. J. Am. Chem. Soc. 119:8916-8920; Kumar et al., 2000, Nucleic Acis Res. 28(14):e71; Lipshutz et al., 1999, Nat. Genet. 21(1 Suppl):20-24; Milner et al., 1997, Nat. Biotechnol. June; 15(6):537-541; Morozov et al., 1999, Anal. Chem. 71(15):3110-3117; Proudnikov et al., 1998, Anal Biochem. 259(1):34-41; Rasmussen et al., 1991, Anal Biochem. 198(1): 138-142; Rogers et al., 1999, Anal. Biochem. 266(1):23-30; Salo et al., 1999, Bioconjug Chem. 10(5):815-823; Singh-Gasson et al., 1999, Nat. Biotechnol. 17(10):974-978, and Pierce Chemical Company Catalog 1994, pp. 155-200), incorporated herein by reference).

Solid Surfaces in Microreactors or Emulsions

One aspect of the invention comprises methods and libraries relating to the attachment of nucleic acids on beads in an microreactors such as in an emulsion. As used herein, a microreactor is a small volume of fluid, generally in the volume range of microliters to nanoliters. The small volumes of the microreactors are isolated from one another allowing reactions to occur within each microreactor without significant contamination from or mixing with other microreactors unless desired. Emulsions or microemulsions comprise one approach to microreactors, in which the individual drops each can represent a microreactor. Microreactors such as emulsions can allow for the clonal amplification from a single molecule of a nucleic acid to produce a population of identical nucleic acids within the microreactor. Generally water-in-oil emulsions, also referred to as inverse emulsions are used. These emulsions have small water droplets dispersed in a hydrophobic medium. As used herein, the term oil is used broadly to refer to a hydrophobic fluid in which aqueous droplets can be dispersed. various exemplary embodiments a hydrophobic medium can be can include an oil (e.g., mineral oil, light mineral oil, silicon oil) or a hydrocarbon (e.g., hexane, heptane, octane, nonane, decane, etc.) and the like. Fluorinated hydrocarbons can also be used.

In some embodiments, solid surfaces can be included within each microreactor. For example, where a bead comprises the solid surface, an emulsion can be produced such that the solid surfaces are included within the emulsion. In some embodiments, an emulsion is produced such that a plurality of microreactors within the emulsion have one or fewer beads. Related methods are described, for example in WO/2004/069849, and WO/05010145A2. In some aspects of the invention, the nucleic acids are attached to the beads by binding of a ligand attached to the nucleic acid to a receptor bound to the solid surface.

The emulsion can be formed either in bulk, for example, by mixing, or can be formed by injection, for example using a microfluidic device. For use with the present invention, beads with or without attached nucleic acid template are suspended in a water-in-oil emulsion. Where the amplification reaction requires thermal cycling, such as a PCR reaction, a heat stable emulsion must be used. Where isothermal amplification is employed, the need for thermal stability may be reduced, expanding the types of emulsions that can be used. In some embodiments, a plurality of the microreactors include only one template nucleic acid species and one bead. There may be many droplets that do not contain a template nucleic acid or which do not contain a bead. Likewise there may be droplets that contain more than one copy of a template. The emulsion may be formed according to any suitable method known in the art. One method of creating emulsion is described below but any method for making an emulsion may be used. These methods are known in the art and include adjuvant methods, counter-flow methods, cross-current methods, rotating drum methods, and membrane methods. Furthermore, the size of the microcapsules may be adjusted by varying the flow rate and speed of the components. For example, in dropwise addition, the size of the drops and the total time of delivery may be varied. In some embodiments, the emulsion contains a density of about 3,000 beads encapsulated per microliter.

Various emulsions that are suitable for biologic reactions are referred to in Griffiths and Tawfik, EMBO, 22, pp. 24-35 (2003); Ghadessy et al., Proc. Natl. Acad. Sci. USA 98, pp. 4552-4557 (2001); U.S. Pat. No. 6,489,103 and WO 02/22869, each fully incorporated herein by reference.

The microreactors should be sufficiently large to encompass sufficient amplification reagents for the degree of amplification required. However, the microreactors should be sufficiently small so that a population of microreactors, each containing a member of a DNA library, can be amplified by conventional laboratory equipment. The use of microreactors as described herein allows amplification of complex mixtures of templates (e.g., genomic DNA samples or whole cell RNA) without intermixing of sequences, or domination by one or more templates (e.g., PCR selection bias; see, Wagner et al., 1994, Suzuki and Giovannoni, 1996; Chandler et al., 1997, Polz and Cavanaugh, 1998).

In some embodiments the micoreactors are produced such that a plurality of microreactors have one bead and one copy of a nucleic acid template. In some embodiments, limiting dilution can be used to isolate polynucleotides in a manner that is suitable for clonal amplification. In some embodiments the beads have the one copy of a nucleic acid bound to the bead. Producing a plurality of microreactors having only one bead and one nucleic acid template can be performed by diluting the bead and the nucleic acid template or the bead with the bound nucleic acid template to a dilution level at which, on average, each microreactor will contain one or fewer beads and/or one or fewer nucleic acid templates per microreactor. Determining the level of dilution at which this condition occurs can be done by calculation, and by experiment. Dilution to single bead and/or single molecule is described, for example in WO/2004/069849. For example, a sample comprising a plurality of beads, each comprising, on average one or fewer nucleic acids can be diluted to a concentration such that aliquots of the diluted sample that can be divided into individual microreactors (e.g., wells of a multi-well plate) can be predicted to comprise on average>0 and <1 nucleic acid molecule. Therefore, a percentage of reaction vessels can be predicted on a statistical basis (e.g., Poisson distribution) to comprise an isolated polynucleotide suitable for clonal amplification. Once isolated within the reaction vessels, polynucleotides can be amplified by various methods as described herein to yield clonal amplification.

Subsequent to amplification, the microreactors can be accessed in order to remove the contents, for example, the beads, for later analysis such as by sequencing. One method of accessing the microreactors comprises breaking the emulsion.

In one embodiment, following amplification of the nucleic acid template and the attachment of amplification copies to the bead, the emulsion is "broken" (also referred to as "demulsification" in the art). There are many methods of breaking an emulsion (see, e.g., U.S. Pat. No. 5,989,892 and references cited therein) and one of skill in the art would be able to select an appropriate method. In the present invention, one preferred method of breaking the emulsion uses additional oil to cause the emulsion to separate into two phases. The oil phase can then be removed, and a suitable organic solvent (e.g., hexanes) is added. After mixing, the oil/organic solvent phase is removed. Subsequently, the aqueous layers above the beads are removed. The beads are then washed, for example, with a mixture of an organic solvent and buffer. Suitable organic solvents include alcohols such as methanol, ethanol, and the like. The beads bound to amplification products may then be resuspended in aqueous solution for use, for example, in a sequencing reaction according to known technologies.

In some embodiments, because the clonal amplicons that are produced are isolated as discrete populations, clonal amplification products can be carried analyzed, for example sequenced, in a parallel manner. Therefore, in some embodiments, at least at least 100, 500, 1000, 10000, 50000, 100000, 300000, 500000, or 1000000 populations of clonal amplification products can be analyzed in parallel. The skilled artisan will appreciate that various methods can be suitable for parallel analysis of clonal amplicons. Generally, such methods can produce a discrete detectable signal that can be associated or linked to individual populations of clonal amplicons.

Determination of Gene Expression Profile

The amplification methods of the invention can be used for use in determining the levels of expression of multiple genes in a sample since the methods described herein are capable of amplifying multiple target RNAs in the same sample. As described above, amplification products can be detected and quantified by various methods, as described herein and/or known in the art. Since RNA is a product of gene expression, the levels of the various RNA species, such as whole transcriptome or total RNAs, in a sample is indicative of the relative expression levels of the various genes (gene expression profile). Thus, determination of the amount of RNA sequences of interest present in a sample, as determined by quantifying amplification products of the sequences, provides for determination of the gene expression profile of the sample source.

The methods of the present invention allow for the storage and subsequent analysis of samples, allowing for a sample to be bound to a solid substrate for archiving, then later to be analyzed by the methods described herein to determine a gene expression profile. In some embodiments, the sample can be analyzed multiple times, and stored between analyses.

Accordingly, the invention provides methods of determining gene expression profile in a sample, said method comprising: amplifying single stranded product from at least one RNA sequence of interest in the sample, using any of the methods described herein; and determining amount of amplification products of each RNA sequence of interest, wherein each said amount is indicative of amount of each RNA sequence of interest in the sample, whereby the expression profile in the sample is determined. Generally, labeled products are generated. In one embodiment, the target RNA is mRNA. It is understood that amount of amplification product may be determined using quantitative and/or qualitative methods. Determining the amount of amplification product includes determining whether amplification product is present or absent. Thus, an expression profile can includes information about presence or absence of one or more RNA sequence of interest. "Absent" or "absence" of product, and "lack of detection of product" as used herein includes insignificant, or de minimus levels. In some cases, the methods further provide for clonal amplification of the target RNA or a subset of the target RNA.

The methods of expression profiling are useful in a wide variety of molecular diagnostic, and especially in the study of gene expression in essentially any mammalian cell (including a single cell) or cell population. A cell or cell population (e.g. a tissue) may be from, for example, blood, brain, spleen, bone, heart, vascular, lung, kidney, pituitary, endocrine gland, embryonic cells, tumors, or the like. Expression profiling is also useful for comparing a control (normal) sample to a test sample, including test samples collected at different times, including before, after, and/or during development, a treatment, and the like.

Libraries

In another embodiment, the invention encompasses a library comprising a plurality of nucleic acid molecules, wherein each nucleic acid molecule is separately immobilized to a different bead. In another embodiment, the invention encompasses a library comprising a plurality of nucleic acid molecules, wherein each nucleic acid molecule is separately immobilized to a different bead and wherein each bead comprises over 100,000 clonal amplification copies of each nucleic acid molecule, wherein the library is contained in a single vessel. As examples, the nucleic acid molecules may be genomic DNA, cDNA, episomal DNA, BAC DNA, or YAC DNA. The genomic DNA may be animal, plant, viral, bacterial, or fungal genomic DNA. Preferably, the genomic DNA is human genomic DNA or human cDNA.

Kits

One aspect of the invention comprises kits useful for carrying out the methods of the invention.

In one aspect, the kit comprises (a) a first primer comprising a 3'-DNA portion and a 5'-RNA portion, wherein the 3'-DNA portion comprises a random sequence or a specific sequence, and the 5' RNA portion further comprises sequence (A), (b) a second primer comprising a 5'-ligand. In some embodiments, the kit may further comprise (c), an RNA dependent DNA polymerase, (d) a DNA dependent DNA polymerase with strand displacement activity, (e) RNase H, (f) an amplification chimeric primer comprising a 3'-DNA portion and a 5'-RNA portion wherein the sequence of the amplification primer is the substantial the same sequence as the (A) sequence, or a combination thereof. In some cases, the kit may further comprise instructions for the use of said kit.

In one aspect, the kit comprises (a) a first primer comprising a 3'-DNA portion and a 5'-RNA portion, wherein the 3'-DNA portion comprises a random sequence and the 5' RNA portion further comprises sequence (A), (b) a second primer comprising a 5'-ligand, and (c) a chimeric oligonucleotide comprising a 3'-DNA portion substantially comprising sequence (A) and a 5'-RNA sequence (C). In some cases, the kit may further comprise (d) RNase H, (e) an RNA dependent DNA polymerase, (f) a DNA dependent DNA polymerase with strand displacement activity, (g) a chimeric amplification primer comprising a 3'-DNA portion and a 5'-RNA portion, wherein the chimeric amplification primer comprises a sequence which is substantially the same as sequence (C), or a combination thereof. In some cases, the kit may further comprise instructions for the use of said kit.

In some embodiments the second primer further comprises a sequence (B) at or near the 5'-end. In some embodiments the kit further comprises solid support with immobilized ligand binding component on it surface.

In some embodiments the kit further comprises solid surface with an oligonucleotide attached to the surface by the 5'-end and comprising a sequence (B). In other embodiment the oligonucleotide attached to the solid surface comprises a sequence hybridizable to sequence (A) and the oligonucleotide is attached by the 5'-end.

In some embodiments the kit comprises (a) a first primer that is a tailed DNA primer comprising a 5'-tail sequence (D), (b) a second primer that is a chimeric primer comprising a 3'-DNA portion and a 5'-RNA portion wherein the 5'-end comprises a tail sequence (E), (c) a third primer which is a tailed primer comprising a 3'-sequence that comprises a sequence substantially the same as sequence (D), optionally a 5'-tail sequence (F), and 5'-ligand. In some cases, the kit may further comprise (d) an RNA dependent DNA polymerase, (e) a DNA dependent DNA polymerase with strand displacement activity, (f) RNase H, (g) a chimeric amplification primer comprising a 3'-DNA portion and a 5'-.RNA portion wherein the chimeric amplification primer comprises a sequence which is substantially a sequence (E), or a combination thereof. In some cases, the kit may further comprise instructions for the use of said kit.

In some embodiments, the kit comprises (a) reagents for forming an emulsion and (b) a DNA polymerase with substantial strand displacement activity. Reagents for forming a suitable water in oil emulsion are known and commercially available for example in emPCR kits II and III (454/Roche LifeSciences). Said emulsion forming reagents may include for example decamethylcyclopentasiloxane, polyphenylmethylsiloxane, water and/or buffer. In some cases, the kit may further comprise (c) one or more RNA-DNA chimeric primers, (d) an all DNA primer, (e) a solid surface such as a bead or set of beads, a substantially planar array, a well or wells in a plate, or an isolated surface or set of isolated surfaces, (f) RNase H, (g) a chimeric oligonucleotide, or a combination thereof. In some cases, the kit may further comprise instructions for the use of said kit.

In some embodiments the kit comprises (a) a first primer that is a tailed DNA primer comprising a 5'-tail sequence (D), (b) a second primer that is a chimeric primer comprising a 3'-DNA portion and a 5'-RNA portion wherein the 5'-end comprises a tail sequence (E), (c) a third primer which is a tailed primer comprising a 3'-sequence that comprises a sequence substantially the same as sequence (D), optionally a 5'-tail sequence (F), and 5'-ligand. In some cases, the kit may further comprise (d) an RNA dependent DNA polymerase, (e) a DNA dependent DNA polymerase with strand displacement activity, (f) RNase H, (g) a chimeric oligonucleotide comprising a 3'-DNA sequence (E) and a 5'-RNA sequence (G), (h) a chimeric amplification primer comprising a 3'-DNA portion and a 5'-RNA portion wherein the chimeric amplification primer comprises a sequence which is substantially the same as sequence (G), or a combination thereof. In some cases, the kit may further comprise instructions for the use of said kit.

The 3'-end sequence of the first and second primer may comprise a specific sequence or a random sequence. In some embodiments the kits useful for carrying out the methods of the invention may further comprise an inhibitor of the DNA dependent DNA polymerase, such as Actinomycin.

The components of the kits may comprise the same aspects and embodiments as described above for the components in the description of methods. For example, the ligands and receptors, the primers, the enzymes and the oligonucleotides can be those described herein to carry out the methods of the invention.

Example 1

Clonal Expansion of RNA

Step 1: Synthesis of First Primer Extension Product 100 ng of an RNA template is provided. The provided RNA template is produced from a biological specimen using a commercially available kit (i.e. Qiagen RNeasy) according to the manufacturer's instructions. A first primer extension reaction mixture is assembled comprising a first primer consisting of a 3' annealing sequence, a portion of which is DNA, and a 5' tail sequence (A), a portion of which is RNA and the following reagents in a total volume of 10 µl:

100 ng of RNA template
20 pmol of primer
0.5 µl dNTPs (25 mM)
0.1 µl RNasin
0.1 µl DTT
2 µl 5×AMV reverse transcriptase reaction buffer
DEPC treated water to 10 µl total volume The reaction mixture is incubated for 2 min at 75° C., and then cooled to 37° C. 1 µl AMV reverse transcriptase (USB 70041Y, 15 U/µl) is added to each reaction and the reaction mixture is further incubated at this temperature for 60 min. The resulting product is a first primer extension product of DNA with a 5' RNA tail sequence (A) annealed to an RNA template. The reaction mixture is heated to 90° C. for 3 min. for enzyme inactivation.

Step 2: Synthesis of Second Primer Extension Product (Formation of (A)/(A') RNA/DNA Heteroduplex)

The first primer extension product is mixed with 10 µl of the second primer extension mixture containing the following:

1 µl 10× Klenow reaction buffer
0.1 µl dNTPs (25 mM)
0.5 µl Klenow Exonuclease free (USB 70057Y 10 U/µl)) DNA polymerase
8.4 µl water The reaction mixture is incubated for 30 min at 37° C., followed by heating to 75° C. for 5 min to stop the reaction by inactivating the enzymes. The resulting primer extension products comprise a double stranded DNA product with a DNA/RNA heteroduplex at one end of sequence (A')/(A) and a partial duplex with a tailed B sequence at the other end.

Step 3: Cleavage of DNA/RNA Hybrid

To the second primer extension product reaction mixture is added 0.02 U Hybridase (RNase H) and the reaction mixture is incubated at 50° C. for 60 min and cooled to 4° C. The resulting RNase H digested primer extension product reaction mixture comprises a first primer extension product of DNA without a 5' RNA tail sequence (A) annealed to the second primer extension product of DNA with a 5' tail sequence (B) and a 3' annealing sequence (A').

Step 4: Annealing of Chimeric Oligonucleotide

Next, a chimeric oligonucleotide comprising a 3' annealing sequence (A), a portion of which is DNA, and a 5' tail sequence (C), a portion of which is RNA is added to the reaction mixture and annealed to the complementary sequence (A'). The annealing step is carried out at 50° C. for 10 min. and the reaction is cooled to 4° C.

Step 5: Extension of the Second Primer Extension Product Along the Chimeric Oligonucleotide To the reaction mixture is added 2.5 units of Exonuclease Free Klenow polymerase and the reaction mixture is incubated for 30 min at 37° C., followed by heating to 75° C. for 5 min to stop the reaction by inactivating the enzymes. The resulting first primer extension product comprises a sequence (A), a 5' tail sequence (C), a portion of which is RNA, and a 3' tail sequence (B') of DNA. The product is a double stranded DNA with a DNA-RNA heteroduplex at one end (C-C').

Step 6: Attachment to a Solid Support

To the reaction mixture is added a solid support in the form of Polystyrene beads which are derivatized with a short DNA oligonucleotide comprised of sequence B. The reaction mixture is heated to 98° C. for 2 minutes and cooled to room temperature to allow for annealing of the first primer extension product to the solid support. The beads are washed in 1×SSC to remove the second primer extension product. To the beads is added 1× Thermopole buffer (NEB), dNTPs, 1×NEB BSA, Bst DNA polymerase, and water in amounts known in the art to promote DNA polymerase activity. The reaction mixture is incubated in a thermocycler at 25° C. for 5 minutes, 50° C. for 30 min, 95° C. for 5 min, and then cooled to 4° C. The resulting double stranded product, illustrated as the final product in FIG. 17, is a SPIA substrate suitable for clonal expansion via SPIA amplification. Enzymes, buffers and salts are removed by washing the solid-support-bound SPIA substrate and resuspending in a suitable volume of water.

Step 7: Clonal Expansion

SPIA amplification is carried out using buffer and enzyme mixtures from NuGEN's WT-Ovation Pico RNA amplification system (NuGen Technologies Inc, San Carlos Calif.). In addition, the SPIA amplification uses a chimeric amplification primer that has a 5' RNA sequence and a short 3' DNA sequence (approximately 7 base pairs) and is complementary to the sequence (C') of the SPIA substrate produced in step 6. The SPIA amplification is set up as follows:
3 µl Amplification primer (50 µM stock)
10 µl Solid-support-bound SPIA substrate
17 µl water
40 µl amplification buffer (WT-Ovation Pico System)
20 µl Amplification Enzyme Mix (WT-Ovation Pico System)

The reactions are incubated in a thermocycler at 50° C. for 60 min, followed by 95° C. for 5 min, and cooled down. The amplification products are generated in close proximity to the remaining unhybridized B-sequence oligonucleotides on the solid support on which the parent SPIA substrate is bound and are therefore also immobilized on the same solid support as they are generated. This process ultimately provides a plurality of solid supports (e.g. beads), each bead with a clonally expanded sequence hybridized therein, such that the hybridized sequence has a known sequence (B') and (C) at each end. The product of this example is useful for such methods as archiving of nucleic acid sequences, reducing the complexity of nucleic acid samples, and providing a set of clonally expanded sequences on beads suitable for use in next generation sequencing platforms such as the SOLiD system by Applied Biosystems.

Example 2

Diagnosis and Prognosis of Cancer

A suggested course of treatment can be determined by RNA expression analysis of a tumor biopsy. A needle biopsy is performed on a subject to obtain tissue from the suspicious mass for further analysis. The biopsied tissue recovered from the subject is processed to extract and purify total RNA using a commercially available Qiagen RNeasy kit according to the manufacturer's instructions.

500 pg of total RNA representing at least a portion of the transcriptome of the biopsied material is amplified by the methods of the present invention as described briefly herein. To the RNA in a reaction mixture is added: 100 pmol of a first primer comprising random first primer and a poly dT first primer, a 5' segment and a 3' segment, a portion of the 5' segment comprising RNA, and a portion of the 3' segment comprising DNA. The 3' DNA segment of the random first primer further comprises an annealing sequence that comprises random hexamers. The 5' RNA segment of the random first primer comprises a tag sequence (A).

To the reaction mixture 10 pmol of a poly-T first primer is also added comprising a 5' segment and a 3' segment, a portion of the 5' segment comprising RNA, and a portion of the 3' segment comprising DNA in the reaction mixture. The 3' DNA segment of this poly-T first primer further comprises an annealing sequence that hybridizes to and is complementary to a portion of the poly A tail of mRNA transcripts present in the total RNA of the reaction mixture, and the 5' RNA segment comprises a tag sequence (A).

The volume of the reaction mixture is adjusted to 10 µl with DEPC treated water, and then the reaction mixture is heated to 75° C. for 2 minutes and cooled. First strand synthesis is carried out using the buffer and enzyme reagents provided with the WT-Ovation Pico RNA Amplification kit, and incubation conditions are as described in the User Guide and Quick Protocol: (http://www.nugeninc.com/tasks/sites/nugen/assets/File/user_guides/userguide_wt_ov_pico.pdf and http://www.nugeninc.com/tasks/sites/nugen/assets/File/quick_protocols/qp_wt_ov_pico.pdf.).

The first primer extension product is mixed with 10 µl of the second primer extension mixture containing the following:
second strand cDNA synthesis enzyme mixture and second strand buffer mixture from the NuGEN's WT-Ovation Pico amplification system (as above)
20 pmol of a second primer comprising a 5' segment and a 3' segment, a portion of the 5' segment comprising a tag sequence (B), and a portion of the 5' segment comprising an annealing sequence.

The reaction mixture is incubated under the conditions described in the use Guide for the WT-Ovation Pico RNA Amplification system, followed by heating to 75° C. for 5 minutes to stop the reaction by inactivating the enzymes. The resulting primer extension products comprise a partial double stranded DNA product with a DNA/RNA heteroduplex at one end of a sequence (A')/(A). The first primer extension product in the reaction mixture is then digested using exonuclease 1 (0.5 µl at 37° C. for 30 min.) followed by inactivation of the enzymes (80° C. for 20 minutes). The first and second primer extension products are then purified using Agencourt magnetic beads as per the manufacturer's instructions (User Guide as above).

Isothermal linear amplification (SPIA) is then carried out in a reaction mixture containing the above purified reaction products (10 µl), 2 µl chimeric amplification primer (100 µM stock solution), 18 µl water, 40 µl amplification buffer and 20 µl amplification enzyme mixture as provided in the WT-Ovation Pico RNA Amplification System (NuGen Technologies). The amplification is carried out according to the instructions provided for the WT-Ovation Pico RNA Amplification System.

The amplified product is then analyzed and quantitated by Real Time qPCR with SYBR Green, using an MJ Opticon thermocycler. Amplification reactions are diluted 1:100 in Tris-EDTA and 2 µl of the diluted DNA are analyzed using primer pairs specific for abl, ras, and her2 in three separate reactions.

The results of the qPCR are analyzed to determine that abl is overexpressed in the cells of the suspicious mass. The results are combined with immunohistochemical and cytological analysis to determine a suggested course of therapy. Alternatively, a gene expression profile of the sample can be obtained using microarrays such as GeneChip (Affymetrix). The amplified reaction products are subjected to fragmentation and labeling with Biotin using NuGEN's Ovation-F/L reagents and protocol. The fragmented and labeled products are used for hybridization to GeneChip according to the manufacturer protocol. The resulting hybridization data provides a gene expression profile of the sample.

Example 3

Personal Genomics

An individual is tested by a personal genomics business using the methods of the present invention for single nucleotide polymorphisms (SNPs) within the BRCA1, BRCA2, p53, MPO, NAT1, NAT2, and ras coding regions that are related to increased risks for specific types of cancer.

The individual supplies a small sample of tissue (i.e. a cheek swab) to the personal genomics business. Genomic DNA from the sample of tissue is isolated using a commercially available kit (i.e. Promega's Wizard® Genomic DNA Purification Kit), according to the manufacturer's protocol.

1 to 10 ng of purified genomic DNA is used to clonally amplify the sequences corresponding to the genomic regions with known, cancer related, SNPs of the BRCA1, BRCA2, p53, MPO, NAT1, NAT2, and ras genes on a solid support (i.e. a bead). The target sequences are clonally amplified by isothermal linear amplification using the steps shown in FIG. 13 steps I(b), II(b), and III(b); FIG. 17 steps IV to X; and FIG. 18 of the present application.

The set of beads comprising the clonally amplified sequences are loaded onto a SOLiD™ Analyzer and the sequences of the regions of interest are determined using the manufacturer's protocol using a primer complementary to the sequence (A) on the 5' end of the amplified product.

The resulting sequences are used to determine the presence or absence of SNPs related to cancer in the genes of interest. A report is generated that includes the SNPs identified, the impact of the SNPs on lifetime risk of developing specific diseases or conditions, and suggestions for prophylactic or therapeutic interventions.

Example 4

Analysis of Fetal DNA

A fetal sample is obtained by amniocentesis. DNA is extracted and purified from the sample using a commercially available kit (i.e. Promega's Wizard® Genomic DNA Purification Kit). The DNA is attached to a solid support according to the method outlined in FIG. 19 and clonally amplified according to the method outlined in FIG. 18. The set of beads comprising the clonally amplified sequences are loaded onto a Genome Sequencer FLX Titanium Series from Roche/454 Life Sciences and the sequences of the regions of interest are determined using the manufacturer's protocol using a primer complementary to the sequence (A) on the 5' end of the amplified product.

The resulting sequences are used to determine the presence or absence of SNPs related to prenatal diseases or conditions. A report is generated that includes the SNPs identified, the impact of the SNPs on lifetime risk of developing specific diseases or conditions, and suggestions for prophylactic or therapeutic interventions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   (a) denaturing a double-stranded target DNA;
   (b) annealing to the target DNA and extending with a DNA polymerase comprising strand displacement activity, a first primer comprising a DNA segment and a 5' RNA segment, wherein a 3' portion of the primer comprises a random sequence, and a 5' portion of the primer comprises a sequence (A), which is not complementary to the target DNA; to form a first primer extension product hybridized to the target DNA and comprising the sequence (A) at its 5' end;
   (c) separating the first primer extension product from the target DNA;
   (d) annealing to the first primer extension product and extending a second primer comprising a 3' complementary DNA region that comprises a random sequence, wherein the second primer is a tailed primer comprising a 5' sequence (B), to form a double-stranded product comprising the first primer extension product and a second primer extension product, whereby a double-stranded product with a DNA/RNA heteroduplex at one end is generated;
   (e) cleaving the RNA in the heteroduplex from the first primer extension product such that a portion of the second primer extension product that is complementary to the sequence (A), a sequence (A'), is single stranded;
   (f) annealing to the second primer extension product an oligonucleotide comprising a 3'-DNA segment that is complementary to the sequence (A') and a 5' RNA segment comprising a sequence (C);
   (g) extending the oligonucleotide along the second primer extension product to form an oligonucleotide extension product comprising a sequence (B'), complementary to the sequence (B) of the second primer extension product wherein a double-stranded DNA product is formed;
   (h) denaturing the double-stranded DNA product of step (g);
   (i) attaching the oligonucleotide extension product to a solid support by annealing the sequence (B') to a bead or isolated area comprising the sequence (B); and (j) extending the sequence (B) on the solid support to produce a third primer extension product hybridized to the oligonucleotide extension product, comprising a 3' sequence (A') and (C'), whereby a DNA/RNA heteroduplex at one end is generated.

2. The method of claim 1 further comprising:

(k) cleaving the RNA from the heteroduplex using RNase H to produce a single-stranded portion of the third primer extension product corresponding to the sequence (C');

(l) annealing an amplification primer to the single-stranded portion of the third primer extension product corresponding to the sequence (C'), wherein the amplification primer has a DNA portion and a 5' RNA portion;

(m) extending the amplification primer with an enzyme having strand displacement activity to produce an amplified product hybridizable to the bead or isolated area; and (n) repeating steps (k) to (m) to produce multiple copies of the amplified product comprising the sequences (A) and (B').

3. The method of claim 2 wherein the amplification is a clonal amplification.

4. The method of claim 2 wherein the bead or isolated area is the only bead or isolated area within an isolated liquid volume such that the amplified product is contained within the liquid volume.

5. The method of claim 4 wherein the liquid volume is an aqueous droplet within a non-aqueous fluid.

6. The method of claim 4 wherein the liquid volume is a well in a plate.

7. The method of claim 1 wherein the solid support is a substantially planar substrate.

8. The method of claim 2 wherein the bead or isolated area comprises multiple covalently attached oligonucleotides comprising the sequence (B) at their 3' ends, whereby upon the amplification of step (m), multiple copies of amplified products comprising the sequence (B') at their 3' end are produced in close proximity to an immobilized sequence (B) so as to enhance hybridization of the amplified products to the immobilized sequence (B) on the bead or isolated area.

9. A method of producing a bead or isolated area with multiple copies of a nucleotide sequence covalently attached thereto by performing the method of claim 8, further comprising extending the (B) sequences to produce multiple polynucleotides covalently attached to the bead or isolated area that are substantially complementary to the amplified product and that comprise the sequence (A') near their 3' ends.

10. A sequencing method comprising performing the method of claim 9, further comprising the steps of removing the amplified product to render the polynucleotides covalently attached to the bead or isolated area single-stranded, and extending a primer hybridized to the sequence (A') to produce detectable oligonucleotide fragments complementary to the sequence of the polynucleotide covalently attached to the bead or isolated area.

11. The method of claim 10 wherein the sequencing method comprises cleavable labeled terminators.

12. The method of claim 10 wherein the sequencing method comprises pyrophosphate detection.

13. The method of claim 10 wherein the sequencing method is an isothermal sequencing method.

14. The method of claim 10 wherein the sequencing method comprises cycle sequencing.

* * * * *